US011433143B2

(12) United States Patent
Nel et al.

(10) Patent No.: US 11,433,143 B2
(45) Date of Patent: Sep. 6, 2022

(54) NANO-ENABLED IMMUNOTHERAPY IN CANCER

(71) Applicant: The Regents of the University of California, Oakland, CA (US)

(72) Inventors: Andre E. Nel, Sherman Oaks, CA (US); Huan Meng, Los Angeles, CA (US); Kuo-Ching Mei, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/687,368

(22) Filed: Nov. 18, 2019

(65) Prior Publication Data
US 2020/0197534 A1    Jun. 25, 2020

Related U.S. Application Data

(63) Continuation-in-part of application No. PCT/US2018/033265, filed on May 17, 2018.
(Continued)

(51) Int. Cl.
*A61K 9/127* (2006.01)
*A61K 47/69* (2017.01)
(Continued)

(52) U.S. Cl.
CPC ........ *A61K 47/6929* (2017.08); *A61K 47/542* (2017.08); *A61K 47/544* (2017.08);
(Continued)

(58) Field of Classification Search
CPC .............. A61K 47/6929; A61K 47/551; A61K 47/542; A61K 47/554; A61K 47/6905;
(Continued)

(56) References Cited

U.S. PATENT DOCUMENTS

| 5,858,397 A * | 1/1999 | Lim ...................... A61K 9/127 424/450 |
| 2002/0192275 A1* | 12/2002 | Zalipsky .............. A61K 9/1271 424/450 |

(Continued)

FOREIGN PATENT DOCUMENTS

| WO | 2004/094409 | * 11/2004 |
| WO | WO 2014/138278 A1 | 9/2014 |

(Continued)

OTHER PUBLICATIONS

Zulfiqar, B., et al in Onco Targets and Therapy, vol. 10, pp. 463-476. 2017.*

(Continued)

*Primary Examiner* — Gollamudi S Kishore
(74) *Attorney, Agent, or Firm* — Tom Hunter; Weaver Austin Villeneuve & Sampson LLP

(57) ABSTRACT

In certain embodiments a platform technology for the facilitating immune therapy in the treatment of cancer is provided. In certain embodiments nanocarriers are provided that facilitate delivery of an IDO inhibitor in conjunction with an inducer of cell death (ICD-inducer). In certain embodiments the IDO inhibitor is conjugated to a component of a lipid bilayer forming a nanovesicle. In still another embodiment, methods and compositions are provided where an ICD-inducing agent (e.g., doxorubicin, oxaliplatin, mitoxantrone etc.) and an IDO pathway inhibitor (e.g., an IDO inhibitor-prodrug) are integrated into a nanocarrier (e.g. a lipid-bilayer (LB)-coated nanoparticle), that allows systemic delivery to orthotopic pancreatic cancer site.

21 Claims, 46 Drawing Sheets

Specification includes a Sequence Listing.

Related U.S. Application Data

(60) Provisional application No. 62/914,950, filed on Oct. 14, 2019, provisional application No. 62/614,325, filed on Jan. 5, 2018, provisional application No. 62/507,996, filed on May 18, 2017.

(51) Int. Cl.
*A61K 47/55* (2017.01)
*A61K 47/54* (2017.01)
*B82Y 5/00* (2011.01)

(52) U.S. Cl.
CPC .......... *A61K 47/551* (2017.08); *A61K 47/554* (2017.08); *A61K 47/6905* (2017.08); *A61K 47/6923* (2017.08); *B82Y 5/00* (2013.01)

(58) Field of Classification Search
CPC .............. A61K 47/6923; A61K 47/544; A61K 47/6911; B82Y 5/00
See application file for complete search history.

(56) References Cited

U.S. PATENT DOCUMENTS

| | | | |
|---|---|---|---|
| 2005/0181037 A1* | 8/2005 | Ahmad | A61K 9/1271 424/450 |
| 2006/0003976 A1* | 1/2006 | Zhang | C07J 43/003 514/176 |
| 2011/0002977 A1* | 1/2011 | Li | A61K 9/1271 424/450 |
| 2011/0092739 A1* | 4/2011 | Chen | A61P 17/06 564/384 |
| 2011/0159017 A1 | 6/2011 | Van Den et al. | |
| 2013/0330399 A1* | 12/2013 | Reisfeld | A61K 9/127 424/450 |
| 2015/0071990 A1* | 3/2015 | Longenecker | A61P 35/00 424/450 |
| 2016/0008283 A1 | 1/2016 | Nel et al. | |
| 2016/0030588 A1* | 2/2016 | Daftarian | A61K 47/646 424/450 |
| 2016/0136289 A1* | 5/2016 | Puri | A61K 9/1271 604/20 |
| 2018/0169268 A1* | 6/2018 | Payne | A61K 47/20 |
| 2019/0269706 A1 | 9/2019 | Lin et al. | |

FOREIGN PATENT DOCUMENTS

| | | |
|---|---|---|
| WO | WO 2017/023667 A1 | 2/2017 |
| WO | WO 2017/201528 A1 | 11/2017 |
| WO | WO 2018/140826 A1 | 8/2018 |
| WO | WO 2018/213631 A1 | 11/2018 |
| WO | WO 2019/173391 A1 | 9/2019 |
| WO | WO 2021/076630 A1 | 4/2021 |

OTHER PUBLICATIONS

PCT International Search Report and Written Opinion dated Aug. 10, 2018 issued in PCT/US2018/033265 [P173WO].
PCT International Preliminary Report on Patentability and Written Opinion dated Nov. 19, 2019 issued in PCT/US2018/033265 [P173WO].
Apetoh et al. (2007) "Toll-like receptor 4-dependent contribution of the immune system to anticancer chemotherapy and radiotherapy." *Nature medicine*, 13(9): 1050-1059.
Bezu et al. (2015) "Combinatorial strategies for the induction of immunogenic cell death," *Frontiers in immunology*, 6: 187 [11 pages].
Casares et al. (2005) "Caspase-dependent immunogenicity of doxorubicin-induced tumor cell death." *The Journal of experimental medicine*, 202(12): 1691-1701.
Fucikova et al. (2011) "Human tumor cells killed by anthracyclines induce a tumor-specific immune response." *Cancer research*, 71(14): 4821-4833,.
Hardacre et al. (2013) "Addition of algenpantucel-L immunotherapy to standard adjuvant therapy for pancreatic cancer: a phase 2 study." *Journal of gastrointestinal surgery: official journal of the Society for Surgery of the Alimentary Tract*, 17(1): 94-101; discussion p. 100-101.
Hou et al. (2007) "Inhibition of indoleamine 2,3-dioxygenase in dendritic cells by stereoisomers of 1-methyl-tryptophan correlates with antitumor responses." *Cancer research*, 67(2): 792-801.
Kershaw et al. (2013) "Enhancing immunotherapy using chemotherapy and radiation to modify the tumor microenvironment." *Oncoimmunology*, 2(9): e25962 [6 pages].
Kroemer et al. (2013) "Immunogenic cell death in cancer therapy." *Annual review of immunology*, 31: 51-72.
Krysko et al. (2012) "Immunogenic cell death and DAMPs in cancer therapy." *Nature reviews Cancer*, 12(12): 860-875.
Lob et al. (2009) "Inhibitors of indoleamine-2,3-dioxygenase for cancer therapy: can we see the wood for the trees?" *Nature Reviews Cancer*, 9(6): 445-452.
Metz et al. (2012) "IDO inhibits a tryptophan sufficiency signal that stimulates mTOR: A novel IDO effector pathway targeted by D-1-methyl-tryptophan." *Oncoimmunology*, 1(9): 1460-1468.
Michaud et al. (2011) "Autophagy-dependent anticancer immune responses induced by chemotherapeutic agents in mice." *Science*, 334(6062): 1573-1577.
Obeid et al. (2007) Calreticulin exposure dictates the immunogenicity of cancer cell death. *Nature medicine*, 13(1): 54-61.
Pfirschke et al. (2016) "Immunogenic Chemotherapy Sensitizes Tumors to Checkpoint Blockade Therapy." *Immunity*, 44(2): 343-354.
Puri et al. (2009) "Lipid-Based Nanoparticles as Pharmaceutical Drug Carriers: From Concepts to Clinic" *Crit Rev Ther Drug Carrier Syst.*, 26(6): 523-580 [NIH Public Access—Author Manuscript—46 pages].
Rossi et al. (2014) "Correlation of anti-calreticulin antibody titers with improved overall survival in a phase 2 clinical trial of algenpantucel-L immunotherapy for patients with resected pancreatic cancer." *J Clin Oncol*, 32(15): Suppl: abstr 3029 [2 pages], DOI: 10.1200/jco.2014.32.15_suppl.3029; Published online Jan. 31, 2017.
Sun et al. (2017) "Programmable co-delivery of the immune checkpoint inhibitor NLG919 and chemotherapeutic doxorubicin via a redox-responsive immunostimulatory polymeric prodrug carrier" *Acta Pharmacotogica Slnica*, 38: 823-834.
Tesniere et al. (2010) "Immunogenic death of colon cancer cells treated with oxaliplatin," *Oncogene*, 29(4): 482-491.
Vacchelli et al. (2014) "Trial watch: IDO inhibitors in cancer therapy." *Oncoimmunology*, 3(10): e957994 [10 pages].
Yamano et al. (2016) "Whole cell vaccination using immunogenic cell death by an oncolytic adenovirus is effective against a colorectal cancer model" *Molecular Therapy—Oncolytics*, 3: 16031 [6 pages].
Zappasodi et al. (2010) "Improved clinical outcome in indolent B-cell lymphoma patients vaccinated with autologous tumor cells experiencing immunogenic death," *Cancer research*, 70(22): 9062-9072.
Zou (2005) "Immunosuppressive networks in the tumour environment and their therapeutic relevance." *Nature reviews Cancer*, 5(4): 263-274.
EP Extended European Search Report dated Jan. 18, 2021 issued in EP 18803111.6 [P173EP].
Liu et al. (2020) "Retraction Notice for: Breast Cancer Chemo-immunotherapy through Liposomal Delivery of an Immunogenic Cell Death Stimulus Plus Interference in the IDO-1 Pathway" *ACS Nano*, 2 pages.
Lu et al. (2018) "Breast Cancer Chemo-immunotherapy through Liposomal Delivery of an Immunogenic Cell Death Stimulus Plus Interference in the IDO-1 Pathway" *ACS Nano*, 12: 11041-11061.
PCT International Search Report and Written Opinion dated Mar. 11, 2021 issued in PCT/US2020/055585 [P213WO].

\* cited by examiner

A
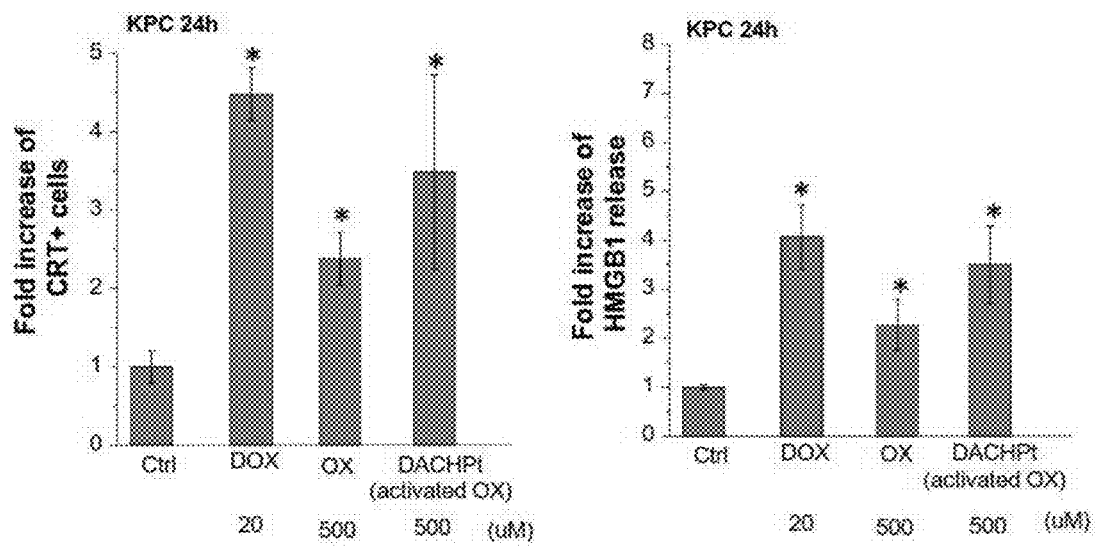
B
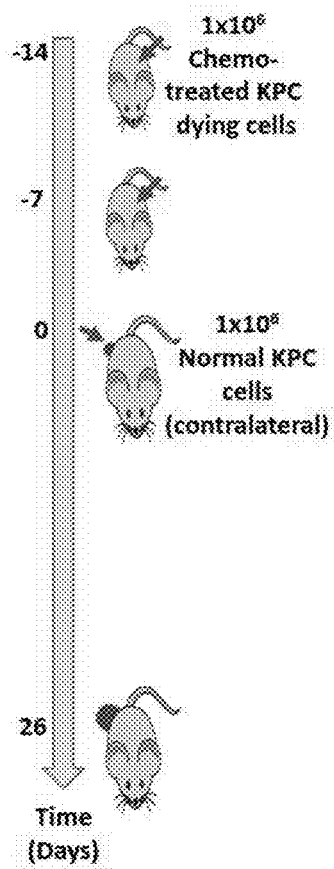
Fig. 6

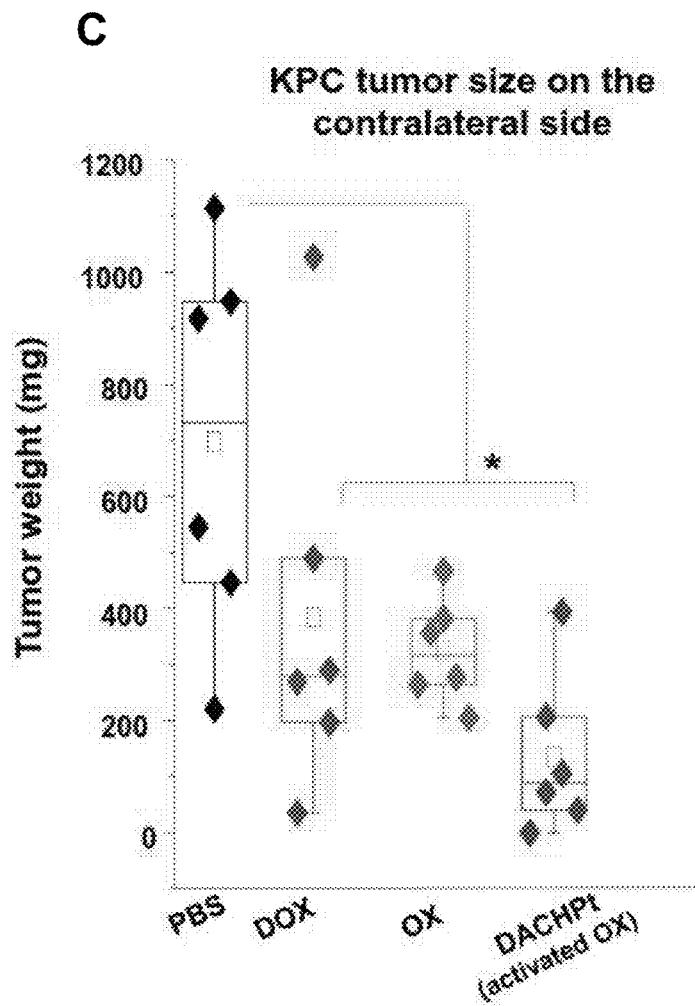
Fig. 6, cont'd.

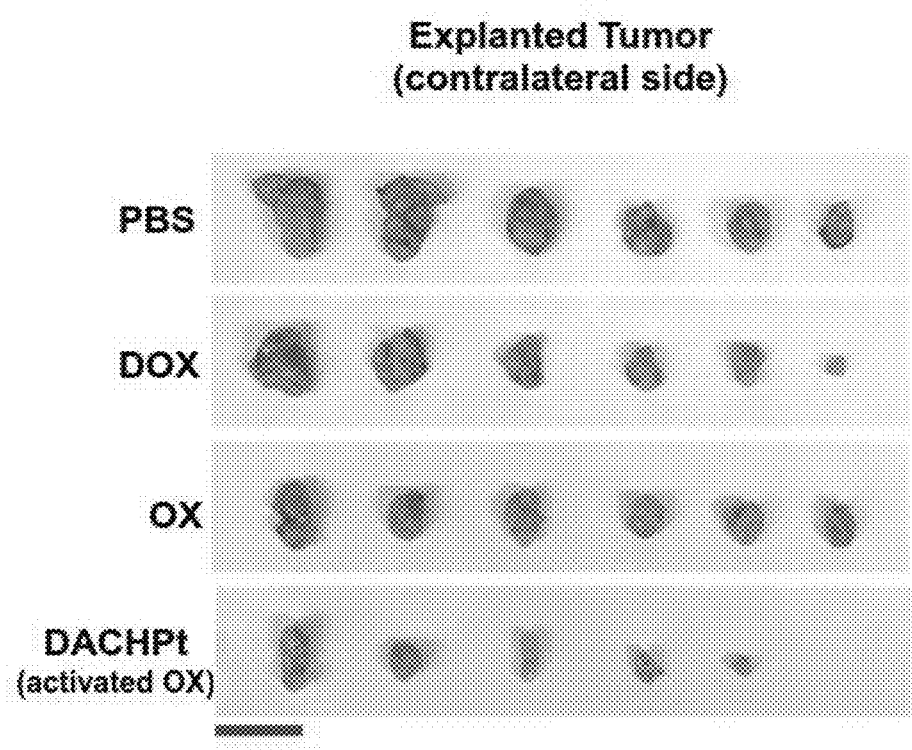
*Fig. 6, cont'd.*

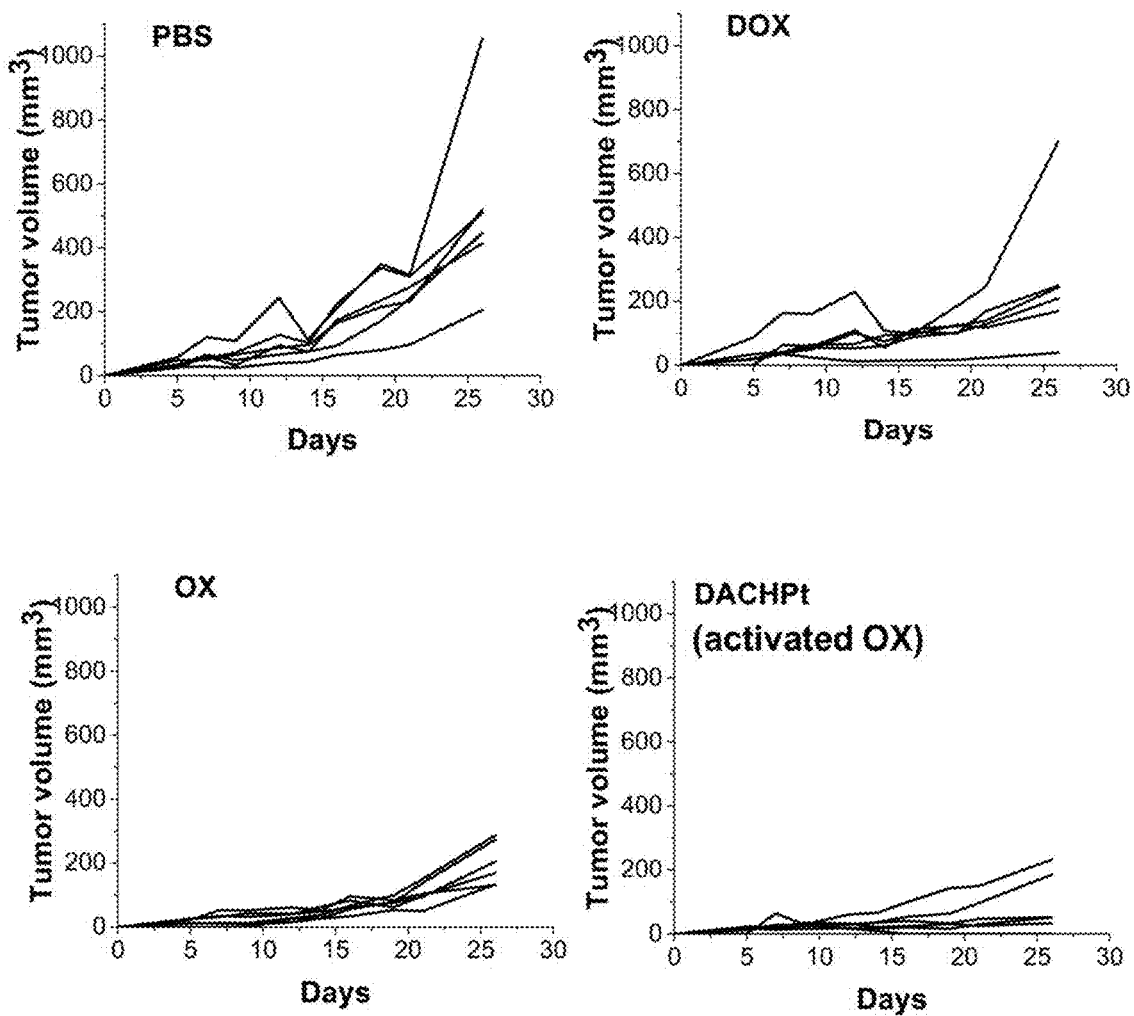
*Fig. 6, cont'd.*

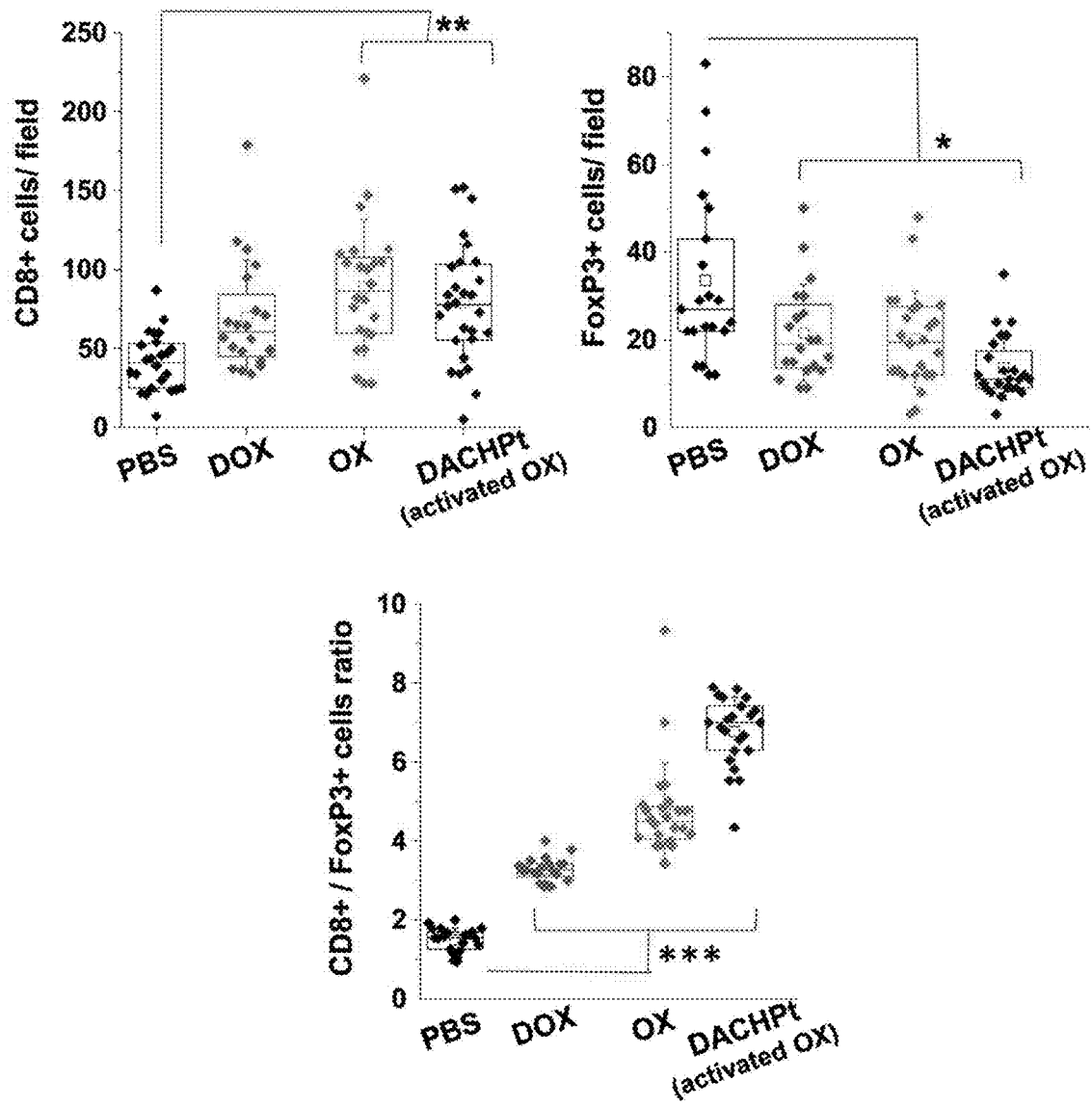
*Fig. 6, cont'd.*

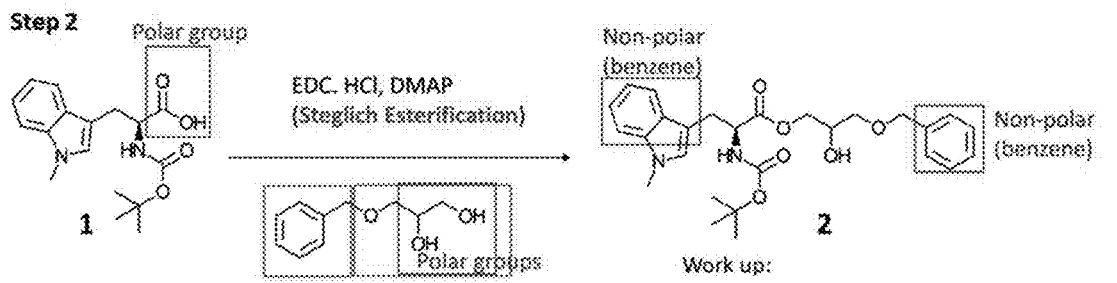
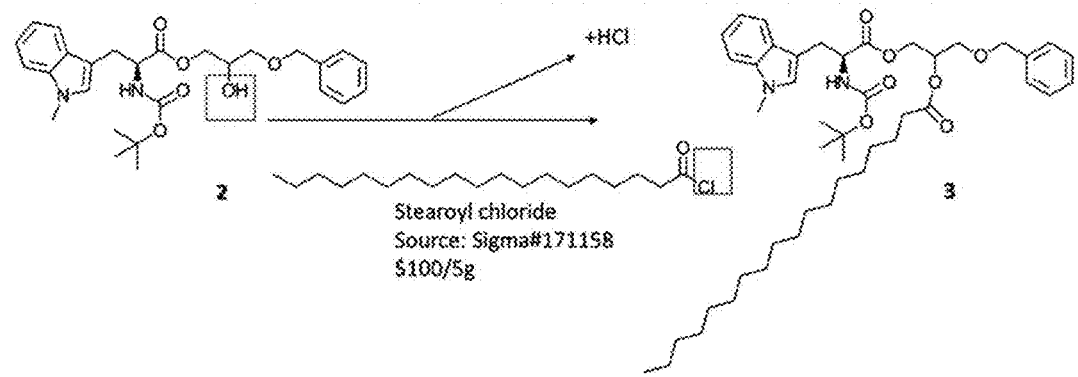
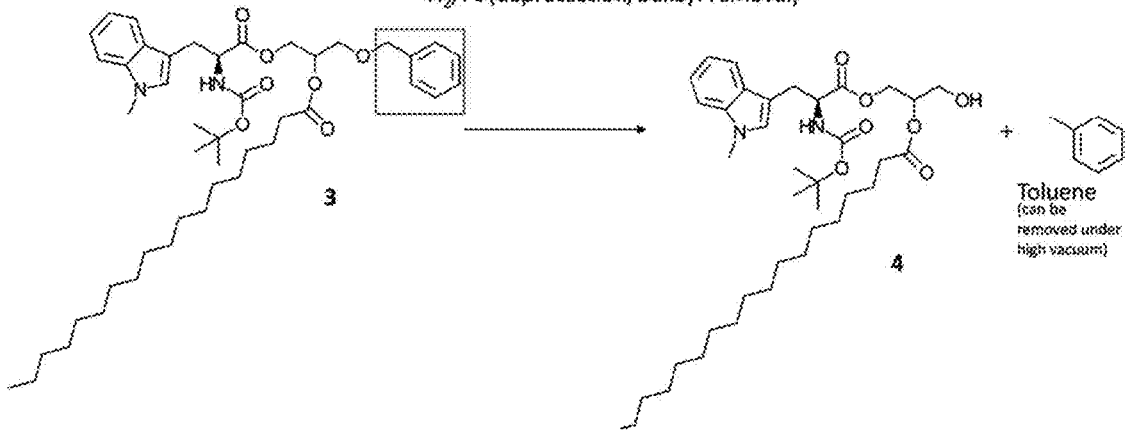
*Fig. 14, cont'd.*

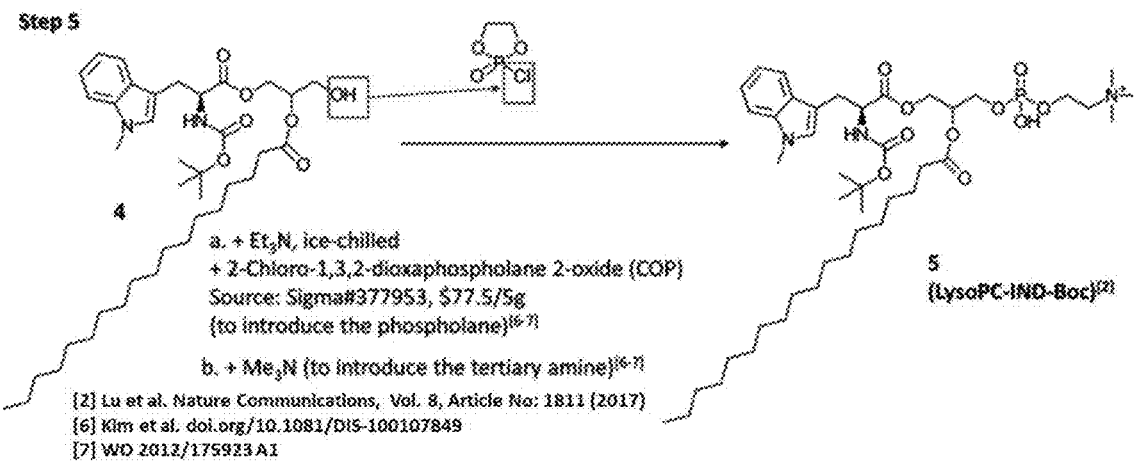
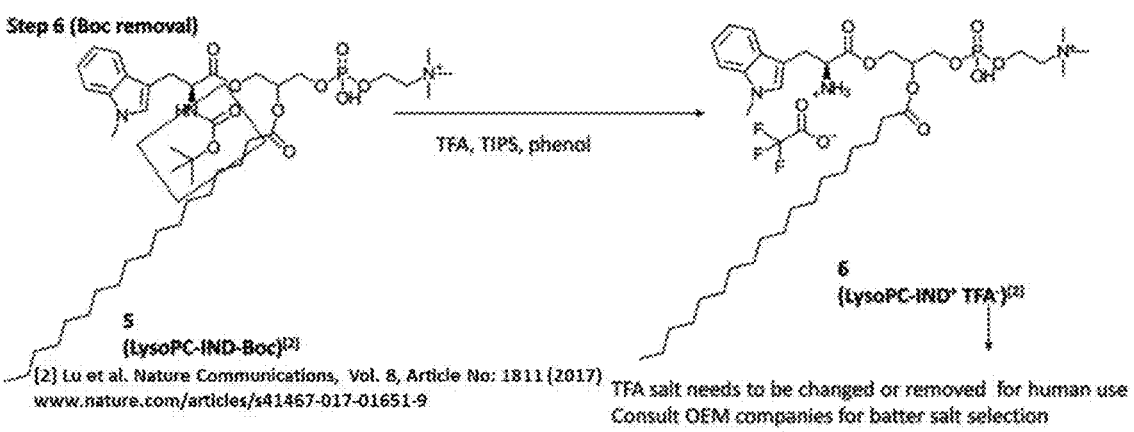
*Fig. 14, cont'd.*
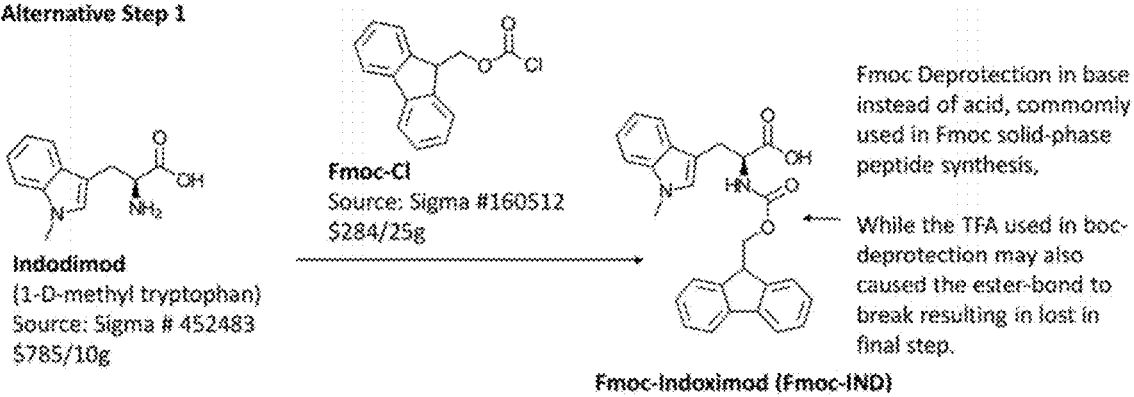
*Fig. 15*

- Formulation: DSPC: Chol-IND: DSPE-PEG2k = 55:40:5
- Size: 90.3 ± 0.9 nm
- PDI: 0.090
- ζ-Potential : +15.03 ± 0.59 mV
- Feed ratio (DOX : Liposome) = 20 wt%
- Loading Capacity: 6.3%
- Loading Efficiency = 33.9%
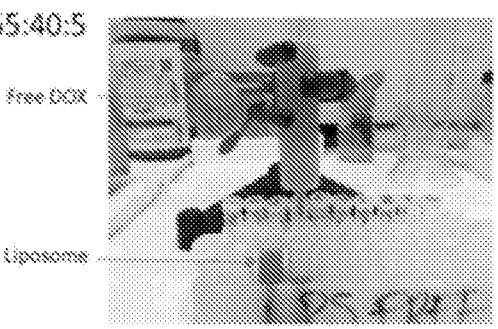
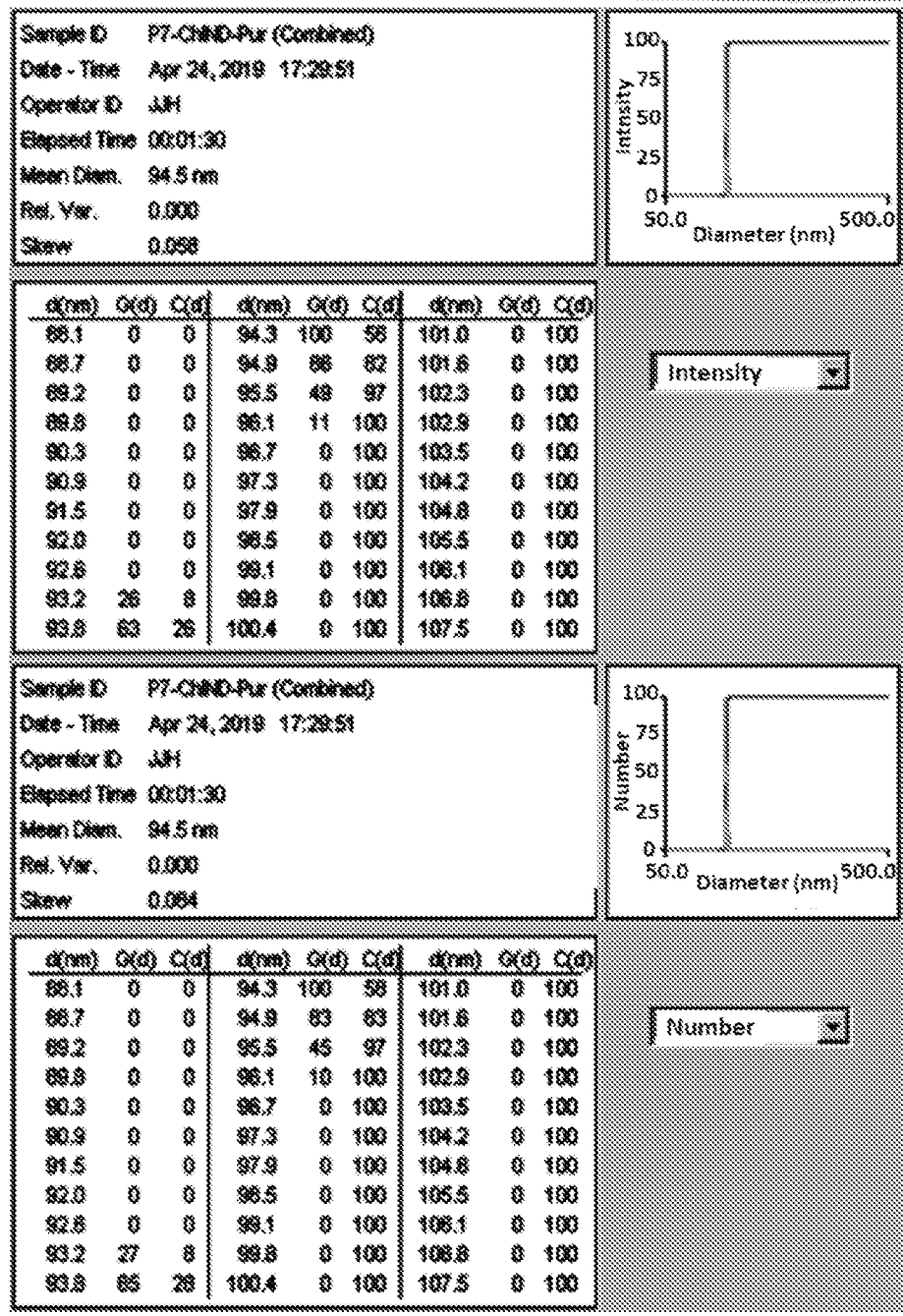
*Fig. 22*

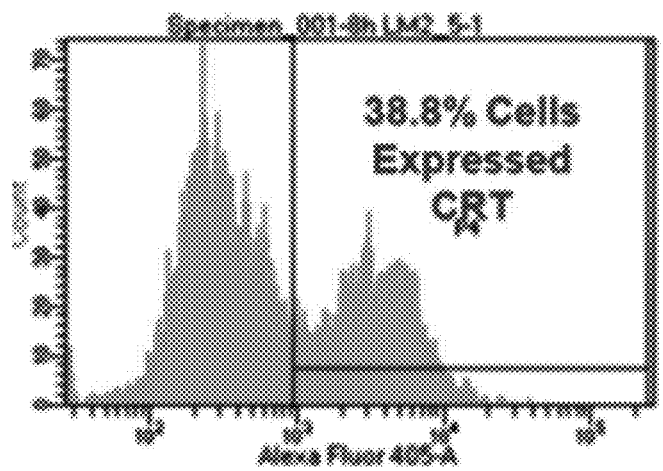
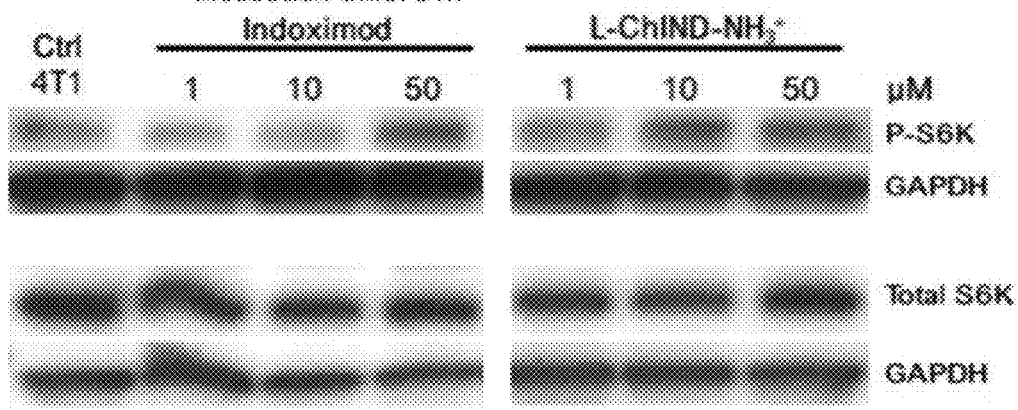
*Fig. 25*

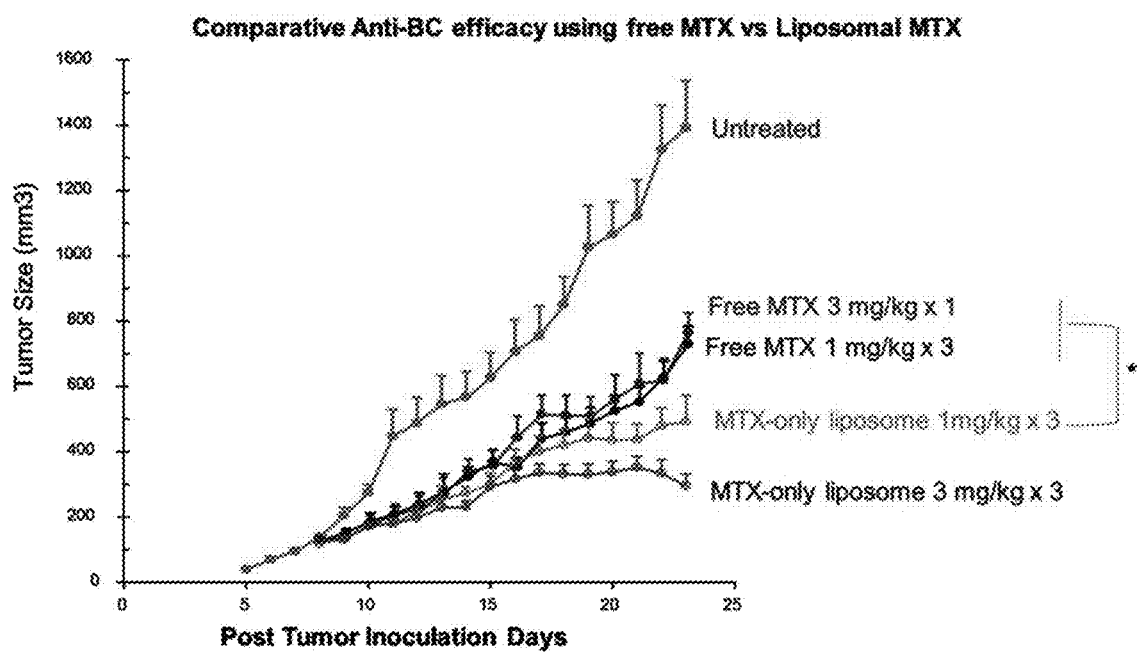
Fig. 26, cont'd.

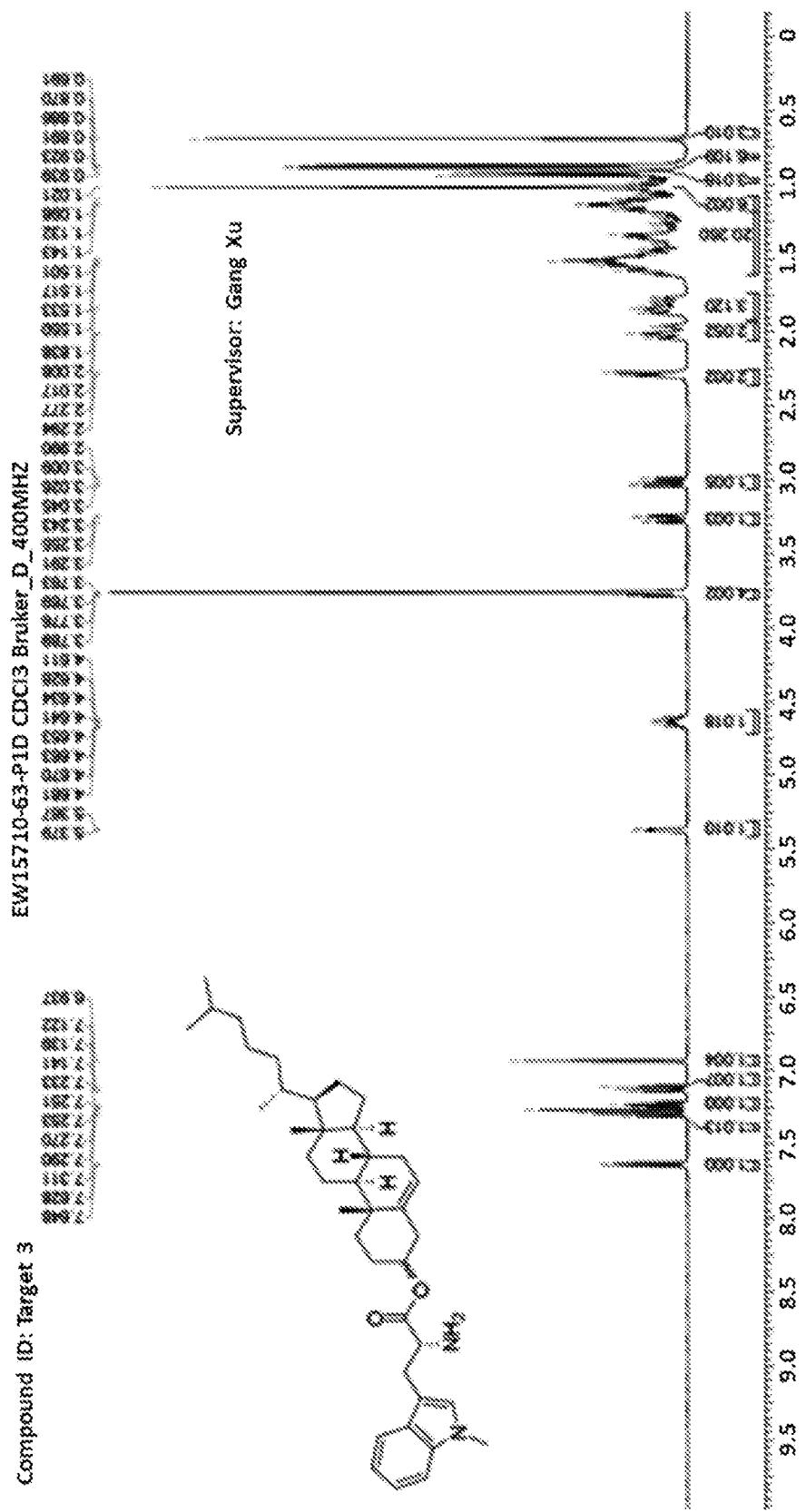
Fig. 27, cont'd.

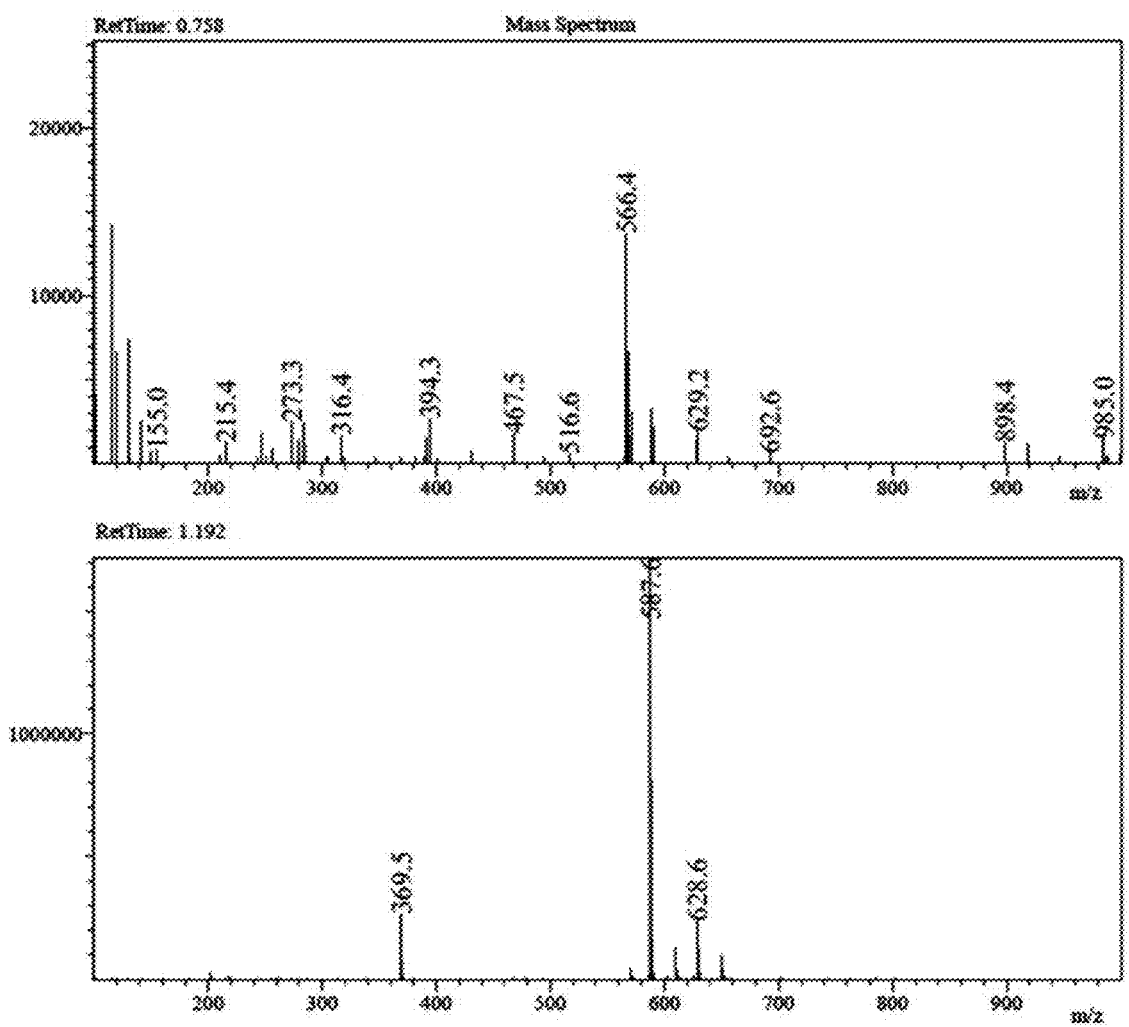
*Fig. 27, cont'd.*

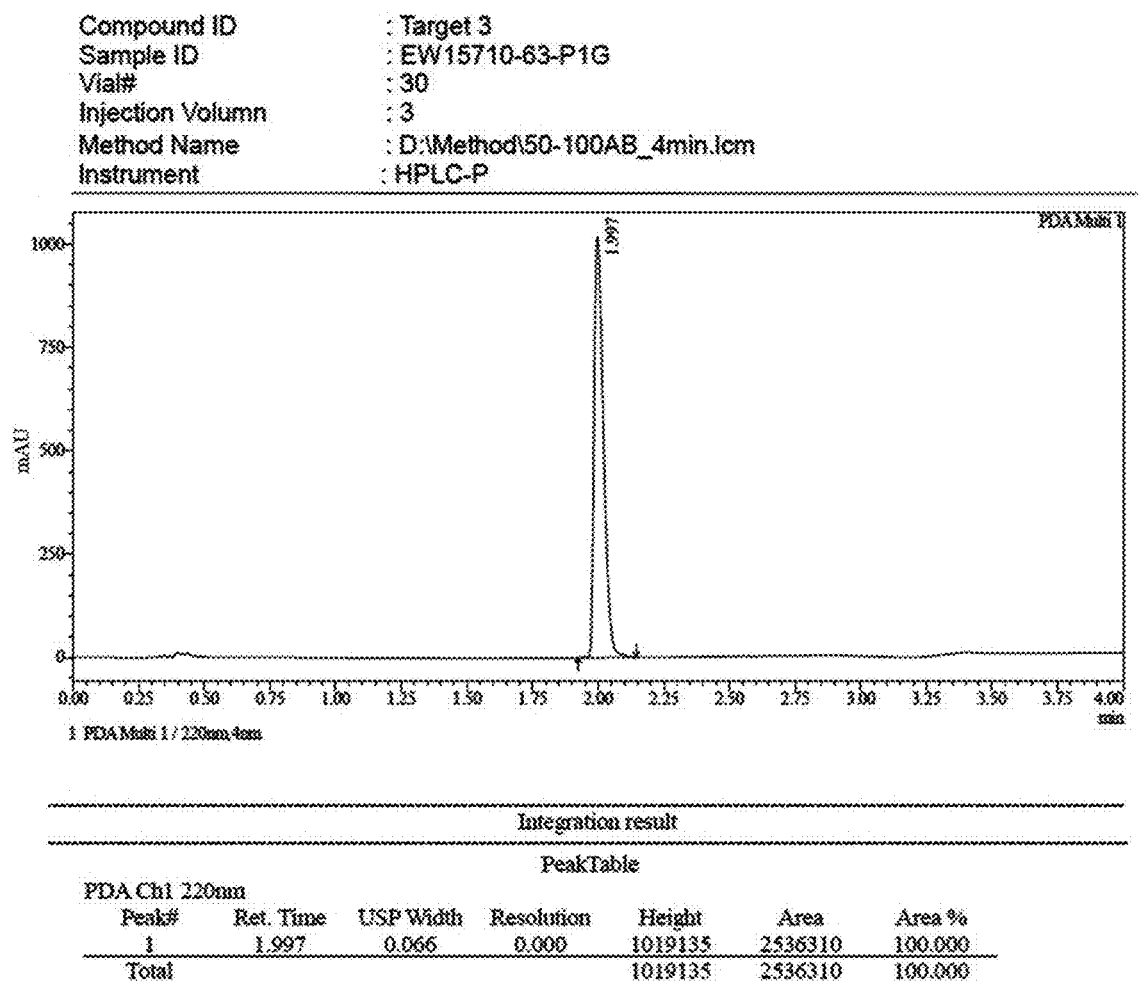
*Fig. 27, cont'd.*

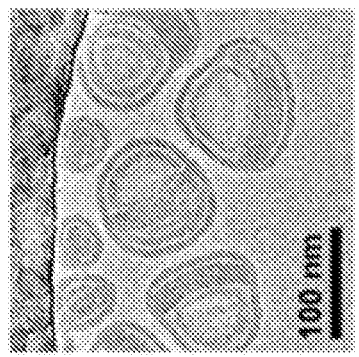
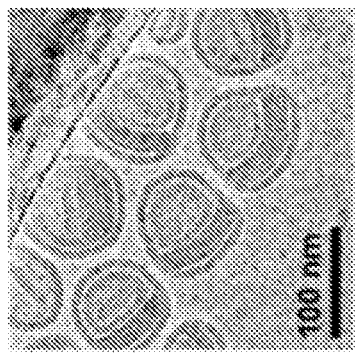
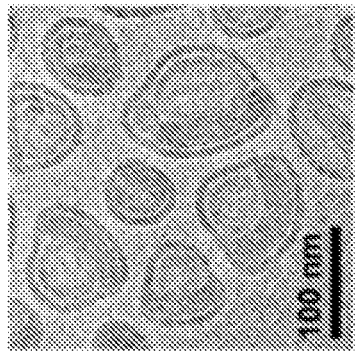
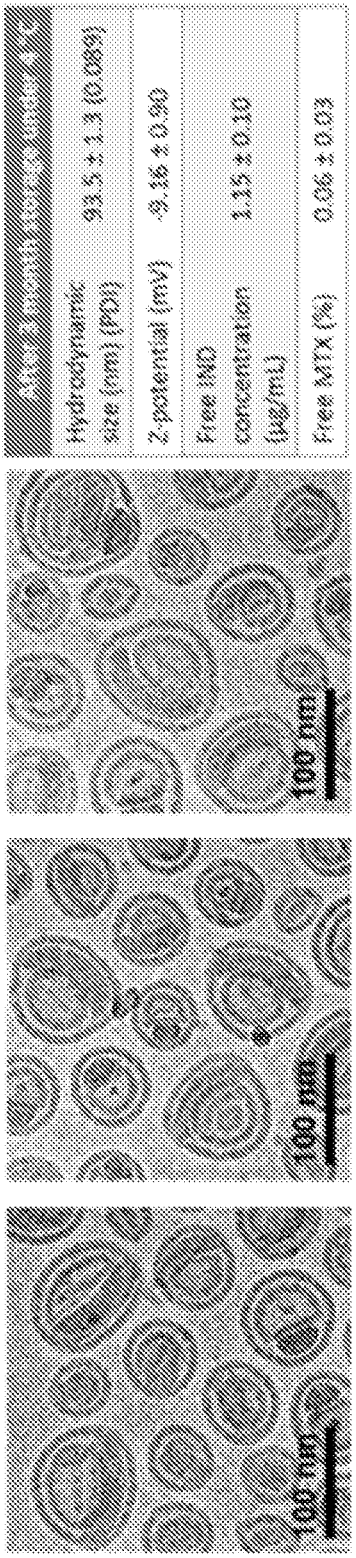
Fig. 28

A

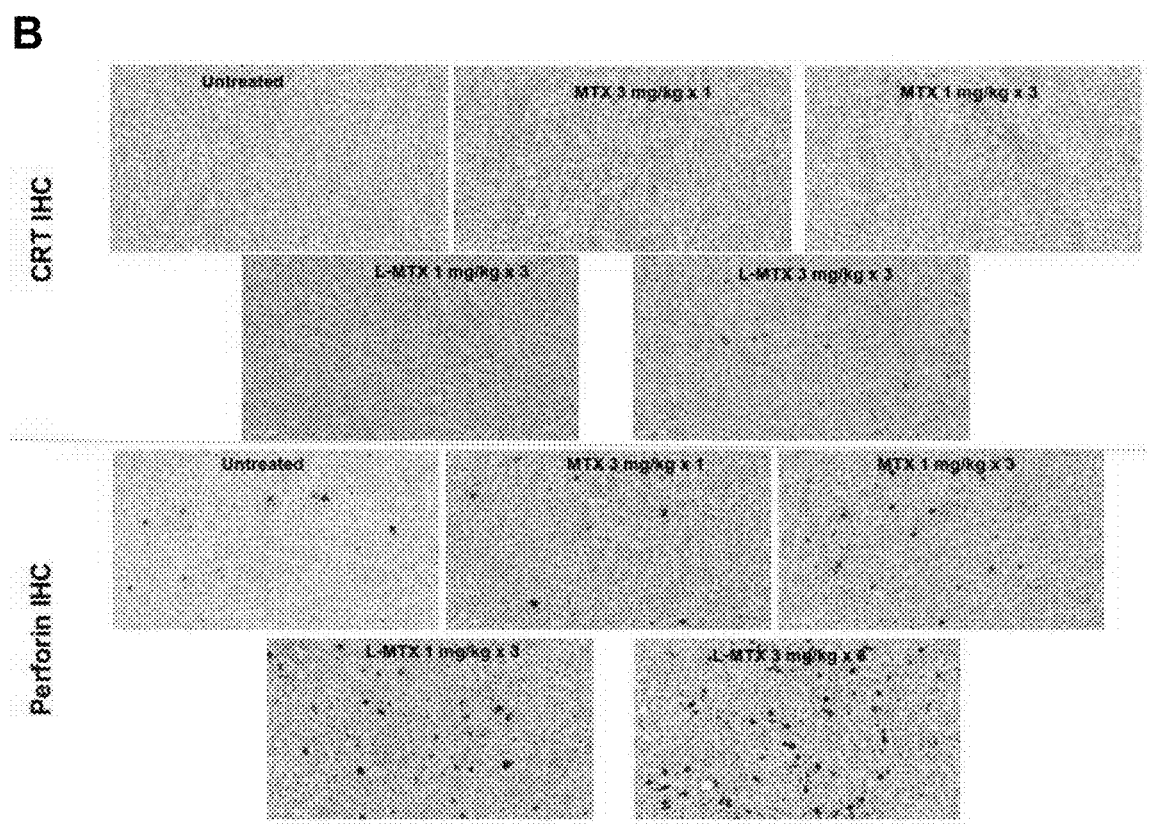
*Fig. 30, cont'd.*

A

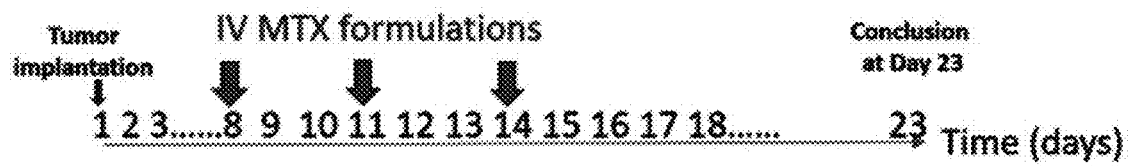

UT: Untreated 4T1 Balb/c

6. L-50%Chol (no MTX)
7. L-20%CHEMS-30%Chol (no MTX)   | MTX (−)
8. L-20%CHEMS-30%Chol-IND (no MTX)

9. L-50%Chol-MTX 3mg/kg x 3
10. L-20%CHEMS-30%Chol-MTX 3 mg/kg x 3   | MTX (+)
11. L-20%CHEMS-30%Chol-IND-MTX 3|3 mg/kg x 3

Formulation (molar ratio):

L-50%Chol = DSPC:Chol:DSPE-PEG$_{2kDa}$ = 45: 50: 5
L-20%CHEMS:30%Chol = DSPC:CHEMS:Chol:DSPE-PEG$_{2kDa}$ = 25: 20: 30: 5
L-20%CHEMS:30%Chol-IND = DSPC:CHEMS:Chol-IND:DSPE-PEG$_{2kDa}$ = 25: 20: 30: 5

MTX loading = 10% (drug/lipid, wt./wt.)
MTX|IND loading = 1: 1 (MTX/cleaved IND, wt./wt.)

*Fig. 31*

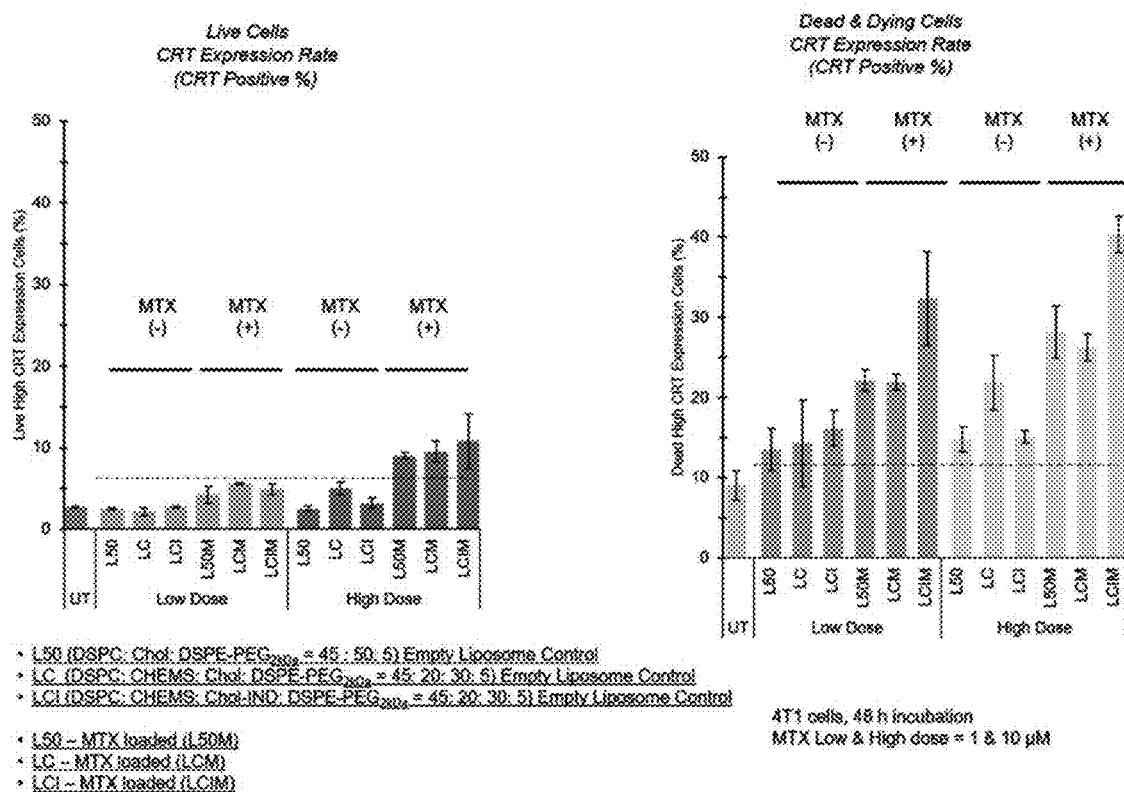
Fig. 31, cont'd.

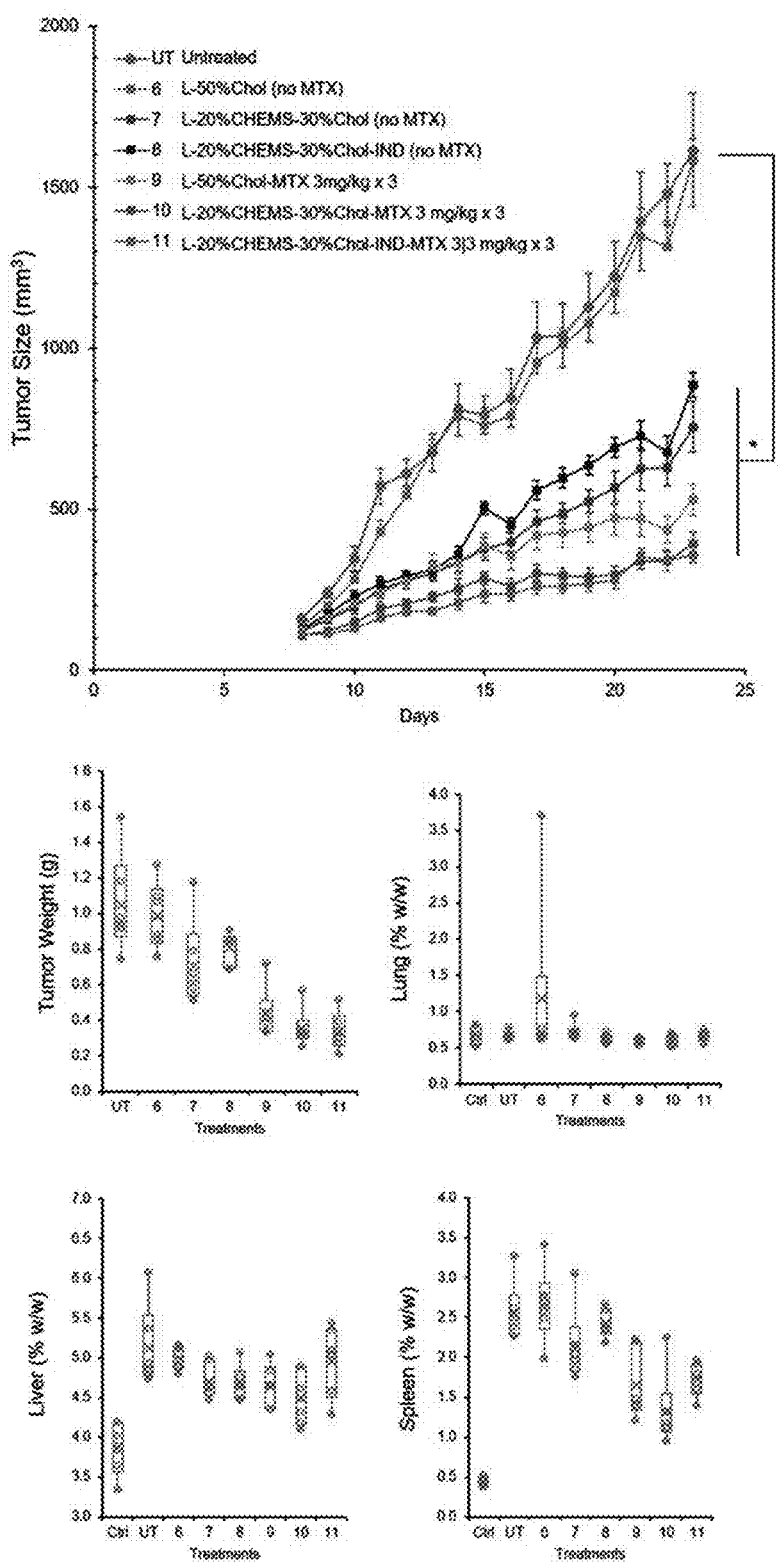
Fig. 31, cont'd.

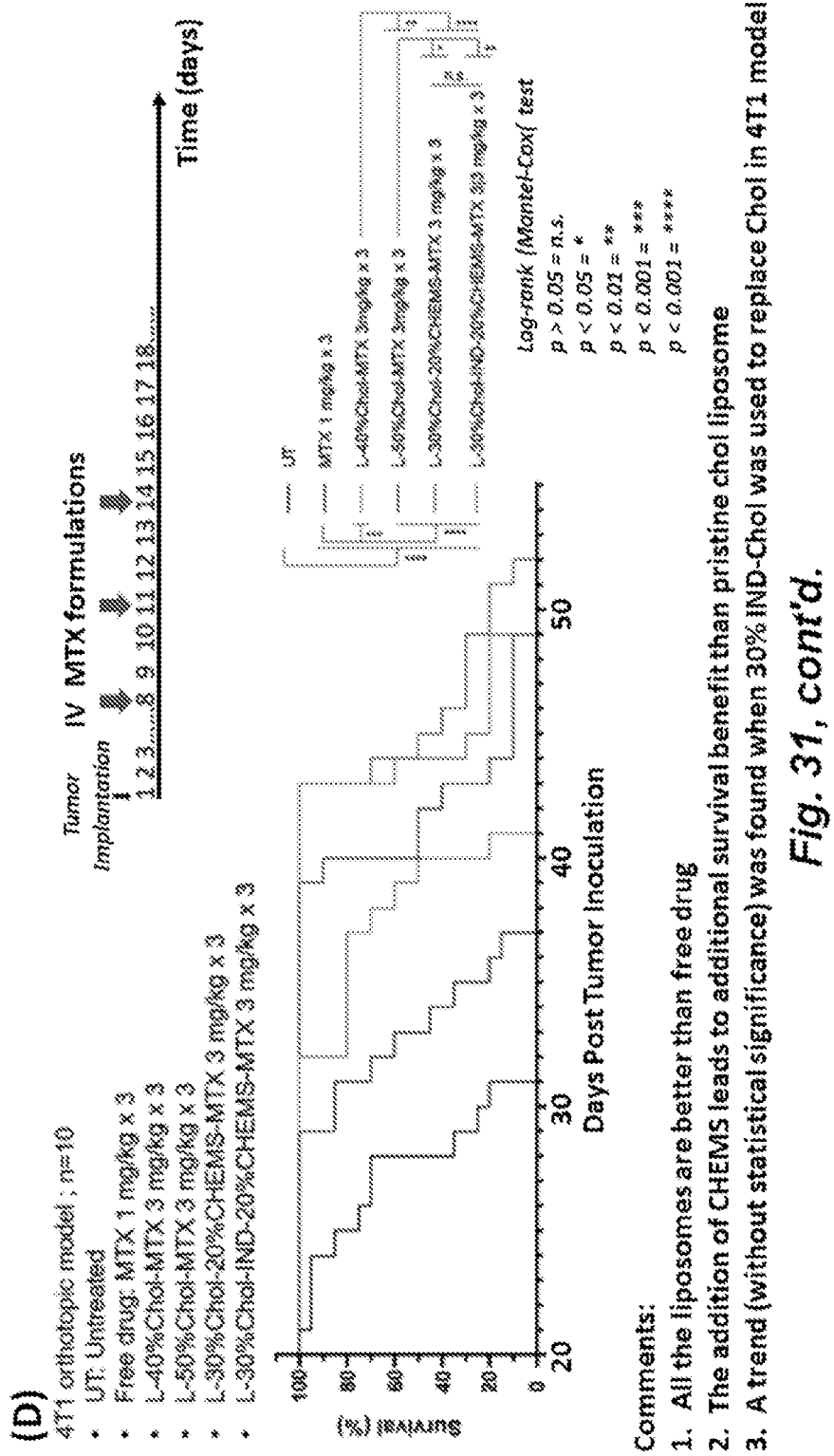
Fig. 31, cont'd.

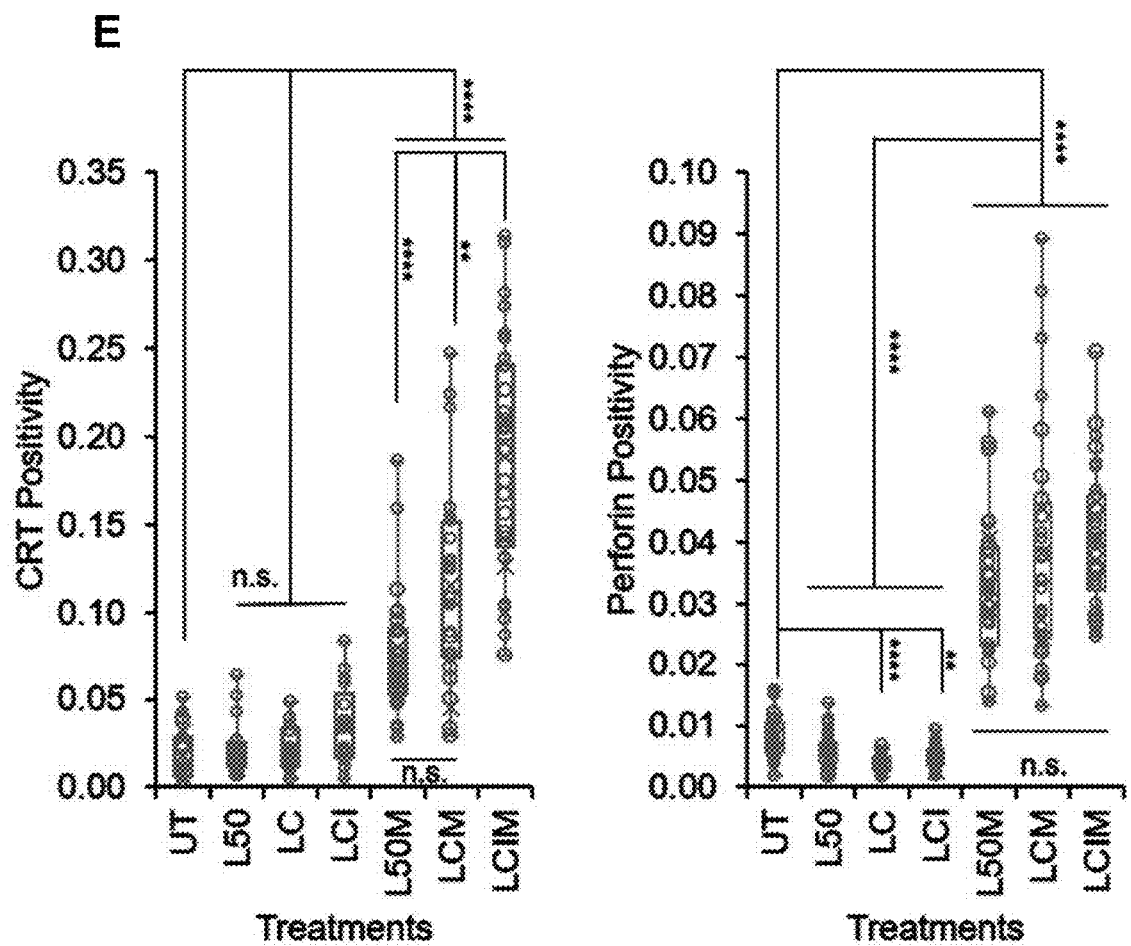
Fig. 31, cont'd.

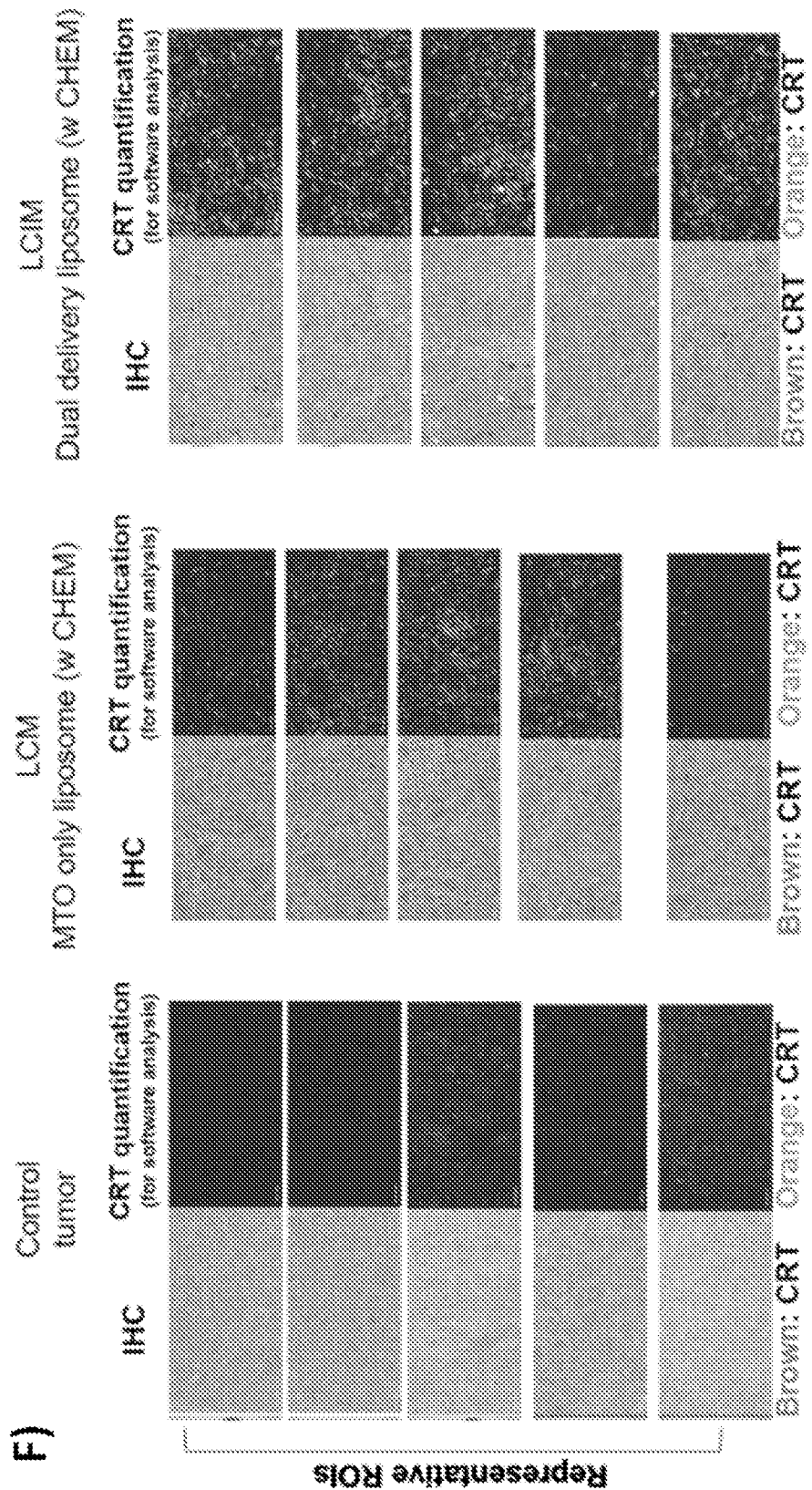
Fig. 31, cont'd.

A

CT26 Tumor Animal Study

- CT26 subQ model establishment: 0.7M cells/mouse
- Treatments (n=8):
    - UT: untreated
    - L50M: MTX-only liposome
       (DSPC : Chol : DSPE-PEG2kDa; 40 : 50 : 5)
    - LCM: MTX-only liposome with CHEMS
       (DSPC : CHEMS : Chol : DSPE-PEG2kDa; 25: 20 : 30 : 5)
    - LCIM: MTX/IND liposome
       (DSPC : CHEMS : Chol-IND : DSPE-PEG2kDa; 25: 20 : 30 : 5)
    - $LCI_2M$: MTX/IND co-delivery plus empty IND-only liposome
       To answer IND dose question
- Endpoints: Tumor size, body weight, survival and IHC if possible
       (CD8, Treg, CRT, HMGB1, cytokines)

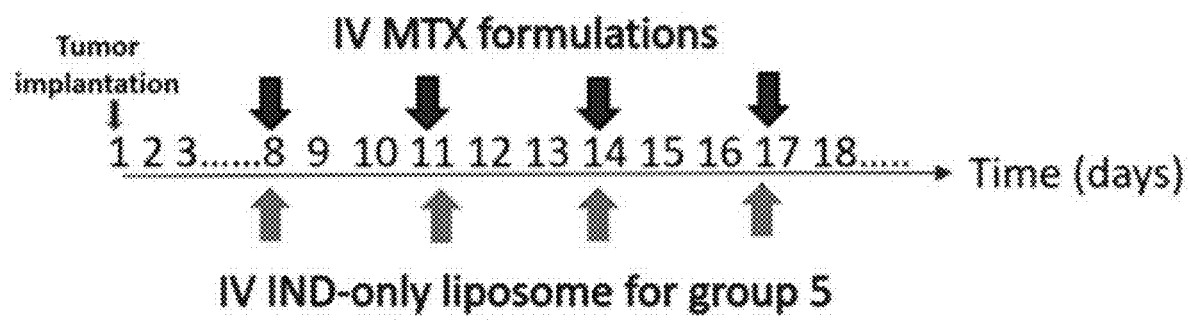

*Fig. 32*

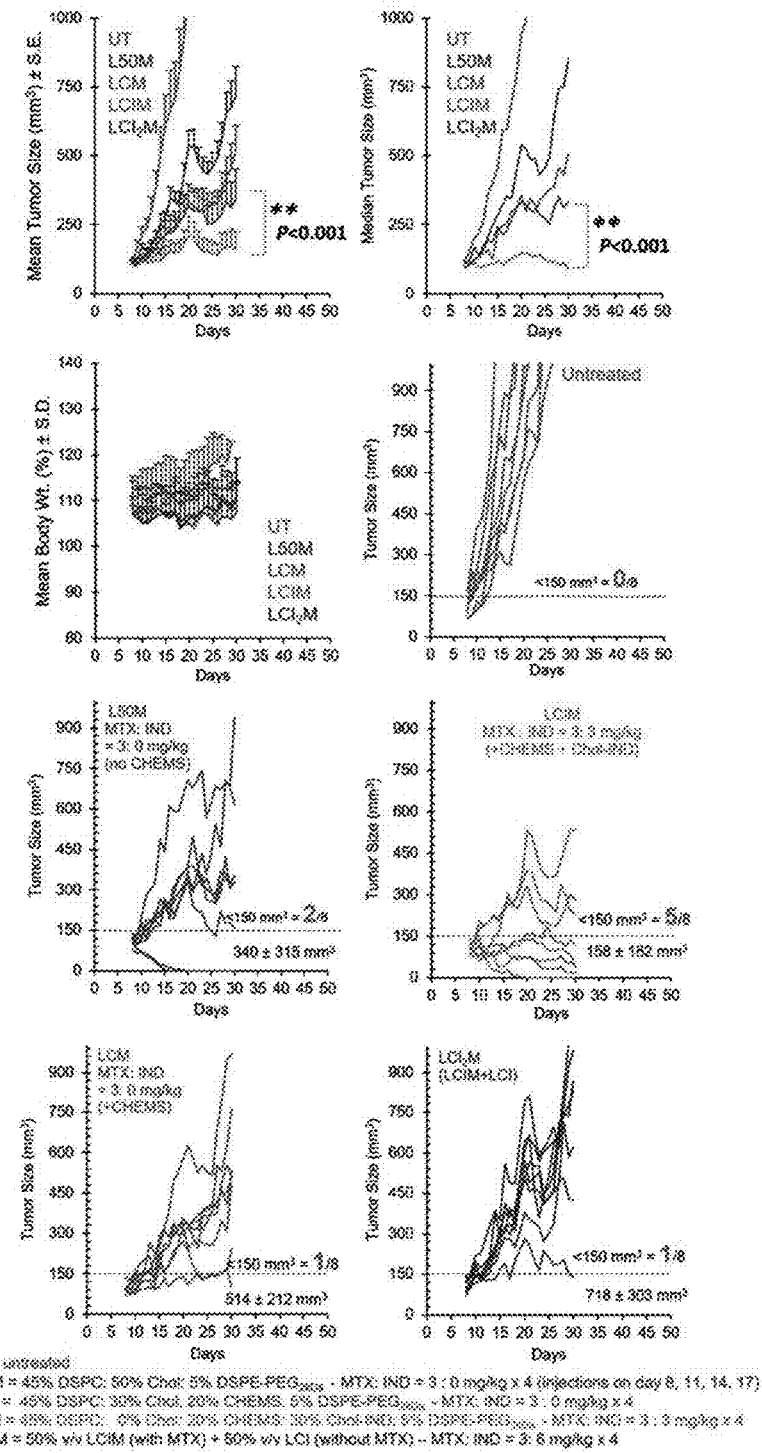
*Fig. 32, cont'd.*

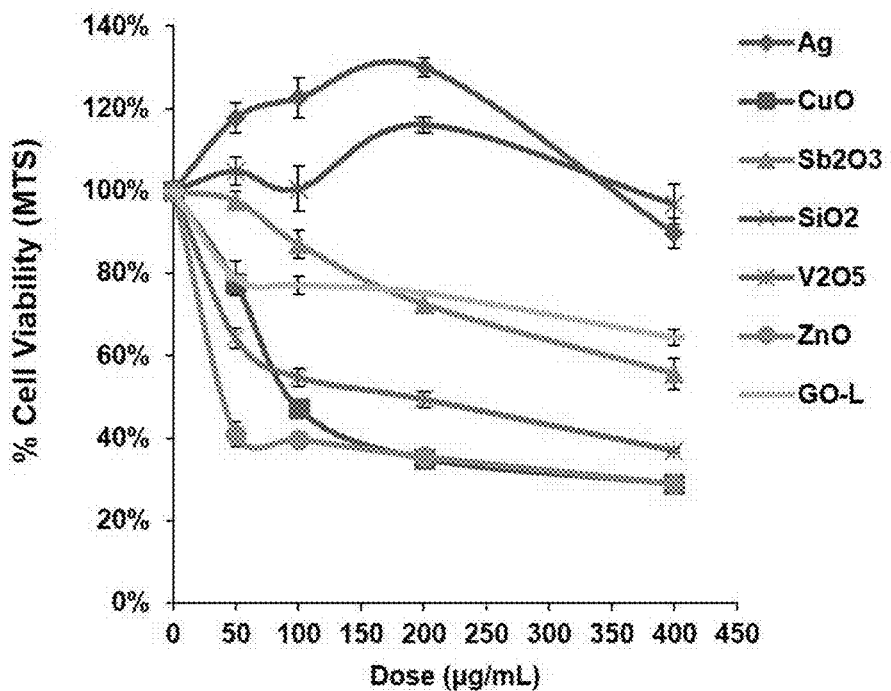
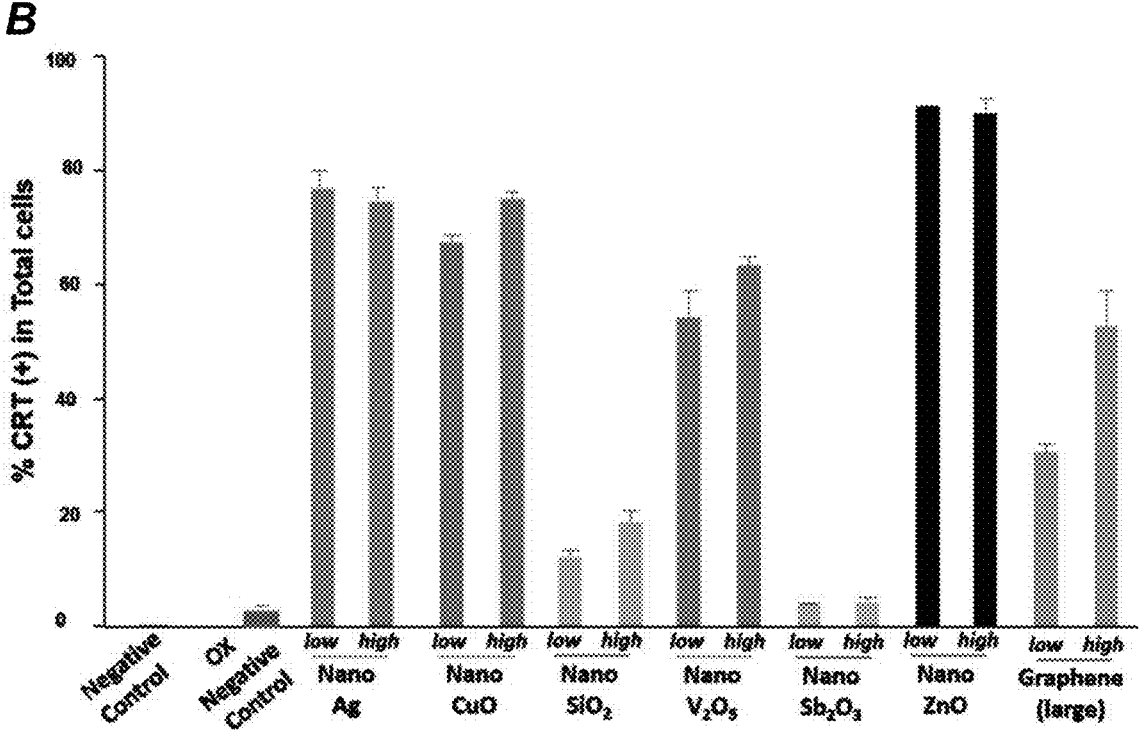
*Fig. 33*

SEQUENCE LISTING

```
<160> NUMBER OF SEQ ID NOS: 10

<210> SEQ ID NO 1
<211> LENGTH: 23
<212> TYPE: PRT
<213> ORGANISM: Artificial
<220> FEATURE:
<223> OTHER INFORMATION: Fusogenic peptide

<400> SEQUENCE: 1

Gly Leu Phe His Ala Ile Ala His Phe Ile His Gly Gly Trp His Gly
1               5                   10                  15

Leu Ile His Gly Trp Tyr Gly
            20

<210> SEQ ID NO 2
<211> LENGTH: 5
```

```
<212> TYPE: PRT
<213> ORGANISM: Artificial
<220> FEATURE:
<223> OTHER INFORMATION: Targeting peptide
<220> FEATURE:
<221> NAME/KEY: misc_feature
<222> LOCATION: (4)..(4)
<223> OTHER INFORMATION: Xaa is dPhe

<400> SEQUENCE: 2

Arg Gly Asp Xaa Lys
1               5

<210> SEQ ID NO 3
<211> LENGTH: 5
<212> TYPE: PRT
<213> ORGANISM: Artificial
<220> FEATURE:
<223> OTHER INFORMATION: Targeting peptide
<220> FEATURE:
<221> NAME/KEY: misc_feature
<222> LOCATION: (4)..(4)
<223> OTHER INFORMATION: Xaa is dTyr

<400> SEQUENCE: 3

Arg Gly Asp Xaa Cys
1               5

<210> SEQ ID NO 4
<211> LENGTH: 5
<212> TYPE: PRT
<213> ORGANISM: Artificial
<220> FEATURE:
<223> OTHER INFORMATION: Targeting peptide
<220> FEATURE:
<221> NAME/KEY: misc_feature
<222> LOCATION: (4)..(4)
<223> OTHER INFORMATION: Xaa is dTyr

<400> SEQUENCE: 4

Arg Gly Asp Xaa Cys
1               5

<210> SEQ ID NO 5
<211> LENGTH: 12
<212> TYPE: PRT
<213> ORGANISM: Artificial
<220> FEATURE:
<223> OTHER INFORMATION: Targeting peptide

<400> SEQUENCE: 5

Tyr His Trp Tyr Gly Tyr Thr Pro Gln Asn Val Ile
1               5                   10

<210> SEQ ID NO 6
<211> LENGTH: 9
<212> TYPE: PRT
<213> ORGANISM: Artificial
<220> FEATURE:
<223> OTHER INFORMATION: Targeting peptide

<400> SEQUENCE: 6

Gly Ser Gly Lys Cys Cys Tyr Ser Leu
1               5

<210> SEQ ID NO 7
<211> LENGTH: 8
<212> TYPE: PRT
<213> ORGANISM: Artificial
```

```
<220> FEATURE:
<223> OTHER INFORMATION: Targeting peptide

<400> SEQUENCE: 7

Gln Trp Ala Val Gly His Met Leu
1               5

<210> SEQ ID NO 8
<211> LENGTH: 8
<212> TYPE: PRT
<213> ORGANISM: Artificial
<220> FEATURE:
<223> OTHER INFORMATION: Targeting peptide

<400> SEQUENCE: 8

Asp Tyr Met Gly Trp Met Asp Phe
1               5

<210> SEQ ID NO 9
<211> LENGTH: 6
<212> TYPE: PRT
<213> ORGANISM: Artificial
<220> FEATURE:
<223> OTHER INFORMATION: Targeting peptide

<400> SEQUENCE: 9

Arg Arg Pro Tyr Ile Leu
1               5

<210> SEQ ID NO 10
<211> LENGTH: 19
<212> TYPE: PRT
<213> ORGANISM: Artificial
<220> FEATURE:
<223> OTHER INFORMATION: Targeting peptide

<400> SEQUENCE: 10

Arg Arg Pro Tyr Ile Leu Gln Leu Tyr Glu Asn Lys Pro Arg Arg Pro
1               5                   10                  15

Tyr Ile Leu
```

NANO-ENABLED IMMUNOTHERAPY IN CANCER

CROSS-REFERENCE TO RELATED APPLICATIONS

This application claims benefit of and priority to U.S. Ser. No. 62/914,950, filed on Oct. 14, 2019 which is incorporated herein by reference in its entirety for all purposes. This application is also a continuation-in-part of PCT/US2018/033265, filed on May 17, 2018 which claims benefit of and priority to U.S. Ser. No. 62/507,996, filed on May 18, 2017, and to U.S. Ser. No. 62/614,325, filed on Jan. 5, 2018, all of which are incorporated herein by reference in their entirety for all purposes.

INCORPORATION BY REFERENCE OF SEQUENCE LISTING PROVIDED AS A TEXT FILE

A Sequence Listing is provided herewith as a text file, "UCLA-P213US_ST25.txt" created on Feb. 11, 2020 and having a size of 2.49 kb. The contents of the text file are incorporated by reference herein in their entirety.

STATEMENT OF GOVERNMENTAL SUPPORT

This invention was made with government support under Grant Number CA198846, awarded by the National Institutes of Health. The Government has certain rights in the invention.

BACKGROUND

While treatment of patients with localized breast cancer (BC) has a survival rate of ~98%, the Breast Cancer Coalition has pointed out that there is marginal improvement on mortality rate since 1975 (DeSantis et al. (2017) *CA Cancer J Clin.* 67: 439-448). This is particularly true for metastatic disease, where none of the current treatments (e.g., radiation, chemotherapy, and estrogen blockers) are capable of eliminating BC once metastatic spread has taken place (Howlader et al. (eds). SEER Cancer Statistics Review, 1975-2010, Nat. Cancer Inst. Bethesda, Md., seer.cancer.gov/csr/1975_2010/, based on November 2012 SEER data submission, posted to the SEER web site, April 2013). Consequently, there is no recognized cure for metastatic disease, which is responsible for ~90% of BC mortality.

Pancreatic ductal adenocarcinoma (PDAC) is an almost uniformly fatal disease with a 5-year survival outcome of less than 6% (American Cancer Society, Cancer Facts & FIGS. 2014, Atlanta: American Cancer Society; 2014). In spite of this dismal prognosis, the introduction of commercial nanocarriers providing paclitaxel (PTX) or irinotecan delivery has had some survival impact (Frese et al. 92012) *Cancer Discov.* 2(3): 260-269; Passero et al. (2016) *Exp. Rev. Anticancer Therap.,* 16(7): 697-703). Thus, while PTX delivery by an albumin-nanocarrier can suppress the drug-resistant tumor stroma, allowing increased gemcitabine uptake, the delivery of irinotecan by a liposome can improve drug pharmacokinetics. Moreover, our own studies using mesoporous silica nanoparticles (MSNP) have shown in a robust orthotopic PDAC animal model that it is possible, in one formulation, to include smart-design features to improve irinotecan loading efficacy, carrier stability and safety over a commercial liposomal equivalent, while a second approach was to develop a ratiometric-designed drug carrier for contemporaneous and synergistic delivery of PTX and gemcitabine (Liu et al. (2016) *ACS Nano,* 10(2): 2702-2715; Meng et al. (2015) *ACS Nano,* 9(4): 3540-3557).

In spite of this bleak picture, newfound optimism has emerged with the advent of cancer immunotherapy, where the power of T-cell immunity can be invoked to treat solid cancers, including, inter alia, breast cancer, and pancreatic cancer. This is best exemplified by the use of immune checkpoint blocking antibodies, that have changed the treatment landscape for melanoma and non-small cell lung cancer (NSCLC). However, in spite of this accomplishment, the overall response rate is only 20-30%, without clear guidance to identify responders.

SUMMARY

To increase the number of responders in the treatment of cancers (e.g., breast cancer), an important strategy that we exploited is to convert immune deplete into immune replete ("hot") tumors as a prelude to further immunomodulatory therapy. One approach was to induce immunogenic conditions at the tumor site by via induced cell death (ICD). ICD is a specialized form of tumor cell death (Kroemer et al. (2013) *Ann. Rev. Immunol.,* 31: 51-72) that can be triggered by specific chemotherapeutic drugs (e.g. anthracyclines, taxanes, oxaliplatin, mitoxantrone), radiation therapy, or cytotoxic viruses. ICD facilitates tumor antigen cross-presentation in. dendritic cells as a result of calreticulin (CRT) expression on the dying tumor cell surface (see, e.g., FIG. 1). CRT expression provides an "eat-me" signal for dendritic cell uptake via the CD91 receptor. In addition, the stepwise release of adjuvant stimuli, including HMGB-1 (a TLR-4 ligand) and/or ATP (a signal that activates the NRLP3 inflammasome), allows dendritic cell maturation and antigen presentation to naive T-cells at the tumor site and regional lymph nodes (Kroemer et al. (2013) *Ann. Rev. Immunol.,* 31: 51-72; Kepp et al. (2014) *Oncoimmunol.,* 3(9): e955691). This response is frequently accompanied by a reduced number of Tregs.

We proposed that ICD will allow more predictable induction of an immune replete status to allow receptor-mediated blockade or perturbation of other immune surveillance pathways to induce durable anti-tumor immunity, which also takes care of metastases. As such, ICD can strengthen the effect of immune checkpoint blocking antibodies as well as indoleamine 2,3-dioxygenase (IDO) inhibitors that interfere in this metabolic immune surveillance pathway. Thus, ICD provides a deliberate means of initiating an immune "hot" start for subsequent response boosting by metabolic and immune checkpoint inhibitors.

In addition to reversal of immune suppression by receptor blocking antibodies to CTLA-4, PD-1 and PD-L1, the IDO pathway is a relevant metabolic immune checkpoint pathway in breast cancer (and other cancers such as pancreatic and colon cancer) because of its overexpression at the tumor site. IDO-1 is the first and rate-limiting enzymatic step in the catabolism of tryptophan in the kynurenine pathway, and exerts potent immunosuppressive effects as a result of the metabolic disturbance of the amino acid ratios (see, e.g., Prendergast et al. (2017) *Canc. Res.,* 77(24): 6795-6811; Lob et al. (2009) *Nat. Rev. Cancer,* 9: 445-452). This allows the IDO effector pathway to control the activity of the mTOR pathway (T-cell activation); activation of the aryl hydrocarbon receptor (AhR) pathway; activation of GCN2 (general control nondereressible), a serine/threonine-protein kinase that senses amino acid deficiency; and development of Tregs. As a result, IDO exerts strong immunosuppressive effects in the TME and regional lymph nodes, culminating in T-cell anergy, decreased cytotoxic killing, and increased accumulation of Tregs at the tumor site (Prendergast et al. (2014) *Cancer Immunol. Immunother.* 63: 721-735; Lob et al. (2009) *Nat. Rev. Cancer,* 9: 445-452). The increased expression of IDO is closely associated with the clinical stage and lymph node metastases in patients with breast cancer.

While a number of small molecule IDO pathway inhibitors have emerged, one of the best studied examples is 1-methyl-tryptophan, a.k.a. indoximod (IND). Although IND has been shown to improve the impact of paclitaxel in a mouse BC model, its modest impact as an adjuvant in human cancer studies has raised concerns about its clinical efficacy. Our own animal studies have demonstrated that the water insolubility of IND contributes to an unfavorable PK, short, circulatory half-life and inadequate tumor retention to effectively interfere in the activity of IDO, which is overexpressed at the tumor site. This served as the impetus to design nanocarriers into which IDO pathway inhibitors (e.g., IND) could be co-delivered with ICD inducers (e.g., doxorubicin, mitoxantrone, etc.).

In one illustrative, but non-limiting embodiment, this goal was accomplished by synthesizing an IDO pathway inhibitor prodrug where the IDO inhibitor (e.g., indoximod) was conjugated to a lipid moiety (e.g., cholesterol or a phospholipid) that can be assembled into a lipid bilayer which can in turn be incorporated into a drug delivery vehicle (e.g., a liposome). In one illustrative embodiment, this can be accomplished by synthesizing IND as a phospholipid-conjugated (or cholesterol-conjugated) prodrug that can self-assembles to form a nanovesicle (e.g., a liposome). Not only did the conjugated IND-lipid bilayer exert a major effect on tumor cell IND levels, but it also provided the lipid bilayer backbone of the carrier into which an ICD inducer (e.g., DOX, mitoxantrone (MTX), etc.) can be loaded, e.g., by remote import.

It is believed that a doxorubicin (DOX) or mitoxantrone (MTX) encapsulating nanocarrier provides a more potent ICD stimulus than the free drug, and can do so synergistically with a small molecule inhibitor (e.g., indoximod) of the IDO-1 pathway. It is believed the nanocarrier is capable of facilitating this task, in part, by improving the PK of DOX and indoximod (IND) at the tumor site. This can provide a next generation nanocarrier providing an ICD stimulus and an IDO inhibitor as a promising synergistic immunotherapy platform for BC, including triple negative BC (TNBC) (most responsive to immune checkpoint inhibitors) as well as ER-positive tumors (numerically the largest BC subtype responsible for mortality) and other cancers (e.g., PDAC, and colon cancer).

Accordingly, in certain embodiments, compositions and methods are provided for systemic and/or for local (peri- or intratumoral) delivery of one or more ICD-inducing agents (e.g., doxorubicin, oxaliplatin, etc.) in conjunction with delivery of an inhibitor of the IDO pathway (e.g., indoximod). In certain embodiments the IDO inhibitor is conjugated to a nanovesicle-forming moiety (e.g., comprising a phospholipid bilayer). In still another embodiment, methods and compositions are provided where an ICD-inducing agent (e.g., oxaliplatin, doxorubicin, mitoxantrone, irinotecan etc.) and an IDO inhibiting agent (e.g., an IDO inhibitor-prodrug) are integrated into a nanocarrier, that allows systemic delivery to a cancer site. Additionally, in certain embodiments, compositions and methods are provided for the treatment or prevention of a cancer via vaccination (e.g., subcutaneous vaccination), utilizing certain cancer cells (e.g., drug-treated cancer cells) in which ICD has been induced ex vivo.

Various embodiments contemplated herein may include, but need not be limited to, one or more of the following:

Embodiment 1

A composition comprising an IDO inhibitor conjugated to a moiety that forms a nanovesicle in aqueous solution.

Embodiment 2

The composition of embodiment 1, wherein said IDO inhibitor is conjugated to a moiety selected from the group consisting of a lipid, a phospholipid, vitamin E, cholesterol, and a fatty acid.

Embodiment 3

The composition according to any one of embodiments 1-2, wherein IDO inhibitor is conjugated directly to said moiety.

Embodiment 4

The composition according to any one of embodiments 1-2, wherein IDO inhibitor is conjugated to said moiety via a linker.

Embodiment 5

The composition of embodiment 4, wherein said IDO inhibitor is conjugated to said moiety via an HO—$(CH_2)_{n=2-5}$—OH linker.

Embodiment 6

The composition according to any one of embodiments 2-5, wherein said IDO inhibitor is conjugated to cholesterol (CHOL).

Embodiment 7

The composition according to any one of embodiments 1-6, wherein said IDO inhibitor comprises an agent selected from the group consisting of D-1-methyl-tryptophan (indoximod, D-1MT), L-1-methyl-tryptophan (L-1MT), a mixture of D-1MT and L-1MT, 1-methyl-L-tryptophan (L-1MT), methylthiohydantoin-dl-tryptophan (MTH-Trp, Necrostatin), β-carbolines (e.g., 3-butyl-β-carboline), Naphthoquinone-based (e.g., annulin-B), S-allyl-brassinin, S-benzyl-brassinin, N-[2-(Indol-3-yl)ethyl]-S-methyl-dithiocarbamate, N-[2-(benzo[b]thiophen-3-yl)ethyl]-S-methyl-dithiocarbamate, N-[3-(Indol-3-yl)propyl]-S-methyl-dithiocarbamate, S-hexyl-brassinin, N-[2-(indol-3-yl)ethyl]-S-benzyl-dithiocarbamate, N-[2-(indol-3-yl)ethyl]-S[(naphth-2-yl)methyl]-dithiocarbamate, N-[2-(indol-3-yl)ethyl]-S-

[(pyrid-3-yl)methyl]-dithiocarbamate, N-[2-(indol-3-yl)ethyl]-S-[(pyrid-4-yl)methyl]-dithiocarbamate, 5-bromo-brassinin, Phenylimidazole-based IDO inhibitors (e.g., 4-phenylimidazole), Exiguamine A, imidodicarbonimidic diamide, N-methyl-N'-9-phenanthrenyl-monohydrochloride (NSC401366), INCB024360 (Epacadostat), 1-cyclohexyl-2-(5H-imidazo[5,1-a]isoindol-5-yl)ethanol (GDC-0919), IDO1-derived peptide, NLG919, Ebselen, Pyridoxal Isonicotinoyl Hydrazone, Norharmane, CAY10581, 2-Benzyl-2-thiopseudourea hydrochloride, and 4-phenylimidazole.

Embodiment 8

The composition of embodiment 7, wherein said IDO inhibitor comprises 1-methyl-tryptophan.

Embodiment 9

The composition of embodiment 8, wherein said IDO inhibitor comprises a D isomer of 1-methyl-tryptophpan.

Embodiment 10

The composition of embodiment 8, wherein said IDO inhibitor comprises an L isomer of 1-methyl-tryptophpan.

Embodiment 11

The composition of embodiment 8, wherein said IDO inhibitor comprises a mixture of D and L isomers of 1-methyl-tryptophpan.

Embodiment 12

The composition of embodiment 8, wherein the IDO inhibitor conjugated to cholesterol comprises a compound having the structure:

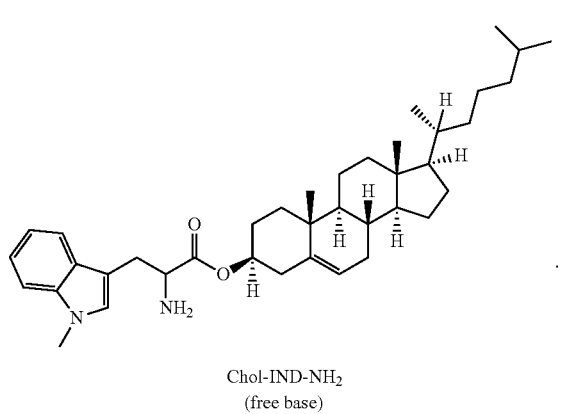

Chol-IND-NH₂
(free base)

Embodiment 13

The composition of embodiment 8, wherein the IDO inhibitor conjugated to cholesterol comprises a compound having the structure:

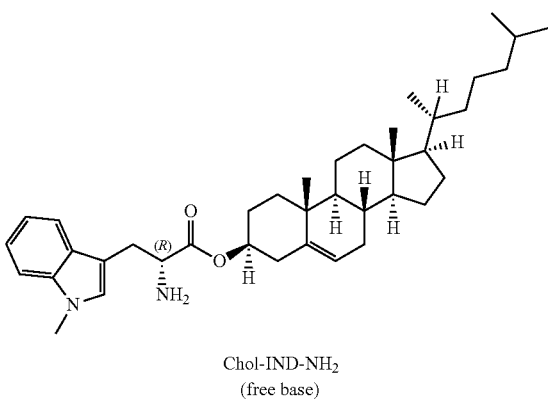

Chol-IND-NH₂
(free base)

Embodiment 14

The composition of embodiment 8, wherein the IDO inhibitor conjugated to cholesterol comprises a compound having the structure:

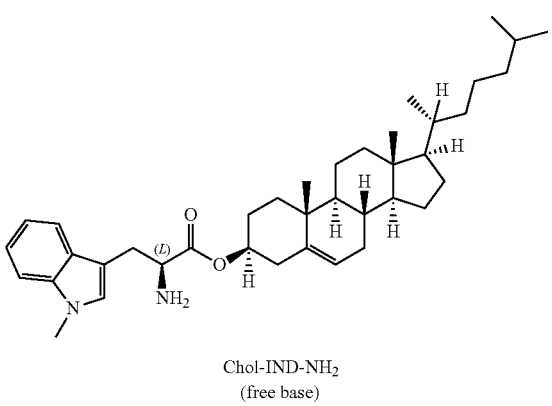

Chol-IND-NH₂
(free base)

Embodiment 15

The composition according to any one of embodiments 1-14, wherein the conjugated IDO inhibitor forms a component of a vesicle.

Embodiment 16

A nanovesicle drug carrier for the combined delivery of an IDO inhibitor and an inducer of immunogenic cell death (ICD), said nanovesicle drug carrier comprising: a lipid vesicle wherein said lipid vesicle comprises a lipid effective to form a vesicle comprising a lipid bilayer in an aqueous solution, where said lipid bilayer comprises a composition according to any one of embodiments 1-15; and a cargo within said vesicle where said cargo comprises an agent that induces immunogenic cell death (ICD) (ICD-inducer).

Embodiment 17

The nanovesicle drug carrier of embodiment 16, wherein said drug carrier contains a predefined ratio of IDO inhibitor to ICD-inducer.

Embodiment 18

The nanovesicle drug carrier of according to any one of embodiments 16-17, wherein said lipid bilayer comprises a phospholipid, and cholesterol (CHOL).

Embodiment 19

The nanovesicle drug carrier according to any one of embodiments 16-18, wherein said lipid bilayer comprises a phospholipid, and cholesterol-IND (Chol-IND).

Embodiment 20

The nanovesicle drug carrier according to any one of embodiments 18-19, wherein said phospholipid comprises a saturated fatty acid with a C14-C20 carbon chain, and/or an unsaturated fatty acid with a C14-C20 carbon chain, and/or a natural lipid comprising a mixture of fatty acids with C12-C20 carbon chains.

Embodiment 21

The nanovesicle drug carrier of embodiment 20, wherein said phospholipid comprises a phospholipid selected from the group consisting of phosphatidylcholine (DPPC), 1,2-dimyristoleoyl-sn-glycero-3-phosphocholine (DMPC), 1,2-dioleoyl-sn-glycero-3-phosphocholine (DOPC), 1,2-distearoyl-sn-glycero-3-phospho-rac-glycerol (DSPG), 1,2-dipalmitoyl-sn-glycero-3-phosphoglycerol (DPPG), distearoylphosphatidylcholine (DSPC), 1,2-dieicosenoyl-sn-glycero-3-phosphocholine, and diactylphosphatidylcholine (DAPC).

Embodiment 22

The nanovesicle drug carrier of embodiment 20, wherein said phospholipid comprises a natural lipid selected from the group consisting of egg phosphatidylcholine (egg PC), and soy phosphatidylcholine (soy PC).

Embodiment 23

The nanovesicle drug carrier of embodiment 20, wherein said phospholipid comprises distearoylphosphatidylcholine (DSPC).

Embodiment 24

The nanovesicle drug carrier according to any one of embodiments 19-23, wherein said lipid bilayer comprises an mPEG phospholipid with a phospholipid C14-C18 carbon chain, and a PEG molecular weight ranging from about 350 Da to 5000 Da.

Embodiment 25

The nanovesicle drug carrier of embodiment 24, wherein said lipid bilayer comprises 1,2-distearoyl-sn-glycero-3-phosphoethanolamine-PEG (DSPE-PEG).

Embodiment 26

The nanovesicle drug carrier of embodiment 25, wherein said DSPE-PEG comprises DPSE-PEG$_{2K}$.

Embodiment 27

The nanovesicle drug carrier of embodiment 25, wherein said DSPE-PEG comprises DPSE-PEG$_{5K}$.

Embodiment 28

The nanovesicle drug carrier according to any one of embodiments 23-27, wherein said lipid bilayer comprises DSPC:Chol-IND:DSPE-PEG.

Embodiment 29

The nanovesicle drug carrier of embodiment 28, wherein the ratio of DSPC:Chol-IND:DSPE-PEG ranges from 40-90% DSPC:10%-50% Chol-IND:1%-10% DSPE-PEG (molar ratio).

Embodiment 30

The nanovesicle drug carrier of embodiment 29, wherein the ratio of DSPC:Chol-IND:DSPE-PEG is about 50:40:5 (molar ratio).

Embodiment 31

The nanovesicle drug carrier according to any one of embodiments 23-27, wherein said lipid bilayer comprises DPPG:Chol-IND:DSPE-PEG.

Embodiment 32

The nanovesicle drug carrier of embodiment 31, wherein the ratio of DPPG:Chol-IND:DSPE-PEG ranges from 40-90% DPPG:10%-50% Chol-IND:1%-10% DSPE-PEG (molar ratio).

Embodiment 33

The nanovesicle drug carrier of embodiment 32, wherein the ratio of DPPG:Chol-IND:DSPE-PEG is about 50:40:5 (molar ratio).

Embodiment 34

The nanovesicle drug carrier according to any one of embodiments 18-33, wherein said lipid bilayer comprises a cholesterol derivative selected from the group consisting of cholesterol hemisuccinate (CHEMS), lysine-based cholesterol (CHLYS), and PEGylated cholesterol (Chol-PEG).

Embodiment 35

The nanovesicle drug carrier of embodiment 34, wherein said lipid bilayer comprises CHEMS.

Embodiment 36

The nanovesicle drug carrier of embodiment 35, wherein said bilayer comprises CHEMS ranging from about 5% (mol percent) up to about 30% total lipid.

Embodiment 37

The nanovesicle drug carrier of embodiment 36, wherein said bilayer comprise about 10% or about 20% CHEMS or about 30% CHEMS or about 40% CHEMS.

Embodiment 38

The nanovesicle drug carrier according to any one of embodiments 16-37, wherein the IDO inhibitor conjugated to cholesterol comprises a compound having the structure

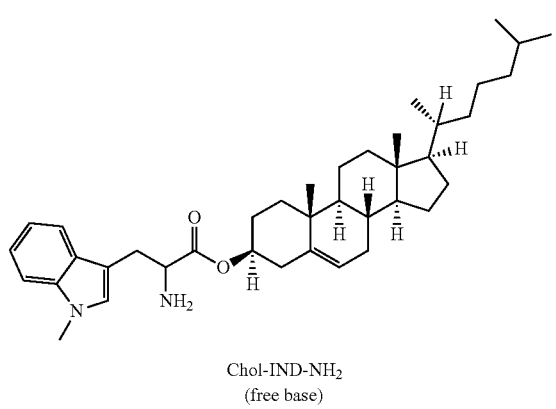

Chol-IND-NH₂
(free base)

Embodiment 39

The nanovesicle drug carrier of embodiment 38, wherein the IDO inhibitor conjugated to cholesterol comprises a compound having the structure:

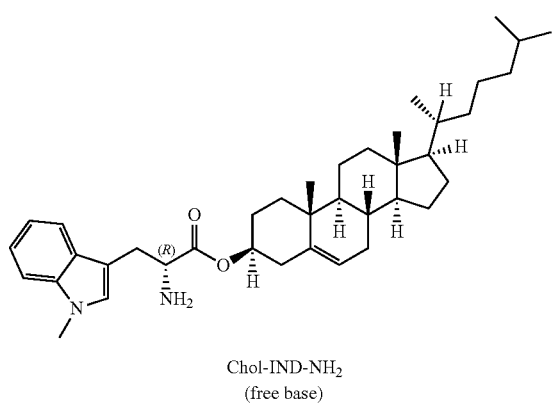

Chol-IND-NH₂
(free base)

Embodiment 40

The nanovesicle drug carrier of embodiment 38, wherein the IDO inhibitor conjugated to cholesterol comprises a compound having the structure:

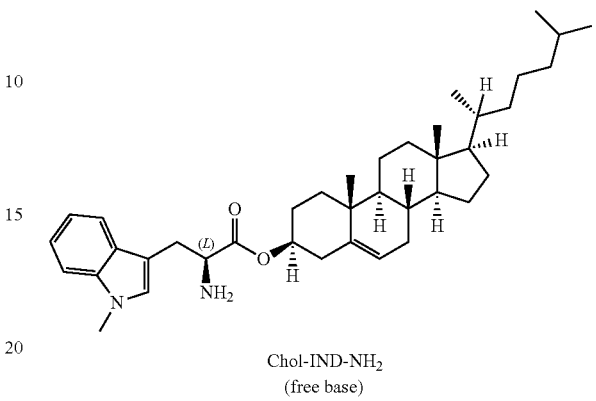

Chol-IND-NH₂
(free base)

Embodiment 41

The nanovesicle drug carrier according to any one of embodiments 16-40, wherein said cargo within said vesicle comprises an agent selected from the group consisting of mitoxantrone (MTX), doxorubicin (DOX), oxaliplatin, anthracenedione, bleomycin, bortezomib, cisplatin, daunorubicin, docetaxel, epirubicin, idarubicin, paclitaxel, R2016, cyclophosphamide, irinotecan and a bioreactive nanomaterial that induces ICD.

Embodiment 42

The nanovesicle drug carrier of embodiment 41, wherein said cargo comprises mitoxantrone (MTX).

Embodiment 43

The nanovesicle drug carrier of embodiment 41, wherein said cargo comprises oxaliplatin.

Embodiment 44

The nanovesicle drug carrier of embodiment 41, wherein said cargo comprises doxorubicin.

Embodiment 45

The nanovesicle drug carrier of embodiment 41, wherein said cargo comprises a bioreactive nanomaterial that induces ICD and/or innate immune activation.

Embodiment 46

The nanovesicle drug carrier of embodiment 45, wherein said cargo comprises a nanomaterial that induces ICD where said nanomaterial is selected from the group consisting of CuO, Cu₂O, Sb₂O₃, As₂O₃, Bi₂O₃, P₂O₃, ZnO, TiO₂, graphene oxide, and bioreactive 2D materials other than graphene or graphene oxide.

Embodiment 47

The nanovesicle drug carrier according to any one of embodiments 16-46, wherein when the cargo in the nanocarrier is a weak base, said carrier comprises a cargo-trapping agent.

Embodiment 48

The nanovesicle drug carrier of embodiment 47, wherein said cargo trapping agent before reaction with the cargo drug loaded in the vesicle, is selected from the group consisting of citric acid, triethylammonium sucrose octasulfate (TEA$_8$SOS), (NH$_4$)$_2$SO$_4$, an ammonium salt, a trimethylammonium salt, and a triethylammonium salt.

Embodiment 49

The nanovesicle drug carrier of embodiment 48, wherein said cargo-trapping agent before reaction with said drug is citric acid.

Embodiment 50

The nanovesicle drug carrier of embodiment 48, wherein said cargo-trapping agent before reaction with said drug is ammonium sulfate.

Embodiment 51

The nanovesicle drug carrier according to any one of embodiments 16-50, wherein said drug carrier is conjugated to a moiety selected from the group consisting of a targeting moiety, a fusogenic peptide, and a transport peptide.

Embodiment 52

The nanovesicle drug carrier of embodiment 51, wherein said drug carrier is conjugated to a peptide that binds a receptor on a cancer cell or tumor blood vessel.

Embodiment 53

The nanovesicle drug carrier of embodiment 52, wherein said drug carrier is conjugated to an iRGD peptide.

Embodiment 54

The nanovesicle drug carrier of embodiment 52, wherein said drug carrier is conjugated to a targeting peptide shown in Table 5.

Embodiment 55

The nanovesicle drug carrier according to any one of embodiments 51-54, wherein said drug carrier is conjugated to transferrin, and/or ApoE, and/or folate.

Embodiment 56

The nanovesicle drug carrier according to any one of embodiments 51-55, wherein said drug carrier is conjugated to a targeting moiety that comprises an antibody that binds to a cancer marker.

Embodiment 57

The nanovesicle drug carrier of embodiment 56, wherein said drug carrier is conjugated to a targeting moiety that comprises an antibody that binds a cancer marker shown in Table 4.

Embodiment 58

The nanovesicle drug carrier according to any one of embodiments 56-57, wherein said antibody is selected from the group consisting of an intact immunoglobulin, an F(ab)'$_2$, a Fab, a single chain antibody, a diabody, an affibody, a unibody, and a nanobody.

Embodiment 59

The nanovesicle drug carrier according to any one of embodiments 16-58, wherein said drug carriers in suspension are stable for at least 1 month, or at least 2 months, or at least 3 months, or at least 4 months, or at least 5 months, or at least 6 months when stored at 4° C.

Embodiment 60

The nanovesicle drug carrier according to any one of embodiments 16-59, wherein said nanoparticle drug carrier forms a stable suspension on rehydration after lyophilization.

Embodiment 61

The nanovesicle drug carrier according to any one of embodiments 16-60, wherein said nanoparticle drug carriers, show reduced drug toxicity as compared to free drug.

Embodiment 62

The nanovesicle drug carrier according to any one of embodiments 16-61, wherein said nanoparticle drug carrier has colloidal stability in physiological fluids with pH 7.4 and remains monodisperse to allow systemic biodistribution and is capable of entering a disease site by vascular leakage (EPR effect) or transcytosis.

Embodiment 63

The nanovesicle drug carrier drug carrier according to any one of embodiments 16-62, wherein said carrier is colloidally stable.

Embodiment 64

The nanovesicle drug carrier according to any one of embodiments 16-63, wherein the IDO inhibitor and the ICD inducer are synergistic in their activity against a cancer.

Embodiment 65

The nanovesicle drug carrier according to any one of embodiments 16-64, wherein said drug carrier, when administered systemically, delivers an amount of an ICD inducer effective to induce or to facilitate induction of immunogenic cell death of a cancer cell at a tumor site.

Embodiment 66

The nanovesicle drug carrier according to any one of embodiments 16-65, wherein said drug carrier, when administered systemically, delivers an amount of an IDO inhibitor to partially or fully inhibit the IDO enzyme or IDO pathway at a cancer site.

Embodiment 67

A nanoparticle drug carrier for the combined delivery of an IDO inhibitor and an inducer of immunogenic cell death (ICD), said nanoparticle drug carrier comprising: a mesoporous silica nanoparticle having a surface and defining a plurality of pores that are suitable to receive molecules therein; a lipid bilayer coating the surface where said lipid bilayer comprises a composition according to any one of embodiments 1-15; and a cargo comprising an agent that induces immunogenic cell death (ICD) (ICD-inducer) disposed within said mesoporous silica particle; wherein the lipid bilayer is substantially continuous and encapsulates said nanoparticle stably sealing the plurality of pores.

Embodiment 68

The nanoparticle drug carrier of embodiment 67, wherein said nanoparticle drug carrier contains a predefined ratio of IDO inhibitor to ICD-inducer.

Embodiment 69

The nanoparticle drug carrier according to any one of embodiments 67-68, wherein the IDO inhibitor and the ICD inducer are synergistic in their activity against a cancer.

Embodiment 70

The nanoparticle drug carrier according to any one of embodiments 67-69, wherein said lipid bilayer comprises a phospholipid, and cholesterol (CHOL).

Embodiment 71

The nanoparticle drug carrier according to any one of embodiments 67-70, wherein said lipid bilayer comprises a phospholipid, and cholesterol-IND (Chol-IND).

Embodiment 72

The nanoparticle drug carrier according to any one of embodiments 70-71, wherein said phospholipid comprises a saturated fatty acid with a C14-C20 carbon chain, and/or an unsaturated fatty acid with a C14-C20 carbon chain, and/or a natural lipid comprising a mixture of fatty acids with C12-C20 carbon chains.

Embodiment 73

The nanoparticle drug carrier of embodiment 72, wherein said phospholipid comprises a phospholipid selected from the group consisting of phosphatidylcholine (DPPC), 1,2-dimyristoleoyl-sn-glycero-3-phosphocholine (DMPC), 1,2-dioleoyl-sn-glycero-3-phosphocholine (DOPC), 1,2-distearoyl-sn-glycero-3-phospho-rac-glycerol (DSPG), 1,2-dipalmitoyl-sn-glycero-3-phosphoglycerol (DPPG), distearoylphosphatidylcholine (DSPC), 1,2-dieicosenoyl-sn-glycero-3-phosphocholine, and diactylphosphatidylcholine (DAPC).

Embodiment 74

The nanoparticle drug carrier of embodiment 72, wherein said phospholipid comprises a natural lipid selected from the group consisting of egg phosphatidylcholine (egg PC), and soy phosphatidylcholine (soy PC).

Embodiment 75

The nanoparticle drug carrier of embodiment 72, wherein said phospholipid comprises distearoylphosphatidylcholine (DSPC).

Embodiment 76

The nanoparticle drug carrier according to any one of embodiments 71-75, wherein said lipid bilayer comprises an mPEG phospholipid with a phospholipid C14-C18 carbon chain, and a PEG molecular weight ranging from about 350 Da to 5000 Da.

Embodiment 77

The nanoparticle drug carrier of embodiment 76, wherein said lipid bilayer comprises 1,2-distearoyl-sn-glycero-3-phosphoethanolamine-PEG (DSPE-PEG).

Embodiment 78

The nanoparticle drug carrier of embodiment 77, wherein said DSPE-PEG comprises DPSE-PEG$_{2K}$.

Embodiment 79

The nanoparticle drug carrier of embodiment 77, wherein said DSPE-PEG comprises DPSE-PEG$_{5K}$.

Embodiment 80

The nanoparticle drug carrier according to any one of embodiments 75-79, wherein said lipid bilayer comprises DSPC:Chol-IND:DSPE-PEG.

Embodiment 81

The nanoparticle drug carrier of embodiment 80, wherein the ratio of DSPC:Chol-IND:DSPE-PEG ranges from 40-90% DSPC:10%-50% Chol-IND:1%-10% DSPE-PEG (molar ratio).

Embodiment 82

The nanoparticle drug carrier of embodiment 81, wherein the ratio of DSPC:Chol-IND:DSPE-PEG is about 50:40:5 (molar ratio).

Embodiment 83

The nanoparticle drug carrier according to any one of embodiments 75-79, wherein said lipid bilayer comprises DPPG:Chol-IND:DSPE-PEG.

Embodiment 84

The nanoparticle drug carrier of embodiment 83, wherein the ratio of DPPG:Chol-IND:DSPE-PEG ranges from 40-90% DSPC:10%-50% Chol-IND:1%-10% DPPG-PEG (molar ratio).

Embodiment 85

The nanoparticle drug carrier of embodiment 84, wherein the ratio of DPPG:Chol-IND:DSPE-PEG is about 50:40:5 (molar ratio).

Embodiment 86

The nanoparticle drug carrier according to any one of embodiments 67-85, wherein said lipid bilayer comprises a cholesterol derivative selected from the group consisting of cholesterol hemisuccinate (CHEMS), lysine-based cholesterol (CHLYS), and PEGylated cholesterol (Chol-PEG).

Embodiment 87

The nanoparticle drug carrier of embodiment 86, wherein said lipid bilayer comprises CHEMS.

Embodiment 88

The nanoparticle drug carrier of embodiment 87, wherein said bilayer comprises CHEMS ranging from about 5% (mol percent) up to about 30% total lipid.

Embodiment 89

The nanoparticle drug carrier of embodiment 88, wherein said bilayer comprises about 10% or about 20% CHEMS or about 30% CHEMS or about 40% CHEMS.

Embodiment 90

The nanoparticle drug carrier according to any one of embodiments 67-89, wherein the IDO inhibitor conjugated to cholesterol comprises a compound having the structure:

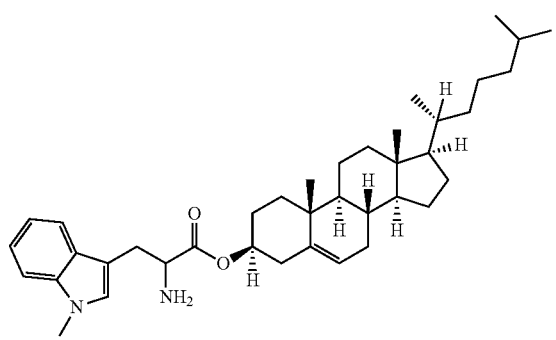

Chol-IND-NH₂
(free base)

Embodiment 91

The nanoparticle drug carrier of embodiment 90, wherein the DO inhibitor conjugated to cholesterol comprises a compound having the structure:

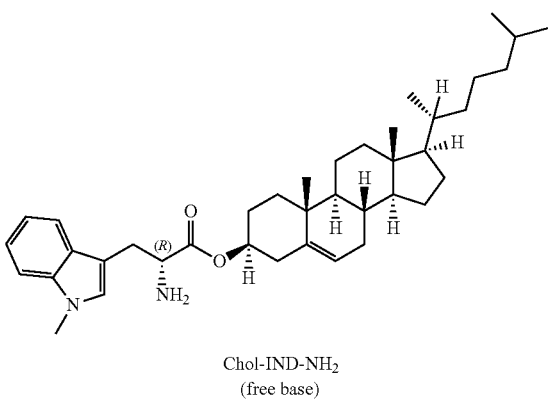

Chol-IND-NH₂
(free base)

Embodiment 92

The nanoparticle drug carrier of embodiment 90, wherein the DO inhibitor conjugated to cholesterol comprises a compound having the structure:

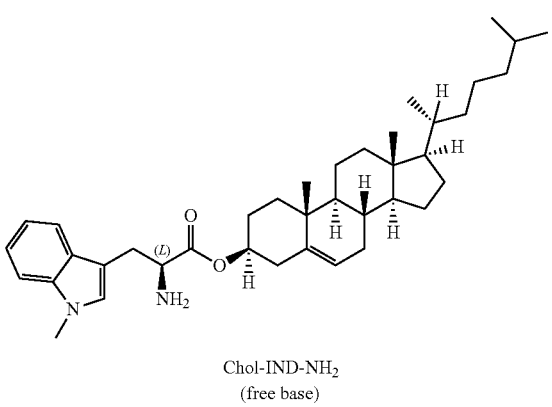

Chol-IND-NH₂
(free base)

Embodiment 93

The nanoparticle drug carrier according to any one of embodiments 67-92, wherein said cargo within said mesoporous silica nanoparticle comprises an agent selected from the group consisting of mitoxantrone (MTX), doxorubicin (DOX), oxaliplatin, anthracenedione, bleomycin, bortezomib, cisplatin, daunorubicin, docetaxel, irinotecan, epirubicin, idarubicin, paclitaxel, R2016, cyclophosphamide, and a bioreactive nanomaterial that induces ICD.

Embodiment 94

The nanoparticle drug carrier of embodiment 93, wherein said cargo comprises mitoxantrone (MTX).

Embodiment 95

The nanoparticle drug carrier of embodiment 93, wherein said cargo comprises oxaliplatin.

Embodiment 96

The nanoparticle drug carrier of embodiment 93, wherein said cargo comprises doxorubicin.

Embodiment 97

The nanoparticle drug carrier according to any one of embodiments 67-96, wherein when the cargo in the nanocarrier is a weak base, said carrier comprises a cargo-trapping agent.

Embodiment 98

The nanoparticle drug carrier of embodiment 97, wherein said cargo trapping agent before reaction with the cargo drug loaded in the vesicle, is selected from the group consisting of citric acid, triethylammonium sucrose octasulfate (TEA$_8$SOS), (NH$_4$)$_2$SO$_4$, an ammonium salt, a trimethylammonium salt, and a triethylammonium salt.

Embodiment 99

The nanoparticle drug carrier of embodiment 98, wherein said cargo-trapping agent before reaction with said drug is citric acid.

Embodiment 100

The nanoparticle drug carrier of embodiment 98, wherein said cargo-trapping agent before reaction with said drug is ammonium sulfate.

Embodiment 101

The nanoparticle drug carrier according to any one of embodiments 67-100, wherein said drug carrier is conjugated to a moiety selected from the group consisting of a targeting moiety, a fusogenic peptide, and a transport peptide.

Embodiment 102

The nanoparticle drug carrier of embodiment 101, wherein said drug carrier is conjugated to a peptide that binds a receptor on a cancer cell or tumor blood vessel.

Embodiment 103

The nanoparticle drug carrier of embodiment 102, wherein said drug carrier is conjugated to an iRGD peptide.

Embodiment 104

The nanoparticle drug carrier of embodiment 102, wherein said drug carrier is conjugated to a targeting peptide shown in Table 5.

Embodiment 105

The nanoparticle drug carrier according to any one of embodiments 101-104, wherein said drug carrier is conjugated to transferrin, and/or ApoE, and/or folate.

Embodiment 106

The nanoparticle drug carrier according to any one of embodiments 101-105, wherein said drug carrier is conjugated to a targeting moiety that comprises an antibody that binds to a cancer marker.

Embodiment 107

The nanoparticle drug carrier of embodiment 106, wherein said drug carrier is conjugated to a targeting moiety that comprises an antibody that binds a cancer marker shown in Table 4.

Embodiment 108

The nanoparticle drug carrier according to any one of embodiments 106-107, wherein said antibody is selected from the group consisting of an intact immunoglobulin, an F(ab)'$_2$, a Fab, a single chain antibody, a diabody, an affibody, a unibody, and a nanobody.

Embodiment 109

The nanoparticle drug carrier according to any one of embodiments 67-108, wherein said drug carriers in suspension are stable for at least 1 month, or at least 2 months, or at least 3 months, or at least 4 months, or at least 5 months, or at least 6 months when stored at 4° C.

Embodiment 110

The nanoparticle drug carrier according to any one of embodiments 67-109, wherein said nanoparticle drug carrier forms a stable suspension on rehydration after lyophilization.

Embodiment 111

The nanoparticle drug carrier according to any one of embodiments 67-110, wherein said nanoparticle drug carriers, show reduced drug toxicity as compared to free drug.

Embodiment 112

The nanoparticle drug carrier according to any one of embodiments 67-111, wherein said nanoparticle drug carrier has colloidal stability in physiological fluids with pH 7.4 and remains monodisperse to allow systemic biodistribution and is capable of entering a disease site by vascular leakage (EPR effect) or transcytosis.

Embodiment 113

The nanoparticle drug carrier drug carrier according to any one of embodiments 67-112, wherein said carrier is colloidally stable.

Embodiment 114

The nanoparticle drug carrier according to any one of embodiments 67-113, wherein the IDO inhibitor and the ICD inducer are synergistic in their activity against a cancer.

Embodiment 115

The nanoparticle drug carrier according to any one of embodiments 67-114, wherein said drug carrier, when administered systemically, delivers an amount of an ICD inducer effective to induce or to facilitate induction of immunogenic cell death of a cancer cell at a tumor site.

Embodiment 116

The nanoparticle drug carrier according to any one of embodiments 67-115, wherein said drug carrier, when administered systemically, delivers an amount of an IDO inhibitor to partially or fully inhibit the IDO enzyme or IDO pathway at a cancer site.

Embodiment 117

A nanomaterial carrier for the combined delivery of an IDO inhibitor and an inducer of immunogenic cell death (ICD), said nanomaterial carrier comprising: a nanomaterial that induces ICD; and a lipid or lipid formulation comprising a composition according to any one of embodiments 1-15, where said lipid or lipid formulation is disposed on the surface of said nanomaterial.

Embodiment 118

The nanomaterial carrier of embodiments 117, wherein said nanomaterial comprises a material selected from the group consisting of CuO, $Cu_2O$, $Sb_2O_3$, $As_2O_3$, $Bi_2O_3$, $P_2O_3$, ZnO, $TiO_2$, graphene oxide, and 2D materials other than graphene or graphene oxide.

Embodiment 119

The nanomaterial carrier according to any one of embodiments 117-118, wherein said lipid or lipid formulation fully encapsulates said nanomaterial.

Embodiment 120

The nanomaterial carrier according to any one of embodiments 117-119, wherein said lipid or lipid formulation is not a lipid bilayer.

Embodiment 121

The nanomaterial carrier according to any one of embodiments 117-119, wherein said lipid or lipid formulation comprises a lipid bilayer.

Embodiment 122

The nanomaterial carrier of according to any one of embodiments 117-121, wherein said lipid or lipid formulation comprises a phospholipid, and cholesterol (CHOL).

Embodiment 123

The nanomaterial carrier according to any one of embodiments 117-122, wherein said lipid or lipid formulation comprises a phospholipid, and cholesterol-IND (Chol-IND).

Embodiment 124

The nanomaterial carrier according to any one of embodiments 18-123, wherein said phospholipid comprises a saturated fatty acid with a C14-C20 carbon chain, and/or an unsaturated fatty acid with a C14-C20 carbon chain, and/or a natural lipid comprising a mixture of fatty acids with C12-C20 carbon chains.

Embodiment 125

The nanomaterial carrier of embodiment 124, wherein said phospholipid comprises a phospholipid selected from the group consisting of phosphatidylcholine (DPPC), 1,2-dimyristoleoyl-sn-glycero-3-phosphocholine (DMPC), 1,2-dioleoyl-sn-glycero-3-phosphocholine (DOPC), 1,2-distearoyl-sn-glycero-3-phospho-rac-glycerol (DSPG), 1,2-dipalmitoyl-sn-glycero-3-phosphoglycerol (DPPG), distearoylphosphatidylcholine (DSPC), 1,2-dieicosenoyl-sn-glycero-3-phosphocholine, and diactylphosphatidylcholine (DAPC).

Embodiment 126

The nanomaterial carrier of embodiment 124, wherein said phospholipid comprises a natural lipid selected from the group consisting of egg phosphatidylcholine (egg PC), and soy phosphatidylcholine (soy PC).

Embodiment 127

The nanomaterial carrier of embodiment 124, wherein said phospholipid comprises distearoylphosphatidylcholine (DSPC).

Embodiment 128

The nanomaterial carrier according to any one of embodiments 123-127, wherein said lipid or lipid formulation comprises an mPEG phospholipid with a phospholipid C14-C18 carbon chain, and a PEG molecular weight ranging from about 350 Da to 5000 Da.

Embodiment 129

The nanomaterial carrier of embodiment 128, wherein said lipid or lipid formulation comprises 1,2-distearoyl-sn-glycero-3-phosphoethanolamine-PEG (DSPE-PEG).

Embodiment 130

The nanomaterial carrier of embodiment 129, wherein said DSPE PEG comprises $DPSE-PEG_{2K}$.

Embodiment 131

The nanomaterial carrier of embodiment 129, wherein said DSPE PEG comprises $DPSE-PEG_{5K}$.

Embodiment 132

The nanomaterial carrier according to any one of embodiments 127-131, wherein said lipid or lipid formulation comprises DSPC:Chol-IND:DSPE-PEG.

Embodiment 133

The nanomaterial carrier of embodiment 132, wherein the ratio of DSPC:Chol-IND:DSPE-PEG ranges from 40-90% DSPC:10%-50% Chol-IND:1%-10% DSPE-PEG (molar ratio).

Embodiment 134

The nanomaterial carrier of embodiment 133, wherein the ratio of DSPC:Chol-IND:DSPE-PEG is about 50:40:5 (molar ratio).

Embodiment 135

The nanomaterial carrier according to any one of embodiments 127-131, wherein said lipid or lipid formulation comprises DPPG:Chol-IND:DSPE-PEG.

Embodiment 136

The nanomaterial carrier of embodiment 135, wherein the ratio of DPPG:Chol-IND:DSPE-PEG ranges from 40-90% DPPG:10%-50% Chol-IND:1%-10% DSPE-PEG (molar ratio).

Embodiment 137

The nanomaterial carrier of embodiment 136, wherein the ratio of DPPG:Chol-IND:DSPE-PEG is about 50:40:5 (molar ratio).

Embodiment 138

The nanomaterial carrier according to any one of embodiments 122-137, wherein said lipid or lipid formulation comprises a cholesterol derivative selected from the group consisting of cholesterol hemisuccinate (CHEMS), lysine-based cholesterol (CHLYS), and PEGylated cholesterol (Chol-PEG).

Embodiment 139

The nanomaterial carrier of embodiment 138, wherein said lipid or lipid formulation comprises CHEMS.

Embodiment 140

The nanomaterial carrier of embodiment 139, wherein said bilayer comprises CHEMS ranging from about 5% (mol percent) up to about 30% total lipid.

Embodiment 141

The nanomaterial carrier of embodiment 140, wherein said bilayer comprise about 10% or about 20% CHEMS.

Embodiment 142

The nanomaterial carrier according to any one of embodiments 117-141, wherein said drug carrier is conjugated to a moiety selected from the group consisting of a targeting moiety, a fusogenic peptide, and a transport peptide.

Embodiment 143

The nanomaterial carrier of embodiment 142, wherein said drug carrier is conjugated to a peptide that binds a receptor on a cancer cell or tumor blood vessel.

Embodiment 144

The nanomaterial carrier of embodiment 143, wherein said drug carrier is conjugated to an iRGD peptide.

Embodiment 145

The nanomaterial carrier of embodiment 143, wherein said drug carrier is conjugated to a targeting peptide shown in Table 5.

Embodiment 146

The nanomaterial carrier according to any one of embodiments 142-145, wherein said drug carrier is conjugated to transferrin, and/or ApoE, and/or folate.

Embodiment 147

The nanomaterial carrier according to any one of embodiments 142-146, wherein said drug carrier is conjugated to a targeting moiety that comprises an antibody that binds to a cancer marker.

Embodiment 148

The nanomaterial carrier of embodiment 147, wherein said drug carrier is conjugated to a targeting moiety that comprises an antibody that binds a cancer marker shown in Table 4.

Embodiment 149

The nanomaterial carrier according to any one of embodiments 147-148, wherein said antibody is selected from the group consisting of an intact immunoglobulin, an F(ab)'$_2$, a Fab, a single chain antibody, a diabody, an affibody, a unibody, and a nanobody.

Embodiment 150

The nanomaterial carrier according to any one of embodiments 117-149, wherein said drug carriers in suspension are stable for at least 1 month, or at least 2 months, or at least 3 months, or at least 4 months, or at least 5 months, or at least 6 months when stored at 4° C.

Embodiment 151

The nanomaterial carrier according to any one of embodiments 117-150, wherein said nanoparticle drug carrier forms a stable suspension on rehydration after lyophilization.

Embodiment 152

The nanomaterial carrier according to any one of embodiments 117-151, wherein said nanoparticle drug carriers, show reduced drug toxicity as compared to free drug.

Embodiment 153

The nanomaterial carrier according to any one of embodiments 117-152, wherein said nanoparticle drug carrier has colloidal stability in physiological fluids with pH 7.4 and remains monodisperse to allow systemic biodistribution and is capable of entering a disease site by vascular leakage (EPR effect) or transcytosis.

Embodiment 154

The nanomaterial carrier drug carrier according to any one of embodiments 117-153, wherein said carrier is colloidally stable.

Embodiment 155

The nanomaterial carrier according to any one of embodiments 117-154, wherein the IDO inhibitor and the ICD inducer are synergistic in their activity against a cancer.

Embodiment 156

The nanomaterial carrier according to any one of embodiments 117-155, wherein said drug carrier, when administered systemically, delivers an amount of an ICD inducer effective to induce or to facilitate induction of immunogenic cell death of a cancer cell at a tumor site.

Embodiment 157

The nanomaterial carrier according to any one of embodiments 117-156, wherein said drug carrier, when administered systemically, delivers an amount of an IDO inhibitor to partially or fully inhibit the IDO enzyme or IDO pathway at a cancer site.

Embodiment 158

A pharmaceutical formulation comprising: a composition according to any one of embodiments 1-15 and a pharmaceutically acceptable carrier; and/or a nanovesicle drug carrier according to any one of embodiments 16-66 and a pharmaceutically acceptable carrier; and/or a nanoparticle drug carrier according to any one of embodiments 67-116 and a pharmaceutically acceptable carrier; and/or a nanomaterial carrier according to any one of embodiments 117-157 and a pharmaceutically acceptable carrier.

Embodiment 159

The pharmaceutical formulation of embodiment 158, wherein said formulation comprises a composition according to any one of embodiments 1-15 and a pharmaceutically acceptable carrier.

Embodiment 160

The pharmaceutical formulation of embodiment 158, wherein said formulation comprises a nanovesicle drug carrier according to any one of embodiments 16-66 and a pharmaceutically acceptable carrier.

Embodiment 161

The pharmaceutical formulation of embodiment 158, wherein said formulation comprises a nanoparticle drug carrier according to any one of embodiments 67-116 and a pharmaceutically acceptable carrier.

Embodiment 162

The pharmaceutical formulation of embodiment 158, wherein said formulation comprises a nanomaterial carrier according to any one of embodiments 117-157 and a pharmaceutically acceptable carrier.

Embodiment 163

The pharmaceutical formulation according to any one of embodiments 158-162, wherein said formulation is an emulsion, dispersion, or suspension.

Embodiment 164

The pharmaceutical formulation of embodiment 163, wherein said suspension, emulsion, or dispersion is stable for at least 1 month, or at least 2 months, or at least 3 months, or at least 4 months, or at least 5 months, or at least 6 months when stored at 4° C.

Embodiment 165

The pharmaceutical formulation according to any one of embodiments 158-164, wherein the nanovesicle drug carriers, and/or the a nanoparticle drug carriers, and/or the a nanomaterial carriers in said formulation show a substantially unimodal size distribution; and/or show a PDI less than about 0.2, or less than about 0.1.

Embodiment 166

The pharmaceutical formulation according to any one of embodiments 158-165, wherein said formulation is formulated for administration via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition.

Embodiment 167

The pharmaceutical formulation according to any one of embodiments 158-165, wherein said formulation is a sterile injectable.

Embodiment 168

The pharmaceutical formulation according to any one of embodiments 158-167, wherein said formulation is a unit dosage formulation.

Embodiment 169

A method of treating a cancer, said method comprising: administering to a subject in need thereof an effective amount of: a composition according to any one of embodiments 1-15; and/or a nanovesicle drug carrier according to any one of embodiments 16-66; and/or a nanoparticle drug carrier according to any one of embodiments 67-116; and/or a nanomaterial carrier according to any one of embodiments 117-157.

Embodiment 170

The method of embodiment 169, wherein said method comprises administering to a subject in need thereof an effective amount of a nanovesicle drug carrier according to any one of embodiments 16-66.

Embodiment 171

The method of embodiment 169, wherein said method comprises administering to a subject in need thereof an effective amount of a nanoparticle drug carrier according to any one of embodiments 67-116.

Embodiment 172

The method of embodiment 169, wherein said method comprises administering to a subject in need thereof an effective amount of a nanomaterial carrier according to any one of embodiments 117-157.

Embodiment 173

The method according to any one of embodiments 170-172, wherein the ICD inducer and the IDO inhibitor are synergistic in their activity against said cancer.

Embodiment 174

The method according to any one of embodiments 170-173, wherein said ICD-inducer is in an amount effective to elevate calreticulin (CRT) expression in cells of said cancer.

Embodiment 175

The method according to any one of embodiments 170-174, wherein said ICD-inducer is in an amount effective to elevate expression and/or release of HMGB1 and/or induction of ATP release.

Embodiment 176

The method according to any one of embodiments 170-175, wherein said method comprises a primary therapy in a chemotherapeutic regimen.

Embodiment 177

The method according to any one of embodiments 170-175, wherein said method comprises an adjunct therapy in a treatment regime that additionally comprises chemotherapy using another chemotherapeutic agent, and/or surgical resection of a tumor mass, and/or radiotherapy.

Embodiment 178

The method according to any one of embodiments 170-177, wherein said composition, a nanovesicle drug carrier, a nanoparticle drug carrier according, and/or nanomaterial carrier is a component in a multi-drug chemotherapeutic regimen.

Embodiment 179

The method according to any one of embodiments 170-178, wherein said cancer is pancreatic ductal adenocarcinoma (PDAC).

Embodiment 180

The method according to any one of embodiments 170-178, wherein said cancer is a cancer selected from the group consisting of breast cancer, lung cancer, melanoma, pancreas cancer, liver cancer, acute lymphoblastic leukemia (ALL), acute myeloid leukemia (AML), adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CIVIL), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 181

The method according to any one of embodiments 170-180, wherein said administration is via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition.

Embodiment 182

The method according to any one of embodiments 170-180, wherein said administration comprises systemic administration via injection or cannula.

Embodiment 183

The method according to any one of embodiments 170-180, wherein said administration is administration to an intra-tumoral or peri-tumoral site.

Embodiment 184

The method according to any one of embodiments 170-183, wherein said mammal is a human.

Embodiment 185

The method according to any one of embodiments 170-183, wherein said mammal is a non-human mammal.

Embodiment 186

The method according to any one of embodiments 170-185, wherein said nanovesicle drug carrier is administered in conjunction with administration of an immune checkpoint inhibitor.

Embodiment 187

The method of embodiment 186, wherein said immune checkpoint inhibitor comprises an inhibitor of PD-1, PD-L1, PD-L2, PD-L3, PD-L4, CTLA-4, LAG3, B7-H3, B7-H4, KIR and/or TIM3.

Embodiment 188

The method of embodiment 187, wherein said checkpoint inhibitor comprises an antibody that inhibits a moiety selected from the group consisting of PD-1, PD-L1, and CTLA4.

Embodiment 189

The method of embodiment 188, wherein said antibody comprises an antibody that inhibits PD-1.

Embodiment 190

The method of embodiment 189, wherein said antibody comprises Pembrolizumab (Keytruda), or Nivolumab (Opdivo).

Embodiment 191

The method of embodiment 188, wherein said antibody comprises an antibody that inhibits PD-L1.

Embodiment 192

The method of embodiment 191, wherein said antibody comprises Atezolizumab (Tecentriq), Avelumab (Bavencio), or Durvalumab (Imfinzi).

Embodiment 193

The method of embodiment 188, wherein said antibody comprises an antibody that inhibits CTLA-4.

Embodiment 194

The method of embodiment 193, wherein said antibody comprises Ipilimumab (Yervoy).

Embodiment 195

The method according to any one of embodiments 186-194, wherein the activity of said composition according to any one of embodiments 1-15; or said nanovesicle drug carrier according to any one of embodiments 16-66; or said nanoparticle drug carrier according to any one of embodiments 67-116; or said a nanomaterial carrier according to any one of embodiments 117-157 and said immune checkpoint inhibitor is synergistic.

Embodiment 196

A method of treating a cancer in a mammal, said method comprising: administering to an intra-tumoral or peri-tumoral site an effective amount of: a composition according to any one of embodiments 1-15; and/or a nanovesicle drug carrier according to any one of embodiments 16-66; and/or a nanoparticle drug carrier according to any one of embodiments 67-116; and/or a nanomaterial carrier according to any one of embodiments 117-157.

Embodiment 197

A kit for the treatment or prophylaxis of a cancer said kit comprising: a container containing: a composition according to any one of embodiments 1-15; and/or a nanovesicle drug carrier according to any one of embodiments 16-66; and/or a nanoparticle drug carrier according to any one of embodiments 67-116; and/or a nanomaterial carrier according to any one of embodiments 117-157.

Embodiment 198

A liposome comprising a lipid bilayer, where said liposome contains mitoxantrone.

Embodiment 199

The liposome of embodiment 198, wherein said lipid bilayer comprises a phospholipid, and cholesterol (CHOL) and/or a cholesterol derivative.

Embodiment 200

The liposome of embodiment 199, wherein said phospholipid comprises a saturated fatty acid with a C14-C20 carbon chain, and/or an unsaturated fatty acid with a C14-C20 carbon chain, and/or a natural lipid comprising a mixture of fatty acids with C12-C20 carbon chains.

Embodiment 201

The liposome of embodiment 200, wherein said phospholipid comprises a phospholipid selected from the group consisting of phosphatidylcholine (DPPC), 1,2-dimyristoleoyl-sn-glycero-3-phosphocholine (DMPC), 1,2-dioleoyl-sn-glycero-3-phosphocholine (DOPC), 1,2-distearoyl-sn-glycero-3-phospho-rac-glycerol (DSPG), 1,2-dipalmitoyl-sn-glycero-3-phosphoglycerol (DPPG), distearoylphosphatidylcholine (DSPC), 1,2-dieicosenoyl-sn-glycero-3-phosphocholine, and diactylphosphatidylcholine (DAPC).

Embodiment 202

The liposome of embodiment 200, wherein said phospholipid comprises a natural lipid selected from the group consisting of egg phosphatidylcholine (egg PC), and soy phosphatidylcholine (soy PC).

Embodiment 203

The liposome of embodiment 200, wherein said phospholipid comprises distearoylphosphatidylcholine (DSPC).

Embodiment 204

The liposome according to any one of embodiments 199-203, wherein said lipid bilayer comprises an mPEG phospholipid with a phospholipid C14-C18 carbon chain, and a PEG molecular weight ranging from about 350 Da to 5000 Da.

Embodiment 205

The liposome of embodiment 204, wherein said lipid bilayer comprises 1,2-distearoyl-sn-glycero-3-phosphoethanolamine-PEG (DSPE-PEG).

Embodiment 206

The liposome of embodiment 205, wherein said DSPE-PEG comprises DPSE-PEG$_{2K}$.

Embodiment 207

The liposome of embodiment 205, wherein said DSPE-PEG comprises DPSE-PEG$_{5K}$.

Embodiment 208

The liposome according to any one of embodiments 203-207, wherein said lipid bilayer comprises DSPC:Chol:DSPE-PEG.

Embodiment 209

The liposome of embodiment 208, wherein the ratio of DSPC:Chol-IND:DSPE-PEG ranges from 40-90% DSPC:10%-50% Chol:1%-10% DSPE-PEG (molar ratio).

Embodiment 210

The liposome of embodiment 209, wherein the ratio of DSPC:Chol:DSPE-PEG is about 50:40:5 (molar ratio).

Embodiment 211

The liposome according to any one of embodiments 203-207, wherein said lipid bilayer comprises DPPG:Chol:DSPE-PEG.

Embodiment 212

The liposome of embodiment 211, wherein the ratio of DPPG:Chol-IND:DSPE-PEG ranges from 40-90% DPPG:10%-50% Chol:1%-10% DSPE-PEG (molar ratio).

Embodiment 213

The liposome of embodiment 212, wherein the ratio of DPPG:Chol:DSPE-PEG is about 50:40:5 (molar ratio).

Embodiment 214

The liposome according to any one of embodiments 199-213, wherein said lipid bilayer comprises a cholesterol derivative selected from the group consisting of cholesterol hemisuccinate (CHEMS), lysine-based cholesterol (CHLYS), and PEGylated cholesterol (Chol-PEG).

Embodiment 215

The liposome of embodiment 214, wherein said lipid bilayer comprises CHEMS.

Embodiment 216

The liposome of embodiment 215, wherein said bilayer comprises CHEMS ranging from about 5% (mol percent) up to about 30% total lipid.

Embodiment 217

The liposome of embodiment 216, wherein said bilayer comprise about 10% or about 20% CHEMS or about 30% CHEMS or about 40% CHEMS.

Embodiment 218

A pharmaceutical formulation comprising: a liposome according to any one of embodiments 198-217; and a pharmaceutically acceptable carrier.

Embodiment 219

The pharmaceutical formulation of embodiment 218, wherein said formulation is an emulsion, dispersion, or suspension.

Embodiment 220

The pharmaceutical formulation of embodiment 219, wherein said suspension, emulsion, or dispersion is stable for at least 1 month, or at least 2 months, or at least 3 months, or at least 4 months, or at least 5 months, or at least 6 months when stored at 4° C.

Embodiment 221

The pharmaceutical formulation according to any one of embodiments 218-220, wherein the liposomes in said formulation show a substantially unimodal size distribution; and/or show a PDI less than about 0.2, or less than about 0.1.

Embodiment 222

The pharmaceutical formulation according to any one of embodiments 218-221, wherein said formulation is formulated for administration via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition.

Embodiment 223

The pharmaceutical formulation according to any one of embodiments 218-221, wherein said formulation is a sterile injectable.

Embodiment 224

The pharmaceutical formulation according to any one of embodiments 218-223, wherein said formulation is a unit dosage formulation.

Embodiment 225

A method of treating a cancer, said method comprising: administering to a subject in need thereof an effective amount a liposome according to any one of embodiments 198-217.

Embodiment 226

The method of embodiment 169, wherein said method comprises a primary therapy in a chemotherapeutic regimen.

Embodiment 227

The method of embodiment 226, wherein said method comprises an adjunct therapy in a treatment regime that additionally comprises chemotherapy using another chemotherapeutic agent, and/or surgical resection of a tumor mass, and/or radiotherapy.

Embodiment 228

The method of embodiment 169, wherein said composition, a nanovesicle drug carrier, a nanoparticle drug carrier according, and/or nanomaterial carrier is a component in a multi-drug chemotherapeutic regimen.

Embodiment 229

The method according to any one of embodiments 169-228, wherein said cancer is triple negative breast cancer.

Embodiment 230

The method according to any one of embodiments 169-228, wherein said cancer is a cancer selected from the group consisting of breast cancer, lung cancer, melanoma, pancreas cancer, liver cancer, acute lymphoblastic leukemia (ALL), acute myeloid leukemia (AML), adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CIVIL), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 231

The method according to any one of embodiments 169-230, wherein said administration is via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition.

Embodiment 232

The method according to any one of embodiments 169-230, wherein said administration comprises systemic administration via injection or cannula.

Embodiment 233

The method according to any one of embodiments 169-230, wherein said administration is administration to an intra-tumoral or peri-tumoral site.

Embodiment 234

The method according to any one of embodiments 169-233, wherein said mammal is a human.

Embodiment 235

The method according to any one of embodiments 169-233, wherein said mammal is a non-human mammal.

In certain embodiments the agent(s) that induce ICD exclude cisplatin, and/or in certain embodiments the agent(s) that induce ICD exclude doxorubicin. In the embodiments above, where a lipid/lipid bilayer comprises a an IDO inhibitor conjugated to cholesterol (e.g., IND-Chol), the use of an IDO inhibitor conjugated to a cholesterol deriviative (e.g., IND-CHEMS) is contemplated. In certain embodiments where the lipid bilayer contains both cholesterol and CHEMS and a conjugated IDO inhibitor, the IDO can be conjugated to the cholesterol (IND-Chol), to the cholesterol derivative (e.g., IND-CHEMS), or to both the cholesterol and to the cholesterol derivative.

DEFINITIONS

The terms "subject," "individual," and "patient" may be used interchangeably and refer to humans, as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for a cancer as described herein. Thus, for example, in certain embodiments the subject is a subject with a cancer (e.g., pancreatic ductal adenocarcinoma (PDAC), breast cancer (e.g., drug-resistant breast cancer), colon cancer, brain cancer, and the like). In certain embodiments the methods described herein are prophylactic and the subject is one in whom a cancer is to be inhibited or prevented. In certain embodiments the subject for prophylaxis is one with a family history of cancer and/or a risk factor for a cancer (e.g., a genetic risk factor, an environmental exposure, and the like).

The term "treat" when used with reference to treating, e.g., a pathology or disease refers to the mitigation and/or elimination of one or more symptoms of that pathology or disease, and/or a delay in the progression and/or a reduction in the rate of onset or severity of one or more symptoms of that pathology or disease, and/or the prevention of that pathology or disease. The term treat can refer to prophylactic treatment which includes a delay in the onset or the prevention of the onset of a pathology or disease.

The terms "coadministration" or "administration in conjunction with" or "cotreatment" when used in reference to the coadministration of a first compound (or component) (e.g., an ICD inducer) and a second compound (or component) (e.g., an IDO inhibitor) indicates that the first compound (or component) and the second compound (or component) are administered so that there is at least some chronological overlap in the biological activity of first compound and the second compound in the organism to which they are administered. Coadministration can include simultaneous administration or sequential administration. In sequential administration there may even be some substantial delay (e.g., minutes or even hours) between administration of the first compound and the second compound as long as their biological activities overlap. In certain embodiments, the coadminstration is over a time frame that permits the first compound and second compound to produce an enhanced therapeutic or prophylactic effect on the organism. In certain embodiments the enhanced effect is a synergistic effect.

The term "immunogenic cell death" or "ICD" refers to a unique form of cell death caused by some cytostatic agents such as anthracyclines (Obeid et al. (2007) *Nature Med.,* 13(1): 54-61), anthracenedione (mitoxantrone, aka MTX), oxaliplatin, irinotecan, and bortezomib, or radiotherapy and/or photodynamic therapy (PDT). Unlike regular apoptosis, which is mostly non-immunogenic or even tolerogenic, immunogenic apoptosis of cancer cells can induce an effective antitumor immune response through activation of dendritic cells (DCs) and consequent activation of specific T cell response (Spisek and Dhodapkar (2007) *Cell Cycle,* 6(16): 1962-1965). Endoplasmic reticulum (ER) stress, reactive oxygen species (ROS) production and induction of autophagy are key intracellular response pathways that govern ICD (Krysko et al. (2012) *Nat. Rev. Canc.* 12(12): 860-875). In addition to facilitating tumor cell death that facilitates antigen presentation by dendritic cells, ICD is characterized by secretion or release of damage-associated molecular patterns (DAMPs), which exert additional immune adjuvant effects. Calreticulin (CRT), one of the DAMP molecules, which is normally in the lumen of the ER, is translocated to the surface of dying cell where it functions as an "eat me" signal for phagocytes. Other important surface exposed DAMPs are heat-shock proteins (HSPs), namely HSP70 and HSP90, which under stress condition are also translocated to the plasma membrane. On the cell surface they have an immunostimulatory effect, based on their interaction with number of antigen-presenting cell (APC) surface receptors like CD91 and CD40 and also facilitate cross-presentation of antigens derived from tumor cells on MHC class I molecule, which then triggers CD8+ T cell activation and expansion. Other important DAMPs, characteristic for ICD are secreted amphoterin (HMGB1) and ATP (see, e.g., Apetoh et al. (2007) Nature Med. 13(9): 1050-1059; Ghiringhelli et al. (2009) Nature Med. 15(10): 1170-1178). HMGB1 is considered to be a late apoptotic marker and its release to the extracellular space appears to be required for the optimal release and presentation of tumor antigens to dendritic cells. It binds to several pattern recognition receptors (PRRs) such as Toll-like receptor (TLR) 2 and 4, which are expressed on APCs. The most recently found DAMP released during immunogenic cell death is ATP, which functions as a "find-me" signal for monocytes when secreted and induces their attraction to the site of apoptosis (see, e.g., Garg et al. (2012) EMBO J. 31(5): 1062-1079). ATP binds to purinergic receptors on APCs.

The terms "IDO inhibitor", "IDO pathway inhibitor", and "inhibitor of the IDO pathway) are used interchangeably and refer to an agent (a molecule or a composition) that either partially or fully blocks the activity of indoleamine-2,3-dioxygenase (IDO) and/or partially or fully suppresses the post-enzymatic signaling cascade(s) in the IDO pathway. IDO is an intracellular heme-containing enzyme that initiates the first and rate-limiting step of tryptophan degradation along the kynurenine pathway. The indoleamine 2,3-dioxygenase (IDO) pathway regulates immune response by suppressing cytotoxic T cell function, enhancing regulatory T cell activity (Tregs) and enabling tumor immune escape, either at the tumor or regional lymphode sites. An IDO pathway inhibitor can inhibit the IDO enzyme directly or by interfering or perturbing IDO effector pathway components. Such components include, but are not limited to: IDO2, tryptophan 2,3-dioxygenase (TDO), the mammalian target of rapamycin (mTOR) pathway, arylhydrocarbon receptor (AhR) pathway, the general control nonderepressible 2 (GCN2) pathway, and the AhR/IL-6 autocrine loop.

The terms "nanocarrier" and "nanoparticle drug carrier" are used interchangeably and refer to a nanostructure having a porous interior core (e.g., a "porous nanoparticle"). In certain embodiments the nanocarrier comprises a lipid bilayer encasing (or surrounding or enveloping) the porous particle core. In certain embodiments the nanoparticle is a porous silica nanoparticle (e.g., mesoporous silica nanoparticle or "MSNP").

As used herein, the term "lipid" refers to conventional lipids, phospholipids, cholesterol, chemically functionalized lipids for attachment of PEG and ligands, etc.

As used herein, the terms "lipid bilayer" or "LB" refers to any double layer of oriented amphipathic lipid molecules in which the hydrocarbon tails face inward to form a continuous non-polar phase.

As used herein, the terms "liposome" or "lipid vesicle" or "vesicle" are used interchangeably to refer to an aqueous compartment enclosed by a lipid bilayer, as being conventionally defined (see, e.g., Stryer (1981) Biochemistry, 2d Edition, W. H. Freeman & Co., p. 213).

A "nanovesicle" refers to a "lipid vesicle" having a diameter (or population of vesicles having a mean diameter) ranging from about 10 nm, or from about 20 nm, or from about 30 nm, or from about 40 nm, or from about 50 nm up to about 500 nm, or up to about 400 nm, or up to about 300 nm, or up to about 200 nm, or up to about 150 nm, or up to about 100 nm, or up to about 80 nm. In certain embodiments a nanovesicle has a diameter ranging from about 10 nm up to about 80 nm, or from about 50 nm up to about 70 nm.

Compared with the lipid bilayer coated on mesoporous silica nanopaticles, the lipid bilayer in a lipid vesicle or liposome can be referred to as an "unsupported lipid bilayer" and the lipid vesicle itself (when unloaded) can be referred to as an "empty vesicle". The lipid bilayer coated on mesoporous silica nanopaticles can be referred to as a "supported lipid bilayer" because the lipid bilayer is located on the surface and supported by a porous particle core. In certain embodiments, the lipid bilayer can have a thickness ranging from about 6 nm to about 7 nm which includes a 3-4 nm thickness of the hydrophobic core, plus the hydrated hydrophilic head group layers (each about 0.9 nm) plus two partially hydrated regions of about 0.3 nm each. In various embodiments, the lipid bilayer surrounding the silica nanoparticle comprises a continuous bilayer or substantially continuous bilayer that effectively encapsulates and seals the nanoparticle.

As used herein, the term "selective targeting" or "specific binding" refers to use of targeting ligands on the surface of a drug delivery nanocarrier (e.g., a LB-coated nanoparticle). In certain embodiments the targeting ligand(s) are on the surface of a lipid bilayer or LB-coated nanoparticle. Typically, the ligands interact specifically/selectively with receptors or other biomolecular components expressed on the target, e.g., a cell surface of interest. The targeting ligands can include such molecules and/or materials as peptides, antibodies, aptamers, targeting peptides, polysaccharides, and the like.

A coated mesoporous silica nanopaticle, having targeting ligands can be referred to as a "targeted nanoparticle or a targeted drug delivery nanocarrier (e.g., LB-coated nanoparticle).

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The term "drug" as used herein refers to a chemical entity of varying molecular size, small and large, naturally occurring or synthetic, that exhibits a therapeutic effect in animals and humans. A drug may include, but is not limited to, an organic molecule (e.g., a small organic molecule), a therapeutic protein, peptide, antigen, or other biomolecule, an oligonucleotide, an siRNA, a construct encoding CRISPR cas9 components and, optionally one or more guide RNAs, and the like.

A "pharmaceutically acceptable carrier" as used herein is defined as any of the standard pharmaceutically acceptable carriers. The pharmaceutical compositions of the subject invention can be formulated according to known methods for preparing pharmaceutically useful compositions. The pharmaceutically acceptable carrier can include diluents, adjuvants, and vehicles, as well as carriers, and inert, non-toxic solid or liquid fillers, diluents, or encapsulating material that does not react with the active ingredients of the invention. Examples include, but are not limited to: phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, Remington's Pharmaceutical Sciences (Martin E W [1995] Easton Pa., Mack Publishing Company, 19th ed.) describes formulations which can be used in connection with the drug delivery nanocarrier(s) (e.g., LB-coated nanoparticle(s)) described herein.

As used herein, an "antibody" refers to a protein consisting of one or more polypeptides substantially encoded by immunoglobulin genes or fragments of immunoglobulin genes or derived therefrom that is capable of binding (e.g., specifically binding) to a target (e.g., to a target polypeptide). The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on a phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405, and 4,956,778). In certain embodiments antibodies should include all that have been displayed on phage (e.g., scFv, Fv, Fab and disulfide linked Fv (see, e.g, Reiter et al. (1995) *Protein Eng.* 8: 1323-1331) as well as affibodies, unibodies, and the like.

The term "specifically binds", as used herein, when referring to a biomolecule (e.g., protein, nucleic acid, antibody, etc.), refers to a binding reaction that is determinative of the presence of a biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

"Two-dimensional materials (2D materials) are materials that do not require a substrate to exist. In other words, they can be isolated as freestanding one atom thick sheets. As a practical matter, this definition can be relaxed to include materials with a thickness of a few atoms (e.g., less than about 10 atoms).

The term "substantially pure isomer" refers to a formulation or composition wherein among various isomers of a compound a single isomer is present at 70%, or greater or at 80% or greater, or at 90% or greater, or at 95% or greater, or at 98% or greater, or at 99% or greater, or said compound or composition comprises only a single isomer of the compound.

A "bioreactive nanomaterial" refers to an engineered biomaterial that induces or catalyzes a biological response. In certain embodiments the nanomaterial induces a response by virtue of one or more properties selected from the group consisting of composition, size, shape, aspect ratio, dissolution, electronic, redox, surface display, surface coating, hydrophobic, hydrophilic, an atomically thin nanosheet, or functionalized surface groups" to catalyze the biological response at various nano/bio interfaces. In certain embodiments the bioreactive nanomaterial has the ability to induce ICD biological responses in cells (e.g., in tumor cells) and/or as well as activating the innate immune system through delivery of "danger signal" and adjuvant effects.

BRIEF DESCRIPTION OF THE DRAWINGS

FIG. 6. Panel A) Flow cytometry experiment showing the induction of the ICD marker, CRT, in cultured KPC pancreatic cancer cells in the presence of PBS, DOX (20 µM), OX (500 µM), and activated DOX (a.k.a. DACHPt, 500 µM) for 24 h. HMBG1 release was measured using ELISA. Panel B) Animal experimentation using 2 rounds of vaccination one week apart, followed by injecting live KPC cells SC on the contralateral side. The details of the animal vaccination experiment are provided in the methods section. Tumors were collected on day 26 for size measurement and IHC analysis. Panel C) Tumor size measurement on the contralateral side. Panel D) Explanted tumor at the contralateral side. Panel E) Spaghetti curves to show KPC tumor growth in the contralateral flank. Panel F) Tumor collection was performed after euthanizing the animal to conduct IHC. IHC staining of CD8 and Foxp3 T cells was used to calculate CD8/FoxP3 T cells ratio in each group. *$p<0.05$; **$p<0.01$

FIG. 15 illustrates and alternative Step 1 for the synthesis strategy shown in FIG. 14.

FIG. 22. Successful synthesis of DOX laden Chol-IND liposome. The synthesis is similar to MTX Chol/IND liposome. In DOX formulation, the trapping agent is $(NH_4)_2SO_4$, similar to Doxil. We used TFA-free Chol-IND in this case. Our synthesis led to a size controlled liposome around ~95 nm. The liposome exhibits positive charge, i.e. +15 mV, which has promoted us to consider introducing charge reversal strategy because we prefer to inject neutral or slightly negatively charged liposome systemically FIG. 23. We synthesized MTX laden liposome using pristine cholesterol or Chol-IND at the identical (40%) molar ratio. The particle charge was measured at different stage during synthesis. Use of prodrug led to positive charge across the board.

FIG. 25. Demonstration of MTX/IND-Chol liposome is capable of ICD induction and IDO inhibition in vitro. 4T1 cells were treated by MTX/IND-Chol liposome at MTX dose of 2.5 µM/mL for 8 h. Representative flow cytometry data was shown to demonstrate effective induction of calreticulin (CRT), a major biomarker during ICD. 4T1 cells were treated with free IND or IND-Chol liposome at the indicated concentrations for 3 h in tryptophan-deficient DMEM. Western blot assays showing the enhanced effect of IND-PL on mTOR signaling, which can be conveniently studied by assessing the phosphorylation of P-S6K.

FIG. 28 shows 3 month stability of an MTX/IND co-delivery liposome.

FIG. 31. Panel A) Orthotopic tumor-bearing 4T1 mice were IV injected with the encapsulated MTX liposomes to deliver indicated MTX dose every 3 days, for a total of 3 administrations. This includes the treatment using IND-Chol/MTX co-delivery (IND: 3 mg/kg; MTX: 3 mg/kg). The animals were sacrificed at day 23. The formulation was provided on the right panel. Panel B) All the particles were fully characterized abiotically and biotically. The capability of CRT induction was confirmed in 4T1 cells. Panel C) Tumor size measurement in the efficacy study. At the conclusion of the experiment, primary tumor and major organs were collected for weighing. Organ index values were calculated. The tumor tissues were fixed and used for IHC staining of CD8, FoxP3, CRT and HMGB1. The IHC staining results are pending. Panel D) In a separate experiment, we also performed an official survival study using these treatments in the same 4T1 orthotopic model. N=10. *, p<0.05; , p<0.01; *, p<0.001. Panel E) We have obtained some IHC data in Experiment (panel C). This includes CRT and perforin. MTX/IND co-delivery (LCIM) led to the strongest CRT induction and perforin staining at tumor site. Panel F) Representative CRT staining was provided.

FIG. 32, panels A-B, illustrates results of an animal study in a CT26 colon cancer model. Panel A) Subcutaneous CT26 colon cancer bearing mice were IV injected with MTX/IND co-delivery liposome to deliver 3 mg/kg MTX and 3 mg/kg IND every 3 days, for a total of 4 administrations. Detailed treatment schedule and group information are discussed in panel A. Panel B) Tumor size measurement in the animal study. A statistically significant difference (p<0.001) emerged as early as day 20 between dual delivery (LCIM) vs MTX only liposome. In the MTX/IND liposome group, five out of eight mice have tumor less than 150 mm3, which outperformed all the control groups including MTX-only liposome w/w CHEMS. The addition of empty IND liposome interfered the effect of co-delivery via a tumor access competition mechanism.

FIG. 33, panels A-B. KPC pancreatic cells were treated by using PBS (negative control), OX (positive control) and indicated engineered nanomaterials at low and high concentrations. The choice of particle concentration is based on an MTS assay (panel A). Twenty-four hours post incubation, the total cells were harvested for CRT analysis through flow cytometry. This suggested a highly strong CRT induction effects (more potent than OX chemo) by nano-sized Ag, Cu, $SiO_2$, $V_2O_5$, ZnO and graphene (panel B).

DETAILED DESCRIPTION

Figure 1:
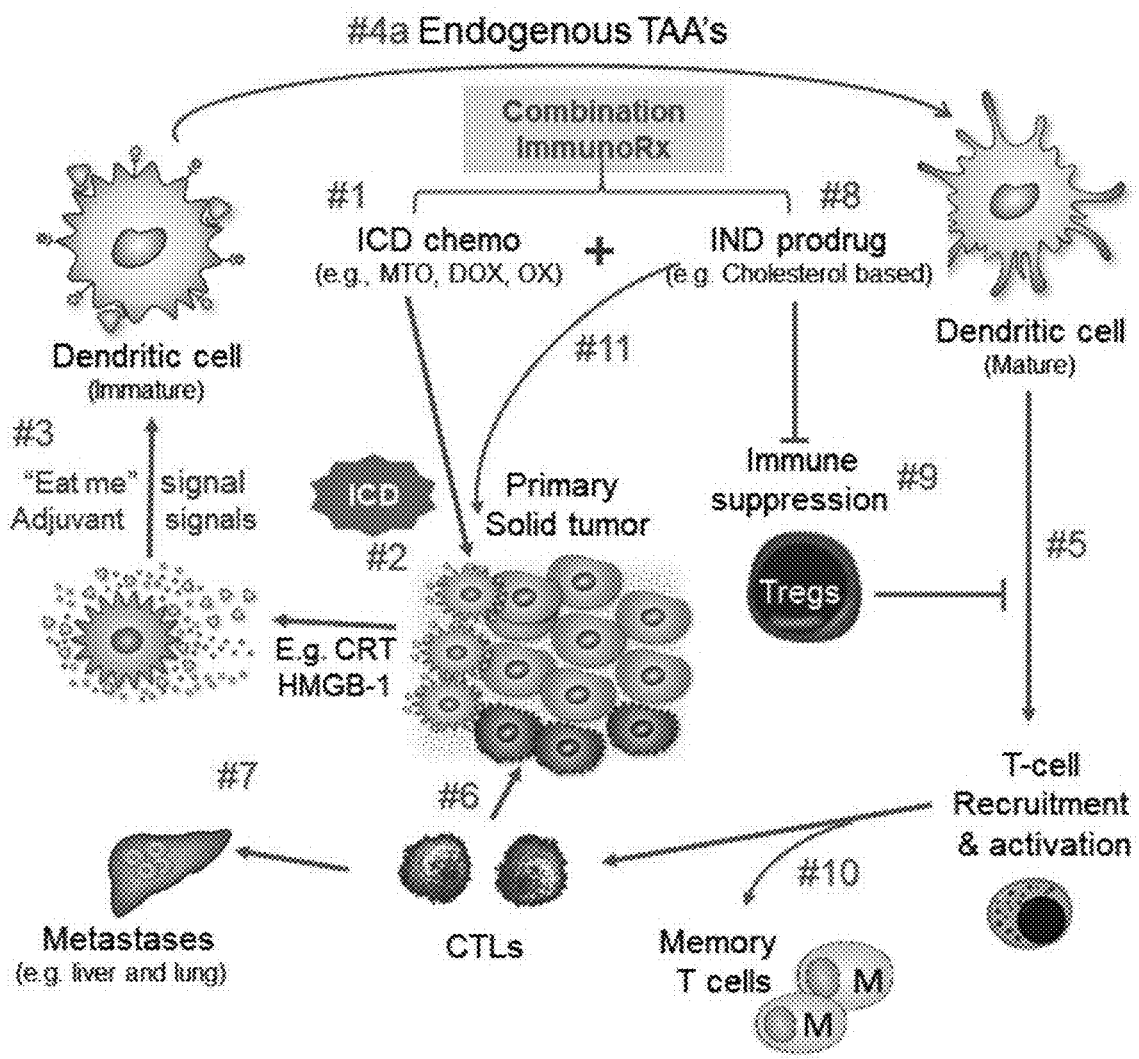
FIG. 1 shows a schematic that illustrates how dual delivery of ICD inducing chemo and IND prodrug may impact the anti-cancer immune response. We hypothesize that nano-enabled co-delivery of a chemotherapeutic agent, which provides an ICD stimulus, and IND, which interferes in the IDO pathway, may combine to trigger a robust PDAC immune response. ICD chemo such as MTO (#1) induces an ICD response (#2) in which CRT expression on the dying tumor cell surfaces provides an "eat-me" signal for DC uptake, as well as the release of HMGB-1 that delivers adjuvant stimuli to DC (#3). Following uptake of the dying tumor cells by DC, their maturation and cross-presentation of endogenous tumor-associated antigens (TAAs) (#4), the recruitment and activation of CD8+ T cells (#5) will lead to granulysin and perforin mediated killing of primary (#6) and metastatic cancer cells (#7). The concomitant delivery of IND prodrug (e.g. IND-Cholesterol) (#8) interferes in the IDO metabolic pathway, which can lead to strengthening the ICD effect by interfering in Treg development and overcome other immunomodulatory effects (#9). The ICD pathway also allows the activation of helper and memory T cells, which may prevent disease recurrence (#10). Following proof-of-principle testing of this scheme, we propose that a co-delivery nanocarrier (i.e. liposome) that contains IND which is capable of synergistically enhancing the ICD effect, providing more than just an additive outcome (#11).

In various embodiments three treatment modalities are provided to generate an anti-cancer response premised, inter alia, on the induction of immunogenic cell death (ICD) in cancer cells. ICD is responsible for enhanced tumor antigen presentation as well as providing stimulatory effects to the participating DCs. This can trigger the activation of cytotoxic T cells and anti-cancer (e.g., anti-PDAC, anti-colon cancer) immunity that can be synergistically enhanced by an intervention in the IDO pathway.

A first treatment modality involves the combination of an ICD inducer (e.g., oxaliplatin or MTX) in combination with an IDO inhibitor (e.g., indoximod) into a single nanocarrier that allows systemic (or local) biodistribution and drug delivery to tumor sites. It is believed the dual-delivery approach can provide synergistic enhancement of adaptive and innate immunity (e.g., anti-PDAC immunity), with a significant improvement in animal survival. In certain embodiments the nanocarrier comprises a vesicle (i.e., a lipid bilayer enclosing a fluid). In certain embodiments the nanocarrier comprises a nanoparticle (e.g., a mesoporous silica nanoparticle (MSNP) surrounded (encapusulated) by a lipid bilayer.

A second treatment modality involves local delivery to a tumor or peri-tumoral region, of an agent that induces ICD (e.g., oxaliplatin) in combination with a lipid (e.g., a nanovesicle) that comprises an inhibitor of the IDO pathway (e.g., indoximod). Without being bound by a particular theory, it is believed that such local delivery of an ICD inducer in combination with an IDO inhibitor induces recruitment of cytotoxic $CD8^+$ lymphocytes, depletion of Tregs, reversal of the $CD8^+/Foxp3^+$ ratio, cytotoxic tumor killing, and tumor shrinkage at the local site. These adaptive immune responses can be accompanied by boosting of the innate immune system, as reflected by CRT and HMGB1 expression, as well as the activation of a DC population, particularly well-suited for generating cytotoxic T cell responses.

A third treatment modality involves vaccination utilizing dying cancer cells (e.g., KPC cells) in which ICD is induced ex vivo. Such vaccination can generate a systemic immune response that can interfere with tumor growth at a remote site as well as allowing adoptive transfer to non-immune animals.

In various embodiments, methods and compositions for performing these treatment modalities are provided.

Approach 1—Systemic Treatment of a Cancer by Combined Delivery of ICD and IDO Inhibition.

The first approach combines an ICD-inducer (e.g., doxirubicin, oxaliplatin, MTX, etc.) and an inhibitor of the IDO pathway (e.g., indoximod) into a single nanocarrier, that can provide systemic biodistribution and drug delivery to orthotopic tumor sites.

In certain embodiments this dual-delivery approach involves the formation of lipid vesicles where a component of the lipid bilayer comprising the vesicle incorporates or is conjugated to an inhibitor of the IDO pathway (e.g., an indoximod prodrug such Chol-IND) and the vesicle contains an ICD inducer (e.g., doxorubicin (DOX), mitoxantrone (MTX), and the like). This approach is illustrated herein in Examples 2 and 3.

Figure 8:
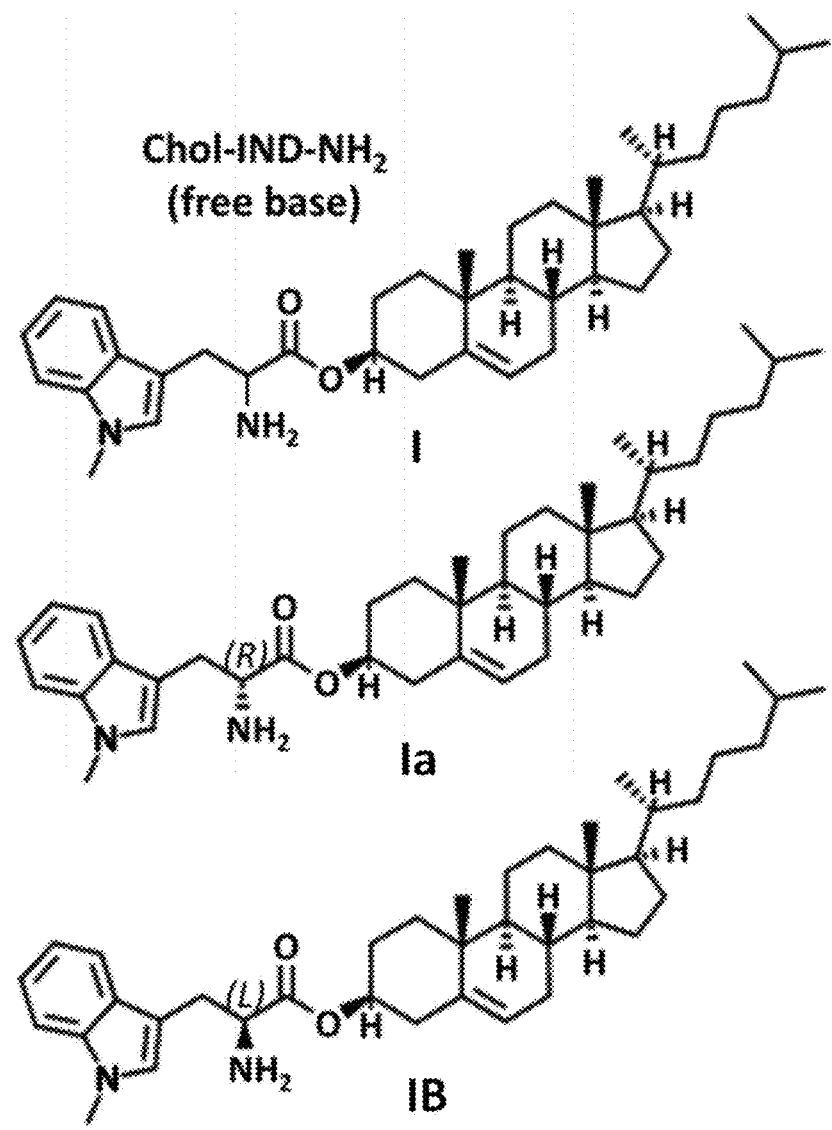
FIG. 8 illustrates a Chol-IND prodrug (Formula II) as well as the R enantiomer (Formula IIa) and L enantiomer (Formula IIb).

In another illustrative, but non-limiting embodiment, the nanocarrier comprises a mesoporous silica nanoparticle (MSNP) containing the ICD inducer (e.g., oxaliplatin) where the silica nanoparticle is surrounded by (encapsulated by) a lipid bilayer containing (or conjugated to) an IDO inhibitor (e.g., indoximod provided as the prodrug Chol-IND (Formula I, FIG. 8). The lipid bilayer (LB) coated MSNP, also known as a silicasome (see, e.g., PCT Patent Application No: PCT/US2017/012625) is designed to provide effective dual delivery of two (or more therapeutics) and can be exploited to provide dual delivery of the ICD inducer and IDO inhibitor. Without being bound by a particular theory, it is believe that this dual-delivery approach achieved synergistic enhancement of adaptive and innate anti-PDAC or anti-colon cancer (CT26) immunity, leading to a significant improvement in animal survival.

A third dual-delivery approach exploits the discovery that certain nanomaterials (e.g., CuO, graphene oxide) can induce immunogenic cell death (ICD) (see, e.g., Example 5). It is also believed that other nanomaterials such as CuO, $Cu_2O$, $Sb_2O_3$, $As_2O_3$, $Bi_2O_3$, $P_2O_3$, ZnO, $TiO_2$, and 2D materials other than graphene or graphene oxide (e.g., graphene, graphyne, borophene, germanene, silicene, $Si_2BN$, stanene, phosphorene, bismuthene, molybdenite, metals, 2D supracrystals, and the like may also induce immunogenic cell death. Nanoparticles formed from these ICD inducers, or combinations thereof, can readily be coated with a lipid that contains (or is conjugated to) an IDO inhibitor (e.g., indoximod provided as the prodrug, Chol-IND (Formula I), and the like). The lipid coated nanomaterial thus forms a dual delivery vehicle for delivery of both an ICD-inducer and an IDO-inhibitor. Accordingly, in certain embodiments, the following dual-delivery vehicles are contemplated herein:

1) ICD-inducer/IDO-inhibitor vesicle;
2) ICD-inducer/IDO-inhibitor silicasome (LB-coated nanoparticle);
3) ICD-inducer nanomaterial (bioreactive nanomaterial) coated with IDO-inhibitor lipid (phospholipid prodrug).

It will be recognized, that in addition to systemic administration, any of these carriers may be considered for local treatment of a tumor. Thus, for example, any of these carriers can be administered topically (e.g., for skin tumors), or directly, e.g., to an intra-tumoral or peri-tumoral site, e.g., via injection or during a surgical procedure.

Dual-Delivery Lipid Vesicles (e.g., ICD/IDO inhibitor-Vesicles)

In certain embodiments dual-delivery nanovesicles are provided for the delivery of an ICD-inducer in combination with an inhibitor of the IDO pathway and/or for the delivery of an ICD inducer and a pharmacological agent other than an ICD inducer or in combination with an ICD inducer in addition to the inhibitor of the IDO pathway.

Accordingly, in certain embodiments, a nanovesicle drug carrier for the combined delivery of an inhibitor of an IDO pathway and an inducer of immunogenic cell death (ICD), is provided where the nanovesicle drug carrier comprises a lipid vesicle where a lipid bilayer effectively forms a vesicle in an aqueous solution, and the lipid or lipid formuation comprising the vesicle is associated with (or conjugated to) an inhibitor of the indoleamine 2,3-dioxygenase (IDO) pathway (IDO pathway inhibitor); and a cargo within the vesicle where the cargo comprises an agent that induces immunogenic cell death (ICD) (ICD-inducer). It is noted that while this embodiment is described with respect to a cargo that induces immunogenic cell death, other cargos are contemplated as an alternative or in addition to the ICD inducer. Such cargos include, inter alia, various cancer chemotherapeutics as described herein. The lipid vesicle is typically formed from a lipid bilayer. However in certain embodiments, a lipid micelle (which does not comprise a lipid bilayer) is contemplated. Thus, for example, in certain embodiments a lipid micelle can be comprise a phospholipid prodrug (e.g., lipid-IDO pathway inhibitor conjugate) and a cargo (typically a lipophilic) cargo can be disposed inside the micelle. In certain embodiments the nanovesicle provides an IDO inhibitor and an ICD inducer that are synergistic in their activity against a cancer. In certain embodiments the nanovesicle drug carrier, when administered systemically, delivers an amount of an ICD inducer effective to induce or to facilitate induction of immunogenic cell death of cancer cells at the tumor site. In certain embodiments the nanovesicle drug carrier, when administered systemically, delivers an amount of IDO inhibitor to partially or fully inhibit an IDO pathway at a cancer site.

In certain embodiments the inhibitor of the IDO pathway comprises an agent selected from the group consisting of 1-methyl-D-tryptophan (indoximod, D-1MT), L-1MT, methylthiohydantoin-dl-tryptophan (MTH-Trp, Necrostatin), β-carbolines (e.g., 3-butyl-β-carboline), naphthoquinone-based (e.g., annulin-B), S-allyl-brassinin, S-benzyl-brassinin, N-[2-(Indol-3-yl)ethyl]-S-methyl-dithiocarbamate, N-[2-(benzo[b]thiophen-3-yl)ethyl]-S-methyl-dithiocarbamate, N-[3-(Indol-3-yl)propyl]-S-methyl-dithiocarbamate, S-hexyl-brassinin, N-[2-(indol-3-yl)ethyl]-S-benzyl-dithiocarbamate, N-[2-(indol-3-yl)ethyl]-N-[2-(indol-3-yl)ethyl]-S-[(pyrid-3-yl)methyl]-dithiocarbamate, N-[2-(indol-3-yl)ethyl]-S-[(pyrid-4-yl)methyl]-dithiocarbamate, 5-bromo-brassinin, Phenylimidazole-based IDO inhibitors (e.g., 4-phenylimidazole), Exiguamine A, imidodicarbonimidic diamide, N-methyl-N'-9-phenanthrenyl-monohydrochloride (NSC401366), INCB024360 (Epacadostat), 1-cyclohexyl-2-(5H-imidazo[5,1-a]isoindol-5-(GDC-0919), IDO1-derived peptide, NLG919, Ebselen, Pyridoxal Isonicotinoyl Hydrazone, Norharmane, CAY10581, 2-Benzyl-2-thiopseudourea hydrochloride, and 4-phenylimidazole. In certain embodiments the IDO inhibitor comprises indoximod. In certain embodiments the IDO inhibitor comprises substantially pure "L" indoximod or substantially pure "R" indoximod, or a racemic mixture of "D" and "L" indoximod.

In certain embodiments the inhibitor of the IDO pathway, is disposed in a lipid comprising the vesicle and/or conjugated to a lipid, or other component, comprising the vesicle. In certain embodiments the vesicle comprises a phospholipid. In certain embodiments the vesicle comprises a phospholipid, and cholesterol (CHOL). In certain embodiments the phospholipid comprises a saturated fatty acid with a C14-C20 carbon chain, and/or an unsaturated fatty acid with a C14-C20 carbon chain, and/or a natural lipid comprising a mixture of fatty acids with C12-C20 carbon chains. In certain embodiments the phospholipid comprises a saturated fatty acid selected from the group consisting of phosphatidylcholine (DPPC), dimyristoylphosphatidylcholine (DMPC), 1,2-dioleoyl-sn-glycero-3-phosphocholine (DOPC), 1,2-Distearoyl-sn-glycero-3-phospho-rac-glycerol (DSPG), dipalmitoylphosphatidylglycerol (DPPG), distearoylphosphatidylcholine (DSPC), diactylphosphatidylcholine (DAPC), and the like. In certain embodiments the phospholipid comprises a natural lipid selected from the group consisting of egg phosphatidylcholine (egg PC), and soy phosphatidylcholine (soy PC). In certain embodiments the phospholipid comprises an unsaturated fatty acid selected from the group consisting of 1,2-dimyristoleoyl-sn-glycero-3-phosphocholine, 1,2-dipalmitoleoyl-sn-glycero-3-phosphocholine, 1,2-dioleoyl-sn-glycero-3-phosphocholine (DOPC), and 1,2-dieicosenoyl-sn-glycero-3-phosphocholine. In certain embodiments the vesicle comprises an mPEG phospholipid with a phospholipid C14-C18 carbon chain, and a PEG molecular weight ranging from about 350 Da to 5000 Da. In certain embodiments the vesicle comprises 1,2-distearoyl-sn-glycero-3-phosphoethanolamine-PEG (DSPE-PEG). In certain embodiments the vesicle comprises DPSE-PEG$_{2K}$. In certain embodiments the IDO inhibitor is conjugated to a component of said vesicle. In certain embodiments the IDO inhibitor is conjugated to a moiety selected from the group consisting of a lipid, PHGP, vitamin E, cholesterol, and a fatty acid. In certain embodiments the IDO inhibitor is conjugated directly to the moiety, while in other embodiments, the IDO inhibitor is conjugated to the moiety via a linker. In certain embodiments the IDO inhibitor is conjugated to a phospholipid. In certain embodiments the IDO inhibitor is conjugated to vitamin E. In certain embodiments the IDO inhibitor is conjugated to cholesterol (CHOL (see, e.g., Formula II)) or to CHEMs, or to squalene. In certain embodiments the IDO inhibitor is conjugated to a fatty acid (e.g., oleic acid or docosahexaenoic acid). In certain embodiments the inhibitor of the IDO pathway is conjugated to oleic acid or docosahexaenoic acid via an HO—$(CH_2)_{n=2-5}$—OH linker. In certain embodiments the inhibitor of the IDO pathway is conjugated to a lipid. In certain embodiments the inhibitor of the IDO pathway is conjugated to a phospholipid comprising the lipid vesicle. In certain embodiments the inhibitor of the IDO pathway is conjugated to cholesterol (e.g., IND-Chol, FIG. 8, Formula I).

In certain embodiments the bilayered vesicle comprises PL/IND-Chol/DSPE-PEG. In certain embodiments the vesicle comprises about 75% PL, about 20% IND-cholesterol, and about 5% DSPE-PEG$_{2K}$. In certain embodiments the ICD inducer comprises a chemotherapeutic agent selected from the group consisting of doxorubicin (DOX), mitoxantrone (MTX), oxaliplatin, anthracenedione, bleomycin, bortezomib, cisplatin, daunorubicin, docetaxel, epirubicin, idarubicin, mitoxanthrone, paclitaxel, R2016, irinotecan and cyclophosphamide. In certain embodiments the ICD inducer comprises doxorubicin. In certain embodiments the ICD inducer comprises mitoxantrone.

In certain embodiments the bilayered vesicle comprises PL/Chol-IND/DSPE-PEG. In certain embodiments the bilayered vesicle comprises DSPC/Chol-IND/DSPE-PEG2K. In certain embodiments the bilayered vesicle comprises DSPC/Chol-IND/DSPE-PEG2K in the molar ratio 50:40:5. It will also be recognized that in certain embodiments the bilyaerd vesicle (e.g., liposome) can additionally include cholesteryl hemisuccinate (CHEMS) and/or the cholesteryl hemisuccinate can be conjugated to an IDO pathway inhibitor (indoximod). In certain embodiments, for systemic administration, a liposome is formatted that is about 100 nm in size, with slightly negative charge, and about 5 to about 20% drug loading capacity. Different lipid compositions can be optimized by, for example, varying the molar ratios of IND-Chol, cholesterol, CHEMS, DSPE, and the like. In certain embodiments the bilayered vesicle comprises IND-Chol (salt free) 30%:CHEMS 20%:DSPC 45%:DSPE-PEG2K 5%. This liposome formulation is now subjected to animal experiment.

Dual-Delivery (ICD-Inducer/IDO-Inhibitor) LB Coated MSNPs (ICD/IDO Silicasomes).

As noted above, in certain embodiments a dual delivery carrier for an ICD inducer (e.g., oxaliplatin, mitoxantrone (MTX), etc.) and an IDO inhibitor (e.g., indoximod) is contemplated where the carrier comprises lipid-bilayer coated nanoparticles (e.g., mesoporous silica nanoparticles). In various illustrative embodiments, the IDO inhibitor (e.g., indoximod) is provided disposed in and/or conjugated to a component of the lipid bilayer (e.g. conjugated to cholesterol) while the ICD inducer is provided on or in (e.g., within the pores) of the nanoparticle, e.g., effectively sealed/encapsulated by the lipid bilayer. However, it will be recognized that in certain embodiments the ICD inducer can be provided in or conjugated to the lipid bilayer while the IDO inhibitor is contained on or within the nanoparticle. Such lipid bilayer coated nanoparticle drug delivery systems (aka silicasomes), are capable of delivering two (or more) active agents in precise concentration ratios as desired.

In one illustrative, but non-limiting embodiment the "dual-delivery carrier" comprises indoximod conjugated to a component of the lipid bilayer (e.g., as IND-Cholesterol (IND-Chol) (Formula I) or IND-Cholesterol hemisuccinate (IND-CHEMS), while the ICD inducer (e.g., doxorubicin (DOX), mitoxantrone (MTX), oxaliplatin, irinotecan etc.) is disposed within the nanoparticle. This leads to stable entrapment of the ICD-inducer (e.g., doxorubicin (DOX), mitoxantrone (MTX), oxaliplatin (OX)) in the pores, with Chol-IND trapped in the bilayer. The coating, procedure(s) described herein provide uniform and instantaneous sealing of all particle pores.

Accordingly in certain embodiments, a nanoparticle drug carrier for the combined delivery of an inhibitor of an IDO pathway and an inducer of immunogenic cell death (ICD) is provided where the nanoparticle drug carrier comprises: a mesoporous silica nanoparticle having a surface and defining a plurality of pores that are suitable to receive molecules therein; a lipid bilayer coating the surface; a first cargo comprising an inhibitor of the indoleamine 2,3-dioxygenase (IDO) pathway (IDO inhibitor); and a second cargo comprising an agent that induces immunogenic cell death (ICD) (ICD-inducer); where the lipid bilayer is substantially continuous and encapsulates the nanoparticle stably sealing the plurality of pores. In certain embodiments the nanoparticle drug carrier contains a predefined ratio of IDO inhibitor to ICD-inducer. As illustrated herein in the Examples, in certain embodiments, the IDO inhibitor and the ICD inducer are synergistic in their activity against a cancer (e.g., against PDAC).

In various embodiments the drug carrier, when administered systemically, is effective to deliver an amount of an ICD inducer effective to initiate or to facilitate induction of immunogenic cell death of a cancer cell. In certain embodiments the drug carrier, when administered systemically, will effectively deliver an amount of IDO inhibitor to partially or fully inhibit an IDO pathway at a cancer site. In certain embodiments, where the activity of the ICD inducer and IDO inhibitor is synergistic, the drug carrier can contain/provide a lower dose ICD inducer and/or IDO inhibitor than when these agents are used individually. In certain embodiments the combination of the ICD inducer and the IDO inhibitor can achieve an anti-cancer activity that cannot be achieved by the use of either agent alone.

In certain embodiments the IDO inhibitor is disposed in the lipid bilayer and/or conjugated to a component (e.g., PL, Chol, Chol derivative (e.g., cholesterol hemisuccinate), etc.) comprising the lipid bilayer while the ICD inducer is disposed in the plurality of pores. In certain embodiments the ICD-inducer comprises a chemical or biological agent described in Table 2, above. In certain embodiments the ICD-inducer comprises a chemotherapeutic agent selected from the group consisting of doxorubicin (DOX), mitoxantrone (MTX), oxaliplatin (OX) anthracenedione, bleomycin, bortezomib, cisplatin, daunorubicin, docetaxel, epirubicin, idarubicin, paclitaxel, R2016, irinotecan and cyclophosphamide. In certain embodiments the ICD-inducer comprises doxirubicin (DOX). In certain embodiments the ICD-inducer comprises mitoxantrone (MTX). In certain embodiments the ICD-inducer comprises oxaliplatin (OX).

In certain embodiments the ICD inducer comprises an ICD inducing nanomaterial (e.g., CuO, $Cu_2O$, $Sb_2O_3$, $As_2O_3$, $Bi_2O_3$, $P_2O_3$, ZnO, $TiO_2$, graphene oxide, 2D materials other than graphene or graphene oxide (e.g., graphene, graphyne, borophene, germanene, silicene, $Si_2BN$, stanene, phosphorene, bismuthene, molybdenite, metals, 2D supracrystals, and the like) as described above or in Example 10. In certain embodiments, the ICD-inducing nanomaterial can be contained on or within the nanoparticle. In certain embodiments an ICD-inducing nanomaterial can be coated with a lipid or with a lipid bilayer. In certain embodiments the ICD-inducing nanomaterial can incorporate one or more drugs as described herein. In certain embodiments, where the ICD-inducing nanomaterial is within a lipid bilayer the nanomaterial may contain the IDO inhibitor, both of which can be released at a target site (e.g., cancer cell). In certain embodiments, where the ICD-inducing nanomaterial comprises graphene oxide, the surface can be functionalized to deliver the IDO-inhibitor.

In certain embodiments, the IDO inhibitor comprises an agent selected from the group consisting of 1-methyl-D-tryptophan (indoximod, D-1MT), L-1MT, methylthiohydantoin-dl-tryptophan (MTH-Trp, Necrostatin), β-carbolines (e.g., 3-butyl-β-carboline), Naphthoquinone-based (e.g., annulin-B), S-allyl-brassinin, S-benzyl-brassinin, N-[2-(Indol-3-yl)ethyl]-S-methyl-dithiocarbamate, N-[2-(benzo[b]thiophen-3-yl)ethyl]-S-methyl-dithiocarbamate, N-[3-(Indol-3-yl)propyl]-S-methyl-dithiocarbamate, S-hexyl-brassinin, N-[2-(indol-3-yl)ethyl]-S-benzyl-dithiocarbamate, N-[2-(indol-3-yl)ethyl]-S[(naphth-2-yl)methyl]-dithiocarbamate, N-[2-(indol-3-yl)ethyl]-S-[(pyrid-3-yl)methyl]-dithiocarbamate, N-[2-(indol-3-yl)ethyl]-S-[(pyrid-4-yl)methyl]-dithiocarbamate, 5-bromo-brassinin, Phenylimidazole-based IDO inhibitors (e.g., 4-phenylimidazole), Exiguamine A, imidodicarbonimidic diamide, N-methyl-N'-9-phenanthrenyl-monohydrochloride (NSC401366), INCB024360 (Epacadostat), 1-cyclohexyl-2-(5H-imidazo[5,1-a]soindol-5-yl)ethanol (GDC-0919), IDO1-derived peptide, NLG919, Ebselen, Pyridoxal Isonicotinoyl Hydrazone, Norharmane, CAY10581, 2-Benzyl-2-thiopseudourea hydrochloride, and 4-phenylimidazole. In certain embodiments the IDO inhibitor comprises an agent shown in Table 3, above. In certain embodiments the IDO inhibitor comprises indoximod.

In certain embodiments, the nanoparticle drug carrier(s) can be fabricated so that a population of the drug carriers in suspension shows essentially a substantially unimodal size distribution; and/or shows a PDI less than about 0.2, or less than about 0.1; and/or shows a coefficient of variation in size less than about 0.1 or less than about 0.05. In certain embodiments, the nanoparticle drug carriers may distribute to developing tumor sites on IV injection. In certain embodiments the nanoparticle drug carrier forms a stable suspension on rehydration after lyophilization. In certain embodiments the nanoparticle drug carriers, show reduced drug toxicity as compared to free drug and/or drug in liposomes. In certain embodiments the nanoparticle drug carrier has colloidal stability in physiological fluids with pH 7.4 and remains monodisperse to allow systemic biodistribution and is capable of entering a disease site by vascular leakage (EPR effect) or transcytosis.

Various nanoparticle (e.g., mesoporous silica core), lipid bilayer formulations, and methods of synthesis are described in the sections below and in the examples.

Nanoparticles.

In various embodiments silicasome drug carriers described herein comprise a porous silica (or other material) nanoparticle (e.g., a silica body having a surface and defining a plurality of pores that are suitable to receive molecules therein) coated with a lipid bilayer. For example, in certain embodiments the silica nanoparticle can be a mesoporous silica nanoparticle. The fact that the nanoparticle is referred to as a silica nanoparticle does not preclude materials other than silica from also being incorporated within the silica nanoparticle. In some embodiments, the silica nanoparticle may be substantially spherical with a plurality of pore openings through the surface providing access to the pores. However, in various embodiments the silica nanoparticle can have shapes other than substantially spherical shapes. Thus, for example, in certain embodiments the silica nanoparticle can be substantially ovoid, rod-shaped, a substantially regular polygon, an irregular polygon, and the like.

Generally, the silica nanoparticle comprises a silica body that defines an outer surface between the pore openings, as well as side walls within the pores. The pores can extend through the silica body to another pore opening, or a pore can extend only partially through the silica body such that that it has a bottom surface of defined by the silica body.

In some embodiments, the silica body is mesoporous. In other embodiments, the silica body is microporous. As used herein, "mesoporous" means having pores with a diameter between about 2 nm and about 50 nm, while "microporous" means having pores with a diameter smaller than about 2 nm. In general, the pores may be of any size, but in typical embodiments are large enough to contain one or more therapeutic compounds therein. In such embodiments, the pores allow small molecules, for example, therapeutic compounds such as anticancer compounds to adhere or bind to the inside surface of the pores, and to be released from the silica body when used for therapeutic purposes. In some embodiments, the pores are substantially cylindrical.

In certain embodiments the nanoparticles comprise pores having pore diameters between about 1 nm and about 10 nm in diameter or between about 2 nm and about 8 nm. In certain embodiments the nanoparticles comprise pores having pore diameters between about 1 nm and about 6 nm, or between about 2 nm and about 5 nm. Other embodiments include particles having pore diameters less than 2.5 nm. In other embodiments, the pore diameters are between 1.5 and 2.5 nm. Silica nanoparticles having other pore sizes may be prepared, for example, by using different surfactants or swelling agents during the preparation of the silica nanoparticles.

In various embodiments the nanoparticles can include particles as large (e.g., average or median diameter (or other characteristic dimension) as about 1000 nm. However, in various embodiments the nanoparticles are typically less than 500 nm or less than about 300 nm as, in general, particles larger than 300 nm may be less effective in entering living cells or blood vessel fenestrations. In certain embodiments the nanoparticles range in size from about 40 nm, or from about 50 nm, or from about 60 nm up to about 100 nm, or up to about 90 nm, or up to about 80 nm, or up to about 70 nm. In certain embodiments the nanoparticles range in size from about 60 nm to about 70 nm. Some embodiments include nanoparticles having an average maximum dimension between about 50 nm and about 1000 nm. Other embodiments include nanoparticles having an average maximum dimension between about 50 nm and about 500 nm. Other embodiments include nanoparticles having an average maximum dimension between about 50 nm and about 200 nm. In some embodiments, the average maximum dimension is greater than about 20 nm, greater than about 30 nm, greater than 40 nm, or greater than about 50 nm. Other embodiments include nanoparticles having an average maximum dimension less than about 500 nm, less than about 300 nm, less than about 200 nm, less than about 100 nm or less than about 75 nm. As used herein, the size of the nanoparticle refers to the average or median size of the primary particles, as measured by transmission electron microscopy (TEM) or similar visualization technique.

Illustrative mesoporous silica nanoparticles include, but are not limited to MCM-41, MCM-48, and SBA-15 (see, e.g., Katiyar et al. (2006) *J. Chromatog.* 1122(1-2): 13-20).

Methods of making porous silica nanoparticles are well known to those of skill in the art. In certain embodiments mesoporous silica nanoparticles are synthesized by reacting tetraethyl orthosilicate (TEOS) with a template made of micellar rods. The result is a collection of nano-sized spheres or rods that are filled with a regular arrangement of pores. The template can then be removed by washing with a solvent adjusted to the proper pH (see, e.g., Trewyn et al. (2007) *Chem. Eng. J.* 137(1): 23-29. In certain embodiments mesoporous particles can also be synthesized using a simple sol-gel method (see, e.g., Nandiyanto, et al. (2009) *Microporous and Mesoporous Mat.* 120(3): 447-453, and the like). In certain embodiments tetraethyl orthosilicate can also be used with an additional polymer monomer (as a template). In certain embodiments 3-mercaptopropyl)trimethoxysilane (MPTMS) is used instead of TEOS.

In certain embodiments the mesoporous silica nanoparticles are cores are synthesized by a modification of the sol/gel procedure described by Meng et al. (2015) *ACS Nano,* 9(4): 3540-3557. To synthesize a batch of ~500 mg of MSNP, 50 mL of CTAC is mixed with 150 mL of $H_2O$ in a flask (e.g., a 500 mL conical flask), followed by stirring (e.g., at 350 rpm for 15 min at 85° C.). This us followed by the addition of 8 mL of 10% triethanolamine for 30 min at the same temperature. Then, 7.5 mL of the silica precursor, TEOS, is added dropwise at a rate of 1 mL/min using a peristaltic pump. The solution is stirred at 350 rpm at 85° C. for 20 min, leading to the formation particles with a primary size of ~65 nm. The surfactant can be removed by washing the particles with a mixture of methanol/HCl (500:19 v/v) at room temperature for 24 h. The particles can be centrifuged at 10 000 rpm for 60 min and washed three times in methanol.

While the methods described herein have been demonstrated with respect to porous silica nanoparticles (e.g., mesoporous silica), it will be recognized that similar methods can be used with other porous nanoparticles. Numerous other mesoporous materials that can be used in drug delivery nanoparticles are known to those of skill in the art. For example, in certain embodiments mesoporous carbon nanoparticles could be utilized. Mesoporous carbon nanoparticles are well known to those of skill in the art (see, e.g., Huang et al. (2016) Carbon, 101: 135-142; Zhu et al. (2014) Asian J. Pharm. Sci., 9(2): 82-91; and the like).

Similarly, in certain embodiments, mesoporous polymeric particles can be utilized. The syntheses of highly ordered mesoporous polymers and carbon frameworks from organic-organic assembly of triblock copolymers with soluble, low-molecular-weight phenolic resin precursors (resols) by an evaporation induced self-assembly strategy have been reported by Meng et al. (2006) *Chem. Mat.* 6(18): 4447-4464 and in the references cited therein.

The nanoparticles described herein are illustrative and non-limiting. Using the teachings provided herein numerous other lipid bilayer coated nanoparticles will be available to one of skill in the art.

Lipid Bilayer and Methods of Coating Nanoparticles with a Lipid Bilayer.

The drug carrier nanoparticles described herein comprise a porous nanoparticle (e.g. a mesoporous silica nanoparticle (MSNP)) coated with a lipid bilayer. In certain embodiments the bilayer composition is optimized to provide a rapid and uniform particle coating, to provide colloidal and circulatory stability, and to provide effective cargo retention, while also permitting a desirable cargo release profile.

In certain embodiments the lipid bilayer comprises a combination of a phospholipid, cholesterol, and in certain embodiments, a IDO-lipid conjugate, a pegylated lipid (e.g., DSPE-PEG$_{2000}$), or a factionalized pegylated lipid (e.g., DSPE-PEG$_{2000}$-maleimide) to facilitate conjugation with targeting or other moieties.

To attach a surface LB coating, a coated lipid film procedure can be utilized in which MSNP suspensions are added to a large lipid film surface, coated on, e.g., a round-bottom flask. Using different lipid bilayer compositions, a series of experiments can be performed to find a composition and optimal lipid/particle ratio that provides rapid and uniform particle wrapping, coating and effective cargo retention and/or release upon sonication. It is believed that this lipid composition and wrapping cannot be achieved by liposomal fusion to the particle surface under low energy vortexing conditions.

Figure 7:
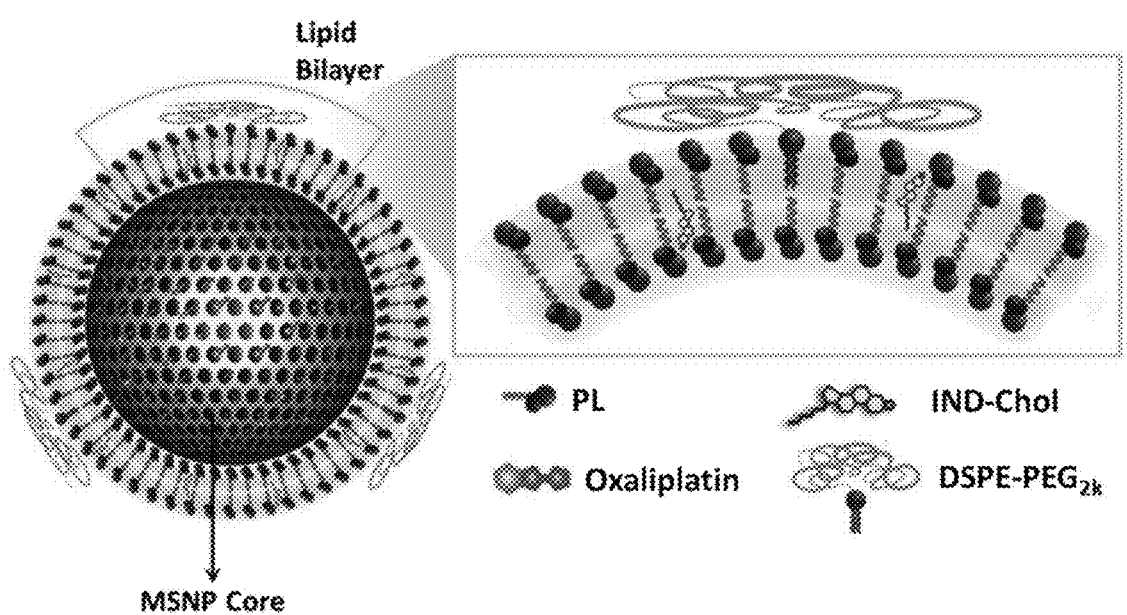
FIG. 7 illustrates the development of a dual delivery carrier for OX plus IND using lipid-bilayer coated mesoporous silica nanoparticles (OX/IND-MSNP). A schematic shows the structure of OX-laden MSNP, in which the drug is trapped by a lipid bilayer containing IND-Chol. This leads to stable entrapment of OX in the pores, with IND-Chol trapped in the bilayer. The coating procedure provides uniform and instantaneous sealing of all particle pores.

In certain embodiments, the mesoporous silica nanoparticles are coated with a lipid bilayer that incorporates the IDO inhibitor coupled to a lipid (e.g., a phospholipid) or to cholesterol. In one illustrated embodiment the mesoporous silica nanoparticles are coated with a lipid bilayer comprising IND-Chol, as well as serving to encapsulate the ICD inducer (e.g., doxorubicin (DOX), mitoxantrone (MTX), oxaliplatin, etc.) in the porous interior (see, e.g., FIG. 7, panel a). In another illustrated embodiment the mesoporous silica nanoparticles are coated with a lipid bilayer comprising Chol-IND, as well as serving to encapsulate doxirubicin, or oxaliplatin in the porous interior (FIG. 7, panel a).

In various embodiments lipid bilayer composition can be optimized for an OX/IND or for an MTX/IND drug delivery carrier (e.g., a bilayer coated nanoparticle). This can accomplished, for example, by using a DSPC/Cho-IND/DSPE-PEG2K or a DSPC/Chol-IND/CHEMS/DSPE-PEG2k mixture at various ratios and measuring the incorporated IND. The biofilm can be laid down at the bottom of a round bottom flask, to which the OX-soaked or MTX-soaked, or other ICD inducer soaked) MSNPs are added, followed by sonication (see, e.g., Liu et al. (2016) ACS Nano, 10(2): 2702-2715; Meng et al. (2015) ACS Nano, 9(4): 3540-3557).

The lipid bilayer formulation described above and in the Examples is illustrative and non-limiting. Depending on the drug(s) being loaded into the drug delivery carrier and the desired release profile, in various embodiments different lipid bilayer formulations can be used and an optimal formulation can be determined.

Accordingly, in certain embodiments the lipid bilayer can comprise: 1) one or more saturated fatty acids with C14-C20 carbon chain, such as dimyristoylphosphatidylcholine (DMPC), dipalmitoylphosphatidylcholine (DPPC), distearoylphosphatidylcholine (DSPC), and diactylphosphatidylcholine (DAPC); and/or 2) One or more unsaturated fatty acids with a C14-C20 carbon chain, such as 1,2-dimyristoleoyl-sn-glycero-3-phosphocholine, 1,2-dipalmitoleoyl-sn-glycero-3-phosphocholine, 1,2-dioleoyl-sn-glycero-3-phosphocholine (DOPC), 1,2-dieicosenoyl-sn-glycero-3-phosphocholine; and/or 3) Natural lipids comprising a mixture of fatty acids with C12-C20 carbon chain, such as Egg PC, and Soy PC, sphingomyelin, and 4) a modified cholesterol (e.g., cholesterol hemisuccinate (CHEMS)) the like. It is noted that, in certain embodiments, in order to compensate a positive charge that introduce during Chol-IND conjugation chemistry, it is possible to use cholesteryl hemisuccinate (CHEMS) that carryies one negative charge at pH >6.5 in the formulation. These lipids are illustrative but non-limiting and numerous other lipids are known and can be incorporated into a lipid bilayer for formation of a drug delivery nanocarrier (e.g., a bilayer-coated nanoparticle).

In certain embodiments the drug carrier comprises bilayer comprising a lipid (e.g., a phospholipid), cholesterol (e.g., IND-Chol), and a PEG functionalized lipid (e.g., a mPEG phospholipid). In certain embodiments the mPEG phospholipids comprises a C14-C18 phospholipid carbon chain from, and a PEG molecular weight from 350-5000 (e.g., MPEG 5000, MPEG 3000, MPEG 2000, MPEG 1000, MPEG 750, MPEG 550, MPEG 350, and the like). In certain embodiments the mPEG phospholipid comprises DSPE-PEG5000, DSPE-PEG3000, DSPE-PEG2000, DSPE-PEG1000, DSPE-PEG750, DSPE-PEG550, or DSPE-PEG350. MPEGs are commercially available (see, e.g., //avantilipids.com/product-category/products/polymers-polymerizable-lipids/mpeg-phospholipids).

In certain embodiments lipid bilayer comprises an mPEG phospholipid with a phospholipid C14-C18 carbon chain, and a PEG molecular weight ranging from about 350 Da to 5000 Da. In certain embodiments the lipid bilayer comprises DPSE-PEG$_{2K}$.

In certain embodiments the lipid bilayer comprises 1,2-distearoyl-sn-glycero-3-phosphoethanolamine-PEG (DSPE-PEG).

In certain embodiments the IDO inhibitor is conjugated to a moiety that forms a component of a vesicle structure in aqueous solution and is provided in the lipid bilayer (see, e.g., conjugated IDO inhibitors, supra.). In certain embodiments the IDO inhibitor is conjugated to a moiety such as a lipid, vitamin E, cholesterol, and a fatty acid (see, e.g., Examples 1 and 2). In various embodiments the IDO inhibitor is conjugated directly to the vesicle-forming moiety and in other embodiments the IDO inhibitor is conjugated to the vesicle-forming moiety via a linker (e.g., via a homo-bifunctional or hetero-bifunctional linker). In certain embodiments the linker comprises an HO—(CH$_2$)$_{n=2-5}$—OH linker.

In certain embodiments the inhibitor of the IDO pathway is conjugated to a lipid, and/or to vitamin E, and/or to cholesterol (CHOL), and/or to a fatty acid (e.g., oleic acid, docosahexaenoic acid, etc.). In certain embodiments the IDO inhibitor is conjugated to a cholesterol.

In certain embodiments the IDO inhibitor is conjugated to a phospholipid comprising the lipid bilayer or to cholesterol comprising said lipid bilayer. In certain embodiments the IDO inhibitor is directly conjugated to cholesterol.

In certain embodiments the ratio of phospholipid:IND-CHOL:PEG, is about phospholipid (50-90 mol %):CHOL (10-50 mol %):PEG (1-10 mol %). In certain embodiments the bilayer comprises DSPC/Cho-IND/DSPE-PEG2K. In certain embodiments the bilayer comprises DSPC/Cho-IND/DSPE-PEG2K in the molar ratio 50:40:5.

In certain embodiments the lipid bilayer is formulated to form a substantially uniform and intact bilayer encompassing the entire nanoparticle. In certain embodiments the lipid bilayer is formulated so that the mesoporous silica nanoparticle is colloidally stable.

Dual Delivery Lipid-Coated ICD-Inducing Nanomaterials.

It was discovered that certain nanomaterials are effective ICD inducers (see, e.g., Example 5). In certain embodiments these ICD-inducing nanomaterials can be administered simply as nanoparticles. However, in other embodiments, the nano particles can be combined with a lipid where the lipid is associated with (e.g., complexed with or conjugated to) an IDO pathway inhibitor (e.g., indoximod). In certain embodiments the lipid can compire an IND conjugated phospholipid (IND-PL) or IND conjugated cholesterol (Chol-IND) (Formula I). The lipid readily coats all or a part of the surface of the nanoparticle.

Accordingly in certain embodiments, a nanomaterial carrier for the combined delivery of an inhibitor of an IDO pathway and an inducer of immunogenic cell death (ICD), is provided where the nanomaterial carrier comprises a nanomaterial that induces ICD; and a lipid or lipid formulation comprising an IDO pathway inhibitor where the lipid or lipid formulation is disposed on the surface of said nanomaterial. In certain embodiments the lipid or lipid formulation fully encapsulates the nanomaterial, while in other embodiments, the lipid or lipid formulation is disposed on a surface of the nanoparticle, but does not fully encapsulate the nanoparticle. In certain embodiments the lipid or lipid formulation can form a lipid bilayer, while more typically, the lipid or lipid formulation is not a lipid bilayer.

In certain embodiments the ICD-inducing nanomaterial comprises one or more ICD-inducing nanomaterials selected from the group consisting of CuO, $Cu_2O$, $Sb_2O_3$, $As_2O_3$, $Bi_2O_3$, $P_2O_3$, ZnO, $TiO_2$, graphene oxide, 2D materials other than graphene or graphene oxide (e.g., graphene, graphyne, borophene, germanene, silicene, $Si_2BN$, stanene, phosphorene, bismuthene, molybdenite, metals, 2D supracrystals, and the like) and other ICD-inducing nanomaterials as described herein. In certain embodiments the nanomaterial comprises copper oxide (CuO). In certain embodiments the nanomaterial comprises graphene oxide (GO).

In certain embodiments the IDO pathway inhibitor associated with the lipid or lipid formulation comprises an agent selected from the group consisting of 1-methyl-D-tryptophan (indoximod, D-1MT), L-1MT, methylthiohydantoin-dl-tryptophan (MTH-Trp, Necrostatin), β-carbolines (e.g., 3-butyl-β-carboline), naphthoquinone-based (e.g., annulin-B), S-allyl-brassinin, S-benzyl-brassinin, N-[2-(Indol-3-yl) ethyl]-S-methyl-dithiocarbamate, N-[2-(benzo[b]thiophen-3-yl)ethyl]-S-methyl-dithiocarbamate, N-[3-(Indol-3-yl) propyl]-S-methyl-dithiocarbamate, S-hexyl-brassinin, N-[2-(indol-3-yl)ethyl]-S-benzyl-dithiocarbamate, N-[2-(indol-3-yl)ethyl]-S[(naphth-2-yl)methyl]-dithiocarbamate, N-[2-(indol-3-yl)ethyl]-S-[(pyrid-3-yl)methyl]-dithiocarbamate, N-[2-(indol-3-yl)ethyl]-S-[(pyrid-4-yl)methyl]-dithiocarbamate, 5-bromo-brassinin, Phenylimidazole-based IDO inhibitors (e.g., 4-phenylimidazole), Exiguamine A, imidodicarbonimidic diamide, N-methyl-N'-9-phenanthrenyl-monohydrochloride (NSC401366), INCB024360 (Epacadostat), 1-cyclohexyl-2-(5H-imidazo[5,1-a]isoindol-S-yl) ethanol (GDC-0919), IDO1-derived peptide, NLG919, Ebselen, Pyridoxal Isonicotinoyl Hydrazone, Norharmane, CAY10581, 2-Benzyl-2-thiopseudourea hydrochloride, and 4-phenylimidazole. In certain embodiments the IDO pathway inhibitor associated with the lipid or lipid formulation comprises 1 methyl-tryptophan (1MT)). In certain embodiments the 1 methyl-tryptophan is a substantially pure "D" isomer of 1-methyl-tryptophan (D-1MT), while in other embodiments, the 1-methyl-tryptophan is a substantially pure "L" isomer of 1-methyl-tryptophan "L-1MT. In certain embodiments the 1-methyl-tryptophan comprises a mixture of the D and L isomers.

In certain embodiments the IDO pathway inhibitor is conjugated to a lipid or to a component of the lipid formulation. In certain embodiments the IDO pathway inhibitor is conjugated to a moiety selected from the group consisting of a lipid (e.g., phospholipid), vitamin E, cholesterol, cholesterol derivative (e.g., cholesterol hemisuccinate (CHEMS)) and a fatty acid. In certain embodiments the IDO inhibitor is conjugated directly to the moiety, while in other embodiments, the IDO inhibitor is conjugated to the moiety via a linker.

In certain embodiments the IDO pathway inhibitor is conjugated to PGHP, vitamin E, cholesterol (CHOL), a fatty acid, (e.g., oleic acid or docosahexaenoic acid), or to a lipid (e.g., a phospholipid). In certain embodiments the IDO pathway inhibitor is conjugated to a phospholipid. Illustrative phospholipids include, but are not limited to phospholipids comprising a saturated fatty acid with a C14-C20 carbon chain, and/or an unsaturated fatty acid with a C14-C20 carbon chain, and/or a natural lipid comprising a mixture of fatty acids with C12-C20 carbon chains. In certain embodiments the phospholipid comprises a saturated fatty acid selected from the group consisting of phosphatidylcholine (DPPC), dimyristoylphosphatidylcholine (DMPC), distearoylphosphatidylcholine (DSPC), and diactylphosphatidylcholine (DAPC). In certain embodiments the phospholipid comprises a natural lipid selected from the group consisting of egg phosphatidylcholine (egg PC), and soy phosphatidylcholine (soy PC). In certain embodiments the phospholipid comprises an unsaturated fatty acid selected from the group consisting of 1,2-dimyristoleoyl-sn-glycero-3-phosphocholine, 1,2-dipalmitoleoyl-sn-glycero-3-phosphocholine, 1,2-dioleoyl-sn-glycero-3-phosphocholine (DOPC), and 1,2-dieicosenoyl-sn-glycero-3-phosphocholine. In certain embodiments the phospholipid comprises 1-palmitoyl-2-hydroxy-sn-glycero-3-phosphocholine.

In certain embodiments the IDO pathway inhibitor comprises an agent selected from the group consisting of 1-methyl-D-tryptophan (indoximod), 1-methyl-L-tryptophan, methylthiohydantoin-dl-tryptophan, Necrostatin-1, Ebselen, Pyridoxal Isonicotinoyl Hydrazone, Norharmane, CAY10581, 2-Benzyl-2-thiopseudourea hydrochloride, Norharmane hydrochloride, INCB024360, S-allyl-brassinin, S-benzyl-brassinin, 5-Bromo-brassinin, 4-phenylimidazole Exiguamine A, and NSC401366. In certain embodiments the IDO pathway inhibitor comprises indoximod. In certain embodiments the IDO pathway inhibitor comprises substantially pure "L" isomer of 1-methyl-tryptophan, or a substantially pure "D" isomer of 1-methyl-tryptophan, or a racemic mixture of "D" and "L" isomers of 1-methyl-tryptophan. In certain embodiments the 1-methyl-tryptophan is conjugated to cholesterol (e.g., Chol-IND, Formula I) and/or to cholesterol hemisuccinate (CHEMS-IND). In certain embodiments where the lipid bilayer comprises both cholesterol and a cholesterol derivative (e.g., CHEMS), the 1-methyl-tryptophan conjugated to the cholesterol or to CHEMS, or to both cholesterol and to CHEMS.

Approach 2—Local Treatment of a Tumor or Peritumor Site to Inhibit the IDO Pathway and to Induce ICD.

A second treatment modality involves local delivery to a tumor or peri-tumoral region, of an agent that induces ICD (e.g., doxirubicin, oxaliplatin, etc.) in combination with an inhibitor of the IDO pathway (e.g., indoximod). In certain embodiments, the IDO inhibitor can be complexed with or conjugated to a moiety (e.g., a lipid) that forms a vesicle (e.g., a nanovesicle). It is believed that such local delivery of an ICD inducer in combination with an IDO inhibitor induces recruitment of cytotoxic CD8+ lymphocytes, depletion of Tregs, reversal of the $CD8^+/Foxp3^+$ ratio, cytotoxic tumor killing, and tumor shrinkage at the local site. It is believed that these adaptive immune responses can be accompanied by boosting of the innate immune system, as reflected by CRT and HMGB1 expression, as well as the activation of a DC population, particularly well-suited for generating cytotoxic T cell responses.

Accordingly in certain embodiments, a method of treating a cancer in a mammal is provided where the method involves administering to an intra-tumoral or peri-tumoral site an effective amount of an inhibitor of the indoleamine 2,3-dioxygenase (IDO) pathway (an IDO inhibitor) in conjunction with an effective amount of an agent that induces immunogenic cell death (ICD) (an ICD-inducer). In certain embodiments, the effective amount of the ICD-inducer is an amount effective to elevate calreticulin (CRT) expression and/or to elevate expression and/or release of HMGB1 and/or introduce ATP release in cells of the cancer.

ICD inducers are well known to those of skill in the art and ICD inducers suitable for this method will readily be recognized in view of the teachings provided herein. Illustrative ICD inducers include, but are not limited to chemotherapeutic agent(s) that induce ICD such as oxaliplatin, anthracenedione, bleomycin, bortezomib, cisplatin, daunorubicin, docetaxel, doxorubicin, epirubicin, idarubicin, mitoxanthrone, oxaliplatin, paclitaxel, R2016 (a heterocyclic quinolone derivative described by Son et al. (2017) *Plos One*, DOI:10.1371, which is incorporated herein by reference for the compounds described therein), irinotecan and cyclophosphamide.

Other suitable ICD inducers include oncolytic viruses (see, e.g., Angelova et al. (2014) *J. Virol.*, 88(10): 5263-52760. One illustrative suitable oncolytic virus is an oncolytic parvovirus (e.g., H-PV).

As explained above, and in Example, 2, it was discovered that certain nanomaterials can induce ICD. In certain embodiments the ability to induce ICD is an intrinsic property of the nanomaterial (e.g., chemical reaction of the material and/or receptor binding of the nanomaterial is not required for induction of ICD). Accordingly, in certain embodiments the tumor or peritumoral space is treated with a nanomaterial that induces ICD. Such materials include, but are not limited to e.g., $CuO$, $Cu_2O$, $51)_2O_3$, $As_2O_3$, $Bi_2O_3$, $P_2O_3$, $ZnO$, $TiO_2$, graphene oxide, 2D materials other than graphene or graphene oxide (e.g., graphene, graphyne, borophene, germanene, silicene, $Si_2BN$, stanene, phosphorene, bismuthene, molybdenite, metals, 2D supracrystals, etc.) and the like) (see, e.g., Example 2) nanoparticles comprising such materials. In certain embodiments the nanoparticle is entirely fabricated from said materials. In certain embodiments the nanoparticle comprises a doped material containing said materials. In certain embodiments the nanoparticle comprises a core-shell structure comprising said ICD inducing materials. Accordingly, in certain embodiments ICD is induced by contacting the cancer cells with a nanomaterial (e.g., $CuO$, $Sb_2O_3$, $ZnO$, $TiO_2$, and graphene oxide) that induced ICD.

It will also be recognized that in various embodiments, two or more ICD inducers can be used to induce ICD via local delivery.

In certain embodiments, the ICD inducer comprises at least oxaliplatin, or doxirubicin e.g., as described in Examples 3 and 4.

As noted above, the ICD inducer can be used in conjunction with an IDO inhibitor. Numerous IDO inhibitors are known to those of skill in the art (see, discussion below) and the use of one or more of these IDO inhibitors is contemplated. In certain embodiments the IDO inhibitor(s) comprise a conjugated IDO inhibitor as described herein. In certain embodiments the IDO inhibitors comprise indoximod or a conjugated indoximod as described below and in Examples 1 and 2. In certain embodiments the IDO inhibitors comprise substantially pure "D" indoximod, or substantially pure "L" indoximod, or conjugated substantially pure "D" indoximod, or conjugated substantially pure "L" indoximod.

In certain embodiments the ICD inducer and the inhibitor of the IDO pathway are delivered locally to a target site. In certain embodiments the ICD inducer and the inhibitor of the IDO pathway can be delivered directly to a tumor site, e.g., by injection, or through a cannula. In certain embodiments the ICD inducer and the inhibitor of the IDO pathway are delivered into a tumor mass and/or into a peritumoral site. In certain embodiments the ICD inducer and the inhibitor of the IDO pathway can be delivered as separate reagents. Alternatively, they can be delivered as a combined formulation. In certain embodiments the combined formulation comprise nanovesicles and/or lipid bilayer coated silica nanoparticles, e.g. as described herein, or suitable other dual delivery carriers that contain an IDO inhibitor plus a nanomaterial capable of inducing ICD.

In certain embodiments the ICD inducer and the IDO pathway inhibitor are delivered via an implantable depot delivery system (e.g., encapsulated in a controlled release polymer, a hydrogel, and the like). In certain embodiments both the ICD inducer and the IDO pathway inhibitor are in implantable depot delivery systems and in other embodiments only the IDO pathway inhibitor or the ICD inducer is in an implantable depot delivery system.

In certain embodiments the ICD inducer and the IDO pathway inhibitor are used in combination as a primary therapy. In certain embodiments the ICD inducer and the IDO pathway inhibitor are used as an adjunct therapy, e.g., in combination with other chemotherapeutics, and/or surgery, and/or radio therapy. In certain embodiments the ICD inducer and the IDO pathway inhibitor are delivered to a surgical site during or after removal of a tumor mass.

In view of the examples and teachings provided herein, it will be recognized that the co-delivery of an ICD inducer and the IDO pathway inhibitor will find use in the treatment of a number of cancers. Illustrative cancers include, but are not limited to pancreatic ductal adenocarcinoma (PDAC), acute lymphoblastic leukemia (ALL), acute myeloid leukemia (AML), Adrenocortical carcinoma, Kaposi sarcoma, anal cancer, appendix cancer, astrocytoma, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CIVIL), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, non-melanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

In certain embodiments the cancer to be treated is cancer pancreatic ductal adenocarcinoma (PDAC) and in certain embodiments, the ICD inducer comprises oxaliplatin and the IDO inhibitor comprises indoximod or a conjugated indoximod as described below in in Example 1.

Approach 3—Vaccination to Prevent or Treat a Cancer.

In various embodiments, methods are provided for the prevention or treatment of a cancer that involve vaccinating a subject (e.g., a human, or a non-human mammal) to induce an immune response directed against one or more cancers. It was a surprising discovery that vaccination of a mammal with cancer cells in which ICD has been induced ex vivo is sufficient to generate a systemic immune response that can interfere with tumor growth at a remote site as well as allowing adoptive transfer to non-immune animals.

Without being bound to a particular theory it is believed that such vaccination methods can be used for the treatment of an existing cancer or prophylactically to prevent or inhibit the formation of a cancer in a subject. In the latter case, for example, subjects that have a family history for cancer in general or for particular cancers, and/or that have a genetic risk for a cancer (e.g., mutations in BRCA1, and/or BRCA2, and/or P53) may be vaccinated prophylactically to prevent the development of a cancer.

In certain embodiments, the vaccination is used as a primary therapy in the treatment of a cancer. In certain embodiments the vaccination is used as an adjunct therapy, e.g., in combination with surgery, and/or other chemotherapy regimen, and/or radiation therapy.

Accordingly, in various embodiments, a method for the treatment and/or prevention of a cancer in a mammal is provided where the method comprises providing cancer cells in which immunogenic cell death (ICD) has been induced ex vivo, and vaccinating the mammal with these cells, where the vaccination induces an anti-cancer immunogenic response.

In certain embodiments, the cancer cells are cells derived from an existing cancer, e.g., obtained during a biopsy, or after surgical resection of a tumor mass). In certain embodiments the cancer cells are cells obtained from the subject that is to be treated and comprise an autologous transplant. In certain embodiments the cells are obtained from a different subject of the same species or can even be obtained from a different species.

In certain embodiments, the cancer cells are cells from a cancer cell line. Typically, where a non-human animal is to be treated (veterinary use) the cell line is an animal cell line from the same species that is to be treated. Similarly, where a human is to be treated a human cell line will typically be used. Numerous cancer cell lines are known to those of skill in the art. Illustrative, but non-limiting examples of suitable cell lines are shown in Table 1.

TABLE 1

Illustrative, but non-limiting, cell lines that can be used to produce dying cancer cells in which immunogenic cell death (ICD) has been induced.

| | |
|---|---|
| KPC | Mouse pancreatic ductal adenocarcinoma (for research purpose only) |
| Patient-derived cancer cells | Primary cancer cells obtained via various diagnosis (i.e. obtained by fine needle biopsy) or surgical procedures |
| SH-SY5Y | Human neuroblastoma |
| Hep G2 | Human Caucasian hepatocyte carcinoma |
| 293 (HEK 293) | Human Embryo Kidney |
| HeLa | Human cervix epitheloid carcinoma |
| MRC-5 (PD 19) | Human foetal lung |
| A2780 | Human ovarian carcinoma |
| CACO-2 | Human Caucasian colon adenocarcinoma |
| THP 1 | Human monocytic leukaemia |
| A549 | Human Caucasian lung carcinoma |
| MRC-5 (PD 30) | Human foetal lung |
| MCF7 | Human Caucasian breast adenocarcinoma |
| Jurkat E6.1 | Human leukaemic T cell lymphoblast |
| U937 | Human Caucasian histiocytic lymphoma |
| HL60 | Human Caucasian promyelocytic leukaemia |
| HT29 | Human Caucasian colon adenocarcinoma |
| OE33 | Human Caucasian oesophageal carcinoma |
| OE19 | Human Caucasian oesophageal carcinoma |
| MDA-MB-231 | Human Caucasian breast adenocarcinoma |
| K562 | Human Caucasian chronic myelogenous leukaemia |

TABLE 1-continued

Illustrative, but non-limiting, cell lines that can be used to produce dying cancer cells in which immunogenic cell death (ICD) has been induced.

| Cell line | Description |
| --- | --- |
| U-87 MG | Human glioblastoma astrocytoma |
| MRC-5 (PD 25) | Human fetal lung |
| A2780cis | Human ovarian carcinoma |
| 1321N1 | Human brain astrocytoma |
| A431 | Human squamous carcinoma |
| U-2 OS | Human Osteosarcoma |
| HCT 116 | Human colon carcinoma |
| BEAS-2B | Human bronchial epithelium, normal |
| T47D | Human breast tumour |
| 1301 | Human T-cell leukaemia |
| PNT2 | Human prostate normal, immortalised with SV40 |
| TF1 | Human erythroleukaemia |
| NCI-H322 | Human Caucasian bronchioalveolar carcinoma |
| SK.N.SH | Human Caucasian neuroblastoma |
| LNCaP.FGC | Human Caucasian prostate carcinoma |
| OE21 | Human Caucasian oesophageal squamous cell carcinoma |
| PSN1 | Human pancreatic adenocarcinoma |
| MFE-280 | Human caucasian endometrial adenocarcinoma |
| MG-63 | Human osteosarcoma |
| EoL-1 cell | Human eosinophilic leukaemia |
| VCaP | Human Prostate Cancer Metastasis |
| tsA201 | Human embryonal kidney, SV40 transformed |
| HT 1080 | Human fibrosarcoma |
| PANC-1 | Human Caucasian pancreas |
| Saos-2 | Human primary osteogenic sarcoma |
| ATCC Pancreatic cell lines: | |
| Capan-2 | ATCC HTB-80 |
| Panc 10.05 | ATCC CRL-2547 |
| CFPAC-1 | ATCC CRL-1918 |
| HPAF-II | ATCC CRL-1997 |
| SW 1990 | ATCC CRL-2172 |
| BxPC-3 | ATCC CRL-1687 |
| AsPC-1 | ATCC CRL-1682 |
| ATCC colon cancer lines | |
| SNU-C1 | ATCC CRL-5972 |
| SK-CO-1 | ATCC HTB-39 |
| SW1116 | ATCC CCL-233 |
| SW948 | ATCC CCL-237 |
| T84 | ATCC CCL-248 |
| LS123 | ATCC CCL-255 |
| LoVo | ATCC CCL-229 |
| SW837 | ATCC CCL-235 |
| SNU-C1 | ATCC CRL-5972 |
| SW48 | ATCC CCL-231 |
| RKO | ATCC CRL-2577 |
| COLO 205 | ATCC CCL-222 |
| SW1417 | ATCC CCL-238 |
| LS411N | ATCC CRL-2159 |
| NCI-H508 | ATCC CCL-253 |
| HT-29 | ATCC HTB-38 |
| CRL-1718 ™ CCF-STTG1 | Human Brain Astrocytoma |
| HTB-12 ™ SW 1088 | Human Brain Astrocytoma |
| HTB-13 ™ SW 1783 | Human Brain Astrocytoma |
| CRL-3020 ™ CHLA-02-ATRT | Human Brain Atypical Teratoid Rhabdoid Tumor (ATRT) |
| CRL-1620 ™ A172 | Human Brain Glioblastoma |
| HTB-16 ™ U-138 MG | Human Brain Glioblastoma |
| CRL-2610 ™ LN-18 | Human Brain Glioblastoma |
| CRL-2611 ™ LN-229 | Human Brain Glioblastoma |
| HTB-14 ™ U-87 MG | Human Brain Glioblastoma, astrocytoma |
| HTB-15 ™ U-118 MG | Human Brain Glioblastoma, astrocytoma |
| CRL-1690 ™ T98G | Human Brain Glioblastoma, multiforme |
| HTB-138 ™ Hs 683 | Human Brain Glioma |
| CRL-3021 ™ CHLA-01-MED | Human Brain Medullomyoblastoma |
| CRL-2273 ™ CHP-212 | Human Brain Neuroblastoma |
| HTB-148 ™ H4 | Human Brain Neuroglioma |
| HTB-187 ™ D341 | Med Human Brain, cerebellum Medulloblastoma |
| HTB-186 ™ Daoy | Human Brain, cerebellum Medulloblastoma, desmoplastic cerebellar |
| CRL-2060 ™ PFSK-1 | Human Brain, cerebellum Tumor, malignant primitive neuroectodermal |
| CRL-2020 ™ DBTRG-05MG | Human Brain, glial cell Glioblastoma |
| CRL-2365 ™ M059K | Human Brain, glial cell Glioblastoma |
| CRL-2366 ™ M059J | Human malignant glioblastoma |

Although not required, in typical embodiments the cancer cells used in the vaccination are of the same type of cancer that is to be treated and/or prevented. It will be recognized however, that vaccination with cells of one type of cancer may generate an immune response directed against a different cancer and/or against multiple cancers. In certain embodiments the vaccination is with cells from multiple different types (e.g., 2 or more cancers, 3 or more cancers, 4 or more cancers, 5 or more cancers, 6 or more cancers, 7 or more cancers, 8 or more cancers, 9 or more cancers, 10 or more cancers, etc.) in which ICD is induced.

In certain embodiments illustrative cancers to be treated or prevented include, but are not limited to pancreatic ductal adenocarcinoma (PDAC), acute lymphoblastic leukemia (ALL), acute myeloid leukemia (AML), Adrenocortical carcinoma, Kaposi sarcoma, anal cancer, appendix cancer, astrocytoma, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CIVIL), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CIVIL), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, non-melanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

In various embodiments the cells used in the vaccination include cells of one or more of these cancers.

Methods of inducing immunogenic cell death (ICD) are well known to those of skill in the art. In certain embodiments ICD is induced by contacting the cells (e.g., primary tumor cells, cancer cell lines, etc.) with one or more chemotherapeutic agent(s) that induce ICD. Such agents include, but are not limited to oxaliplatin, anthracenedione, bleomycin, bortezomib, cisplatin, daunorubicin, docetaxel, doxorubicin, epirubicin, idarubicin, mitoxantrone, paclitaxel, irinotecan, R2016 (a heterocyclic quinolone derivative described by Son et al. (2017) Plos One, DOI:10.1371, which is incorporated herein by reference for the compounds described therein), and cyclophosphamide. In certain embodiments the ICD chemo reagents may also include the drug derivatives, i.e. prodrugs, that are capable of releasing the abovementioned chemotherapeutics in biological environments.

Another method of inducing ICD involves infecting the cells with an oncolytic virus. Illustrative, but non-limiting oncoviruses that induce ICD include, but are not limited to Parvovirus (e.g., H-PV (see, e.g., Angelova et al. (2014) J. Virol., 88(10): 5263-5276), and the like), Adenovirus (AD) (e.g., hTERT-Ad (see, e.g., Boozari et al. (2010) Gut. 59: 1416-1426), Ad5/3-D24-GMCSF (see, e.g., Liikanen et al. (2013) Mol. Ther. 21: 1212-1223), and the like), Herpes simplex virus (HSV) (e.g., G207 (see, e.g., Toda et al. (1999) Hum. Gene. Ther. 10: 385-393), HSV-1716 (see, e.g., Benencia et al. (2005)Mol. Ther., 12: 789-8020, T-VEC (see, e.g., Hu et al. (2006) Clin. Cancer Res. 12: 6737-67470), HSV-2 ΔPK mutant (see, e.g., Colunga et al. (2010) Gene Ther., 17: 315-327), and the like), Poxvirus (e.g., vSP (see, e.g., Guo et al. (2005) Cancer Res. 65: 9991-9998, vvDD (see, e.g., John et al. (2012) Cancer Res., 72: 1651-1660), Pexa-Vec (see, e.g., Heo et al. (2013) Nat. Med., 19: 329-336), and the like), Arbovirus (see, e.g., VSV-GFP (Indiana serotype) (see, e.g., Wongthida et al. (2010) Cancer Res. 70: 4539-4549), VSVgm-icv (see, e.g., Lemay et al. (2012) Mol. Ther., 20: 1791-1799), and the like), Paramyxovirus (e.g., MV-eGFP (Edmonston strain) (see, e.g., Donnelly et al. (2013) Gene Ther. 20: 7-15), and the like). A review of such oncoviruses is found in Bartlett et al. (2013) Mol. Cancer. 12: 103).

Other methods of inducing ICD involve exposure to radiation (e.g., gamma radiation, UVC radiation).

In certain embodiments ICD induction is accomplished using any of the compounds and/or modalities described in Table 2.

TABLE 2

Illustrative compounds and/or modalities to induce immunogenic cell death (ICD).

| ICD Inducer | DAMPs released |
|---|---|
| Mitoxantrone<br>Oxaliplatin<br>UVC irradiation<br>γ-irradiation<br>anthracyclines (e.g., Daunorubicin, Doxorubicin, Epirubicin, Idarubicin) | Pre-apoptotic ecto-CRT and ERp57; early apoptotic secreted ATP; mid to late apoptotic ecto-HSP70; late apoptotic passively released HMGB1 |
| Shikonin | Early to mid apoptotic ecto-CRT; early to mid apoptotic ecto-HSP70; early to mid apoptotic ecto-GRP78 |
| 7A7 (EGFR-specific antibody) | Pre-apoptotic ecto-CRT and ERp57; early to mid apoptotic ecto-HSP70; early to mid apoptotic ecto-HSP90 |
| Cyclophosphamide | Pre-apoptotic ecto-CRT; late apoptotic passively released HMGB1 |
| Bortezomib | Early to mid apoptotic ecto-HSP90 |
| Cardiac glycosides | Pre-apoptotic ecto-CRT; early to mid apoptotic ATP release; late apoptotic passively released HMGB1 |
| Hypericin-based PDT | Pre-apoptotic ecto-CRT; pre-apoptotic secreted ATP; pre-apoptotic ecto-HSP70; tate apoptotic passively released HSP70, HSP90 and CRT |
| Coxsackievirus B3 | Early apoptotic ecto-CRT; early apoptotic secreted ATP; late apoptotic passively released HMGB1 |
| Oncolytic parvovirus (e.g., H-PV)<br>Anthracenedione<br>Bleomycin<br>Docetaxel<br>Paclitaxel<br>R2016<br>Irinotecan | |

In other embodiments, the methods of inducing ICD can involve contacting the cells with materials, e.g., nanomaterials that induce ICD. It was a surprising discovery that certain materials (e.g., nanomaterials), as a result of intrinsic nanomaterial properties, are capable of inducing ICD, e.g., as determined by CRT induction, in a manner comparable to the positive control, oxaliplatin. Such materials include, but are not limited to CuO, graphene oxide, and certain others (see, e.g., Example 3). Accordingly, in certain embodiments ICD is induced by contacting the cancer cells with a nanomaterial that induces ICD (e.g., CuO, $Cu_2O$, $As_2O_3$, $Bi_2O_3$, $P_2O_3$, ZnO, $TiO_2$, graphene oxide, 2D materials other than graphene or graphene oxide (e.g., graphene, graphyne, borophene, germanene, silicene, $Si_2BN$, stanene, phosphorene, bismuthene, molybdenite, metals, 2D supracrystals, and the like)). In certain embodiments, the nanomaterial comprises copper oxide. In certain embodiments, the nanomaterial comprises graphene oxide (GO), CuO, $Cu_2O$, $Sb_2O_3$, $As_2O_3$, $Bi_2O_3$, $P_2O_3$, ZnO, $TiO_2$, graphene oxide, and 2D materials other than graphene or graphene oxide Extensive high throughput screening of a large number of nanomaterial libraries (including metals, metal oxides, rare earth oxides, graphene, graphene oxide, multi- and single walled carbon nanotubes, fumed silica, long aspect ratio nanomaterials, redox active nanomaterials, nanomaterials with functionalized catalytic surfaces and coatings etc) in our nanomaterial safety screening laboratory in the California Nano Systems Institute at UCLA have demonstrated a variety of mechanisms, involving intrinsic nanomaterial properties, that can induce a wide variety of different types of cell death, including apoptosis, necrosis, pyroptosis, and immunogenic cell death.

In view of the results demonstrated herein, it is believed that numerous other 2-dimensional (2D) materials can similarly induce ICD.

In this regard, it is noted that a number of 2D materials other than graphene are known to those of skill in the art (see, e.g., Mas Balleste et al. (2011) *Nanoscale,* 3: 20-30). Such materials include, but are not limited to graphene, graphyne, borophene, germanene, silicene, $Si_2BN$, stanene, phosphorene, bismuthene, molybdenite, metals, 2D supracrystals, and the like. Other 2D materials include, but are not limited to BN, $MoS_2$, $NbSe_2$, $Bi_2Sr_2CaCu_2O$—(Id.), single layers of single layers of manganese (see, e.g., Omomo et al. (2003) *J. Am. Chem. Soc.,* 125: 3568-3575), oxides of cobalt (see, e.g., Kim et al. (2009) *Chem. Eur. J.,* 15: 10752-10761), tantalum (Fukuda et al. (2007) *Inorg. Chem.* 46: 4787-4789), ruthenium (Fukuda et al. (2010) *Inorg. Chem.* 49: 4391-4393), and titanium (Tanaka et al. (2003) *Chem. Mater.* 15: 3564-3568) as well as sheets of several perovskite type structures, e.g., $H_2[A_{n-1}B_nO_{3n+1}]$ where A is Na, CA, Sr, or LA, and B is Ta or Ti, $K_2LN_2Ti_3O_{10}A$, $KLnNb_2O_7$, or $RbLNTa_2O_7$ where Ln is lanthanide ion, $MWO_6$ where M is Nb or Ta, $KCa_2Nb_3O_{10}$, $KSr_2Nb_3O_{10}$, $Bi_2SrTa_2O_9$, and the like.

It is noted that these ICD-inducing nanomaterials exhibit a range of tunable physicochemical properties that can readily be adapted to achieve the optimal ICD-inducing catalytic outcomes. For example, for graphene oxide these properties include, inter alia, nanosheet size, surface oxidation status, and the like, while for metal oxides these properties include, inter alia, the particle size, dissolution characteristics, zeta potential, and the like.

The list of nanomaterials above that induce immunogenic cell death is illustrative and non-limiting. It is believed there are numerous other materials that have the capability of inducing ICD based on property-activity relationships, such as the induction of oxidative stress, mitochondrial damage, lysosomal damage, surface membrane damage, DNA damage, photo activation, oxygen radical generation, activation of the NRLP3 inflammasome, induction or interference in autophagy flux, etc.

It will also be recognized that in various embodiments, two or more agents can (e.g., two or more of the agents or modalities described above) can be used to induce ICD.

Methods of determining whether DC is induced in the cells are known to those of skill in the art. For example, ICD is characterized by elevated expression of calreticulin (CRT), and/or elevated expression and/or release of e.g., HMGB1 or ATP as compared to the same cells in which ICD is not induced. Illustrative, but non-limiting methods of inducing ICD in cancer cells (e.g., KPC cells) and evaluation of the ICD are described in Example 1.

These methods and agents for inducing ICD are illustrative and non-limiting. Numerous other agents and compositions for inducing ICD are known.

Modes of Vaccination.

Methods of vaccination of humans or non-human mammals are well known to those of skill in the art. Most typically, the vaccination will be by intramuscular, subcutaneous, or intradermal injection. In various embodiments injection may be performed by needle or pressure.

In certain embodiments mucosal immunization can be performed and such modalities include, but are not limited to intraocular, intranasal and/or oral.

In certain embodiments jet injectors, such as Antares Pharma's MediJector VISION, deliver medication through high-speed, pressurized liquid penetration of the skin without a needle. These have been developed as single-use devices and multiuse systems. A high peak pressure behind the liquid is required so it can drill a hole in the skin, and then the pressure is reduced to allow the rest of the liquid to enter the skin.

Other transdermal approaches deliver the antigen in a solid form. These approaches have the added benefit that the therapeutic agent is more stable and therefore may not need cold storage.

Another illustrative, but non-limiting approach uses the pharmaceutical formulation itself to puncture the skin. Glide Pharma has developed a low-velocity, spring-powered administrator that pushes a pointed rod of pharmaceutical material through the skin in a fraction of a second. This administrator enables constant, reliable delivery of a solid dosage form and could be applied to various vaccines including vaccines comprising cancer ICD-induced cancer cells as described herein.

In another illustrative, but non-limiting embodiment, the antigen (e.g., ICD-induced cancer cells) can be delivered by injection or implantation in a hydrogel. In certain embodiments the hydrogel is an injectible hydrogel.

Injectable hydrogels can be prepared using a wide range of materials. Cyto- and bio-compatibility as well as reactive chemistries are typical factors considered for selecting base materials that can be used in hydrogels for cell delivery. Material crosslinking (formation and concentration of physical or covalent linkages), biodegradability, and biochemical properties can influence the structural, mechanical, and biological properties of the hydrogels initially and over time. Hydrophilic polymers used for hydrogel construction generally can be divided into two categories: natural polymers derived from tissues or other natural sources and synthetic polymers fabricated using organic chemistry and molecular engineering principles. Biocompatible natural polymers such as hyaluronic acid, chitosan, heparin, alginate, fibrin, collagen, chondroitin sulfate, and silk, mimic aspects of the native microenvironment, including its mechanical and biochemical properties for modulating cell adhesion, migration, and other functions (see, e.g., Munarin et al. (2012) J. Appl. Biomater. Funct. Mater. 10(2): e67-81). These natural polymers have been used as building blocks for injectable hydrogel formation by physical (e.g., ionic, hydrogen bonding) or covalent crosslinking (e.g., reaction of functional groups on modified polymers) (see, e.g., Kharkar et al. (2013) Chem. Soc. Rev. 42(17): 7335-7372.

Synthetic polymers such as poly(ethylene glycol) (PEG), poly(vinyl alcohol) (PVA), poly(N-isopropylacrylamide) (PNIPAAm), and polycaprolactone (PCL) have frequently been used for the design of injectable, cell-compatible hydrogels due to their commercial availability, low batch-to-batch variation, versatility for chemical modification, and consequently, the ease of tuning the mechanical properties of the resulting hydrogels. Since synthetic polymers lack the inherent biochemical cues for interaction with cells, In certain embodiments they can be used in combination with natural polymers or biomimetic peptides to facilitate cell adhesion, migration, and protein secretion.

In certain illustrative, but non-limiting embodiments, the cells can be delivered by use of an injectable (or implantable) cryogel. Cryogels are a type of hydrogel made up of cross-linked hydrophilic polymer chains that can hold up to 99 percent water. They are created by freezing a solution of the polymer that is in the process of gelling. When thawed back again to room temperature, the substance turns into a highly interconnected pore-containing hydrogel, which is similar in composition to bodily soft tissues in terms of their water content, structure, and mechanics. By adjusting their shape, physical properties, and chemical composition sponge-like, porous cryogels can be formed that can be infused with living cells, biological molecules or drugs. One illustrative, but non-limiting cyrogel is formed from methacrylated alginate (MA-alginate) as described by Bencherif et al. (2016) Nat. Comm., 6: 7556.

Adjuvants.

In certain embodiments the vaccination utilizing cancer cells in which ICD has been induced is performed using one or more adjuvants to increase the subject's immune response to the vaccination. Typically, adjuvants enhance and direct the adaptive immune response to vaccine antigens.

Adjuvants may exert their effects through different mechanisms. Some adjuvants, such as alum and emulsions (e.g., MF59®), function as delivery systems by generating depots that trap antigens at the injection site, providing slow release in order to continue the stimulation of the immune system. These adjuvants enhance the antigen persistence at the injection site and increase recruitment and activation of antigen presenting cells (APCs). Particulate adjuvants (e.g., alum) have the capability to bind antigens to form multimolecular aggregates that encourage uptake by APCs (see, e.g., Leroux-Roels (2010) Vaccine. 28S(3):C25-3).

Some adjuvants are also capable of directing antigen presentation by the major histocompatibility complexes (MHC) (Id.). Other adjuvants, essentially ligands for pattern recognition receptors (PRR), act by inducing the innate immunity, predominantly targeting the APCs and consequently influencing the adaptive immune response. AlOOH described below is one such example. Members of nearly all of the PRR families are potential targets for adjuvants. These include Toll-like receptors (TLRs), NOD-like receptors (NLRs), RIG-I-like receptors (RLRs) and C-type lectin receptors (CLRs). They signal through pathways that involve distinct adaptor molecules leading to the activation of different transcription factors. These transcription factors (e.g., NF-κB, IRF3) induce the production of cytokines and chemokines that play a key role in the priming, expansion and polarization of the immune responses. Activation of some members of the NLR family, such as NLRP3 and NLRC4, triggers the formation of a protein complex, called inflammasome, implicated in the induction of the pro-inflammatory cytokines IL-1β (see, e.g., Li et al. (2008) J. Immunol. 181(1): 17-21.) and IL-18. The NLRP3 and NLRC4 inflammasomes have been involved in the innate immunity induced by certain adjuvants. Much of our high throughput discovery on material such as AOOH, multiwall carbon nanotubes, singlewall carbon nanotubes, graphene, rare earth oxide nanoparticles, metal oxide nanorods, and the like function via the NRLP3 pathway. Most of the adjuvant effects fit into the category of stimulating DAMP pathways, which overlaps with the concept of ICD.

Alum & Emulsions

Alum is the most commonly used adjuvant in human vaccination. Alum provokes a strong Th2 response. Alum induces the immune response by a depot effect and activation of APCs. The NLRP3 inflammasome has been linked to the immunostimulatory properties of alum.

In certain embodiments a high aspect ratio AlOOH variant of alum can be used as an adjuvant. We have also made a much-improved variant of alum by high throughput screening that identified high aspect ration AlOOH for use as an adjuvant. The high aspect ratio AlOOH that is 1-2 orders of magnitude better than Alum, based, inter alia, on the principle that the long aspect ratio of the material and its surface reactivity provide superior stimulation to the NRLP3 inflammasome in dendritic cells (see, e.g., Sun et al. (2013) ACS Nano, 7(12): 10834-10849).

Additionally, emulsions (either oil-in-water or water-in-oil), such as Freund's Incomplete Adjuvant (IFA) and MF59®, can trigger depot generation and induction of MHC responses. IFA induces a predominantly Th2 biased response with some Th1 cellular response. MF59® is a potent stimulator of both cellular (Th1) and humoral (Th2) immune responses.

PRR Ligands

New adjuvants are being developed that are natural ligands or synthetic agonists for PRRs, either alone or with various formulations. PRR activation stimulates the production of pro-inflammatory cytokines/chemokines and type I IFNs that increase the host's ability to eliminate the pathogen. Thus, the incorporation of pathogens associated molecular patterns (PAMPs) in vaccine formulations can improve and accelerate the induction of vaccine-specific responses. A number of these agonists are now in clinical or late preclinical stages of development (see, e.g., Steinhagen et al. (2011) 29(17): 3341-3355; Mbow et al. (2010) Curr. Opin. Immunol. 22(3): 411-416). When used in combination with alum or classical emulsion adjuvants, the immune response can be biased towards a Th1 response (see, e.g., Didierlaurent et al. (2009) J. Immunol. 183(10): 6186-6197).

TLR3 and RLR Ligands

Double-stranded RNA (dsRNA), which is produced during the replication of most viruses, is a potent inducer of innate immunity. Synthetic analogs of dsRNA, such as poly(I:C), have been utilized as adjuvants. They act through TLR 3 and RIG-I/MDA-5, inducing IL-12 and type I IFNs production, facilitating antigen cross-presentation to MHC class II molecules, and improving generation of cytotoxic T cells.

TLR4 Ligands

Bacterial lipopolysaccharides (LPS), which are ligands for TLR4, have long been recognized as potent adjuvants. The development of less toxic derivatives led to the production of MPLA (monophosphoryl lipid A), which formulated with alum (AS04) triggers a polarized Th1 response and is approved for clinical use in Europe. We also have demonstrated that graphene oxide can interact with TLR4.

TLR5 Ligands

The TLR5 ligand, bacterial flagellin, is a potent T-cell antigen and has been utilized as a vaccine adjuvant. Unlike other TLR agonists, flagellin tends to produce mixed Th1 and Th2 responses rather than strongly Th1 responses. Flagellin can be used as an adjuvant mixed with the antigen.

TLR7/8 Ligands

The TLR7/8 pathway, specialized in the recognition of single stranded viral RNA, has also been explored for use as vaccine adjuvants. Imidazoquinolines (e.g., imiquimod, gardiquimod, and R848) are synthetic compounds that activate TLR7/8 in multiple subsets of dendritic cells leading to the production of IFN-α and IL-12 thus promoting a Th1 response. In this regard, is noted that the formulations and/or drug delivery nanocarriers described herein can easily include imiquimod.

TLR9 Ligands

Oligodeoxynucleotides containing specific CpG motifs (CpG ODNs such as ODN 1826 and ODN 2006) are recognized by TLR9. They enhance antibody production and strongly polarize the cell responses to Th1 and away from Th2 responses. In this regard, it is noted that various drug delivery nanocarriers described herein (e.g., a bilayer-coated nanoparticle) can readily be modified to present CPG oligonucleotides on the surface (e.g., LB-coated nanoparticles can present CPG oligo's on the lipid bilayer).

NOD2 Ligands

Fragments of bacterial cell walls, such as muramyl dipeptide (MDP), have long been recognized as adjuvants. More recently, it was discovered that MDP triggers the activation of NOD2 and the NLRP3 inflammasome.

Adjuvants may be combined to achieve a stronger effect or a more potent skewing of immune responses. For example, alum has been combined with TLR9 agonists (see, e.g., Siegrist et al. (2004) *Vaccine*, 23(5): 615-622). In experimental models, administration of other combinations such as CpG ODNs with MDP or MPLA has proven effective (see, e.g., Kim et al. (2000) *Vaccine*, 19: 530-537).

In various embodiments, any one or more of the these adjuvants may be used to enhance response to the vaccination with cancer cells in which ICD has been induced.

The foregoing vaccination methods are illustrative and non-limiting. Using the teachings provided herein, numerous other methods and compositions for vaccinating subjects with cancer cells in which ICD is induced will be available to one of skill in the art.

IDO Inhibitors

Figure 2:
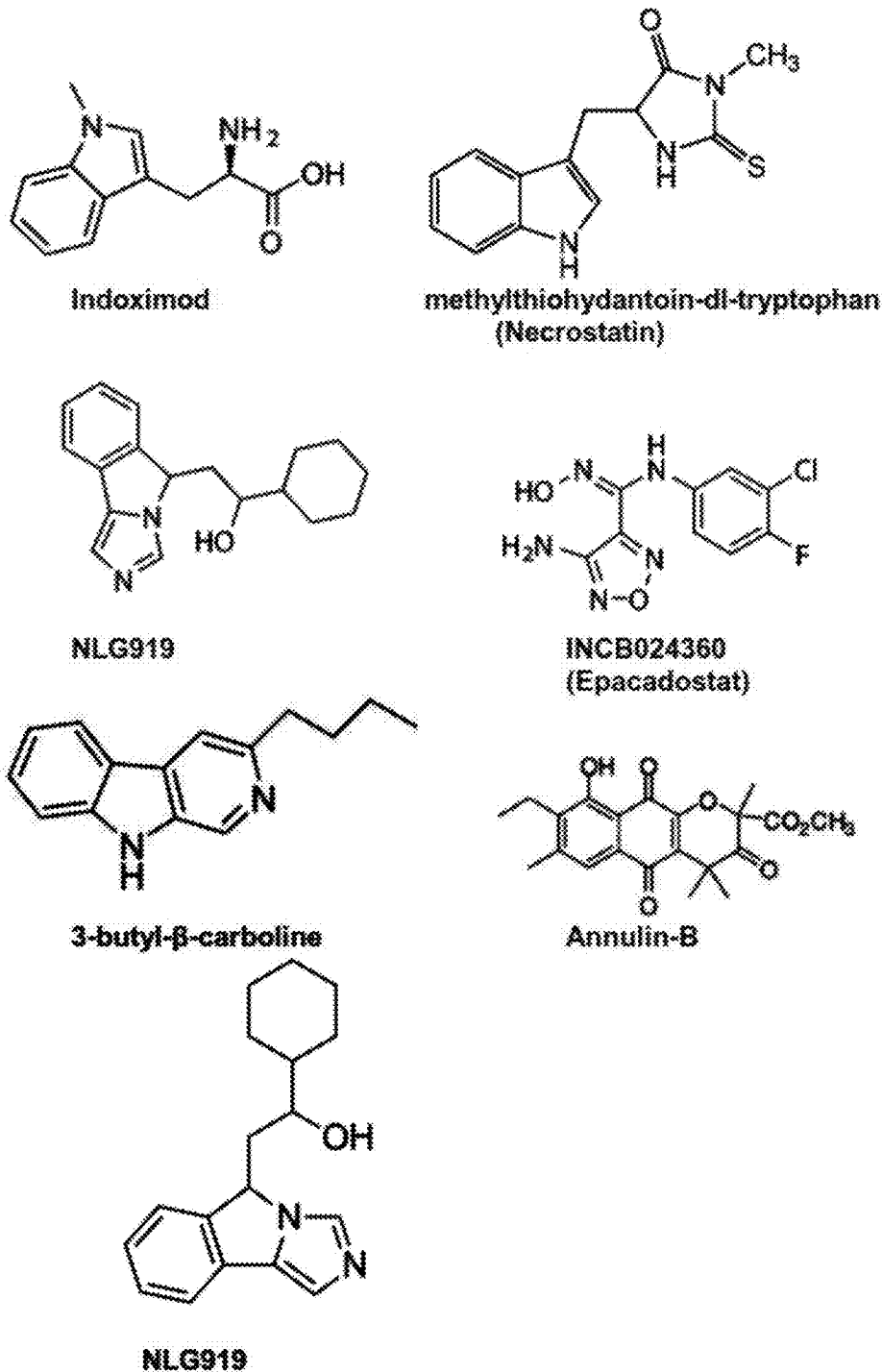
FIG. 2 illustrates the structure of indoximod and various other IDO pathway inhibitors.

A number of IDO inhibitors are well-known to those of skill in the art and useful in the methods described herein. Illustrative, but non-limiting examples of IDO inhibitors are shown in Table 3 and the structures of several of these are shown in FIG. 2.

TABLE 3

Illustrative, but non-limiting IDO inhibitors.

| IDO Inhibitor | Mechanism | Reference |
|---|---|---|
| Indoximod (D-1MT) | Tryptophan mimetic; D isoform of MT; Transcriptional suppressor of IDO | Metz et at. (2012) *Oncoimmunology*, 1(9): 1460-1468 |
| L-1MT | Tryptophan mimetic; L isoform of MT; selective IDO1 inhibitor | Opitz et at. (2011) *Nature*, 478(7368): 197-203 |
| methylthiohydantoin-dl-tryptophan (MTH-Trp) (Necrostatin) | Tryptophan mimetic; transcriptional suppressor of IDO | Okamoto (2007) *Cytotechnology*, 54(2): 107-113 |
| β-carbolines (e.g., 3-butyl-β-carboline) | Tryptophan mimetic; IDO and TDO inhibitor | Eguchi et at. (1984) *Arch. Biochem. Biophys.* 232(2): 602-609 |
| Naphthoquinone-based (e.g., annulin-B) | Pharmacophore of natural product annulin B; indole mimetic; IDO inhibitor | Kumar et at. (2008) *J. Med. Chem.*, 51(6): 1706-1718 |
| S-allyl-brassinin | Phytoalexin; indole mimetic | U.S. Pat. No. 7,705,022 |
| S-benzyl-brassinin | Phytoalexin; indole mimetic | U.S. Pat. No. 7,705,022 |
| N-[2-(Indol-3-yl)ethyl]-S-methyl-dithiocarbamate | | U.S. Pat. No. 7,705,022 |
| N-[2-(benzo[b]thiophen-3-yl)ethyl]-S-methyl-dithiocarbamate | | U.S. Pat. No. 7,705,022 |
| N-[3-(Indol-3-yl)propyl]-S-methyl-dithiocarbamate | | U.S. Pat. No. 7,705,022 |
| S-Hexyl-brassinin | | U.S. Pat. No. 7,705,022 |
| N-[2-(indol-3-yl)ethyl]-S-benzyl-dithiocarbamate | | U.S. Pat. No. 7,705,022 |
| N-[2-(indol-3-yl)ethyl]-S[(naphth-2-yl)methyl]-dithiocarbamate | | U.S. Pat. No. 7,705,022 |
| N-[2-(indol-3-yl)ethyl]-S-[(pyrid-3-yl)methyl]-dithiocarbamate | | U.S. Pat. No. 7,705,022 |
| N-[2-(indol-3-yl)ethyl]-S-[(pyrid-4-yl)methyl]-dithiocarbamate | | U.S. Pat. No. 7,705,022 |
| 5-Bromo-brassinin | Phytoalexin; indole mimetic | Banerjee et al. (2008) *Oncogene*, 27(20): 2851-2857 |
| Phenylimidazole-based (e.g., 4-phenylimidazole) | Heme ligand in IDO enzyme | Sono et al. (1989) *Biochemistry* (Mosc), 8(13): 5392-5399 |
| Exiguamine A | Non-tryptophan analogue | Brastianos et at. (2006) J. Am. Chem. Soc. 128(50): 16046-1647 |

TABLE 3-continued

Illustrative, but non-limiting IDO inhibitors.

| IDO Inhibitor | Mechanism | Reference |
| --- | --- | --- |
| imidodicarbonimidic diamide,N-methyl-N'-9-phenanthrenyl-, monohydrochloride (NSC401366) | Non-indolic IDO inhibitor | Vottero et at. (2006) Biotechnol. J. 1(3): 282-288 |
| INCB024360 (Epacadostat) | | |
| 1-cyclohexyl-2-(5H-imidazo[5,1-a]isoindol-5-yl)ethanol (GDC-0919) | | |
| IDO1-derived peptide NLG919 | | |
| Ebselen | | |
| Pyridoxal Isonicotinoyl Hydrazone | | |
| Norharmane | | |
| (3R,4S)-4-(benzylamino)-3-hydroxy-2,2-dimethyl-3,4-dihydrobenzo[g]chromene-5,10-dione (CAY 10581) | | |
| 2-Benzyl-2-thiopseudourea hydrochloride | | |

Still other IDO inhibitors include, but are not limited to the inhibitors described in U.S. Patent Publication Nos: US 2016/0362412, US 2016/0289171, US 2016/0200674, US 2016/0143870, US 2016/0137595, US 2016/0060237, US 2016/0002249, US 2014/0323740, US 2014/0066625, US 2013/0289083, US 2013/0183388, US 2012/0277217, US 2011/0136796, US 2011/0112282, US 2011/0053941, US 2010/0233166, US 2010/0166881, US 2010/0076066, US 2009/0042868, US 2007/0173524, US 2007/0105907, which are all incorporated herein by reference for the IDO inhibitors described therein.

It is contemplated that the methods described herein can use one or more of these IDO inhibitors and/or any other IDO inhibitors known to those of skill in the art. In certain embodiments the one or more IDO inhibitors comprise indoximod.

Conjugated IDO Inhibitors and Vesicles Thereof.

In certain embodiments one or more IDO inhibitors (e.g., any one or more of the IDO inhibitors shown in Table 3) are conjugated to a moiety that forms a vesicle (e.g., a liposome or a micelle) structure in aqueous solution or that can form a component of a lipid bilayer comprising a liposome. The conjugated IDO inhibitors can be used directly (e.g., described in approach 2 above), provided as components in a combined formulation (e.g., in combination with an ICD inducer), and in certain embodiments, the IDO inhibitor is conjugated to a moiety that forms a component of a lipid bilayer that can be disposed on a nanoparticle, e.g., as described below and in Example 1).

In certain embodiments the moiety that is conjugated to the IDO pathway inhibitor comprises a lipid (e.g., a phospholipid), vitamin E, cholesterol, and/or a fatty acid. In certain embodiments the IDO pathway inhibitor can be conjugated directly to the moiety (see, e.g., FIG. 3), while in other embodiments the IDO inhibitor can be conjugated to the moiety using a linker (e.g., a HO—(CH$_2$)$_{n=2-5}$—OH linker as shown in FIG. 4).

Figure 3:
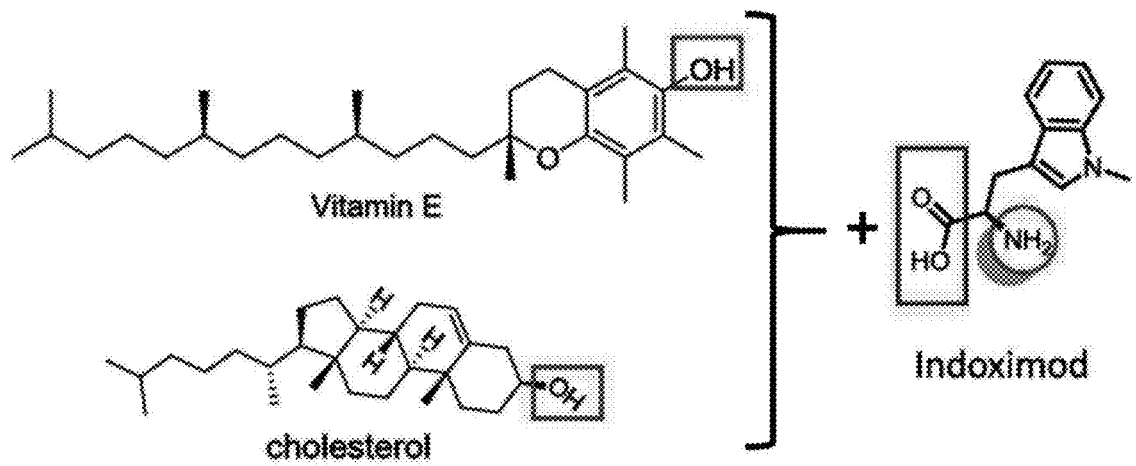
FIG. 3 illustrates representative examples to show the use of an ester bond to make IDO inhibitor (e.g., indoximod) pro-drug conjugates. As a general strategy, the $NH_2$ group (highlighted by circle) in the indoximod is protected before the conjugation reaction. The —COOH (green box) in indoximod can then robustly react with the —OH (blue box) in, for example, vitamin E or cholesterol, leading to a list of pro-drugs, that can self-assemble as vesicles (or micellar structures) in aqueous solution. It can also be used in the lipid mixture for MSNP coating.
Figure 4:
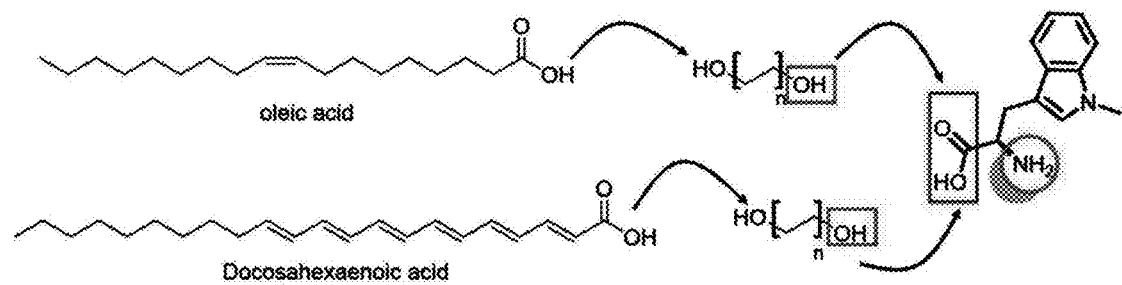
FIG. 4 illustrates representative examples to show the combined use of HO—$(CH_2)_{n=2-5}$—OH linker and ester bond to make IDO inhibitor (e.g., indoximod) pro-drug conjugates. As illustrated in this example, the $NH_2$ group (highlighted by red circle) is protected in the indoximod before the conjugation reaction. The —COOH (in box) in indoximod can robustly react with one —OH group (blue box) in the linker compound, which can also readily react with —COOH in the oleic acid or DHA molecule via the other —OH group.

In the illustrative embodiments shown in FIG. 3, the an ester bond is used to make the conjugate. As a general strategy in the case of indoximod, the NH$_2$ group in the indoximod is protected before the conjugation reaction. The —COOH in indoximod can then robustly react with the in the conjugating moiety (e.g., phospholipid, Vitamin E, cholesterol, a fatty acid, etc.). Similarly, FIG. 34 illustrates representative examples to show the combined use of HO—(CH$_2$)$_{n=2-5}$—OH linker and ester bond to make IDO inhibitor (e.g., indoximod) pro-drug conjugates. Again, as illustrated, the NH$_2$ group can be protected.

Examples 8 and 9 illustrate various conjugation strategies. These reactions, however, are illustrative and non-limiting. Numerous IDO inhibitors have other groups readily available for conjugation directly to a vesicle-forming moiety or to a linker. Such groups include for example, H, OH, CH$_2$, and the like (see, e.g., FIG. 2).

In certain embodiments, particularly for rapid and easy incorporation into a lipid bilayer the IDO pathway inhibitor can be conjugated to a lipid (e.g., a phospholipid), or cholesterol. Of course, in certain embodiments, the other vesicle-forming agents having conjugated IDO inhibitor(s) can also be incorporated into a lipid bilayer.

In certain embodiments, the inhibitor of the IDO pathway is conjugated to cholesterol or to a modified cholesterol (e.g., cholesterol hemisuccinate (CHEMS), lysine-based cholesterol (CHLYS), PEGylated cholesterol (Chol-PEG), and the like). In certain embodiments the IDO pathway inhibitor is conjugated to cholesterol by a linker. In certain embodiments the IDO pathway inhibitor is conjugated directly to cholesterol (see, e.g., Formulas II, IIa, and IIb in FIG. 8).

In certain embodiments, the inhibitor of the IDO pathway is conjugated to a phospholipid comprising a saturated fatty acid with a C14-C20 carbon chain, and/or an unsaturated fatty acid with a C14-C20 carbon chain, and/or a natural lipid comprising a mixture of fatty acids with C12-C20 carbon chains. In certain embodiments, the phospholipid comprises a saturated fatty acid selected from the group consisting of phosphatidylcholine (DPPC), dimyristoylphosphatidylcholine (DMPC), distearoylphosphatidylcholine (DSPC), and diactylphosphatidylcholine (DAPC). In certain embodiments, the phospholipid comprises a natural lipid selected from the group consisting of egg phosphatidylcholine (egg PC), and soy phosphatidylcholine (soy PC). In certain embodiments, the phospholipid comprises an unsaturated fatty acid selected from the group consisting of 1,2-dimyristoleoyl-sn-glycero-3-phosphocholine, 1,2-dipalmitoleoyl-sn-glycero-3-phosphocholine, 1,2-dioleoyl-sn-glycero-3-phosphocholine (DOPC), and 1,2-dieicosenoyl-sn-glycero-3-phosphocholine, and the like.

It will be recognized that as shown above, in various embodiments, the 1-methyl-tryptophan component of the conjugated IND (e.g., Chol-IND, or any other moiety conjugated IND), can be a "D" isomer or an L isomer.

In certain embodiments the IDO pathway inhibitors can be incorporated into the lipid bilayer forming the vesicle without conjugation to a lipid bilayer component. For example, epacadostat is a potent direct IDO enzyme inhibitor with an IC50 of ~125 nM in a whole blood assay (Yue et al. (2017) *ACS Med. Chem. Letts.* 8: 486-491). Although the drug showed good synergy with anti-PD1 antibody (nivolumab) in a phase II clinical trial in melanoma patients, the success could not be duplicated in a recent phase 3 clinical trial for the same disease. This has raised questions about the exact role and efficacy of IDO inhibitors, their pharmacology and explaining the divergent effects. Epacadostat is highly soluble in ethanol (>20 mg/mL), which allows its incorporation into a liposomal membrane through the use of the ethanol injection method ((see, e.g., Pons, et al. (1993) *J. Pharmaceutic.* 95: 51-56). The ethanol injection method produces homogeneous unilamellar liposomes (Pereira et al. (2016) *Int. J. Pharmaceutics,* 514: 150-159). In this method, water is poured into a concentrated lipid-ethanol solution (e.g., containing docetaxel and possibly IND-Chol in a ratiometric designed strategy), following which ethanol is removed in an evaporator (Id.). Dilution with water causes spontaneous formation of small and homogenous unilamellar liposomes from the micellar aggregate. The size of the liposomes can be controlled by the ratio of ethanol to water.

It will be recognized that the foregoing conjugates and lipid bilayers incorporating IDO inhibitors are illustrative and non-limiting. Using the teaching provided herein, numerous other IDO inhibitor conjugates and/or IDO-containing lipid bilayers (vesicles) will be available to one of skill in the art.

MTX Only Liposomes.

It is noted that the use of both of the mitoxantrone-only and mitoxantrone/IND liposomes were extremely effective in a 4T1 breast cancer model (see, e.g., Example 8), and much better than the results with a Doxil equivalent liposome delivering doxorubicin only. Without being bound to a particular theory, it is believed that the effect can be attributed to the superior ICD inducing effect of mitoxantrone over doxirubicin, rendering a liposomal mitoxantrone candidate that can be used for multiple cancer types. Additionally, in the 4T1 model, the mitoxantrone-only liposome was so effective that an additional effect for cholesterol-IND was not observed, reflecting the possibility that the 4T1 triple negative breast cancer model may represent a TN cancer subset in which IDO-1 does not play a major role. In this regard, it is noted that the same triple negative cancer also fails to respond to anti-PD1, the ligand of which is controlled by the same IFN-gamma response pathway that is responsible for the expression of PD-1 ligand. In this sense, TN breast cancer may be no different from a series of solid cancers in which there is only a 25-30% response rate to checkpoint inhibitors, likely due to a variable contribution by different immune escape mechanisms.

We have clear evidence that in spite of the lack of a synergistic effect for IND in the 4T1 model, that there is a strong ICD response in the Immunohistochemistry data, implying that the contribution of turning the cold tumor hot provides a strong contribution irrespective of an apparent lack of IDO-1 involvement.

Without being bound by a particular theory, it is believed that a potent ICD agent such as mitoxantrone can exert similar effects on other solid tumors, increasing the 25% response rate.

In view of this observation, it is believed that there is also a role for a mitoxantrone-only liposome in addition to a mitoxantrone/IND liposome. While not required, the use of an MTX-only liposome would be facilitated by the identification of a biomarker to identify whether tumors are potentially IDO-1 responsive, similar to the manner in which the expression of PD-1 ligand is currently used to decide who should receive anti-PD1 therapy for lung cancer.

Accordingly, in certain embodiments, the use of liposomes containing mitoxantrone where the lipid bilayer does not contain IND or other IDO inhibitor. In certain embodiments the liposome formulations are the same as liposome formulations described herein comprising IND, but the lipid bilayer components do not comprise a conjugated IDO inhibitor.

Remote Loading of Silicasomes, and Vesicles/Liposomes

In certain embodiments, the encapsulation of, e.g., the ICD inducer in the nanoparticle and/or in the nanovesicle can be optimized by using a "remote loading" strategy in which the addition of the drug (e.g., ICD-inducer such as doxorubicin) to preformed vesicles or silicasomes (LB-coated nanoparticles) which achieves high loading levels using a a pH gradient or an ion gradient capable of generating a pH gradient (see, e.g., Ogawa et al. (2009) *J. Control. Rel.* 1(5): 4-10; Fritze et al. (2006) *Biochimica et Biophys Acta.* 1758: 1633-1640). In general, the remote loading method involves adding a cargo-trapping reagent (e.g., protonating reagent such as $TEA_8SOS$, ammonium sulfate, etc.) which can be added to the lipid biofilm prior to the sonication in the formation of silicasomes, or can be incorporated into the nanovesicle lipids prior to the formation of the nanovesicle e.g., as described in Example 2.

Thus for example, using an IND-Cholesterol (IND-Chol) prodrug, a DOX/IND nanovesicle can be prepared as follows: 1) a total of 50 mg lipids of IND-Chol plus other vesicle-forming lipids (e.g., DPPC/Chol-IND/DPPG/DSPE-PEG (e.g., DSPE-PEG2k, DSPE-PEG5k, and the like), in certain embodiments at a molar ratio of ~40% (DPPC): ~35% (Chol-IND):~20% DPPG:~5% DSPE-PEG) can be dissolved in 5 mL chloroform in a 50 mL round bottom glass flask. The solvent can be evaporated under a rotatory vacuum to form a uniform thin lipid film that can be dried further under vacuum overnight. 2) The film can be hydrated with a cargo-trapping agent (e.g., with 2 mL of ammonium sulfate (123 mM) and probe sonicated, e.g., for 1 h, then subsequently extruded, e.g., 15 times, through a Mini-Extruder (Avanti Polar Lipids), using, e.g., a polycarbonate membrane with 100 nm pores (Avanti Polar Lipids) at 80° C. IND nanovesicle (IND-NV) size and morphology can be assessed by dynamic light scattering and cryoEM, respectively as desired. Unincorporated cargo-trapping agent (e.g., ammonium sulfate) can be removed, e.g., by running through a PD-10 size exclusion column. The drug to be loaded (e.g., 6.4 mg of DOX.HCl (10 mg/mL) in DI water) can be incubated with the above prepared IND-NVs, e.g., at 65° C. for 40 min. The nanovesicles can be fractionated across a PD-10 column, allowing the removal of free DOX. Their size and morphology can be assessed by dynamic light scattering, cryoEM and UPLC/MS-MS, respectively. In another illustrative, but non-limiting embodiments, citrate can be used to load mitoxantrone.

Of course, this protocol is illustrative and non-limiting. Using this teaching, numerous other nanovesicles comprising an ICD-inducer and various lipid formulations can be produced by one of skill in the art.

Similarly, preparation and remote-loading of a silicasome comprising an IDO pathway inhibitor and an ICD-inducer is illustrated in example 2. A DOX/IND-MSNP dual-delivery carrier is designed by trapping DOX in the mesoporous interior of a ~65 nm MSNP, using a lipid bilayer into which IND-Chol can be incorporated. In order to apply the lipid coating, we use the previously described biofilm method for rapid encapsulation, by sonication (Meng et al. (2015) *ACS Nano*, 9(4): 540-3557; Liu et al. (2016) *ACS Nano*, 10: 2702-2715). DOX was then remotely loaded using the protocol as previously described (Id).

Typically this involves preparing the MSNPs, e.g., by a sol-gel synthesis process (see. e.g., Meng et al. (2015) *ACS Nano*, 9(4): 540-3557). The MSNPs are then soaked in the cargo-trapping agent (e.g., ammonium sulfate) to load the agent into the pores of the MSNPs. The lipid formulation that will comprise the bilayer surrounding the silicasome is prepared, e.g., as described in Example 2, where the lipid formulation incorporates the IDO inhibitor (e.g., IND-Chol). The cargo-trapping agent loaded MSNPs are added to the IDO-inhibitor lipid film followed by sonication (e.g., 30 min probe sonication) to provide the trapping agent (e.g., ammonium sulfate)-loaded IND-Chol coated MSNP. To remove the free ammonium sulfate, the particle suspension can be passed through a PD-10 size exclusion column. Ammonium sulfate-containing IND-LB coated MSNPs will elute from column faster than free ammonium sulfate due to its large size. Remote Dox loading can be accomplished by incubating 6.5~32.4 mg of DOX.HCl (10 mg/mL) in DI water with cargo-trapping agent loaded laden IND-LB components coated MSNP at 65° C. for 40 min. The pure MSNPs can be collected by centrifuging at 15,000 rpm for 15 min, three times.

This protocol also is illustrative and non-limiting. Using this teaching, numerous other silicasomes comprising an IDO pathway inhibitor and ICD-inducer and various lipid formulations can be produced by one of skill in the art.

In this regard, it is noted that the lipid conjugation technology described herein can be used to make prodrugs out of chemo agents, which can be folded into a liposome. Thus, for example, ICD chemo agents like the taxanes can be incorporated into a phospholipid bilayer based on hydrophobicity, and this has been demonstrated for a MSNP where we used paclitaxel incorporation into the encapsulating phospholipid bilayer. The same can be done for a liposome.

Thus, the versatility of the liposomal platform described herein allows the encapsulation of ICD-inducing drugs such as paclitaxel, docetaxel, mitroxantrone, irinotecan and etoposide through the use different loading strategies that depend on the chemical structure of the drugs. For example, it is believed that mitoxantrone, which is a weak basic molecule with MW of 444.4, water solubility of 89 mg/mL and log P value of −3.1 (mitoxantrone. www.drugbank.ca/drugs/DB01204), can be remotely loaded into the Chol-IND liposome via a proton gradient, using $(NH_4)_2SO_4$ or citric acid. The same is possible for etoposide. Since docetaxel has high ethanol solubility (~100 mg/mL), this lends itself to constructing liposomes by an ethanol injection method that can produce homogeneous unilamellar liposomes as described. In this method, water is poured into a concentrated lipid-ethanol solution (containing docetaxel and possibly Chol-IND in a ratiometric designed strategy), following which ethanol is removed in an evaporator (see, e.g., Pereira et al. (2016) *Int. J. Pharmaceutics*, 514: 150-159). Dilution with water causes spontaneous formation of small and homogenous unilamellar liposomes from the micellar aggregate. The size of the liposomes can be controlled by the ratio of ethanol to water. While paclitaxel (PTX) is moderately soluble in ethanol (1.5 mg/mL), up to ~5 wt % PTX can be loaded into the liposomal membrane by ethanol injection (Koudelka & Turánek (2012) *J. Control. Release*, 163: 322-334).

These embodiments are illustrative and non-limiting. Using the teachings provided herein numerous variants will be available to one of skill in the art.

Cargo Trapping Reagents.

As explained above, in certain embodiments a cargo-trapping reagent can be utilized to facilitate incorporation of a cargo (e.g., DOX, MTX, OX, irinotecan etc. (see, e.g., Table 2)) into the dual-delivery (ICD-inducer/IDO-inhibitor) LB coated MSNP (ICD/IDO silicasome), and/or the dual-delivery lipid vesicles (e.g., ICD/IDO-lipid vesicles). The cargo-trapping reagent can be selected to interact with a desired cargo. In some embodiments, this interaction can be an ionic or protonation reaction, although other modes of interaction are contemplated. The cargo-trapping agent can have one or more ionic sites, i.e., can be mono-ionic or poly-ionic. The ionic moiety can be cationic, anionic, or in some cases, the cargo-trapping agent can include both cationic and anionic moieties. The ionic sites can be in equilibrium with corresponding uncharged forms; for example, an anionic carboxylate (—COO$^-$) can be in equilibrium with its corresponding carboxylic acid (—COOH); or in another example, an amine (—NH$_2$) can be in equilibrium with its corresponding protonated ammonium form (—NH$_3^+$). These equilibriums are influenced by the pH of the local environment. Certain ICD-inducing weak-base reagents, such as doxorubicin, can be loaded using a trapping agent mediated approach for loading (see, e.g., Example 2).

Likewise, in certain embodiments, the cargo can include one or more ionic sites. The cargo-trapping agent and cargo can be selected to interact inside the dual-delivery (ICD-inducer/IDO-inhibitor) LB coated MSNP (ICD/IDO silicasome), and/or the dual-delivery lipid vesicle (e.g., ICD/IDO-lipid vesicle). This interaction can help retain the cargo within the nanoparticle until release of the cargo is desired. In some embodiments, the cargo can exist in a pH-dependent equilibrium between non-ionic and ionic forms. The non-ionic form can diffuse across the lipid bilayer and enter the vesicle or the pores of the MSNP. There, the cargo-trapping agent (e.g., a polyionic cargo-trapping agent) can interact with the ionic form of the cargo and thereby retain the cargo within the nanocarrier, e.g., within the vesicle or within the pores of the MSNP (provided the ionic forms of the cargo and cargo-trapping agent have opposite charges). The interaction can be an ionic interaction, and can include formation of a precipitate. Trapping of cargo within the nanocarrier can provide higher levels of cargo loading compared to similar systems, e.g., nanocarriers that omit the cargo-trapping agent, or liposomes that do include a trapping agent. Release of the cargo can be achieved by an appropriate change in pH to disrupt the interaction between the cargo and cargo-trapping agent, for example, by returning the cargo to its non-ionic state which can more readily diffuse across the lipid bilayer. In one embodiment, the cargo is irinotecan and the cargo-trapping agent is TEA$_8$SOS.

The cargo trapping agent need not be limited to TEA$_8$SOS. In certain embodiments the cargo trapping comprises small molecules like citric acid, $(NH_4)_2SO_4$, and the like (see, e.g., Examples 2 and 9). Other trapping agents include, but are not limited to, ammonium salts (e.g., ammonium sulfate, ammonium sucrose octasulfate, ammonium α-cyclodextrin sulfate, ammonium β-cyclodextrin sulfate, ammonium γ-cyclodextrin sulfate, ammonium phosphate, ammonium α-cyclodextrin phosphate, ammonium β-cyclodextrin phosphate, ammonium γ-cyclodextrin phosphate, ammonium citrate, ammonium acetate, and the like), trimethylammonium salts (e.g., trimethylammonium sulfate, trimethylammonium sucrose octasulfate, trimethylammonium α-cyclodextrin sulfate, trimethylammonium β-cyclodextrin sulfate, trimethylammonium γ-cyclodextrin sulfate, trimethylammonium phosphate, trimethylammonium α-cyclodextrin phosphate, trimethylammonium β-cyclodextrin phosphate, trimethylammonium γ-cyclodextrin phosphate, trimethylammonium citrate, trimethylammonium acetate, and the like), triethylammonium salts (e.g., triethylammonium sulfate, triethylammonium sucrose octasulfate, triethylammonium α-cyclodextrin sulfate, triethylammonium β-cyclodextrin sulfate, triethylammonium γ-cyclodextrin sulfate, triethylammonium phosphate, triethylammonium α-cyclodextrin phosphate, triethylammonium β-cyclodextrin phosphate, triethylammonium γ-cyclodextrin phosphate, triethylammonium citrate, triethylammonium acetate, and the like).

It is also worth pointing out that, in addition to TEA$_8$SOS, transmembrane pH gradients can also be generated by acidic buffers (e.g. citrate) (Chou et al. (2003) *J. Biosci. Bioengineer.*, 95(4): 405-408; Nichols et al. (1976) *Biochimica et Biophysica Acta (BBA)-Biomembranes*, 455(1): 269-271), proton-generating dissociable salts (e.g. $(NH_4)_2SO_4$) (Haran et al. (1993) *Biochimica et Biophysica Acta (BBA)-Biomembranes*, 1151(2): 201-215; Maurer-Spurej et al. (1999) *Biochimica et Biophysica Acta (BBA)-Biomembranes*, 1416 (1): 1-10; Fritze et al. (2006) *Biochimica et Biophysica Acta (BBA)-Biomembranes*, 1758(10): 1633-1640), or ionophore-mediated ion gradients from metal salts (e.g. A23187 and MnSO$_4$) (Messerer et al. (2004) *Clinical Cancer Res.* 10(19): 6638-6649; Ramsay et al. (2008) *Eur. J. Pharmaceut. Biopharmaceut.* 68(3): 607-617; Fenske et al. (1998) *Biochimica et Biophysica Acta (BBA)-Biomembranes*, 1414 (1): 188-204). Moreover, it is possible to generate reverse pH gradients for drug loading, such as use a calcium acetate gradient to improve amphiphilic weak acid loading in LB-MSNP, a strategy that has been utilized in liposomes (Avnir et al. (2008) *Arthritis & Rheumatism*, 58(1): 119-129).

In certain embodiments the cargo-trapping reagent is particular suitable for use with a cargo that comprises an organic compound that includes at least one primary amine group, or at least one secondary amine group, or at least one tertiary amine group, or at least one quaternary amine group, or any combination thereof, capable of being protonated.

In certain embodiments the general characteristics of these cargo molecules include the following chemical properties:

(i) organic molecular compounds that include primary, secondary, tertiary or quaternary amine(s);
(ii) a pKa <11 to allow protonation and entrapment behind the LB (Zucker et al. (2009) *J. Control. Release*, 139(1): 73-80; Cern et al. (2012) *J. Control. Release*, 160(2): 147-157; Xu et al. (2014) *Pharmaceut. Res.* 31(10): 2583-2592);
(iii) a water solubility index of 5-25 mg/mL and amphipathic characteristics that allow diffusion across the LB;
(iv) an octanol/water partition coefficient or log P value of −3.0 to 3.0 (Zucker et al. (2009) *J. Control. Release*, 139(1): 73-80; Cern et al. (2012) *J. Control. Release*, 160(2): 147-157);
(v) suitable molecular weight with a geometric size less than MSNP pore size (2-8 nm), to allow entry into the MSNP pores (Li et al. (2012) *Chem. Soc. Rev.* 41(7): 2590-2605; Tang et al. (2012) *Adv. Mat.* 24(12): 1504-1534; Tarn et al. (2013) *Acc. Chem. Res.* 46(3): 792-801).

Remote loading utilizing doxorubicin, with ammonium sulfate as a cargo trapping agent is described in Example 2. This is illustrative, but non-limiting. In addition to DOX loading into nanovesicles or silicasomes, there are other possible drugs that can be imported across the lipid bilayer of these carriers. These include, but are not limited to, weak basic compounds, with medicinal chemical features. Such compounds include, but are not limited to alkaloids (e.g. irinotecan, topotecan, 10-hydroxycamptothecin, belotecan, rubitecan, vinorelbine, LAQ824, vinblastine, vincristine, homoharringtonine, trabectedin), anthracyclines (e.g. doxorubicin, epirubicin, pirarubicin, daunorubicin, rubidomycin, valrubicin, amrubicin), alkaline anthracenediones (e.g. mitoxantrone), alkaline alkylating agents (e.g. cyclophosphamide, mechlorethamine, temozolomide), purine or pyrimidine derivatives (e.g. 5-fluorouracil, 5'-deoxy-5-fluorouridine, gemcitabine, capecitabine) and protein kinase inhibitors (e.g., pazopanib, enzastaurin, vandetanib erlotinib, dasatinib, nilotinib, sunitinib, osimertinib, palbociclib, ribociclib), and the like.

Using the teachings provided herein, numerous other agents can be remote loaded (e.g., loaded using a cargo trapping agent) into the silicasomes (e.g., dual-delivery (ICD-inducer/IDO-inhibitor) LB coated MSNP (ICD/IDO silicasome)), and vesicles (e.g., the dual-delivery lipid vesicles (e.g., ICD/IDO-lipid vesicles)) described herein.

Targeting Ligands and Immunoconjugates.

In certain embodiments the dual-delivery (ICD-inducer/IDO-inhibitor) LB coated MSNPs (ICD/IDO silicasomes), and/or the dual-delivery lipid vesicles (e.g., ICD/IDO-lipid vesicles), and/or dual delivery lipid-coated ICD-inducing nanomaterial carriers can be conjugated to one or more targeting ligands, e.g., to facilitate specific delivery in endothelial cells, to cancer cells, to fusogenic ligands, e.g., to facilitate endosomal escape, ligands to promote transport across the blood-brain barrier, and the like.

In one illustrative, but non-limiting embodiment, the nanocarrier (e.g., ICD/IDO silicasome, ICD/IDO lipid vesicle, ICD-inducing nanomaterial carrier, etc.) is conjugated to a fusogenic peptide such as histidine-rich H5WYG (H$_2$N-GLFHAIAHFIHGGWHGLIHGWYG-COOH, (SEQ ID NO:1)) (see, e.g., Midoux et al., (1998) *Bioconjug. Chem.* 9: 260-267).

In certain embodiments the nanocarrier (e.g., ICD/IDO silicasome, ICD/IDO lipid vesicle, ICD-inducing nanomaterial carrier, etc.) is conjugated to one or more targeting ligand(s) that can include antibodies as well as targeting peptides. Targeting antibodies include, but are not limited to intact immunoglobulins, immunoglobulin fragments (e.g., F(ab)'$_2$, Fab, etc.) single chain antibodies, diabodies, affibodies, unibodies, nanobodies, and the like. In certain embodiments antibodies will be used that specifically bind a cancer marker (e.g., a tumor associated antigen). A wide variety of cancer markers are known to those of skill in the art. The markers need not be unique to cancer cells, but can also be effective where the expression of the marker is elevated in a cancer cell (as compared to normal healthy cells) or where the marker is not present at comparable levels in surrounding tissues (especially where the chimeric moiety is delivered locally).

Illustrative cancer markers include, for example, the tumor marker recognized by the ND4 monoclonal antibody. This marker is found on poorly differentiated colorectal cancer, as well as gastrointestinal neuroendocrine tumors (see, e.g., Tobi et al. (1998) *Cancer Detection and Prevention*, 22(2): 147-152). Other important targets for cancer immunotherapy are membrane bound complement regulatory glycoproteins CD46, CD55 and CD59, which have been found to be expressed on most tumor cells in vivo and in vitro. Human mucins (e.g. MUC1) are known tumor markers as are gp100, tyrosinase, and MAGE, which are found in melanoma. Wild-type Wilms' tumor gene WT1 is expressed at high levels not only in most of acute myelocytic, acute lymphocytic, and chronic myelocytic leukemia, but also in various types of solid tumors including lung cancer.

Acute lymphocytic leukemia has been characterized by the TAAs HLA-Dr, CD1, CD2, CD5, CD7, CD19, and CD20. Acute myelogenous leukemia has been characterized by the TAAs HLA-Dr, CD7, CD13, CD14, CD15, CD33, and CD34. Breast cancer has been characterized by the markers EGFR, HER2, MUC1, Tag-72. Various carcinomas have been characterized by the markers MUC1, TAG-72, and CEA. Chronic lymphocytic leukemia has been characterized by the markers CD3, CD19, CD20, CD21, CD25, and HLA-DR. Hairy cell leukemia has been characterized by the markers CD19, CD20, CD21, CD25. Hodgkin's disease has been characterized by the Leu-M1 marker. Various melanomas have been characterized by the HMB 45 marker. Non-hodgkins lymphomas have been characterized by the CD20, CD19, and Ia marker. And various prostate cancers have been characterized by the PSMA and SE10 markers.

In addition, many kinds of tumor cells display unusual antigens that are either inappropriate for the cell type and/or its environment, or are only normally present during the organisms' development (e.g., fetal antigens). Examples of such antigens include the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. GD2 is thus a convenient tumor-specific target for immunotherapies.

Other kinds of tumor cells display cell surface receptors that are rare or absent on the surfaces of healthy cells, and which are responsible for activating cellular signaling pathways that cause the unregulated growth and division of the tumor cell. Examples include (ErbB2) HER2/neu, a constitutively active cell surface receptor that is produced at abnormally high levels on the surface of breast cancer tumor cells.

Other useful targets include, but are not limited to CD20, CD52, CD33, epidermal growth factor receptor and the like.

An illustrative, but not limiting list of suitable tumor markers is provided in Table 4. Antibodies to these and other cancer markers are known to those of skill in the art and can be obtained commercially or readily produced, e.g. using phage-display technology. Such antibodies can readily be conjugated to the drug delivery nanocarrier (e.g., LB-coated nanoparticle) described herein, e.g., in the same manner that iRGD peptide is conjugated in Example 3.

TABLE 4

Illustrative cancer markers and associated references, all of which are incorporated herein by reference for the purpose of identifying the referenced tumor markers.

| Marker | Reference |
| --- | --- |
| 5 alpha reductase | Délos et al. (1998) *Int J Cancer*, 75:6 840-846 |
| α-fetoprotein | Esteban et al. (1996) *Tumour Biol.*, 17(5): 299-305 |
| AM-1 | Harada et al. (1996) *Tohoku J Exp Med.*, 180(3): 273-288 |
| APC | Dihlmann et al. (1997) *Oncol Res.*, 9(3) 119-127 |
| APRIL | Sordat et al. (998) *J Exp Med.*, 188(6): 1185-1190 |
| BAGE | Böel et al. (1995) *Immunity*, 2: 167-175. |
| β-catenin | Hugh et al. (1999) *Int J Cancer*, 82(4): 504-11 |
| Bcl2 | Koty et al. (1999) *Lung Cancer*, 23(2): 115-127 |
| bcr-abl (b3a2) | Verfaillie et al.( 996) *Blood*, 87(11): 4770-4779 |
| CA-125 | Bast et al. (998) *Int J Biol Markers*, 13(4): 179-187 |
| CASP-8/FLICE | Mandruzzato et al. (1997) *J Exp Med.*, 186(5): 785-793. |
| Cathepsins | Thomssen et al. (1995) *Clin Cancer Res.*, 1(7): 741-746 |
| CD19 | Scheuermann et al. (1995) *Leuk Lymphoma*, 18(5-6): 385-397 |
| CD20 | Knox et al. (1996) *Clin Cancer Res.*, 2(3): 457-470 |
| CD21, CD23 | Shubinsky et at. (1997) *Leuk Lymphoma*, 25(5-6): 521-530 |
| CD22, CD38 | French et al. (1995) *Br J Cancer*, 71(5): 986-994 |
| CD33 | Nakase et al. (1996) *Am J Clin Pathol.*, 105(6): 761-768 |
| CD35 | Yamakawa et al. *Cancer*, 73(11): 2808-2817 |
| CD44 | Naot et at. (1997) *Adv Cancer Res.*, 71: 241-319 |
| CD45 | Buzzi et al. (1992) *Cancer Res.*, 52(14): 4027-4035 |
| CD46 | Yamakawa et al. (1994) *Cancer*, 73(11): 2808-2817 |
| CD5 | Stein et al. (1991) *Clin Exp Immunol.*, 85(3): 418-423 |
| CD52 | Ginaldi et al. (1998) *Leuk Res.*, 22(2): 185-191 |
| CD55 | Spendlove et al. (1999) *Cancer Res.*, 59: 2282-2286. |
| CD59 (791Tgp72) | Jarvis et al. (1997) *Int J Cancer*, 71(6): 1049-1055 |
| CDC27 | Wang et al. (1999) *Science*, 284(5418): 1351-1354 |
| CDK4 | Wölfel et al. (1995) *Science*, 269(5228): 1281-1284 |
| CEA | Kass et at. (1999) *Cancer Res.*, 59(3): 676-683 |
| c-myc | Watson et al. (1991) *Cancer Res.*, 51(15): 3996-4000 |
| Cox-2 | Tsujii et al. (1998) *Cell*, 93: 705-716 |

TABLE 4-continued

Illustrative cancer markers and associated references, all of which are incorporated herein by reference for the purpose of identifying the referenced tumor markers.

| Marker | Reference |
| --- | --- |
| DCC | Gotley et al. (1996) Oncogene, 13(4): 787-795 |
| DcR3 | Pitti et at. (1998) Nature, 396: 699-703 |
| E6/E7 | Steller et al. (1996) Cancer Res., 56(21): 5087-5091 |
| EGFR | Yang et al. (1999) Cancer Res., 59(6): 1236-1243. |
| EMBP | Shiina et at. (1996) Prostate, 29(3): 169-176. |
| Ena78 | Arenberg et at. (1998) J. Clin. Invest., 102: 465-472. |
| FGF8b and FGF8a | Dorkin et al. (1999) Oncogene, 18(17): 2755-2761 |
| FLK-1/KDR | Annie and Fong (1999) Cancer Res., 59: 99-106 |
| Folic Acid Receptor | Dixon et at. (1992) J Biol Chem., 267(33): 24140-72414 |
| G250 | Divgi et at. (1998) Clin Cancer Res., 4(11): 2729-2739 |
| GAGE-Family | De Backer et at. (1999) Cancer Res., 59(13): 3157-3165 |
| gastrin 17 | Watson et al. (1995) Int J Cancer, 61(2): 233-240 |
| Gastrin-releasing hormone (bombesin) | Wang et al. (1996) Int J Cancer, 68(4): 528-534 |
| GD2/GD3/GM2 | Wiesner and Sweeley (1995) Int J Cancer, 60(3): 294-299 |
| GnRH | Bahk et al. (1998) Urol Res., 26(4): 259-264 |
| GnTV | Hengstler et at. (1998) Recent Results Cancer Res., 154: 47-85 |
| gp100/Pmel17 | Wagner et at. (1997) Cancer Immunol Immunother., 44(4): 239-247 |
| gp-100-in4 | Kirkin et at. (1998) APMIS, 106(7): 665-679 |
| gp15 | Maeurer et at. (1996) Melanoma Res., 6(1): 11-24 |
| gp75/TRP-1 | Lewis et al. (1995) Semin Cancer Biol., 6(6): 321-327 |
| hCG | Hoermann et al. (1992) Cancer Res., 52(6): 1520-1524 |
| Heparanase | Vlodaysky et at. (1999) Nat Med., 5(7): 793-802 |
| Her2/neu | Lewis et al. (1995) Semin Cancer Biol., 6(6): 321-327 |
| Her3 | |
| HMTV | Kahl et al. (1991) Br J Cancer, 63(4): 534-540 |
| Hsp70 | Jaattela et at. (1998) EMBO J., 17(21): 6124-6134 |
| hTERT (telomerase) | Vonderheide et at. (1999) Immunity, 10: 673-679. 1999. |
| IGFR1 | Ellis et al. (1998) Breast Cancer Res. Treat., 52: 175-184 |
| IL-13R | Murata et at. (1997) Biochem Biophys Res Commun., 238(1): 90-94 |
| iNOS | Klotz et al. (1998) Cancer, 82(10): 1897-1903 |
| Ki 67 | Gerdes et al. (1983) Int J Cancer, 31: 13-20 |
| KIAA0205 | Gueguen et al. (1998) J Immunol., 160(12): 6188-6194 |
| K-ras, H-ras, N-ras | Abrams et al. (1996) Semin Oncol., 23(1): 118-134 |
| KSA (CO17-1A) | Zhang et al. (1998) Clin Cancer Res., 4(2): 295-302 |
| LDLR-FUT | Caruso et al. (1998) Oncol Rep., 5(4): 927-930 |
| MAGE Family (MAGE1, MAGE3, etc.) | Marchand et at. (1999) Int J Cancer, 80(2): 219-230 |
| Mammaglobin | Watson et al. (1999) Cancer Res., 59: 13 3028-3031 |
| MAP17 | Kocher et at. (1996) Am J Pathol., 149(2): 493-500 |
| Melan-A/MART-1 | Lewis and Houghton (1995) Semin Cancer Biol., 6(6): 321-327 |
| mesothelin | Chang et at. (1996) Proc. Natl. Acad. Sc., USA, 93(1): 136-140 |
| MIC A/B | Groh et al. (1998) Science, 279: 1737-1740 |
| MT-MMP's, such as MMP2, MMP3, MMP7, MMP9 | Sato and Seiki (1996) J Biochem (Tokyo), 119(2): 209-215 |
| Mox1 | Candia et at. (1992) Development, 116(4): 1123-1136 |
| Mucin, such as MUC-1, MUC-2, MUC-3, and MUC-4 | Lewis and Houghton (1995) Semin Cancer Biol., 6(6): 321-327 |
| MUM-1 | Kirkin et at. (1998) APMIS, 106(7): 665-679 |
| NY-ESO-1 | Jager et al. (1998) J. Exp. Med., 187: 265-270 |
| Osteonectin | Graham et at. (1997) Eur J Cancer, 33(10): 1654-1660 |
| p15 | Yoshida et al. (1995) Cancer Res., 55(13): 2756-2760 |
| P170/MDR1 | Trock et at. (1997) J Natl Cancer Inst., 89(13): 917-931 |
| p53 | Roth et al. (1996) Proc. Natl. Acad. Sci., USA, 93(10): 4781-4786. |
| p97/melanotransferrin | Furukawa et at. (1989) J Exp Med., 169(2): 585-590 |
| PAI-1 | Grondahl-Hansen et al. (1993) Cancer Res., 53(11): 2513-2521 |
| PDGF | Vassbotn et al. (1993) Mol Cell Biol., 13(7): 4066-4076 |
| Plasminogen (uPA) | Naitoh et al. (1995) Jpn J Cancer Res., 86(1): 48-56 |
| PRAME | Kirkin et at. (1998) APMIS, 106(7): 665-679 |
| Probasin | Matuo et at. (1985) Biochem Biophys Res Commun., 130(1): 293-300 |
| Progenipoietin | — |
| PSA | Sanda et at. (1999) Urology, 53(2): 260-266. |
| PSM | Kawakami et al. (1997) Cancer Res., 57(12): 2321-2324 |
| RAGE-1 | Gaugler et al. (1996) Immunogenetics, 44(5): 323-330 |
| Rb | Dosaka-Akita et al. (1997) Cancer, 79(7): 1329-1337 |
| RCAS1 | Sonoda et al. (1996) Cancer, 77(8): 1501-1509. |

TABLE 4-continued

Illustrative cancer markers and associated references, all of which are incorporated herein by reference for the purpose of identifying the referenced tumor markers.

| Marker | Reference |
|---|---|
| SART-1 | Kikuchi et at. (1999) *Int J Cancer*, 81(3): 459-466 |
| SSX gene Family | Gure et at. (1997) *Int J Cancer*, 72(6): 965-971 |
| STAT3 | Bromberg et al. (1999) *Cell*, 98(3): 295-303 |
| STn (mucin assoc.) | Sandmaier et at. (1999) *J Immunother.*, 22(1): 54-66 |
| TAG-72 | Kuroki et al. (1990) *Cancer Res.*, 50(16): 4872-4879 |
| TGF-α | Imanishi et at. (1989) *Br J Cancer*, 59(5): 761-765 |
| TGF-β | Picon et at. (1998) *Cancer Epidemiol Biomarkers Prev*, 7(6): 497-504 |
| Thymosin β 15 | Bao et al. (1996) *Nature Medicine*. 2(12), 1322-1328 |
| IFN-α | Moradi et at. (1993) *Cancer*, 72(8): 2433-2440 |
| TPA | Maulard et al. (1994) *Cancer*, 73(2): 394-398 |
| TPI | Nishida et al. (1984) *Cancer Res* 44(8): 3324-9 |
| TRP-2 | Parkhurst et al. (1998) Cancer Res., 58(21) 4895-4901 |
| Tyrosinase | Kirkin et at. (1998) *APMIS*, 106(7): 665-679 |
| VEGF | Hyodo et al. (1998) *Eur J Cancer*, 34(13): 2041-2045 |
| ZAG | Sanchez et al. (1999) *Science*, 283(5409): 1914-1919 |
| p16INK4 | Quelle et at. (1995) *Oncogene* Aug. 17, 1995; 11(4): 635-645 |
| Glutathione S-transferase | Hengstler (1998) et al. *Recent Results Cancer Res.*, 154: 47-85 |

Any of the foregoing markers can be used as targets for the targeting moieties comprising the nanocarrier (e.g., ICD/IDO silicasomes, ICD/IDO lipid vesicles, ICD-inducing nanomaterial carriers, etc.) constructs described herein. In certain embodiments the target markers include, but are not limited to members of the epidermal growth factor family (e.g., HER2, HER3, EGF, HER4), CD1, CD2, CD3, CD5, CD7, CD13, CD14, CD15, CD19, CD20, CD21, CD23, CD25, CD33, CD34, CD38, 5E10, CEA, HLA-DR, HM 1.24, HMB 45, 1a, Leu-M1, MUC1, PMSA, TAG-72, phosphatidyl serine antigen, and the like.

The foregoing markers are intended to be illustrative and not limiting. Other tumor associated antigens will be known to those of skill in the art.

Where the tumor marker is a cell surface receptor, a ligand to that receptor can function as targeting moieties. Similarly, mimetics of such ligands can also be used as targeting moieties. Thus, in certain embodiments peptide ligands can be used in addition to or in place of various antibodies. An illustrative, but non-limiting list of suitable targeting peptides is shown in Table 5. In certain embodiments any one or more of these peptides can be conjugated to a drug delivery vehicle described herein.

TABLE 5

Illustrative, but non-limiting peptides that target membrane receptors expressed or overexpressed by various cancer cells.

| Target Membrane Receptor | Targeting Peptide | SEQ ID NO |
|---|---|---|
| Integrin receptor $A_I\beta_3$ | c(RGDfK) | 2 |
| | c(RGDfC) | 3 |
| | c(RGDyC) | 4 |
| | RGD | |
| GFR | GE11 (YHWYGYTPQNVI) | 5 |
| GFR | GSG-KCCYSL | 6 |
| SSTR2 | Ostreotide | |
| GRP | QWAVGHML | 7 |
| CCK | DYMGWMDF | 8 |
| NT | RRPYIL | 9 |
| | RRPYILQLYENKPRRPYIL | 10 |
| LHRH | Gondaorelin | |
| GPRC family members | Antagonist G | | c() indicates cyclopeptide. Lower case indicates "D" amino acid.

In certain embodiments the nanocarrier (e.g., ICD/IDO silicasome, ICD/IDO lipid vesicle, ICD-inducing nanomaterial carrier, etc.) can be conjugated to moieties that facilitate stability in circulation and/or that hide the nanocarrier from the reticuloendothelial system (REC) and/or that facilitate transport across a barrier (e.g., a stromal barrier, the blood brain barrier, etc.), and/or into a tissue. In certain embodiments the nanocarriers are conjugated to transferrin or ApoE to facilitate transport across the blood brain barrier. In certain embodiments the nanocarriers are conjugated to folate.

Methods of coupling the nanocarrier (e.g., ICD/IDO silicasome, ICD/IDO lipid vesicle, ICD-inducing nanomaterial carrier, etc.) to targeting (or other) agents are well known to those of skill in the art. Examples include, but are not limited to the use of biotin and avidin or streptavidin (see, e.g., U.S. Pat. No. 4,885,172 A), by traditional chemical reactions using, for example, bifunctional coupling agents such as glutaraldehyde, diimide esters, aromatic and aliphatic diisocyanates, bis-p-nitrophenyl esters of dicarboxylic acids, aromatic disulfonyl chlorides and bifunctional arylhalides such as 1,5-difluoro-2,4-dinitrobenzene; p,p'-difluoro m,m'-dinitrodiphenyl sulfone, sulfhydryl-reactive maleimides, and the like. Appropriate reactions which may be applied to such couplings are described in Williams et al. Methods in Immunology and Immunochemistry Vol. 1, Academic Press, New York 1967. In one illustrative but non-limiting approach a peptide (e.g., iRGD) is coupled to the (e.g., ICD/IDO silicasome, ICD/IDO lipid vesicle, ICD-inducing nanomaterial carrier, etc.) by substituting a lipid (e.g., DSPE-PEG$_{2000}$) with a lipid coupled to a linker (e.g., DSPE-PEG$_{2000}$-maleimide), allowing thiol-maleimide coupling to the cysteine-modified peptide. It will also be recognized that in certain embodiments the targeting (and other) moieties can be conjugated to other moieties comprising the lipid bilayer on a silicasome or vesicle, or comprising the nanomaterial carrier. It is also possible to improve tumor delivery of the IDO inhibitor-ICD inducing nanoparticle, (e.g., OX laden IND-Lipid bilayer-MSNP (IND-LB-MSNP), MTX loaded Chol-IND-MSNP, etc.), through co-administration (not conjugated) of the iRGD peptide to enhance particle transcytosis.

The former conjugates and coupling methods are illustrative and non-limiting. Using the teachings provided herein, numerous other moieties can be conjugated to, for instance, ICD/IDO silicasome, ICD/IDO lipid vesicle, ICD-inducing nanomaterial carrier, etc., described herein by any of a variety of methods.

Pharmaceutical Formulations, Administration and Therapy
    Pharmaceutical Formulations.

In some embodiments, the nanocarrier (e.g., ICD/IDO silicasome, ICD/IDO lipid vesicle, ICD-inducing nanomaterial carrier, etc.) and/or the ICD-inducing nanomaterials are administered alone or in a mixture with a physiologically-acceptable carrier (such as physiological saline or phosphate buffer) selected in accordance with the route of administration and standard pharmaceutical practice. For example, when used as an injectable, the nanocarriers can be formulated as a sterile suspension, dispersion, or emulsion with a pharmaceutically acceptable carrier. In certain embodiments normal saline can be employed as the pharmaceutically acceptable carrier. Other suitable carriers include, e.g., water, buffered water, 0.4% saline, 0.3% glycine, 5% glucose and the like, including glycoproteins for enhanced stability, such as albumin, lipoprotein, globulin, etc. In compositions comprising saline or other salt-containing carriers, the carrier is preferably added following nanocarrier formation. Thus, after the nanocarrier is formed and loaded with suitable drug(s), the nanocarrier can be diluted into pharmaceutically acceptable carriers such as normal saline.

Similarly, the ICD-inducing nanomaterials can be introduced into carriers that facilitate suspension of the nanomaterials (e.g., emulsions, dilutions, etc.).

The pharmaceutical compositions may be sterilized by conventional, well-known sterilization techniques. The resulting aqueous solutions, suspensions, dispersions, emulsions, etc., may be packaged for use or filtered under aseptic conditions. In certain embodiments the drug delivery nanocarriers (e.g., LB-coated nanoparticles) are lyophilized, the lyophilized preparation being combined with a sterile aqueous solution prior to administration. The compositions may also contain pharmaceutically acceptable auxiliary substances as required to approximate physiological conditions, such as pH-adjusting and buffering agents, tonicity adjusting agents and the like, for example, sodium acetate, sodium lactate, sodium chloride, potassium chloride, calcium chloride, etc.

Additionally, in certain embodiments, the pharmaceutical formulation may include lipid-protective agents that protect lipids against free-radical and lipid-peroxidative damage on storage. Lipophilic free-radical quenchers, such as alpha-tocopherol and water-soluble iron-specific chelators, such as ferrioxamine, are suitable.

The concentration of the nanocarrier (e.g., ICD/IDO silicasome, ICD/IDO lipid vesicle, ICD-inducing nanomaterial carrier, etc.) (or ICD-inducing nanomaterial particles) in the pharmaceutical formulations can vary widely, e.g., from less than approximately 0.05%, usually at least approximately 2 to 5% to as much as 10 to 50%, or to 40%, or to 30% by weight and are selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, nanocarriers composed of irritating lipids may be diluted to low concentrations to lessen inflammation at the site of administration. The amount of nanocarriers administered will depend upon the particular drug used, the disease state being treated and the judgment of the clinician but will generally be between approximately 0.01 and approximately 50 mg per kilogram of body weight, preferably between approximately 0.1 and approximately 5 mg per kg of body weight.

In some embodiments, e.g., it is desirable to include polyethylene glycol (PEG)-modified phospholipids in the LB-coated nanoparticles or vessicles. Alternatively, or additionally, in certain embodiments, PEG-ceramide, or ganglioside $G_{M1}$-modified lipids can be incorporated in the nanocarrier (e.g., ICD/IDO silicasome, ICD/IDO lipid vesicle, ICD-inducing nanomaterial carrier, etc.). Addition of such components helps prevent nanocarrier aggregation and provides for increasing circulation lifetime and increasing the delivery of the loaded nanocarriers to the target tissues. In certain embodiments the concentration of the PEG-modified phospholipids, PEG-ceramide, or $G_{M1}$-modified lipids in the nanocarriers will be approximately 1 to 15%.

In some embodiments, overall nanocarrier charge is an important determinant in nanocarrier clearance from the blood. It is believed that highly charged nanocarriers (i.e. zeta potential >+35 mV) will be typically taken up more rapidly by the reticuloendothelial system (see, e.g., Juliano (1975), *Biochem. Biophys. Res. Commun.* 63: 651-658 discussing liposome clearance by the RES) and thus have shorter half-lives in the bloodstream. Nanocarriers with prolonged circulation half-lives are typically desirable for therapeutic uses. For instance, in certain embodiments, drug delivery nanocarriers (e.g., LB-coated nanoparticles) that are maintained from 8 hrs, or 12 hrs, or 24 hrs, or greater are desirable.

In another example of their use, nanocarriers (e.g., ICD/IDO silicasome, ICD/IDO lipid vesicle, ICD-inducing nanomaterial carrier, etc.) can be incorporated into a broad range of topical dosage forms including but not limited to gels, oils, emulsions, and the like, e.g., for the treatment of a topical cancer. For instance, in some embodiments the suspension containing the nanocarrier is formulated and administered as a topical cream, paste, ointment, gel, lotion, and the like.

In some embodiments, pharmaceutical formulations comprising nanocarrier (e.g., ICD/IDO silicasome, ICD/IDO lipid vesicle, ICD-inducing nanomaterial carrier, etc.) described herein additionally incorporate a buffering agent. The buffering agent may be any pharmaceutically acceptable buffering agent. Buffer systems include, but are not limited to citrate buffers, acetate buffers, borate buffers, and phosphate buffers. Examples of buffers include, but are not limited to citric acid, sodium citrate, sodium acetate, acetic acid, sodium phosphate and phosphoric acid, sodium ascorbate, tartaric acid, maleic acid, glycine, sodium lactate, lactic acid, ascorbic acid, imidazole, sodium bicarbonate and carbonic acid, sodium succinate and succinic acid, histidine, and sodium benzoate, benzoic acid, and the like.

In some embodiments, pharmaceutical formulations comprising nanocarrier (e.g., ICD/IDO silicasome, ICD/IDO lipid vesicle, ICD-inducing nanomaterial carrier, etc.) described herein additionally incorporate a chelating agent. The chelating agent may be any pharmaceutically acceptable chelating agent. Chelating agents include, but are not limited to ethylene diaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid (e.g., citric acid monohydrate) and derivatives thereof. Derivatives of citric acid include anhydrous citric acid, trisodiumcitrate-dihydrate, and the like. Still other chelating agents include, but are not limited to, niacinamide and derivatives thereof and sodium deoxycholate and derivatives thereof.

In some embodiments, pharmaceutical formulations comprising nanocarrier (e.g., ICD/IDO silicasome, ICD/IDO lipid vesicle, ICD-inducing nanomaterial carrier, etc.) described herein additionally incorporate an antioxidant. The antioxidant may be any pharmaceutically acceptable antioxidant. Antioxidants are well known to those of ordinary skill in the art and include, but are not limited to, materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, sodium sulfite and N-acetyl cysteine. In certain embodiments such materials, when present, are typically added in ranges from 0.01 to 2.0%.

In some embodiments, pharmaceutical formulations comprising nanocarrier (e.g., ICD/IDO silicasome, ICD/IDO lipid vesicle, ICD-inducing nanomaterial carrier, etc.) described herein are formulated with a cryoprotectant. The cryoprotecting agent may be any pharmaceutically acceptable cryoprotecting agent. Common cryoprotecting agents include, but are not limited to, histidine, polyethylene glycol, polyvinyl pyrrolidine, lactose, sucrose, mannitol, polyols, and the like.

In some embodiments, pharmaceutical formulations comprising nanocarrier (e.g., ICD/IDO silicasome, ICD/IDO lipid vesicle, ICD-inducing nanomaterial carrier, etc.) described herein are formulated with an isotonic agent. The isotonic agent can be any pharmaceutically acceptable isotonic agent. This term is used in the art interchangeably with iso-osmotic agent, and is known as a compound that is added to the pharmaceutical preparation to increase the osmotic pressure, e.g., in some embodiments to that of 0.9% sodium chloride solution, which is iso-osmotic with human extracellular fluids, such as plasma. Illustrative isotonicity agents include, but are not limited to, sodium chloride, mannitol, sorbitol, lactose, dextrose and glycerol.

In certain embodiments pharmaceutical formulations of the nanocarrier (e.g., ICD/IDO silicasome, ICD/IDO lipid vesicle, ICD-inducing nanomaterial carrier, etc.) described herein may optionally comprise a preservative. Common preservatives include, but are not limited to, those selected from the group consisting of chlorobutanol, parabens, thimerosol, benzyl alcohol, and phenol. Suitable preservatives include but are not limited to: chlorobutanol (e.g., 0.3-0.9% w/v), parabens (e.g., 0.01-5.0%), thimerosal (e.g., 0.004-0.2%), benzyl alcohol (e.g., 0.5-5%), phenol (e.g., 0.1-1.0%), and the like.

In some embodiments, pharmaceutical formulations comprising the nanocarriers (e.g., ICD/IDO silicasome, ICD/IDO lipid vesicle, ICD-inducing nanomaterial carrier, etc.) described herein are formulated with a humectant, e.g., to provide a pleasant mouth-feel in oral applications. Humectants known in the art include, but are not limited to, cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Administration

The nanocarrier (e.g., ICD/IDO silicasome, ICD/IDO lipid vesicle, ICD-inducing nanomaterial carrier, etc.) described herein can be administered to a subject (e.g., patient) by any of a variety of techniques.

In certain embodiments the nanocarrier (e.g., ICD/IDO silicasome, ICD/IDO lipid vesicle, ICD-inducing nanomaterial carrier, etc.) and/or pharmaceutical formulations thereof are administered parenterally, e.g., intraarticularly, intravenously, intraperitoneally, subcutaneously, or intramuscularly. In some embodiments, the pharmaceutical compositions are administered intravenously, intraarteraly, or intraperitoneally by a bolus injection (see, e.g., U.S. Pat. Nos. 3,993,754; 4,145,410; 4,235,871; 4,224,179; 4,522,803; and 4,588,578 describing administration of liposomes). Particular pharmaceutical formulations suitable for this administration are found in *Remington's Pharmaceutical Sciences*, Mack Publishing Company, Philadelphia, Pa., 17th ed. (1985). Typically, the formulations comprise a solution of the drug delivery nanocarrier suspended in an acceptable carrier, preferably an aqueous carrier. As noted above, suitable aqueous solutions include, but are not limited to physiologically compatible buffers such as Hanks solution, Ringer's solution, or physiological (e.g., 0.9% isotonic) saline buffer and/or in certain emulsion formulations. The solution(s) can contain formulatory agents such as suspending, stabilizing and/or dispersing agents. In certain embodiments the active agent(s) can be provided in powder form for constitution with a suitable vehicle, e.g., sterile pyrogen-free water, before use. For transmucosal administration, and/or for blood/brain barrier passage, penetrants appropriate to the barrier to be permeated can be used in the formulation. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc., e.g., as described above.

In other methods, the pharmaceutical formulations containing the nanocarrier (e.g., ICD/IDO silicasome, ICD/IDO lipid vesicle, ICD-inducing nanomaterial carrier, etc.) described herein may be contacted with the target tissue by direct application of the preparation to the tissue. The application may be made by topical, "open" or "closed" procedures. By "topical" it is meant the direct application of the pharmaceutical preparation to a tissue exposed to the environment, such as the skin, oropharynx, external auditory canal, and the like. Open procedures are those procedures that include incising the skin of a patient and directly visualizing the underlying tissue to which the pharmaceutical formulations are applied. This is generally accomplished by a surgical procedure, such as a thoracotomy to access the lungs, abdominal laparotomy to access abdominal viscera, or other direct surgical approaches to the target tissue. Closed procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrizamide imaging of the spinal cord. Alternatively, the preparations may be administered through endoscopic devices. In certain embodiments the pharmaceutical formulations are introduced via a cannula.

In certain embodiments the pharmaceutical formulations comprising the nanocarrier (e.g., ICD/IDO silicasome, ICD/IDO lipid vesicle, ICD-inducing nanomaterial carrier, etc.) described herein are administered via inhalation (e.g., as an aerosol). Inhalation can be a particularly effective delivery route for administration to the lungs and/or to the brain. For administration by inhalation, the drug delivery nanocarriers are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator may be formulated containing a powder mix of the compound and a suitable powder base such as lactose or starch.

In certain embodiments, the nanocarrier (e.g., ICD/IDO silicasome, ICD/IDO lipid vesicle, ICD-inducing nanomaterial carrier, etc.) described herein are formulated for oral administration. For oral administration, suitable formulations can be readily formulated by combining the drug delivery nanocarriers) with pharmaceutically acceptable carriers suitable for oral delivery well known in the art. Such carriers enable the active agent(s) described herein to be formulated as tablets, pills, dragees, caplets, lozenges, gelcaps, capsules, liquids, gels, syrups, slurries, suspensions and the like, for oral ingestion by a patient to be treated. For oral solid formulations such as, for example, powders, capsules and tablets, suitable excipients can include fillers such as sugars (e.g., lactose, sucrose, mannitol and sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose), synthetic polymers (e.g., polyvinylpyrrolidone (PVP)), granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. The preparation of enteric-coated particles is disclosed for example in U.S. Pat. Nos. 4,786,505 and 4,853,230.

In various embodiments the nanocarrier (e.g., ICD/IDO silicasome, ICD/IDO lipid vesicle, ICD-inducing nanomaterial carrier, etc.) described herein can be formulated in rectal or vaginal compositions such as suppositories or retention enemas, e.g., containing conventional suppository bases such as cocoa butter or other glycerides. Methods of formulating active agents for rectal or vaginal delivery are well known to those of skill in the art (see, e.g., Allen (2007) *Suppositories*, Pharmaceutical Press) and typically involve combining the active agents with a suitable base (e.g., hydrophilic (PEG), lipophilic materials such as cocoa butter or Witepsol W45), amphiphilic materials such as Suppocire AP and polyglycolized glyceride, and the like). The base is selected and compounded for a desired melting/delivery profile.

The route of delivery of the nanocarrier (e.g., ICD/IDO silicasome, ICD/IDO lipid vesicle, ICD-inducing nanomaterial carrier, etc.) described herein can also affect their distribution in the body. Passive delivery of nanocarrier (e.g., ICD/IDO silicasome, ICD/IDO lipid vesicle, ICD-inducing nanomaterial carrier, etc.) involves the use of various routes of administration e.g., parenterally, although other effective administration forms, such as intraarticular injection, inhalant mists, orally active formulations, transdermal iontophoresis, or suppositories are also envisioned. Each route produces differences in localization of the drug delivery nanocarrier.

Because dosage regimens for pharmaceutical agents are well known to medical practitioners, the amount of the liposomal pharmaceutical agent formulations that is effective or therapeutic for the treatment of a disease or condition in mammals and particularly in humans will be apparent to those skilled in the art. The optimal quantity and spacing of individual dosages of the formulations herein will be determined by the nature and extent of the condition being treated, the form, route and site of administration, and the particular patient being treated, and such optima can be determined by conventional techniques. It will also be appreciated by one of skill in the art that the optimal course of treatment, e.g., the number of doses given per day for a defined number of days, can be ascertained by those skilled in the art using conventional course of treatment determination tests.

Typically, the nanocarrier (e.g., ICD/IDO silicasome, ICD/IDO lipid vesicle, ICD-inducing nanomaterial carrier, etc.) and/or pharmaceutical formations thereof described herein are used therapeutically in animals (including man) in the treatment of various cancers. In certain embodiments the nanocarriers and/or pharmaceutical formations thereof described herein are particularly well suited in conditions that require: (1) repeated administrations; and/or (2) the sustained delivery of the drug in its bioactive form; and/or (3) the decreased toxicity with suitable efficacy compared with the free drug(s) in question. In various embodiments the nanocarriers and/or pharmaceutical formations thereof are administered in a therapeutically effective dose. The term "therapeutically effective" as it pertains to the nanocarriers described herein and formulations thereof means that the combination of ICD inducer and IDO inhibitor produces a desirable effect on the cancer. Such desirable effects include, but are not limited to slowing and/or stopping tumor growth and/or proliferation and/or slowing and/or stopping proliferation of metastatic cells, reduction in size and/or number of tumors, and/or elimination of tumor cells and/or metastatic cells, and/or prevention of recurrence of the cancer following remission.

Exact dosages will vary depending upon such factors as the particular ICD inducer(s) and IDO inhibitors and the desirable medical effect, as well as patient factors such as age, sex, general condition, and the like. Those of skill in the art can readily take these factors into account and use them to establish effective therapeutic concentrations without resort to undue experimentation.

For administration to humans (or to non-human mammals) in the curative, remissive, retardive, or prophylactic treatment of diseases the prescribing physician will ultimately determine the appropriate dosage of the drug for a given human (or non-human) subject, and this can be expected to vary according to the age, weight, and response of the individual as well as the nature and severity of the patient's disease. In certain embodiments the dosage of the drug provided by the nanocarrier(s) can be approximately equal to that employed for the free drug. However as noted above, the nanocarriers described herein can significantly reduce the toxicity of the drug(s) administered thereby and significantly increase a therapeutic window. Accordingly, in some cases dosages in excess of those prescribed for the free drug(s) will be utilized.

In certain embodiments, the dose of each of the drug(s) (e.g., ICD inducer, IDO inhibitor) administered at a particular time point will be in the range from about 1 to about 1,000 mg/m$^2$/day, or to about 800 mg/m$^2$/day, or to about 600 mg/m$^2$/day, or to about 400 mg/m$^2$/day. For example, in certain embodiments a dosage (dosage regiment) is utilized that provides a range from about 1 to about 350 mg/m$^2$/day, 1 to about 300 mg/m$^2$/day, 1 to about 250 mg/m$^2$/day, 1 to about 200 mg/m$^2$/day, 1 to about 150 mg/m$^2$/day, 1 to about 100 mg/m$^2$/day, from about 5 to about 80 mg/m$^2$/day, from about 5 to about 70 mg/m$^2$/day, from about 5 to about 60 mg/m$^2$/day, from about 5 to about 50 mg/m$^2$/day, from about 5 to about 40 mg/m$^2$/day, from about 5 to about 20 mg/m$^2$/day, from about 10 to about 80 mg/m$^2$/day, from about 10 to about 70 mg/m$^2$/day, from about 10 to about 60 mg/m$^2$/day, from about 10 to about 50 mg/m$^2$/day, from about 10 to about 40 mg/m$^2$/day, from about 10 to about 20 mg/m$^2$/day, from about 20 to about 40 mg/m$^2$/day, from about 20 to about 50 mg/m$^2$/day, from about 20 to about 90 mg/m$^2$/day, from about 30 to about 80 mg/m$^2$/day, from about 40 to about 90 mg/m$^2$/day, from about 40 to about 100 mg/m$^2$/day, from about 80 to about 150 mg/m$^2$/day, from about 80 to about 140 mg/m$^2$/day, from about 80 to about 135 mg/m$^2$/day, from about 80 to about 130 mg/m$^2$/day, from about 80 to about 120 mg/m$^2$/day, from about 85 to about 140 mg/m$^2$/day, from about 85 to about 135 mg/m$^2$/day, from about 85 to about 135 mg/m$^2$/day, from about 85 to about 130 mg/m$^2$/day, or from about 85 to about 120 mg/m$^2$/day. In certain embodiments the does administered at a particular time point may also be about 130 mg/m$^2$/day, about 120 mg/m$^2$/day, about 100 mg/m$^2$/day, about 90 mg/m$^2$/day, about 85 mg/m$^2$/day, about 80 mg/m$^2$/day, about 70 mg/m$^2$/day, about 60 mg/m$^2$/day, about 50 mg/m$^2$/day, about 40 mg/m$^2$/day, about 30 mg/m$^2$/day, about 20 mg/m$^2$/day, about 15 mg/m$^2$/day, or about 10 mg/m$^2$/day.

Dosages may also be estimated using in vivo animal models, as will be appreciated by those skill in the art. In this regard, with respect to the irinotecan-loaded drug delivery nanocarriers described herein, it is noted that the effective therapeutic dose of the OX/IND nanocarrier in a KPC-derived orthotopic animal model is about 5 mg OX/kg with 50 mg IND/kg, which is equivalent to 15.5 mg OX/m$^2$ IND 150 mg/m$^e$ in a 60 kg human subject. Fibonacci analysis indicates this dose can be achieved by starting and intermediary OX doses of 37.5 and 75 mg/m$^2$. It is noted that 75 mg/m$^2$ OX is quite conservative and higher dosages are contemplated.

The dose administered may be higher or lower than the dose ranges described herein, depending upon, among other factors, the bioavailability of the composition, the tolerance of the individual to adverse side effects, the mode of administration and various factors discussed above. Dosage amount and interval may be adjusted individually to provide plasma levels of the composition that are sufficient to maintain therapeutic effect, according to the judgment of the prescribing physician. Skilled artisans will be able to optimize effective local dosages without undue experimentation in view of the teaching provided herein.

Multiple doses (e.g., continuous or bolus) of the compositions as described herein may also be administered to individuals in need thereof of the course of hours, days, weeks, or months. For example, but not limited to, 1, 2, 3, 4, 5, or 6 times daily, every other day, every 10 days, weekly, monthly, twice weekly, three times a week, twice monthly, three times a month, four times a month, five times a month, every other month, every third month, every fourth month, etc.

Methods of Treatment.

In various embodiments methods of treatment using the nanocarrier (e.g., ICD/IDO silicasome, ICD/IDO lipid vesicle, ICD-inducing nanomaterial carrier, etc.) and/or pharmaceutical formulation(s) comprising nanoparticle drug carriers described herein are provided. In certain embodiments the method(s) comprise a method of treating a cancer. In certain embodiments the method can comprise administering to a subject in need thereof an effective amount of a nanocarrier (e.g., ICD/IDO silicasome, ICD/IDO lipid vesicle, ICD-inducing nanomaterial carrier, etc.), and/or a pharmaceutical formulation comprising a nanocarrier as described herein, where the drug(s) comprising the nanocarrier and/or said pharmaceutical formulation comprises an anti-cancer drug.

In certain embodiments the nanocarrier (e.g., ICD/IDO silicasome, ICD/IDO lipid vesicle, ICD-inducing nanomaterial carrier, etc.) and/or pharmaceutical formulation is a primary therapy in a chemotherapeutic regimen. In certain embodiments the nanoparticle drug carrier and/or pharmaceutical formulation is a component in an adjunct therapy in addition to chemotherapy using one or more other chemotherapeutic agents, and/or surgical resection of a tumor mass, and/or radiotherapy.

In certain embodiments the nanocarrier (e.g., ICD/IDO silicasome, ICD/IDO lipid vesicle, ICD-inducing nanomaterial carrier, etc.) and/or pharmaceutical formulation is a component in a multi-drug chemotherapeutic regimen. In certain embodiments the multi-drug chemotherapeutic regimen comprises at least two drugs selected from the group consisting of irinotecan oxaliplatin (OX), 5-fluorouracil (5-FU), and leucovorin (LV). In certain embodiments the multi-drug chemotherapeutic regimen comprises at least three drugs selected from the group consisting of irinotecan (IRIN), oxaliplatin (OX), 5-fluorouracil (5-FU), and leucovorin (LV). In certain embodiments the multi-drug chemotherapeutic regimen comprises at least irinotecan oxaliplatin (OX), 5-fluorouracil (5-FU), and leucovorin (LV).

In various embodiments nanocarrier (e.g., ICD/IDO silicasome, ICD/IDO lipid vesicle, ICD-inducing nanomaterial carrier, etc.) and/or pharmaceutical formulation(s) thereof described herein are effective for treating any of a variety of cancers. In certain embodiments the cancer is pancreatic ductal adenocarcinoma (PDAC). In certain embodiments the cancer is a cancer selected from the group consisting of acute lymphoblastic leukemia (ALL), acute myeloid leukemia (AML), adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, glioblastoma, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, chronic myeloid leukemia (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

In certain embodiments the nanocarrier (e.g., ICD/IDO silicasome, ICD/IDO lipid vesicle, ICD-inducing nanomaterial carrier, etc.) described herein is not conjugated to an iRGD peptide and the nanocarrier is administered in conjunction with an iRGD peptide (e.g., the nanocarrier and the iRGD peptide are co-administered as separate formulations).

In various embodiments of these treatment methods, the nanocarrier (e.g., ICD/IDO silicasome, ICD/IDO lipid vesicle, ICD-inducing nanomaterial carrier, etc.) and/or pharmaceutical formulation is administered via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition. In certain embodiments the nanocarrier and/or pharmaceutical formulation is administered as an injection, from an IV drip bag, or via a drug-delivery cannula. In various embodiments the subject is a human and in other embodiments the subject is a non-human mammal.
Combined Treatment with Checkpoint Inhibitors.

It is believed that the nanocarriers described herein (e.g., comprising an inducer of immunogenic cell death (ICD), and an IDO inhibitor) showed synerstistic anti-cancer activity when administered in combination with one or more checkpoint inhibitors, and this has been demonstrated for an Irinotecan silicasome and anti-PD1. Accordingly, certain embodiments, methods contemplated herein include the administration of a drug delivery nanovesicle and/or a drug delivery nanocarrier as described herein in conjunction with one or more checkpoint inhibitors.

Illustrative checkpoint inhibitors include, but are not limited to inhibitors of PD-1, PD-L1, PD-L2, PD-L3, PD-L4, CTLA-4, LAG3, B7-H3, B7-H4, KIR and/or TIM3 receptors.

In some embodiments, the immune checkpoint inhibitor can be a small peptide agent that can inhibit regulatory T cell function, including any one or a combination of the inhibitory receptors listed above. In some embodiments, the immune checkpoint inhibitor can be a small molecule (e.g. less than 500 Daltons) that can inhibit T regulatory cell function. including the immune checkpoint receptors listed above. In some embodiments, the immune checkpoint inhibitor can be a molecule providing co-stimulation of T-cell activation. In some embodiments, the immune checkpoint inhibitor can be a molecule providing co-stimulation of natural killer cell activation. In some embodiments, the immune checkpoint inhibitor can be an antibody. In some embodiments, the immune checkpoint inhibitor is a PD-1 antibody. In some embodiments, the immune checkpoint inhibitor is a PD-L1 antibody. In some embodiments, the immune checkpoint inhibitor is a PD-L2 antibody. In some embodiments, the immune checkpoint inhibitor is a PD-L3 antibody. In some embodiments, the immune checkpoint inhibitor is a PD-L4 antibody. In some embodiments, the immune checkpoint inhibitor is a CTLA-4 antibody. In some embodiments, the immune checkpoint inhibitor is an antibody of CTLA-4, LAG3, B7-H3, B7-H4, KIR, or TIM3.

In certain embodiments the antibody can be selected from α-CD3-APC, α-CD3-APC-H7, α-CD4-ECD, α-CD4-PB, α-CD8-PE-Cy7, α-CD-8-PerCP-Cy5.5, α-CD11c-APC, α-CD11b-PE-Cy7, α-CD11b-AF700, α-CD14-FITC, α-CD16-PB, α-CD19-AF780, α-CD19-AF700, α-CD20-PO, α-CD25-PE-Cy7, α-CD40-APC, α-CD45-Biotin, Streptavidin-BV605, α-CD62L-ECD, α-CD69-APC-Cy7, α-CD80-FITC, α-CD83-Biotin, Streptavidin-PE-Cy7, α-CD86-PE-Cy7, α-CD86-PE, α-CD123-PE, α-CD154-PE, α-CD161-PE, α-CTLA4-PE-Cy7, α-FoxP3-AF488 (clone 259D), IgG1-isotype-AF488, α-ICOS (CD278)-PE, α-HLA-A2-PE, α-HLA-DR-PB, α-HLA-DR-PerCPCy5.5, α-PD1-APC, VISTA, co-stimulatory molecule OX40, CD137, and the like.

Any of a variety of antibodies can be used in the methods described herein, including, but nor limited to antibodies having high-affinity binding to PD-1 PD-L1, PD-L2, PD-L3, or PD-L4. Human mAbs (HuMAbs) that bind specifically to PD-1 (e.g., bind to human PD-1 and may cross-react with PD-1 from other species, such as cynomolgus monkey) with high affinity have been disclosed in U.S. Pat. No. 8,008,449, which is incorporated herein by reference for the antibodies described herein. HuMAbs that bind specifically to PD-L1 with high affinity have been disclosed in U.S. Pat. No. 7,943,743, which is incorporated herein by reference for the antibodies described herein. Other anti-PD-1 mAbs have been described in, for example, U.S. Pat. Nos. 6,808,710, 7,488,802 and 8,168,757, and PCT Publication No. WO 2012/145493, all of which are incorporated herein by reference for the antibodies described herein. Anti-PD-L1 mAbs have been described in, for example, U.S. Pat. Nos. 7,635,757 and 8,217,149, U.S. Publication No. 2009/0317368, and PCT Publication Nos. WO 2011/066389 and WO 2012/14549, all of which are incorporated herein by reference for the antibodies described herein.

In some embodiments, the anti-PD-1 HuMAbs can be selected from 17D8, 2D3, 4H1, 5C4 (also referred to herein as nivolumab), 4A1 1, 7D3 and 5F4, all of which are described in U.S. Pat. No. 8,008,449. In some embodiments, the anti-PD-1 HuMAbs can be selected from 3G10, 12A4 (also referred to herein as BMS-936559), 10A5, 5F8, 10H10, 1B12, 7H1, 1 1E6, 12B7, and 13G4, all of which are described in U.S. Pat. No. 7,943,743.

In certain embodiments the antibodies comprises antibodies that are approved for clinical use. Such antibodies include, but are not limited to antibodies that target PD-1 (e.g., Pembrolizumab (Keytruda), Nivolumab (Opdivo)), antibodies that target PD-L1 (e.g., Atezolizumab (Tecentriq), Avelumab (Bavencio), Durvalumab (Imfinzi), and the like), and/or antibodies that target CTLA-4 (e.g., Ipilimumab (Yervoy)).

The foregoing checkpoint inhibitors are illustrative and not limiting. Using the teaching provided herein numerous other checkpoint inhibitors can be used in conjunction with the delivery vehicles described herein.

Kits.

In certain embodiments, kits are provided containing reagents for the practice of any of the methods described herein. In certain embodiments the kit comprises a container containing an inhibitor of the indoleamine 2,3-dioxygenase (IDO) pathway (IDO inhibitor); and/or a container containing an agent that induces immunogenic cell death (ICD) (ICD-inducer). In certain embodiments the IDO inhibitor comprises an agent selected from the group consisting of 1-methyl-D-tryptophan (indoximod), 1-methyl-L-tryptophan, methylthiohydantoin-dl-tryptophan, Necrostatin-1, Ebselen, Pyridoxal Isonicotinoyl Hydrazone, Norharmane, CAY10581, 2-Benzyl-2-thiopseudourea hydrochloride, Norharmane hydrochloride, INCB024360, S-allyl-brassinin, S-benzyl-brassinin, 5-Bromo-brassinin, 4-phenylimidazole Exiguamine A, and NSC401366. In certain embodiments the IDO inhibitor comprises an agent shown in Table 3, supra. In certain embodiments the IDO inhibitor comprises indoximod. In certain embodiments the IDO inhibitor is conjugated to an agent that forms a vesicle. In certain embodiments the agent is selected from the group consisting of a lipid, PHGP, vitamin E, cholesterol, and a fatty acid. In certain embodiments the agent comprises a phospholipid. In certain embodiments the IDO inhibitor is IDO-PL.

In certain embodiments the ICD inducer comprises a chemotherapeutic agent selected from the group consisting of oxaliplatin, cisplatin, doxorubicin, epirubicin, idarubicin, mitoxantrone, anthracenedione, bleomycin, bortezomib, R2016, irinotecan and cyclophosphamide. In certain embodiments the ICD inducer comprises oxaliplatin. In certain embodiments the ICD inducer is a compound or a biological agent in Table 2.

In certain embodiments the kit contains both an IDO inhibitor and an ICD inducer. In certain embodiments the IDO inhibitor and the ICD inducer are in separate containers. In certain embodiments the IDO inhibitor and said ICD inducer are in the same container. In certain embodiments the IDO inhibitor and said ICD inducer are provided as a nanoparticle drug carrier (e.g., a drug delivery nanocarrier) as described herein.

In certain embodiments the kit contains an ICD inducer that comprise a nanomaterial or a formulation thereof (e.g., a sterile formulation). In certain embodiments the nanomaterial comprises a material selected form the group consisting of CuO, $Sb_2O_3$, ZnO, $TiO_2$, and graphene oxide.

In certain embodiments the kit comprises a container containing a nanocarrier (e.g., ICD/IDO silicasome, ICD/IDO lipid vesicle, ICD-inducing nanomaterial carrier, etc.) described herein.

Additionally, in certain embodiments, the kits can include instructional materials disclosing the means of the use of the ICD inducer to induce immunogenic death in cancer cells for vaccination, and/or the use of the ICD inducer and the IDO inhibitor as a cancer therapeutic for local administration, and/or the use of a drug-loaded drug delivery nanocarrier (e.g., LB-coated nanoparticle) or nanocarrier immunoconjugate as a therapeutic for a cancer (e.g., a pancreatic cancer, gastric cancer, cervical cancer, ovarian cancer, etc.).

In addition, the kits optionally include labeling and/or instructional materials providing directions (e.g., protocols) for the use of the materials described herein, e.g., alone or in combination for the treatment of various cancers. Instructional materials can also include recommended dosages, description(s) of counterindications, and the like.

While the instructional materials in the various kits typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

IDO Inhibitor Prodrugs

Indoleamine-2,3-dioxygenase (IDO) is an intracellular heme-containing enzyme that initiates the first and rate-limiting step of tryptophan degradation along the kynurenine pathway. In mammalian organisms, tryptophan is an essential amino acid for cell survival; it cannot be synthesized de novo. IDO was shown to be expressed in normal tissues such as the endothelial cells in the placenta and lung, the epithelial cells in the female genital tract, and the lymphoid tissues in mature dendritic cells. Munn et al. showed that IDO has a central role in preventing T cell-driven rejection of allogeneic fetuses during pregnancy as trophoblast expressing IDO was found to induce maternal tolerance to fetal allograft (see, e.g., Munn et al. (1998) *Science*, 281(5380): 1191-1193). This discovery broke ground for further research addressing the immunomodulatory potential of IDO, including the discovery of IDO inhibitor for cancer treatment. The immunosuppressive roles of IDO have also been investigated for elucidation of therapeutic targets in the management of many diseases including cancer (Gajewski et al. (2013) *Nature Immunol.* 14: 1014-1022; Moon et al. (2015) *J. ImmunoTherapy Cancer*, 3: 51).

Based on a summary of clinical trials (Vacchelli et al. (2014) *Oncoimmunology*, 3(10): e957994), we found that:
1) Use of indoximod as a standalone agent often fails to cause tumor eradication; and
2) Combination therapy, i.e. chemo+indoximod, showed promising results. This includes the use of an IDO inhibitor plus many standard chemoagents, such as MTX, paclitaxel, docetaxel, etc. In PDAC, a clinical trial using IDO inhibitor plus GEM and PTX is ongoing.

Synthesis of IDO Inhibitor Indoximod Prodrug

Indoximod is a potent IDO pathway inhibitor. It is currently used as its free form in NaOH solution and/or pellets in clinical trials. However, in order to achieve an effective therapeutic dose, extremely high concentrations of Indoximod are required to be used (e.g. oral formulation, 1200-2000 mg/day). We propose to use a bio-conjugation or supramolecular assembly approach to further improve the PK/PD, local retention and potency of Indoximod in vivo, either via local intratumoral injection or systemic IV injection.

Bio-Conjugation Approach

Indoximod has a functional carboxyl group (see, e.g., FIG. 2), that can be readily conjugated to other compounds containing a hydroxyl moiety. A few representative compounds are provided (see, e.g., FIG. 3). The resulting prodrugs can form nanovesicles in an aqueous solution at certain concentrations (e.g. >CMC) or be used as a component to coat MSNPs as described herein, leading to a variety of immunotherapy drug delivery nanocarrier(s) (e.g., LB-coated nanoparticle(s)). Since the resulting conjugates are amphipathic molecules, they are readily incorporated into lipid vesicles and can also self-assemble as micellar structures, both of which are pharmaceutically active.

In certain embodiments a little more complicated ester-mediated conjugation could include the use of linkers such as an HO—$(CH_2)_{n=2-5}$—OH as a linker in the reaction. The cases of oleic acid and docosahexaenoic acid (DHA) fall into this category (see, e.g., FIG. 4).

Supramolecular Approach:

It is possible to take advantage of the chemical structure of indoximod or other IDO inhibitors, allowing the supramolecular assembly of this compound onto a nanostructured surface mediated by individual or combined molecule-nanomaterial interactions, such as pi-pi stacking, electrostatic interactions, van der Waals' force and/or physical absorption. One example is graphene oxide, which is also an inducer of ICD in our HTS studies.

While the above-identified methods are illustrated with respect to indoximod, it will be recognized that these or similar methods can be utilized with numerous other IDO inhibitors (see, e.g., Table 3, above, and FIG. 2).

Example 2

Self-Asssembled Nanovesicles for the Co-Delivery of an IDO Pathway Inhibitor Prodrug and Remote Loading of an Immunogenic Cell Death Inducing Agent A potential limitation of the OX/IND-MSNP carrier is its relatively low loading capacity for Pt-based drugs, such as OX (i.e. <10% wt). Since Pt-drugs are coordination complex compounds, they are usually not suitable for remote loading by a proton gradient, such as has been reported for irinotecan encapsulation in LB-coated MSNPs (see, e.g., Liu et al. (2016) *ACS Nano*, 10: 2702-2715). We therefore developed new particle iterations capable of achieving a higher loading capacity for ICD-inducing chemo agents.

Synthesis of a DOX Nanovesicle Carrier that Co-Delivers IND-PL.

DOX is chosen to illustrate remote loading of IND-NVs based on its composition as a weak basic substance. Following its import into the vesicles, DOX typically precipitates as crystals, yielding a carrier that morphologically resembles the DOXIL® liposome. We consider the DOX/IND liposome or an MTX/IND liposome as leading carrier prototypes for initiating antitumor immunotherapy in settings such as breast cancer and other cancer types.

Synthesis of DOX/IND Nanovesicle:

The IND-Chol prodrug synthesis and preparation of liposomes comprising IND-Chol is described in Example 7. Using the IND-Chol liposome prodrug, a DOX/IND nanovesicle can be prepared as follows: 1) a total of 50 mg lipids of IND-Chol plus other vesicle-forming lipids (e.g., DPPC/Chol-IND/DPPG/DSPE-PEG (e.g., DSPE-PEG2k, DSPE-PEG5k, and the like), in certain embodiments at a molar ratio of ~40% (DPPC):~35% (Chol-IND):~20% DPPG:~5% DSPE-PEG) can be dissolved in 5 mL chloroform in a 50 mL round bottom glass flask. The solvent is evaporated under a rotatory vacuum to form a uniform thin lipid film, which is dried further under vacuum overnight. 2) The film is hydrated with 2 mL of ammonium sulfate (123 mM) and probe sonicated for 1 h, which is subsequently extruded 15 times through a Mini-Extruder (Avanti Polar Lipids), using a polycarbonate membrane with 100 nm pores (Avanti Polar Lipids) at 80° C. IND-NV size and morphology were assessed by dynamic light scattering and cryoEM, respectively. 3) Unincorporated ammonium sulfate can be removed by running through a PD-10 size exclusion column. 4) 6.4 mg of DOX.HCl (10 mg/mL) in DI water is incubated with the above prepared IND-NVs at 65° C. for 40 min. 5) The nanovesicles are fractionated across a PD-10 column, allowing the removal of free DOX. Their size and morphology can be assessed by dynamic light scattering, cryoEM and UPLC/MS-MS, respectively. The final product is was stored at 4° C. in the dark prior to biological testing.

Figure 5:
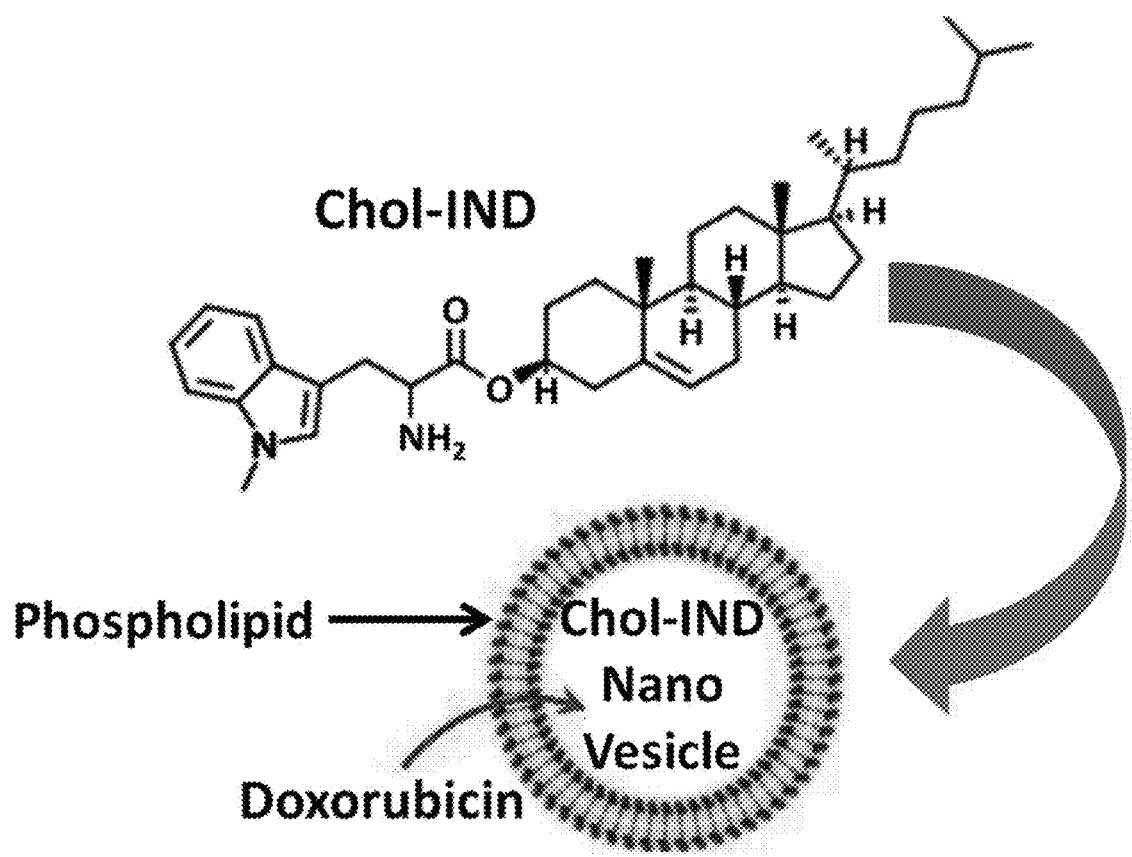
FIG. 5 shows construction of an IND nanovesicle by self-assembly of Chol-IND+Phospholipid.

The DOX/IND nanovesicle can be constructed by self-assembly of IND-Chol/LP (see, e.g., FIG. 5). The prodrug is amphipathic, allowing self-assembly into nanovesicles (IND-NV) in the presence of an aqueous biological buffer. Moreover, the entrapment of a protonating agent (such as ammonium sulfate) at the time of self-assembly, permits the nanovesicle to import DOX from the surrounding drug suspension. DOX can precipitate as crystals in the nanovesicle. This provides a nanocarrier that morphologically resembles the DOXIL® liposome.

Additional Possible Weak Base Laden Co-Delivery IND-NVs.

In addition to DOX loading into nanovesicles, there are other possible drugs that can be imported across the lipid bilayer of this carrier. These include, but are not limited to weak basic compounds with medicinal chemical features. Such compounds include, but are not limited to alkaloids (e.g. irinotecan, topotecan, 10-hydroxycamptothecin, belotecan, rubitecan, vinorelbine, LAQ824, vinblastine, vincristine, homoharringtonine, trabectedin), anthracyclines (e.g. doxorubicin, epirubicin, pirarubicin, daunorubicin, rubidomycin, valrubicin, amrubicin), alkaline anthracenediones (e.g. mitoxantrone), alkaline alkylating agents (e.g. cyclophosphamide, mechlorethamine, temozolomide), purine or pyrimidine derivatives (e.g. 5-fluorouracil, 5'-deoxy-5-fluorouridine, gemcitabine, capecitabine) and protein kinase inhibitors (e.g., pazopanib, enzastaurin, vandetanib erlotinib, dasatinib, nilotinib, sunitinib, osimertinib, palbociclib, ribociclib), etc.

Example 3

Doxorubicin is an ICD-Inducing Chemoagent in Breast Cancer Leading to Development of a Co-Delivery Liposome for Breast Cancer Nano-Immunotherapy by Contemporaneous Triggering of Immunogenic Cell Death and Restraining the IDO Pathway While treatment of patients with localized breast cancer (BC) has a survival rate of ~98%, the Breast Cancer Coalition has pointed out that there is marginal improvement on mortality rate since 1975 (DeSantis et al. (2017) *CA Cancer J Clin.* 67: 439-448). This is particularly true for metastatic disease, where none of the current treatments (e.g., radiation, chemotherapy, and estrogen blockers) are capable of eliminating BC once metastatic spread has taken place (Howlader et al. (eds). *SEER Cancer Statistics Review,* 1975-2010, Nat. Cancer Inst. Bethesda, Md., seer.cancer.gov/csr/1975_2010/, based on November 2012 SEER data submission, posted to the SEER web site, April 2013). Newfound optimism has emerged with the advent of cancer immunotherapy, where the power of T-cell immunity can be invoked to treat solid cancers, including breast cancer (Emens (2018) *Clin. Canc. Res.* 24: 511-520). This is best exemplified by the use of immune checkpoint blocking antibodies, which have changed the treatment landscape for melanoma and non-small cell lung cancer (NSCLC) (Id.). However, in spite of this accomplishment, the overall response rate is only 20-30%, without clear guidance to identify responders (see, e.g., Solinas et al. (2017) *ESMO Open,* 2: e000255).

The overarching challenge that we address to improve BC mortality is to improve the response rate to immunotherapy through the delivery of immunogenic cell death (ICD) stimuli by nanocarriers (see, e.g., FIG. 1). Our data show reproducible induction of tumor infiltrating lymphocytes (TILs) in an orthotopic BC animal model by an ICD-inducing nanocarrier. The advantage of using a nanocarrier to deliver ICD-inducing chemotherapy to the cancer site lies in its improved pharmacokinetics, and decreased toxicity of the drugs. This will eliminate the guesswork to find responders, who are postulated to be patients with a high mutational load, in whom non-synonymous mutations generate a "hot" immune environment (TME) (Nagarsheth et al. (2017) *Nat. Rev. Immunol.* 17: 559). This facilitates boosting of the immune response by antibodies that block CTLA-4, PD-1 and, PD-L1 receptors.

We propose that ICD will allow more predictable induction of an immune replete status to allow receptor-mediated blockade or perturbation of other immune surveillance pathways to induce durable anti-tumor immunity, which also takes care of metastases. As such, ICD could strengthen the effect of immune checkpoint blocking antibodies as well as indoleamine 2,3-dioxygenase (IDO) inhibitors that interfere in this metabolic immune surveillance pathway.

It is believed that a doxorubicin (DOX) encapsulating nanocarrier provides a more potent ICD stimulus than the free drug, and can do so synergistically with a small molecule inhibitor (indoximod) of the IDO-1 pathway. The nanocarrier is capable of facilitating this task by improving the PK of DOX and indoximod (IND) at the tumor site. This provides us with a first generation nanocarrier providing an ICD stimulus and an IDO inhibitor as a promising synergistic immunotherapy platform for BC, including triple negative BC (TNBC) (most responsive to immune checkpoint inhibitors) as well as ER-positive tumors (numerically the largest BC subtype responsible for mortality).

Doxorubicin (DOX) and Mitoxantrone (MTX) are ICD-Inducing Chemoagents in Breast Cancer In addition to improved intratumor drug content, we envisage the use of nanocarriers to deliver chemotherapy with a view to also implement breast cancer (BC) immunotherapy. One possible approach is to use chemotherapy to induce immunogenic cell death or ICD. Consensus guidelines have been developed is to identify drug and chemo agents that can trigger ICD in vitro and in vivo (Kepp et al. (2014) *OncoImmunol.* 3: e955691). This allowed us to identify doxorubicin (DOX) and MTX as potent ICD inducing chemotherapeutic agents for BC immunotherapy, using 4T1 cells in a syngeneic BALB/c vaccination model. Multi-parameter cellular screening demonstrated that DOX and MTX can induce calreticulin (CRT expression), and release of HMGB1 during nuclear disintegration of cancer cells. In addition to DOX and MTX, we also identified paclitaxel (PTX) as an ICD inducer in 4T1 cells. In contrast, cisplatin (Cis) and 5-FU failed to induce the same effect.

In certain embodiments the ability of the DOX- or PTX-treated cells to significantly suppress tumor growth at the challenge site is compared to the negative control. Additional in vitro ICD profiling (HMGB1 and ATP release as well as CRT cell surface visualization) has been determined. In certain embodiments tumors are excised from the mice from each group and the averaged tumor weight determined. Additionally, bioluminescence visualization of 4T1 tumor development in the vaccination experiment can be performed using IVIS imaging at different time points. Mouse body weight monitoring can be provided.

Synthesis of a DOXIL® Look-Like DOX-Laden IND-Liposome (DOX/IND-Liposome).

In certain embodiments synthesis of a DOXIL® look-like DOX-laden IND-Liposome (DOX/IND-Liposome) is contemplated. DOXIL® is a PEGylated liposome for the delivery of DOX and has been in the marketplace for two decades. Encapsulated DOX delivery holds significant advantages over free DOX in patients with Kaposi's sarcoma, ovarian carcinoma and BC (Barenholz et al. (2012) *J. Control. Rel.* 160: 117-134). This advantage is in part derived from the improved PK of DOX at the tumor site as well as a reduction in cardiovascular and systemic DOX toxicity (Id.). DOX is loaded into DOXIL® by using a trapping agent, which generates a proton gradient that allows the import of weak-basic DOX through the liposomal lipid bilayer. One potential downside of DOXIL® is the preferential concentration of DOX in the skin, which can result in the hand-foot syndrome (redness and inflammation) (Id.). Clinical guidelines to avoid this side effect by adapting the DOXIL® dosing schedule exist. Against this background of this FDA-approved technology, we asked whether it was possible to develop a liposome for dual DOX and indoximod (IND) delivery. In addition to the improving the PK of DOX, we hypothesized that we would also be able to improve the circulatory half-life ($T_{1/2}$) and tumor levels of indoximod (IND).

This challenge can be met by using bio-conjugation chemistry to synthesize a cholesterol-conjugated IND prodrug (IND-Chol). IND (D-1-methyl tryptophan or D-1MT) can be covalently linked to cholesterol which is then incorporated into a liposome.

Briefly, to construct the DOX/IND-liposome, a classic DOX remote loading strategy can be employed using ammonium sulfate as gradient. Following the evaporation of organic solvent that contains phospholipids, IND-Cholesterol, and DSPE-PEG$_{2K}$, a uniform lipid film is formed along the bottom of the round flask. A protonating agent $(NH_4)_2SO_4$ can be added into the flask afterwards, followed by probe sonication and PD-10 desalting column purification to render the pure $(NH_4)_2SO_4$-loaded IND-Liposome. Then DOX.HCl solution is incubated with $(NH_4)_2SO_4$-loaded IND-Liposome at 65° C. for the active loading of DOX into the hydrophilic pocket of IND-Liposome.

DOX, a weak basic molecule, can easily be loaded into the liposome by using ammonium sulfate as a protonating agent in the self-assembly solution. The proton gradient allows amphiphilic DOX to be imported across the liposomal membrane. This provides dual drug delivering liposome that visually resembles DOXIL®. To determine the optimal DOX/IND-Liposome, a mixture of lipids containing varied molar ratios of IND-Chol, PL, and DSPE-PEG$_{2K}$ can be tested when encapsulating a fixed amount of DOX.

Example 4

Pancreas Cancer Immunotherapy Using Synergistic Immunogenic Cell Death and Immunomodulatory Responses While chemotherapy delivery by nanocarriers has modestly improved the survival prospects of pancreatic ductal adenocarcinoma (PDAC), additional engagement of the immune response could be game changing. We describe a nano-enabled approach for accomplishing robust anti-PDAC immunity in syngeneic mice through the induction of immunogenic cell death (ICD) as well as interfering in the immunosuppressive indoleamine 2,3-dioxygenase (IDO) pathway (see, e.g., FIG. 1).

This can be accomplished by conjugating the IDO inhibitor, indoximod (IND), to Cholesterol (Chol) or another component of a lipid bilayer that allows the prodrug to self-assemble into nanovesicles (IND-NV) or to be incorporated into a lipid bilayer that encapsulates mesoporous silica nanoparticles (MSNP). The porous MSNP interior allows contemporaneous delivery of the ICD-inducing chemotherapeutic agent, oxaliplatin (OX). It is believed that IND-NV plus free OX or OX/IND-MSNP can induce effective innate and adaptive anti-PDAC immunity when used in a vaccination approach, direct tumor injection or intravenous biodistribution to an orthotopic PDAC site. It is believed that significant tumor reduction or eradication cajn accomplished by recruited cytotoxic T lymphocytes, concomitant with downregulation of FoxP3$^+$ T-cells.

In this Example, we report the design of nanocarriers to facilitate the induction of ICD and interference in the Kynurenin pathway, either through the development of nanovesicle that delivers an IND pro-drug or a lipid-coated MSNP, that co-delivers cholesterol-conjugated IND plus OX. It is believed that the synergy between ICD and interference in the IDO pathway can boost innate and adaptive immunity in the syngeneic animal KPC model. It is believed that this leads to effective killing of pancreatic cancer cells by CD8$^+$ cytotoxic T cells at the tumor site, as well as interfering in metastatic spread. The cytotoxic response can be accompanied by disappearance of Tregs at the tumor site. The systemic immune response could also be adoptively transferred to non-immune animals.

Results

Oxaliplatin-Induced ICD Provides a Successful Vaccination Approach for PDAC

ICD is a modified form of apoptosis that can be used to initiate an effective immune response against endogenous tumor antigens (Kroemer et al. (2013) *Ann. Rev. Immunol.*, 31: 51-72).[1] Since this model was 1$^{st}$ proposed against the backdrop of a select number of cancer drugs (Id.), we focused on the use of OX, because it is FDA-approved for PDAC treatment. As a component of the FOLFIRINOX regimen (in combination with irinotecan, 5-FU and folinic acid). For comparison, we also included the anthracycline antibiotic, DOX, as a positive control and cisplatin (Cis) as a negative control for the screening of PDAC cell lines, using cell surface CRT expression (Obeid et al. (2017) *Nat. Med.*, 13(1): 54-61; Casares et al. (2005) *J. Exp. Med.* 202(12): 1691-1701; Fucikova et al. (2011) *Canc. Res.* 71(14): 4821-4833; Tesniere et al. (2010) *Oncogene,* 29(4): 482-491; Galluzzi et al. (2012) *Oncogene,* 31(15): 1869-1883; Martins et al. (2011) *Oncogene,* 30(10): 1147-1158). CRT is an endoplasmic reticulum (ER) stress protein that translocates to the surface membrane of cancer cells undergoing ICD (Obeid et al. (2017) *Nat. Med.*, 13(1): 54-61; Fucikova et al. (2011) *Canc. Res.* 71(14): 4821-4833). Screening for CRT expression was performed in murine KPC cells, derived from a spontaneous tumor that developed in a transgenic Kras$^{LSL-G12D/+}$/Trp53$^{LSL-R172H/+}$/Pdx-1-Cre (KPC) mouse (Hingorani et al. (2005) *Cancer cell,* 7(5): 469-483).

The KPC model recapitulates many of disease features of human PDAC, including oncogene expression, development of a robust cancer stroma, extensive local invasion and distant metastases (Tones et al. (2013) *PloS one,* 8(11): e80580; Tseng et al. (2010) *Clin. Canc. Res.* 16(14): 3684-3695). DOX and OX and activated DOX induced the ICD marker CRT in cultured KPC pancreatic cancer cells (FIG. 6, panel A). Similarly, in the presence of DOX, OX, and activated DOX (a.k.a. DACHPt) HMGB1 release was increased (FIG. 6, panel A).

Animal experiments were performed using two rounds of vaccination one week apart, followed by injecting live KPC cells SC on the contralateral side (FIG. 6, panel B). Tumors were collected on day 26 for size measurement and IHC analysis. KPC tumor size showed significant reduction on treatment with DOX, OX, and activated DOX (FIG. 6, panel C).

FIG. 6, panel D shows explanted tumors at the contralateral side. Spaghetti curves show a decrease in KPC tumor growth in the contralateral flank in animals treated with DOX, OX, and activated DOX (6, panel E).

Tumor collection was performed after euthanizing the animals to conduct IHC. IHC staining of CD8 and Foxp3 T cells was used to calculate CD8/FoxP3 T cell ratio in each group (see, e.g., FIG. 6, panel F).

Discussion

PDAC is an often-fatal and notoriously treatment-resistant disease, in desperate need of new treatment approaches for dealing with the primary tumor growth as well as metastatic spread. We demonstrate a first treatment modality to generate an anti-PDAC response, premised on the ability of OX to induce ICD. ICD is responsible for enhanced tumor antigen presentation as well as providing stimulatory effects to the participating DCs. This triggers the activation of cytotoxic T cells and anti-PDAC immunity that was synergistically enhanced by an intervention in the IDO pathway. The first treatment modality comprises a subcutaneous vaccination approach that utilizes ex vivo induction of ICD by OX in a KPC cell line, it is sufficient to a generate systemic immune response that can interfere with tumor growth at a remote site as well as allowing adoptive transfer to non-immune animals.

In view of these results it is believed that two additional treatment modalities are available. The second treatment modality involves local injection of OX plus an IND-nanovesicle (e.g., and IND-Chol nanovesicle) to induce the recruitment of cytotoxic $CD8^+$ lymphocytes, depletion of Tregs, reversal of the $CD8^+/Foxp3^+$ ratio, cytotoxic tumor killing, and tumor shrinkage at the local injection site. It is believed these adaptive immune responses are accompanied by boosting of the innate immune system, as reflected by CRT and HMGB1 expression, as well as the activation of a DC population, particularly well-suited for generating cytotoxic T cell responses. The $3^{rd}$ treatment approach combines OX and an IND-nanovesicle (e.g., and IND-Chol nanovesicle) into a single MSNP-based nanocarrier, that allows systemic biodistribution and drug delivery to orthotopic KPC tumor sites. It is believed the dual delivery approach can achieved synergistic enhancement of adaptive and innate anti-PDAC immunity, leading to a significant improvement in animal survival.

Our proposed nano-enabled approach for boosting immunotherapy offers distinct advantages over current immunotherapy strategies for PDAC, including peptide and protein vaccines (e.g., mutant Kras, survivin, vascular endothelial growth factor receptor, gastrin and heat shock proteins) (Paniccia et al. (2015) *Chinese J. Canc. Res.*, 27(4): 376-391), whole-cell vaccination approaches (e.g., PDAC cell lines engineered to express GM-CSF)[18], dendritic cell vaccines (Koido et al. (2014) *Clin. Canc. Res.*, 20(16): 4228-4239), microorganisms (e.g., expression of antigenic peptides by vaccinia virus or heat-killed *Mycobacterium obuense*) (Strug et al. (2008) *J. Proteome Res.*, 7(7): 2703-2711) and immune checkpoint blockade (e.g., anti-CTLA-4 or anti-PD1 or monoclonal antibodies) (McCormick et al. (2016) *Hum. Vacc. Immunother.*, 12(3): 563-575). While most of these approaches rely on select antigens chosen from the large repertoire of potential immunogenic PDAC components, the reality is that there is a dynamic interplay between the tumor and the immune system, which could render the use of specific antigens redundant, including through the process of immune editing or the display of T cell antigen receptors (TCR) of sub-optimal affinity or on/off rates (Dunn et al. (2004) *Ann. Rev. Immunol.* 22: 329-360). In contrast, the use of ICD prepares the dying cancer cells for uptake and processing by local APCs, with the possibility that the full complement of mutant or neo-antigens can participate in dynamically fashion in T cell selection, allowing effective TCR proofreading for immune activation. This allows the cognitive immune system to adapt to an array of continuously evolving tumor antigens rather than restricting the immune response to selected antigens.

The idea that ICD could be advantageous to mounting an anti-PDAC immune response is reflected by studies employing the whole cell vaccine, Algenpantucel-L; this vaccine is comprised of two irradiated PDAC cells, genetically engineered to express the murine enzyme, α (1, 3)-galactosyl-transferase (αGT) (McCormick et al. (2016) *Hum. Vacc. Immunother.*, 12(3): 563-575). αGT is responsible for the synthesis of the αGal epitope, e.g., in normal gut flora. This immune challenge leads to a constitutive anti-αGal response in the human host, in the form of a high titer of αGT antibodies. Thus, vaccination with the αGal-expressing cell lines leads to the induction of These antibodies lead to a hyper-acute immune response upon vaccination with Algenpantucel-L. The death of these cell lines leads to CRT-mediated tumor cell uptake and processing by DCs, which also receive adjuvant input in subsequent phases of tumor cell death (Obeid et al. (2017) *Nat. Med.*, 13(1): 54-61; Tesniere et al. (2010) *Oncogene*, 29(4): 482-491). Noteworthy, data from a phase II clinical trial, using the αGal vaccine, have demonstrated the ability to induce a high titer of anti-CRT antibodies, which correlates with increased survival in PDAC patients (Rossi et al. (2014) *J. Clin. Oncol.* 32(5s): Suppl: abstr 3029).

Instead of using genetically engineered PDAC cells, we propose that ICD induction by a an already FDA-approved chemotherapeutic agent (such as OX or irinotecan) constitutes a more effective means to achieve anti-PDAC immunity because it targets autologous cancer cells rather than preselected PC cell lines (which may not dynamically display the full complement of tumor antigens). We also propose that it may be easier to adjust the dosimetry of chemotherapy-induced ICD rather than relying on a hyper-acute immune response that may not always induce ICD. Good experimental data have recently been collected to show the feasibility of using chemotherapy to induce ICD in lung or colon carcinoma, with the ability to amplify these responses by immune checkpoint blockade (Pfirschke et al. (2016) *Immunity*, 44(2): 343-354; Rossi et al. (2014) *J. Clin. Oncol.* 32(5s): Suppl: abstr 3029). Also, for colon cancer it has been demonstrated that core-shell nanoparticles, comprised of an OX core and a photosensitizing pyrolipid conjugate in the shell, can synergize to deliver an ICD response, which may be useful for a vaccination approach or an abscopal effect (He et al. (2016) *Nat. Comm.* 7: 12499).

It is believed that the third approach described herein is the first to use an ICD approach in PDAC through the use of nanocarriers. Our work also introduces the novel principle of using a nanocarrier to simultaneously induce ICD and immunomodulation. OX is an integral component of the FOLFIRINOX regimen, and constitutes one of a short list of chemotherapeutics capable of inducing ICD, other than anthracyclines (Kepp et al. (2014) *Oncatarget*, 5(14): 5190-5191). The unique ability of these chemotherapeutics to induce ICD is dependent on their ability to initiate a sequence of events that differ from regular apoptosis. Integral to ICD, is triggering of ER stress, which leads to CRT expression at the pre-mortem stage (Id.). CRT expression serves as an "eat me" signal for antigen-presenting DCs, which also receive adjuvant signals at subsequent stages of ICD by the release of the nuclear protein, HMGB1, and ATP from the dying tumor cells (Obeid et al. (2017) *Nat. Med.,* 13(1): 54-61; Kroemer et al. (2013) *Ann. Rev. Immunol.,* 31: 51-72). CRT and HMGB-1 interacts with CD91 and TLR4, respectively.

Immune activation in the PDAC microenvironment has to overcome a number of immune suppressive mechanisms, including the presence of $CD4^+/Foxp3^+$ Tregs, secretion of anti-inflammatory cytokines, expression of checkpoint inhibitors and overproduction of IDO. While our results indicate that OX alone is capable of increasing the $CD8^+/Foxp3^+$ ratio at local and systemic tumor sites, it is believed the co-administration of a vesicle-conjugated IDO inhibitor, (e.g., IND-Chol liposome) can significantly enhance this integrative response parameter, which reflects the transition from an immune suppressive to an immune stimulatory TME. This synergy reflects the importance of the IDO metabolic effect in the TME, in much the same way as regional expression of this enzyme plays an immune surveillance role in the placenta to protect the fetus.

IDO inhibitors are currently undergoing clinical trials in several cancer types, including breast, prostate, melanoma, brain and pancreas. This includes the use of IND together with gemcitabine, nab-paclitaxel and anti-PDL1 antibody. [31] It is believed a major advantage of our nanocarrier approach is the improvement of the PK and intratumoral accumulation of IND-Chol (or other IND-prodrug). Free IND is relatively water insoluble and has unfavorable PK characteristics. In contrast, it is believed an IND-NV can significantly increase the uptake and release of IND in tumor cells which translates to a more robust interference in IDO-mediated immune suppressive signaling pathways in vitro and in vivo. In addition to improving the circulatory $t_{1/2}$ and PK of IND, it is believed the dual delivery carrier can also improve the PK of OX (FIG. 7, panel c). It is also believed that the harmonized PK and contemporaneous delivery can further contribute to the in vivo synergy of the OX/IND-MSNP at the tumor site.

How can this discovery be practically implemented to provide PDAC immunotherapy in the clinic? Based on our animal studies, possible ways to improve immunotherapy in patients could include: (i) tumor cell harvesting from resected cancer tissues during surgery, with the possibility of developing a cell culture-based vaccine approach; (ii) local injection of OX and IND-Chol (or other IND conjugated prodrug) into the tumor under remote guidance, during collection of biopsies or direct visualization during surgery; (iii) systemic administration of one or a combination of treatment modalities, which may include the use of free drugs, IND-NV or the dual-delivery carrier. In addition, it is also possible to enhance treatment efficacy by nanomaterials that exhibit intrinsic nanoscale properties and functions that lead to sequential induction of ER stress, ICD, autophagy and the release of adjuvants. It is also possible to use nanocarriers to deliver other FDA-approved drugs (e.g., cardiac glycosides, GADD34/PP1 inhibitors, $Ca^{2+}$-activated K-channel agonists, poly-PC, etc.)[14] to achieve ICD, individually or in combination with chemotherapeutics or ICD-inducing nanoparticles. Another approach could be to combine chemotherapy and IND delivering nanoparticles with immune checkpoint blockers, irradiation, photodynamic therapy or cytotoxic viruses to achieve additional immune response enhancement. The same principles could also apply to the treatment of a host of other cancers.

Example 5

Nanomaterial ICD Inducers

A number of immunogenic cell death (ICD) inducers are known to those of skill in the art. Illustrative ICD inducers include, but are not limited to oxaliplatin, anthracenedione, bleomycin, bortezomib, cisplatin, daunorubicin, docetaxel, doxorubicin, doxorubicin, epirubicin, idarubicin, mitoxanthrone, oxaliplatin, paclitaxel, R2016, irinotecan and cyclophosphamide (see, e.g., Moon et al. (2015) *J. Immuno-Therapy Cancer,* 3: 51; Bezu et al. (2015) Front. Immunol., 6:187).

Use of Nanoparticles for the Induction of Immunogenic Cell Death.

The principles according to which various drugs listed are capable of inducing immunogenic cell death is the induction of an apoptosis-like cell death, which is accompanied by an early cell stress response and effects on autophagy. This combination of cell stress with apoptosis (which is generally non-immunogenic), leads to a cell death process where there is an early expression of the cell stress response marker, calreticulum, which serves as an "eat me" signal for dendritic cells. This changes the response from non-immunogenic to immunogenic, further assisted by the release of HMGB1 from the nucleus and ATP from the endoplasmic reticulum, which serves as immune adjuvants that stimulate the TLR4 and pure magic receptors, respectively.

Through high throughput screening discovery aimed at understanding the hazard and safety of a vase number of nanomaterials in our nanomaterial safety laboratory, have taught us important lessons about nanomaterial physicochemical properties that can trigger cell death response pathways. These include nanomaterial properties (e.g., from transition metal oxides, rare earth oxides, graphene oxide) that induce oxidative stress, which can induce mitochondrial triggering and the initiation of apoptosis. Another example are rare earth oxide nanoparticles that can trigger a cell death response pathway by triggering lysosomal damage and interference in autophagy flux. These particles can induce cellular pyroptosis, which is a different form of inflammatory cell death. There are also nanoparticles such as fumed silica that could trigger cell death through disruption of the surface membrane. We used our nanomaterial libraries, to screen for materials that can induce immunogenic cell death, which can be assayed by following calreticulin (CRT) expression, HMGB1 release etc.

FIG. 33 shows the results of screening of nanomaterials (NMs) for induced immunogenic cell death (ICD) in KPC pancreatic cancer cell after 24 h treatment with engineered nanoparticles. Calreticulin (CRT), one of the hallmarks dictating ICD, is translocated onto the cell surface membrane from endoplasmic reticulum following ICD inducer treatment. Flow cytometry analysis was performed to quantitatively measure the induction of CRT level compared to control group. This suggested a highly strong CRT induction effects (more potent than OX chemo) by nano-sized Ag, Cu, $SiO_2$, $V_2O_5$, ZnO, graphene, and the like. Illustrative nanomaterials believed to induce immunogenic cell death include, but are not limited to $Al_2O_3$, $CeO_2$, $CoO$, $Co_3O_4$, $Cr_2O_3$, $CuO$, $Dy_2O_3$, $Er_2O_3$, $Eu_2O_3$, $Fe_2O_3$, $Fe_3O_4$, $Gd_2O_3$, $HfO_2$, $Ln_2O_3$, $La_2O_3$, $Mn_2O_3$, $Nd_2O_3$, $NiO$, $Ni_2O_3$, $SiO_2$, $Sm_2O_3$, $SnO_2$, $TiO_2$, $WO_3$, $Y_2O_3$, $Yb_2O_3$, $ZnO$, $ZrO_2$, AP-WMCNT, PF108-MWCNT, COOH-MWCNT, GO-S, GO-L, and the like.

FIG. 33 shows the results of vaccination experiment using metal and metal oxide. Animal were treated using 2 rounds of vaccination (dying KPC cells treated with metal oxide nanoparticles) one week apart, followed by injecting live KPC cells SC on the contralateral side. FIG. 33, panel A, shows spaghetti curves to show KPC tumor growth in the contralateral flank. FIG. 33, panel B, shows percent CRT.

Example 6

Regarding the transition from lab scale synthesis to industrial scale production of lysolipid-conjugated 1-MT (either D- or L-form), we have conceptualized a total synthesis approach as a more economic approach for prodrug synthesis. This results in better scalability, reduced cost by using more economical synthetic building blocks, reduction of the number of potential side reactions that provides improved yield, as well as better-quality control. By using the total synthesis approach, it is possible to adjust the position of the drug (1-MT) conjugation to the glycerol backbone of the phospholipid or other lipid bilayer component (e.g., cholesterol).

In addition, we further expanded the prodrug conjugation strategies from lysolipid conjugation (saturated and non-saturated lipid with various chain length) to fatty acid (both saturated and non-saturated lipid with various chain length) as well as cholesterol conjugations (via ester or carbamate or amide conjugations). These are known excipients commonly being used in liposomal formulations (US FDA approved pharmaceutical excipient), and other nano-formulations, e.g. emulsions, micelles, polymers, hydrogels, polymersomes, solid lipid nanoparticles, PLGA±PEG nanoparticles/nanocapsules, and other lipid, amphiphilic, hydrophilic/hydrophobic formulation blends (see, e.g., FIGS. 23-27).

1. Total Synthesis of Lipid-Conjugated 1-MT

The lysolipid (single chain phosphatidylcholine, a.k.a. LysoPC) conjugated 1-MT is essentially a conjugation of 4 building blocks: i) the drug (1-MT), ii) a glycerol backbone, iii) a fatty acid lipid chain, and iv) a phosphocholine head group. The following idealized example can be used for block-by-block assembly of 1-MT, glycerol, fatty acid, and phosphocholine, wherein the order of the building blocks can be swapped around if needed. The following idealized example consists of six synthesis steps, linking together the key building blocks. The sequence of procedures could be carried out commercially or synthesized in-house, using the most economic acquisition of the required starting materials as needed. Through the use of the full synthetic approach, one is able to obtain the desired molecule (e.g., "6c", shown in FIG. 11, which is the 16:0 LysoPC-indoximod (IND-PL); this is the material tested in our previous disclosure and patent (PCT/US2018/033265). With the invention of a total synthetic approach, this strategy allows the design and construction of a series of conjugations that can be used for design of indoximod prodrugs as described below.

Stage I

In brief, the first stage of the total synthesis starts from the protection of the amine (—NH2) group of the 1-(D/L)-MT using di-tert-butyl decarbonate ($Boc_2O$) or other amine protection groups (e.g. fluorenylmethyloxycarbonyl chloride (Fmoc-Cl)) to obtain Boc-1MT (or Fmoc-1MT). The amine protection avoids self-reaction when conjugating to other building blocks via ester bonds (1-MT can undergo amidation to form amide bond between to —NH2 and —COOH of two 1-MT molecules). $Boc_2O$ protection was shown in the following example, yielding compound (1) (FIG. 9, Stage I).

Stage II—a/b

Figure 9:
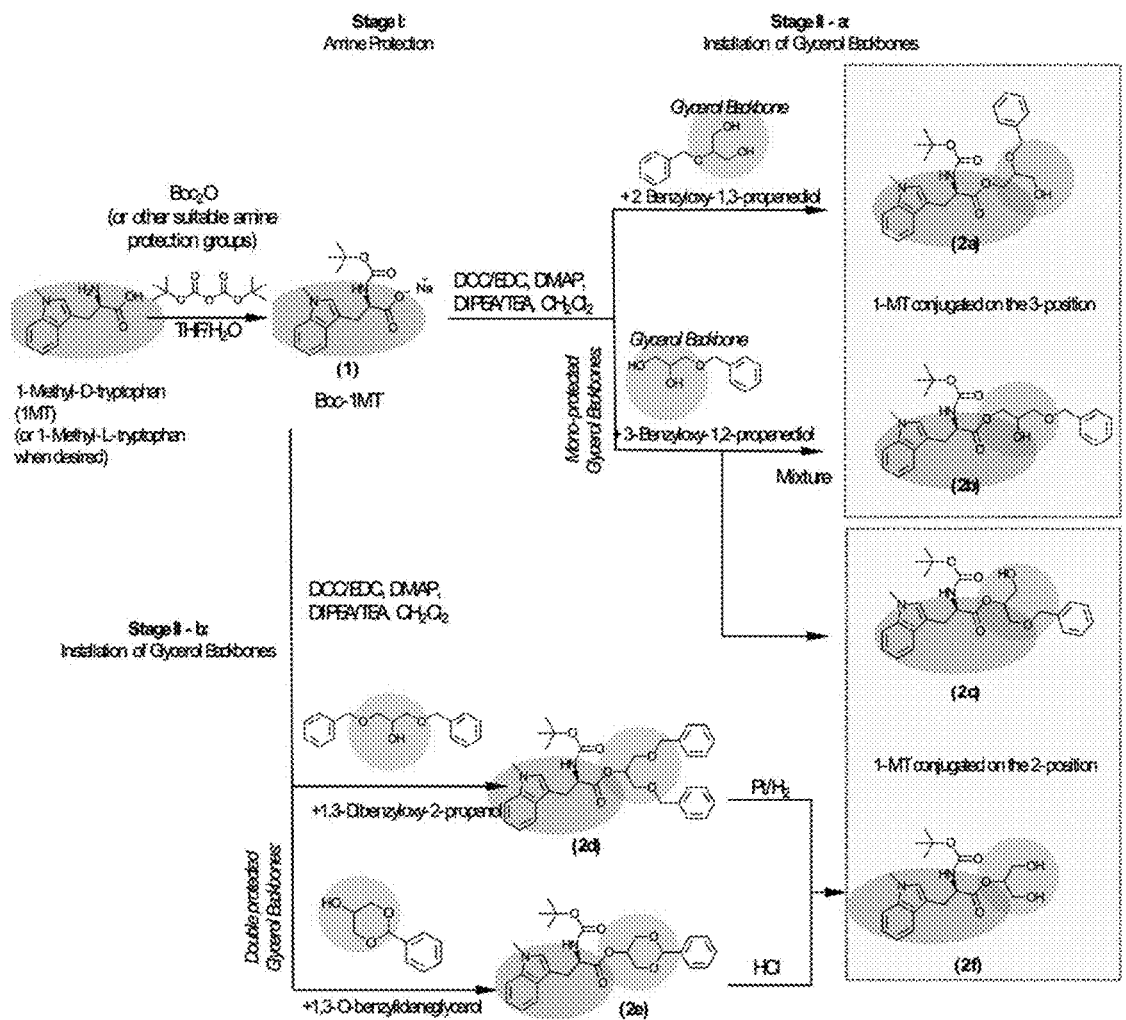
FIG. 9 illustrates synthesis of lysolipid conjugated 1-MT prodrugs: Stage I-II.

The second stage of the synthesis is to conjugate compound (1) with a glycerol building block via Steglich esterification reaction (FIG. 9). In the approach of Stage II—a, mono-hydroxyl protected glycerol, e.g. 2 Benzyloxy-1,3-propanediol and 3-Benzyloxy-1,2-propanediol were used yielding compound (2a) and compound (2b/2c) mixture, respectively. In the approach of Stage II—b, dual-hydroxyl protected glycerol, e.g. 1,3-Dibenzyloxy-2-propanol and 1,3-O-benzylideneglycerol were used, both lead to compound (2f).

Common alcohol protecting groups, e.g. benzyloxy or suitable alternatives can be used when desired. Double-(hydroxyl) protected glycerol via the formation of isopropylidene acetal (e.g. solketal), or 1,3-O-benzylidene, or mono-choloro substituted double-hydroxyl protected glycerol (e.g. 4-chloromethyl-2,2-dimethyl-1,3-dioxolane) can also be used for sequential lipid prodrug conjugation through similar approaches.

Stage III-IV

Figure 10:
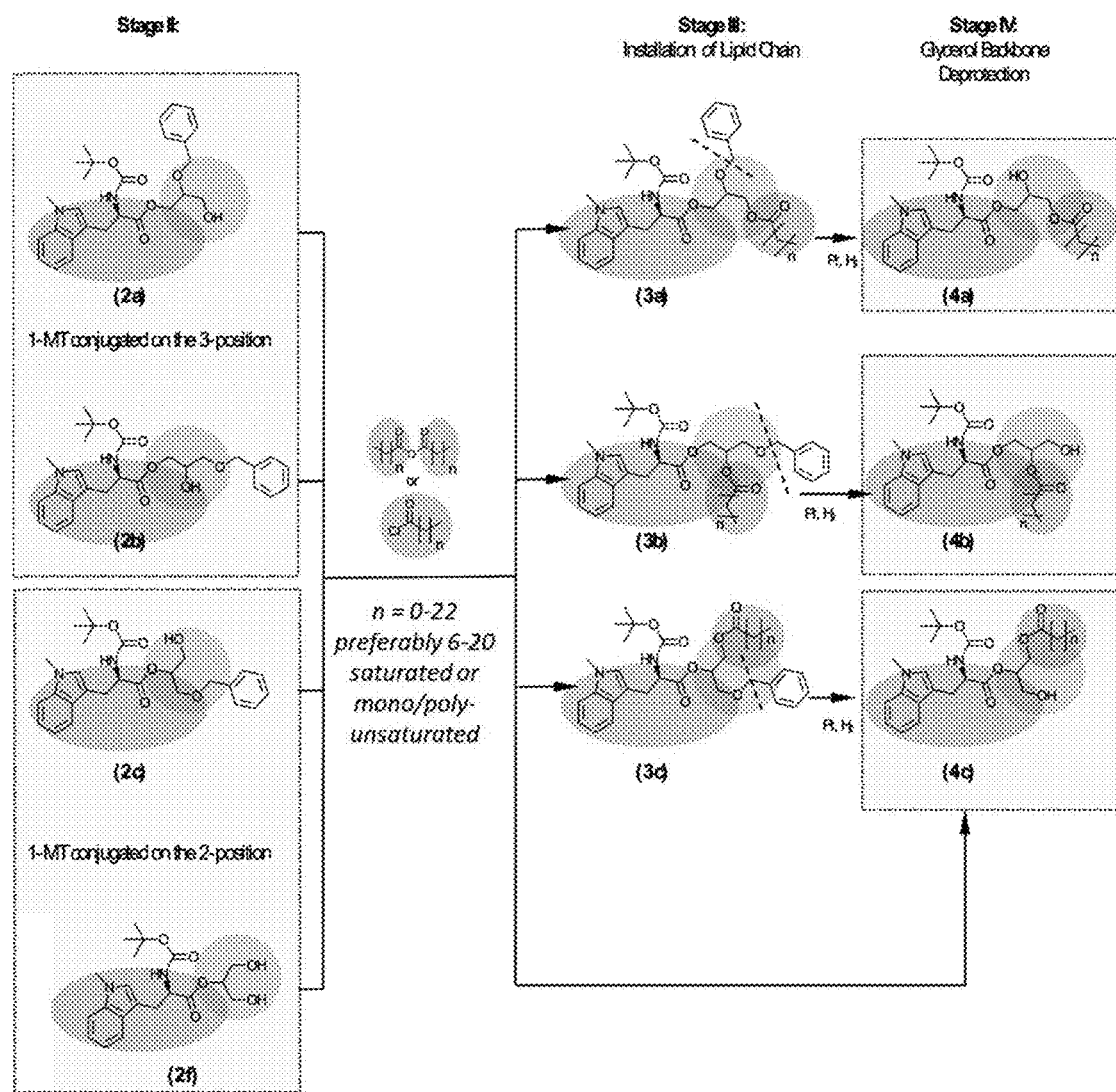
FIG. 10 illustrates synthesis of lysolipid conjugated 1-MT prodrugs: Stage III-IV.

The next stage of the synthesis aims for the installation of a lipid (fatty acid) chain on to the 1-MT-conjugated glycerol backbone (Stage II compounds). This was achieved via a nucleophilic addition/elimination reaction between the alcohol (hydroxyl group from the glyceryl) and an acyl chloride yielding an ester, or can be achieved by using an acid anhydride. The acyl chloride used here is a fatty acid chloride, either saturated fatty acid chlorides with a general formula of $CH3(CH2)nCOCl$, n=0-22, e.g., butyryl/valeroyl/hexanoyl/heptanoyl/octanoyl/pelargonic/caprylic/ . . . stearic chloride, or non-saturated fatty acid chloride, e.g. oleic chloride. The fatty acid chloride equivalent version of fatty acid anhydride could also be used as a source of reactive acyl groups. Once the fatty acid chain was installed on compound (2a), (2b), and (2c), yielding compound (3a), (3b), and (3c), the glycerol was deprotected (benzyloxy removal) to free up the third conjugation site of the glycerol backbone, yielding compound (4a), (4b), and 4(c), respectively. (FIG. 10). Compound (2f) will generate compound (4c) directly the glycerol backbone was deprotected in Stage II—b.

Stage V-VI

Figure 11:
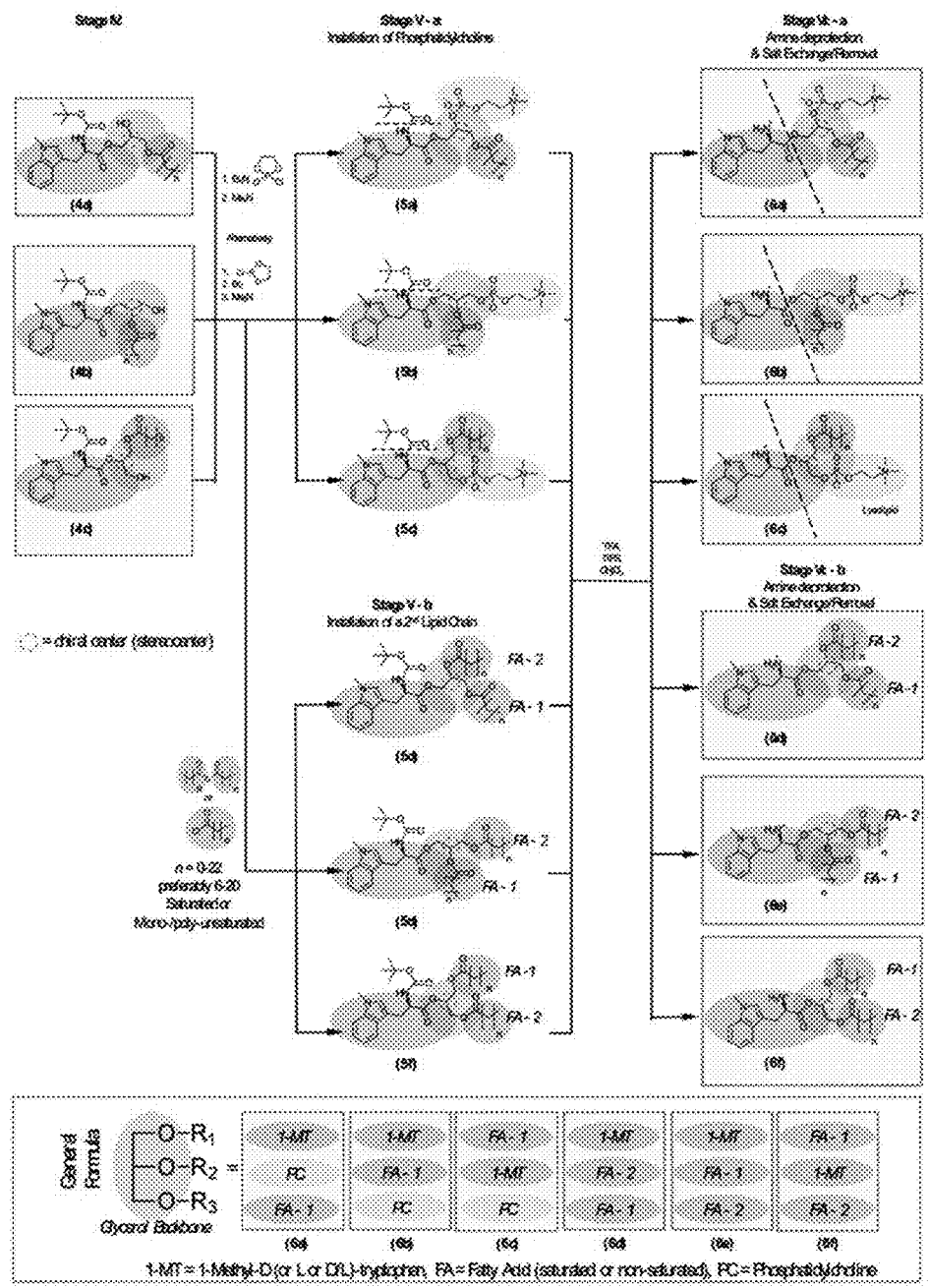
FIG. 11 illustrates synthesis of lysolipid conjugated 1-MT prodrugs: Stage V-VI. Through the use of the full synthetic approach, one should be able to obtain 16:0 LysoPC-indoximod (IND-PL) (see box 6c) that was tested in our previous studies described in PCT Publication No: WO/2018/213631 (PCT/US2018/033265). Because we now disclosed a total synthetic approach, this strategy has opened up the whole library for all other similar conjugations, which have also been delineated as below.

Stage V focuses on two synthesis options: Stage V—a, to install a phosphatidylcholine head group onto the 1MT conjugated glycerol backbone yielding lyso-phosphatidylcholine (LysoPC) derivative drug conjugates); alternatively, in Stage V—b, a secondary lipid (fatty acid) chain was conjugated, yielding mono-substitute triglyceride (TG) derivative drug conjugates, i.e. drug conjugated diglyceridediacylglycerol (DAG) derivatives. Stage V—a is achieved by first attaching a dioxaphospholane ring via 2-Chloro-1,3,2-dioxaphospholane 2-oxide or 2-chloro-1,3,2-dioxaphospholane followed by a ring opening reaction and the addition of a choline head via trimethylamine (Me3N, a.k.a. TMA), yielding compound (5a), (5b), and (5c). Stage V—b is essentially the same reaction as Stage III, which the second fatty acid (FA-2) could be the same as the first fatty acid installed (FA-1) or different from FA-1 to mimic natural triglyceride configurations, yielding compound (5d), (5e), and (5f). Compounds (5d) and (5e) will be the same if FA-1 is identical to FA-2. Finally, the amine protection on the 1MT was removed by suitable methods, e.g. to use TFA/TIPS for Boc removal yielding compounds (6a-f) (Stage VI—a/b). The overall reactions and the general formula of compounds (6a-f) is shown in FIG. 11.

Single Fatty Acid-Conjugated and Cholesterol-Conjugated 1-MT

Figure 12:
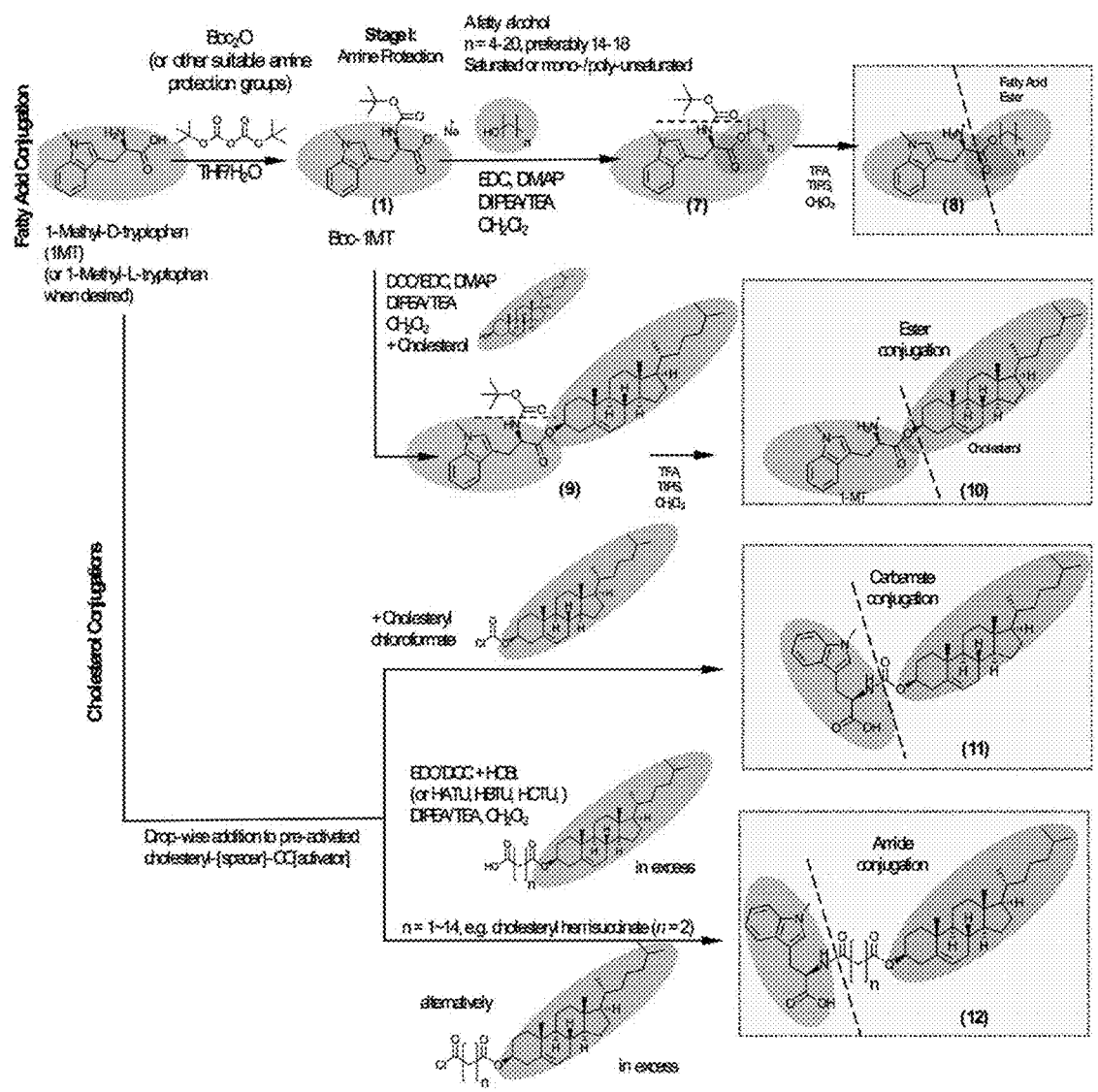
FIG. 12 illustrates synthesis of fatty acid and cholesterol conjugated 1-MT prodrugs.

In addition to the 1MT-LysoPC and 1MT-DAG conjugations, we also devised single fatty acid drug-conjugation and cholesterol conjugation derivatives (FIG. 12). The single fatty acid conjugation is simply achieved by performing a Steglich esterification reactions between compound (1), the Boc-1MT and a fatty alcohol (saturated or poly-/mono-unsaturated), yielding compound (7) followed by amine deprotection to afford compound (8) as the final drug conjugate. Ester conjugated 1MT-cholesterol is simply synthesized by conjugating Boc-1MT and cholesterol followed by amine deprotection, yielding compound (9) and (10), respectively. Alternatively, 1MT can be directly conjugated with a cholesteryl chloroformate yielding a 1MT-Cholesterol conjugate via carbamate as compound (11). Finally, we prepared the 1MT-amide-[spacer]-Cholesterol conjugations by using cholesteryl-[spacer]-OH via amidation, where the spacer is [—CO—(CH2)n-CO—], or by using a cholesteryl-[spacer]-Cl, yielding compound (12).

Conclusion.

The resulting lipid/chol prodrugs could apply to the preparation of all nanomedicine formulations. To name a few, we can use the prodrug to coat nanoparticle surface or make self-assembly nanocarrier in which the interior or surface can be used for payload delivery.

Issues and Solutions.

Figure 13:
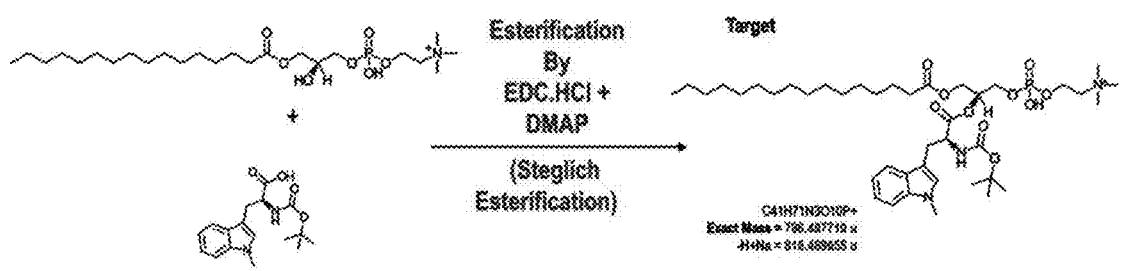
FIG. 13 illustrates a Steglich esterification (see, e.g., Steglich (1078) *Agnew. Chem. Int. Ed.* 17(7): 522-524).

One difficulty for certain embodiments is that the Steglich Esterification (FIG. 13) works for targets that have only one ester bonds in the end, otherwise, trans-esterification will take place resulting in many different esters.

Figure 14:
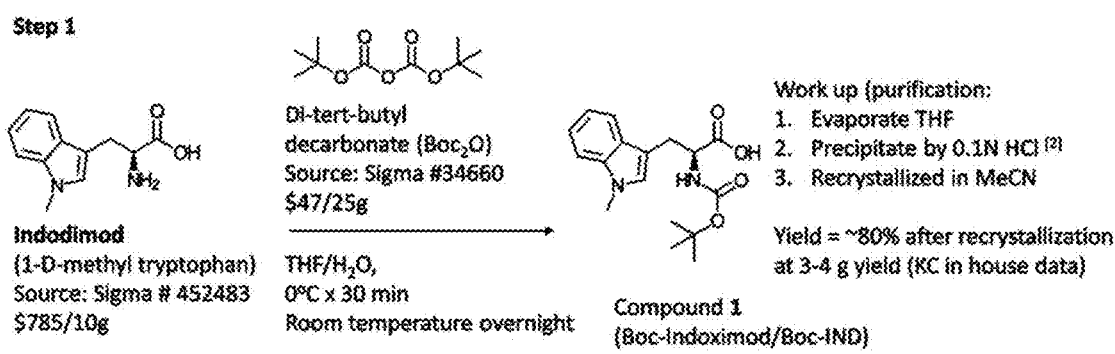
FIG. 14 illustrates an alternative synthetic strategy.

For academic discovery research this is acceptable, but it can be problematic for industrial scale production. An alternative synthetic strategy is a total synthesis approach (e.g, as described above). In this approach one esterification step is used to produce the intermediate compound where trans-esterification side reactions less likely. The largue components can be built first and the small components attached later (see, e.g., FIG. 14, Steps 1-6 and alternative Step 1.

Example 7

Synthesis and Testing of Chol-Ind Liposomes

This example describes the synthesis of a cholesterol-based indoximod prodrug. The design is based on the use of medicinal chemistry criteria such as presence of reactive functional groups, steric hindrance, analysis of side products, product yield and avoidance of toxic/unstable/expensive chemicals to identify API candidate(s) to direct prodrug design. This prodrug can be used to formulate dual delivery liposomes, capable of co-delivery of mitoxantrone (MTX) and doxorubicin (DOX), which have the potential to act as ICD stimuli.

Synthesis of Cholesterol-Indoximod Through an Ester Bond (Chol-IND)

Figure 16:
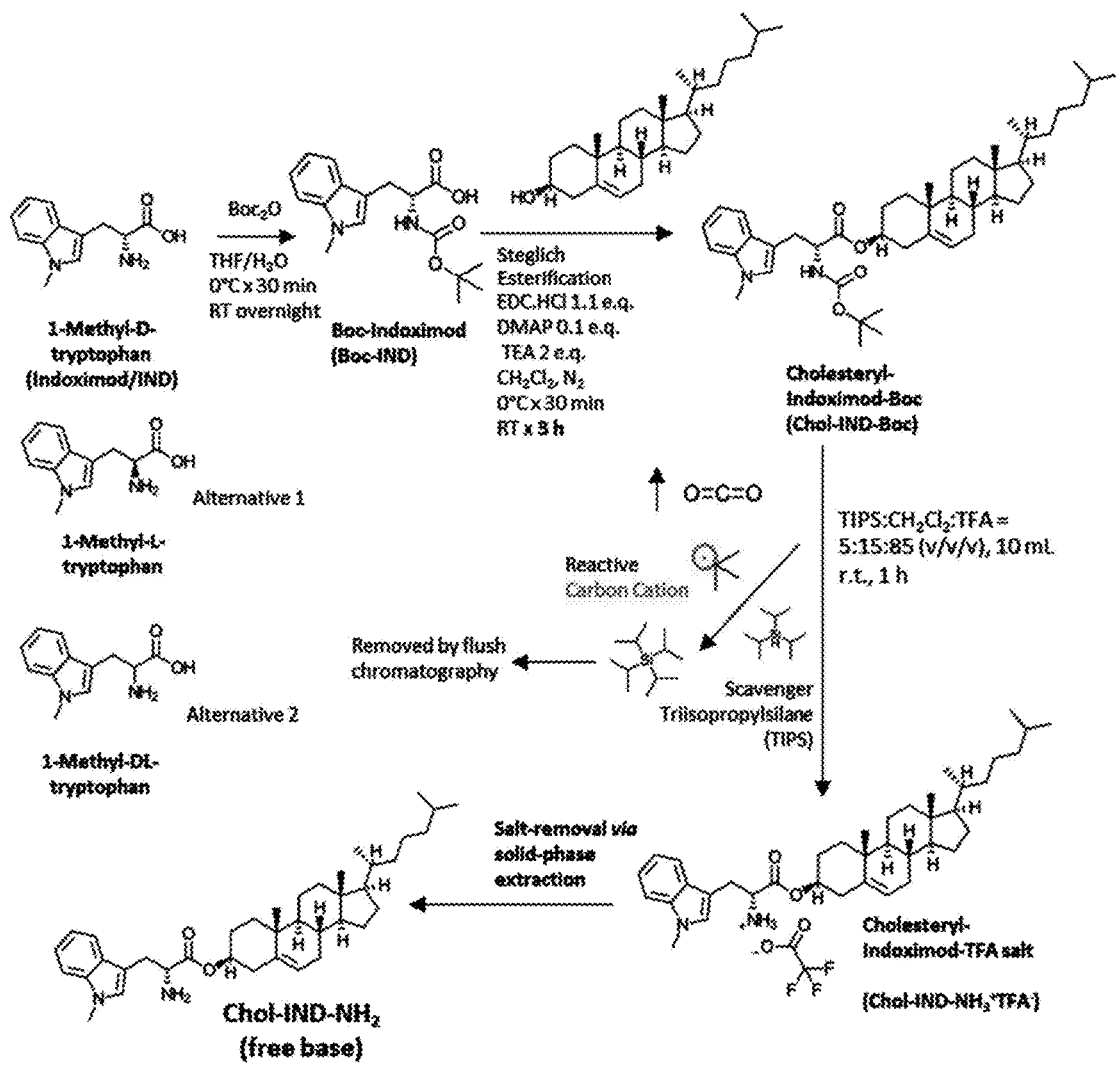
FIG. 16 illustrates the synthesis of Chol-IND.

The major steps for making Chol-IND are summarized in FIG. 16. The synthesis involves 4 simple steps: Boc-protection of IND, Cholesterol conjugation, Boc removal and de-salting. The raw materials and supplies that were used to make Chol-IND are summarized in Table 6. The overall yield is 20~30%.

TABLE 6

Raw Materials and supplies for making Chol-IND.

| # | Name | Supplier | Catalog Number |
|---|------|----------|----------------|
| 1 | Cholesterol from sheep wool | Sigma-Aldrich | C8503 |
| 2 | Indoximod (1-methyl-D-tryptophan) | | 452483 |
| 3 | Di-tert-butyl decarbonate ($Boc_2O$) | | 205249 |
| 4 | 4-(dimethylamino)pyridine (DMAP) | | 8204990025 |
| 5 | Sand, 50-70 mesh | | 274739 |
| 6 | $MgSO_4$ (magnesium sulfat) anhydrous | | M7506 |
| 7 | TEA (triethalamine) | | T0886 |
| 8 | Sodium bicarbonate ($NaHCO_3$) | | S6014 |
| 9 | Triisopropylsilane (TIPS), 98% | | 233781 |
| 10 | Tetrahydrofuran (THF) | Fisher Scientific | |
| 11 | Hydrochloric Acid (HCl) 12 N | | A144-500 |
| 12 | Dichloromethane, anhydrous, >99.7%, Alfa Aesar ™ | | AA41835K2 |
| 13 | Ethyl acetate (EtOAc) | | |
| 14 | Hexane | | |
| 15 | Acetonnitrile (MeCN) | | |
| 16 | 1-ethyl-3-(3-dimethylaminopropyl)carbodiimide hydrochloride (EDC.HCl) | ThermalFisher Scientific | 22980 |
| 17 | Trifluoroacetic acid, 99% (TFA), Alfa Aesar ™ | | L06374 |
| 18 | TLC Siliga gel 60 $F_{254}$ x 25 Aluminum sheets (20 x 20 cm) | Millipore | 1.05554.0001 |
| 19 | Microcapillary Pipettes Disposable Soda-lime Glass, 20 µL, 250 pipets | Kimble Glass Inc. | 71900-20 |
| 20 | Disposable culture tubes (250 borosilicate glass tubes, 13 x 100 mm) | Globe Scientific Inc. | 1510 |
| 21 | Column, Chromatography, 24/40 Outer Joint, 250 mL Reservoir, 1 in ID X 12 in E.L., 2 mm Stpk | Chemglass Life Sciences | CG-1197-14 |
| 22 | Column, Chromatography, 24/40 Outer Joint, 500 mL Reservoir, 1 1/2 in ID X 12 in E.L., 2 mm Stpk | | CG-1197-17 |
| 23 | SilicaFlash ® P60 40-63 µm (230-400 mesh) for <1 kDa, UltraPure Silica Gel | Silicycle | R12030B |

TABLE 6-continued

Raw Materials and supplies for making Chol-IND.

| # | Name | Supplier | Catalog Number |
|---|------|----------|----------------|
| 24 | SiliaPrep ™ Carbonate (or Si-CO3) | | SPE-R66030B |
| 25 | PoraPak ™ Rxn CX Cartridges (alternative for SiliaPrep carbonate) | Waters | 1860045-41/42/43/44 |

Step 1: Synthesis of Boc-Indoximod (Boc-IND).

Figure 17:
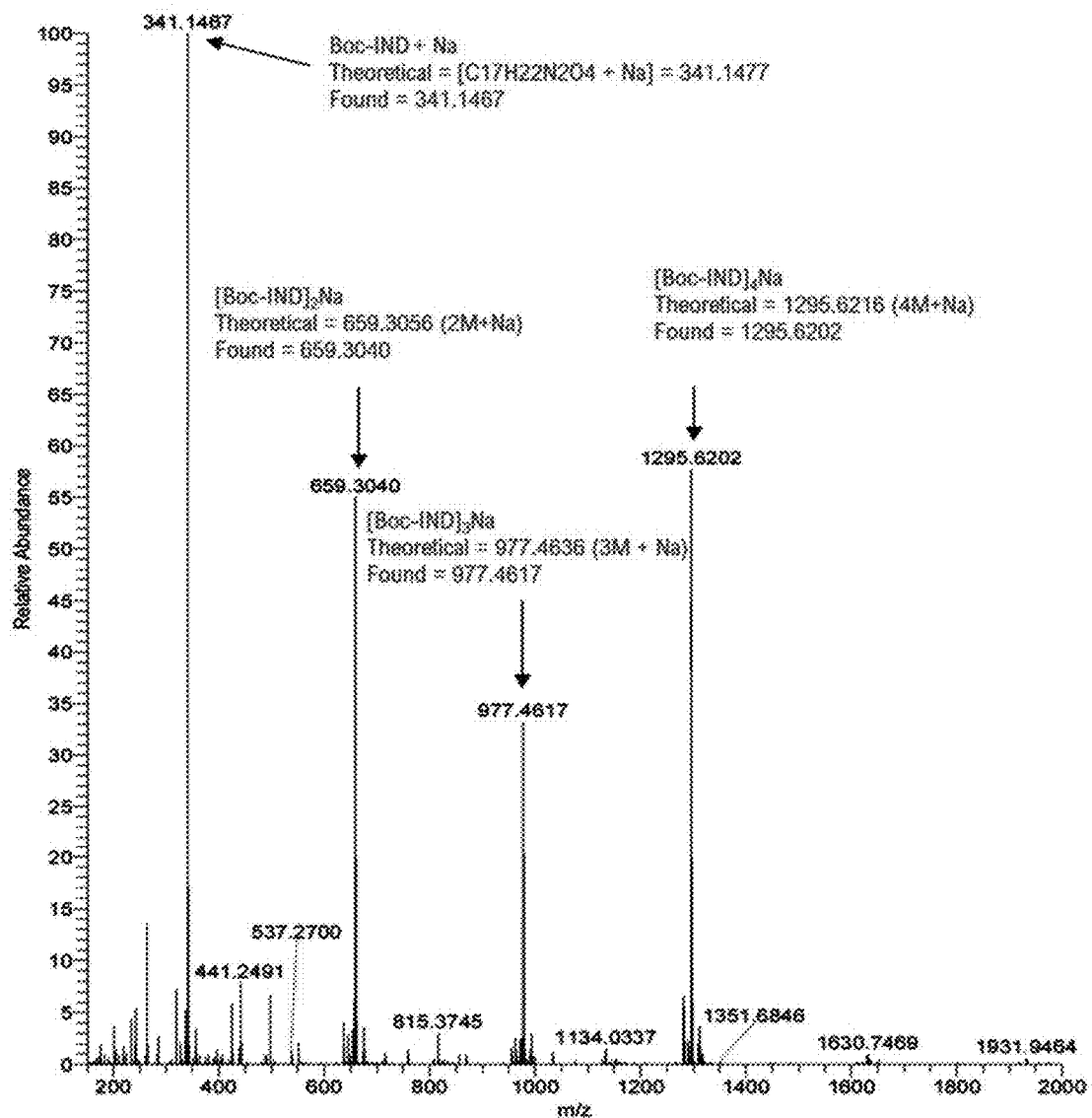
FIG. 17 shows ESI-MS results for synthesis of Boc-Indoximod (BOc-IND).

Indoximod (1-Methyl-D-tryptophan, 95%) powder 3.2 g (13.93 mmol) and sodium bicarbonate ($NaHCO_3$) were suspended in 80 mL $THF/H_2O$ (1:1 v/v) and chilled on ice. Di-tert-butyl decarbonate ($Boc_2O$ anhydride) 4.16 g (19 mmol) was pre-dissolved in 20 mL $THF/H_2O$ (1:1 v/v) and added drop-wise to the suspension. The ice-bath was removed, and the mixture was stirred overnight at room temperature under nitrogen in which Boc-IND was precipitated by adding 0.1N HCl without stirring. This yielded a sticky, brownish precipitate. The precipitate was recovered by filtration, dried in vacuum, and recrystallized in MeCN to yield pale-yellow crystalline compound 3.779 g (11 mmol)= 78.98%. Accurate mass measurement by ESI-MS (Thermo Scientific™ Q Exactive™ hybrid quadrupole-Orbitrap mass spectrometer) was performed. We observed multiple MS peaks that represent to the complexes that contain one sodium (Na) together with 1~4 $C_{17}H_{22}N_2O_4$ molecules. This includes: i) $[C_{17}H_{22}N_2O_4Na]$ (theoretical: 341.1477, experiential: 341.1467), ii) $[(C_{17}H_{22}N_2O_4)_2Na]$ (theoretical: 659.3056, experiential 659.3040), iii) $[C_{17}H_{22}N_2O_4)_3Na]$ (theoretical: 977.4636, experimental: 977.4617) and iv) $[(C_{17}H_{22}N_2O_4)_4Na]$ (theoretical: 1295.6216, found: 1295.6202) (FIG. 17).

Figure 18:
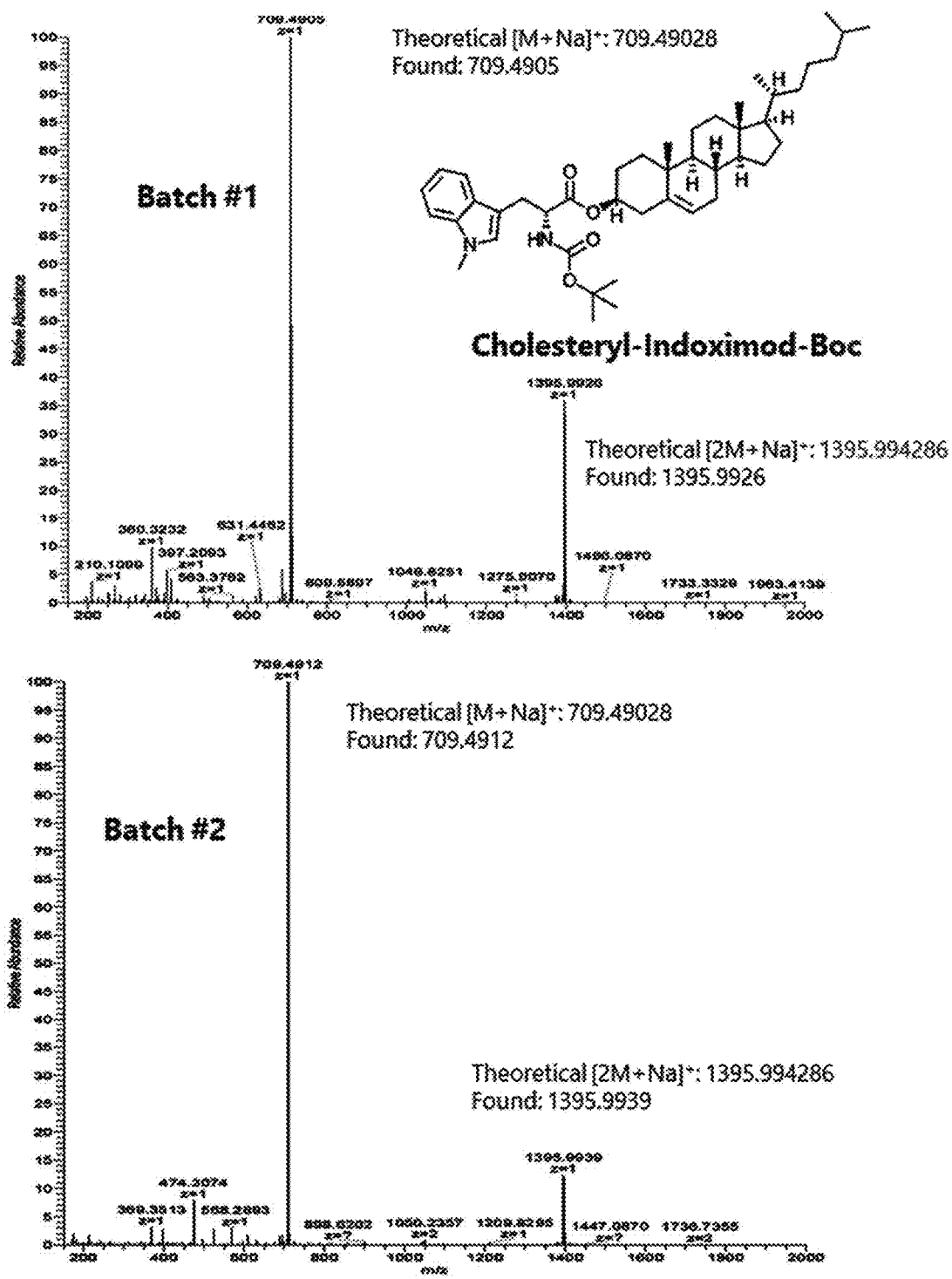
FIG. 18 shows ESI-MS results for synthesis of cholesteryl-indoximod-Boc (Chol-IND-Boc).

Step 2: Synthesis of Cholesteryl-Indoximod-Boc (Chol-IND-Boc):

Recrystallized Boc-IND (purity ~90%, 900 mg, 1 mmol) was loaded into a 100 mL round bottom flask containing anhydrous dichloromethane (25 mL) with a magnetic stir. This was followed by the addition of a catalytic amount of DMAP (12 mg, 0.1 mmol), and cholesterol (purity 92.5%, 836 mg, 2 mmol) powder to form a solution that was chilled on ice. The solution was kept under nitrogen during the reaction. EDC HCl (210 mg, 1.1 mmol) was pre-dissolved in anhydrous dichloromethane (5 mL) and triethylamine (202 mg/279 μL, 2 mmol) in a glass vial, chilled on ice, and then loaded drop lies into the reaction solution. The reaction was allowed to proceed at room temperature for 3 h. Formation of the Ch-IND-Boc can be monitored by TLC (mobile phase: EtOAC:MeOH=9:1 v/v, Rf 0.73-0.93, UV and iodine double positive). The reaction mixture was purified by sequential extraction with 0.5N HCl (50 mL×2), saturated $NaHCO_3$ (50 mL×2), and an optional brine wash (50 mL×1). The residual water in the organic phase was absorbed by anhydrous $MgSO_4$, from which the $MgSO_4$ hydrate was removed by filtration. The dichloromethane was evaporated in a rotary evaporator, the crude residual was dissolved in minimal solvents and purified by flush chromatography (mobile phase: EtOAc:Hexane=4:6 v/v, Rf=0.67, UV and iodine double positive). The elution fractions containing the Ch-IND-Boc were pooled and solvent was removed in a rotary evaporator. This yielded a transparent gel, which was further dried in high vacuum overnight to afford a dried transparent solid that turned into white powder when scrapped off. Batch #1 yielding 421.71 mg (59.44%), Batch #2 yielding 469.09 mg (66.12%). Average yield=62.78% (n=2). Accurate mass measurement by ESI-MS (Thermo Scientific™ Q Exactive™ hybrid quadrupole-Orbitrap mass spectrometer): [C44H66N2O4Na=M+Na]+ theoretical: 709.49203, found 709.4905; [(C44H66N2O4)2Na=2M+Na]+ theoretical 1935.9943, found ~1395.99. (FIG. 18).

Step 3: Synthesis of Ch-IND-$NH_3^+$TFA" (TFA Salt).

Figure 19:
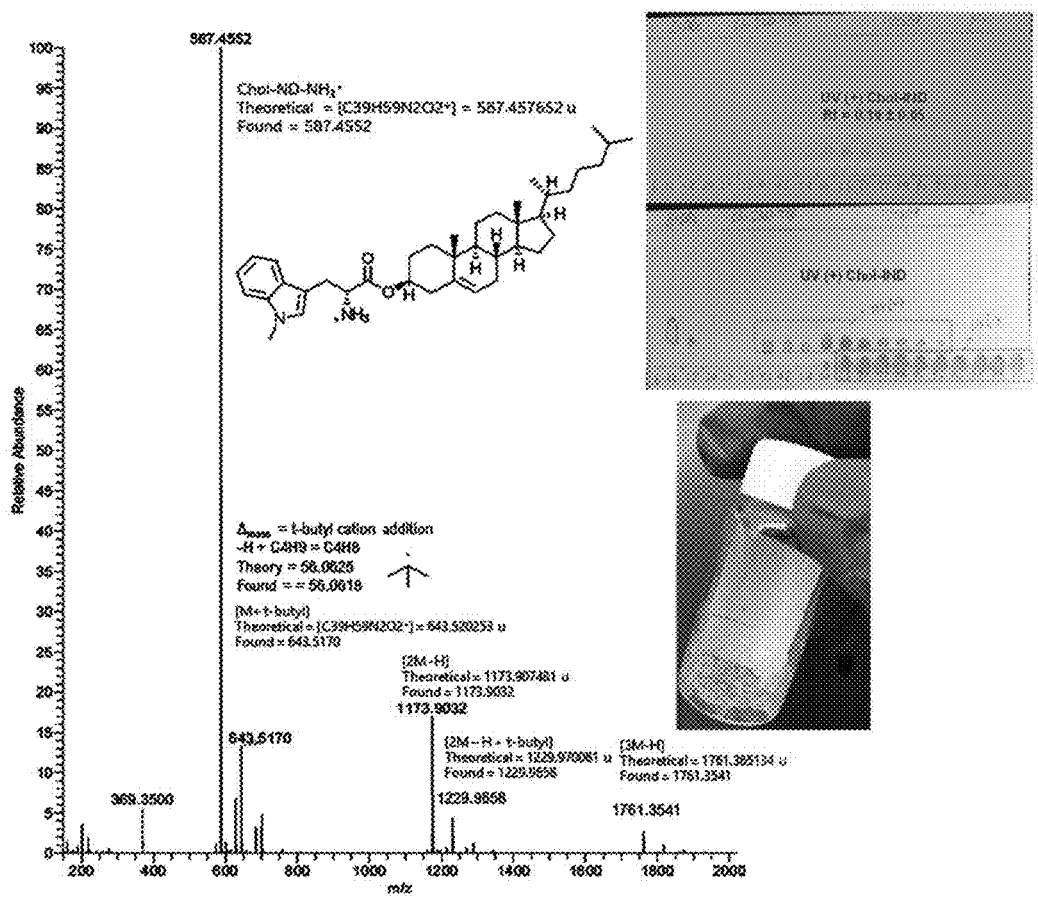
FIG. 19 shows. ESI-MS data of Chol-IND-NH3+TFA− salt. Thin layer chromatography profile of Chol-IND-NH3+ TFA− salt was showed on the top right corner. Chol-IND-NH3+TFA− salt is a yellow color paste.

Chol-IND-$NH_2$—Boc (700 mg, ~1 mmol) was dissolved in a mixture solution of triisopropylsilane (TIPS), $CH_2Cl_2$, and TFA (10 mL, 5:15:85 v/v) and stirred for 1 h. $CH_2Cl_2$ and the TFA excess was removed in a rotary evaporator. Residuals were purified by flush chromatography to obtain the Ch-IND-$NH_3^+$TFA$^-$ salt (mobile phase: EtOAc for impurity removal, and EtOAc plus TEA 99:1 v/v for Ch-IND-$NH_3^+$TFA$^-$ salt, Rf=0.15, UV and iodine double positive). Accurate mass measurement by ESI-MS (Thermo Scientific™ Q Exactive™ hybrid quadrupole-Orbitrap mass spectrometer): $[C_{39}H_{59}N_2O_2^+=M^+]$ theoretical: 587.457652, found 587.4552; $[(C_{39}H_{59}N_2O_2^+)_2—H=2M^+-H]$ theoretical 1173.907481, found 1173.9032; $[(C_{39}H_{59}N_2O_2^+)_3—H=3M^+-H]$ theoretical 1761.365134, found 1761.3541 (FIG. 19).

Step 4: TFA Removal.

TFA removal can be done using a commercially available resin (siliaPrep™ Carbonate (or Si—CO3) resin) or purification column, according to the manufacturer's instructions (see Item #24 in Table 6). Using a different industrial protocol a TFA removal % of 99.96% was observed.

Figure 20:
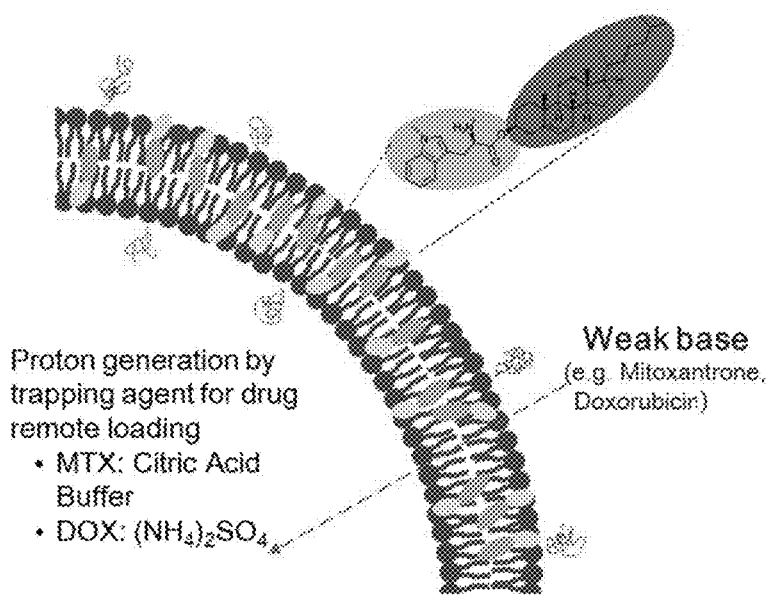
FIG. 20 illustrates one design of Chol-IND liposome for ICD inducing agent delivery via a trapping agent mediated approach.
Figure 21:
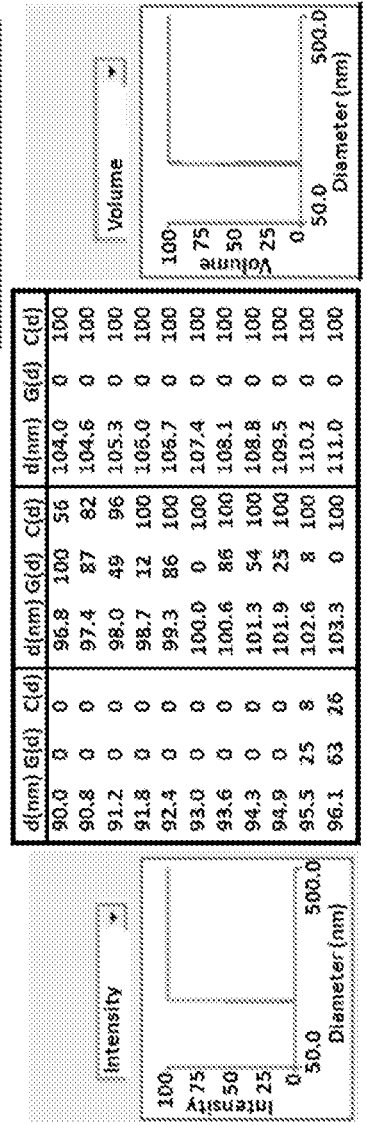
FIG. 21 shows the successful synthesis of MTX laden Chol-IND liposome. The synthesis involved preparation of lipid biofilm, rehydration in citrate solution (trapping agent), extrusion (100 nm pore size), removal of free citrate acid, drug import, and purification. CyroEM visualization is provided. The final prodrug shows single peak in the DLS analysis, suggesting the formation of a liposome formulation with low PDI. The MTX loading is 14.1 wt %. The loading efficiency is determined to be 78%. The liposome exhibits slight positive charge, i.e. +4 mV. Note: This sample was made using the IND prodrug as a Chol-IND TFA salt. We are currently also making a liposome with salt free Chol-IND.

Use of Chol-IND to Make Dual Delivery Liposome for Concurrent ICD Induction and IDO Inhibition We have experimentally demonstrated the feasibility of making co-delivery liposomes that incorporate indoximod (IND) as well as MTX and DOX. The ICD inducing chemo agents are loaded into the liposome by trapping agents, which include citric acid for MTX and ammonium sulfate for DOX (FIG. 20). The data are summarized in FIGS. 21 and 22.

Use of Cholesteryl Hemisuccinate (CHEMS) to Reduce the Positive Charge in the Co-Delivery Liposome.

Figure 23:
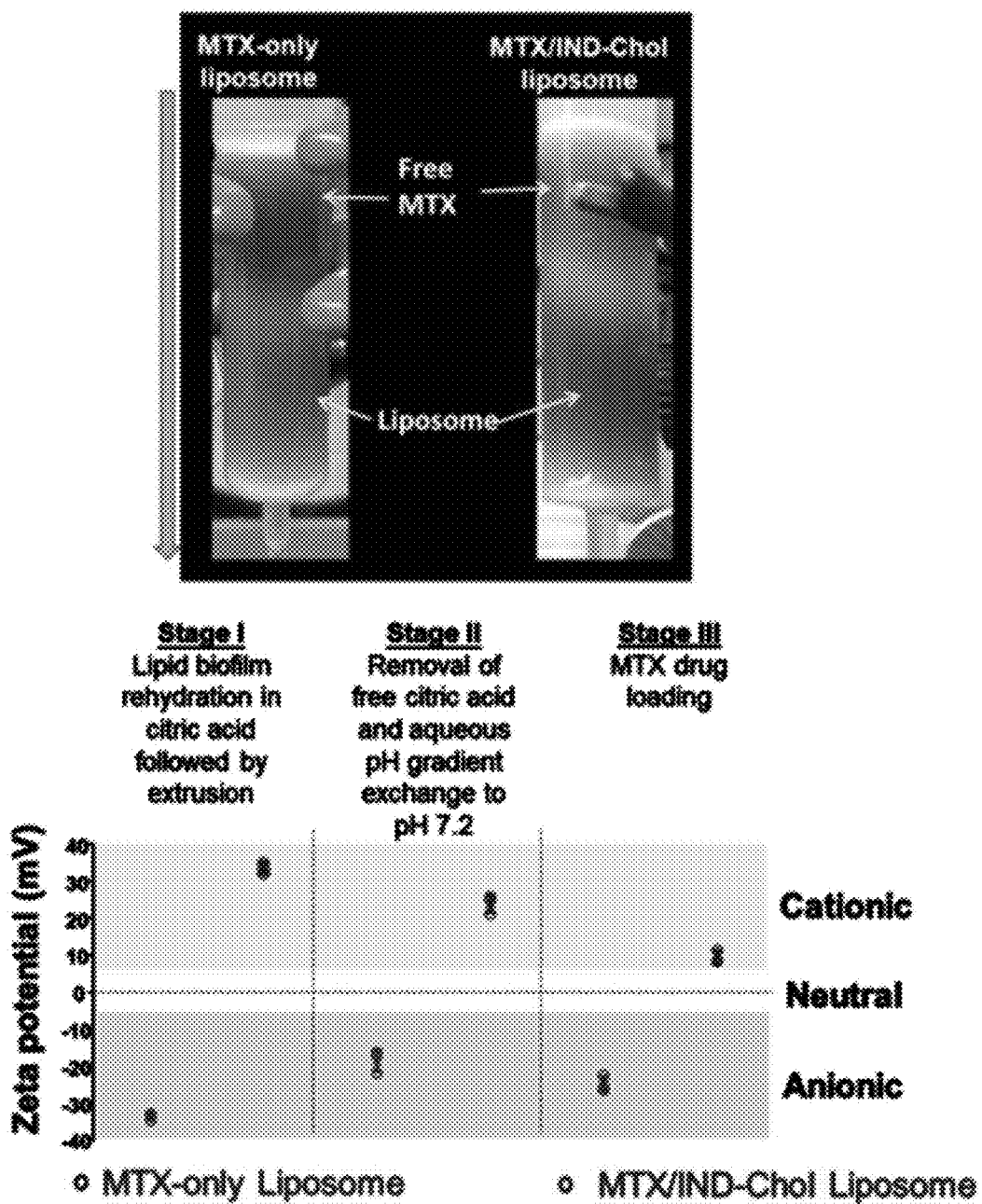

Liposomal construction with the Chol-IND salt leads to the formation of a cationic liposome. The cationic charge is due to the presence of an amine group in the prodrug. For drug delivery purposes, we prefer a liposomal charge close to neutral. Construction of a liposome containing MTX-only (without the prodrug) yields a negatively charged carrier (FIG. 23). However, a liposome formulation containing MTX and Chol-IND yields a positively charged formulation at each step of construction as shown in FIG. 23.

Figure 24:
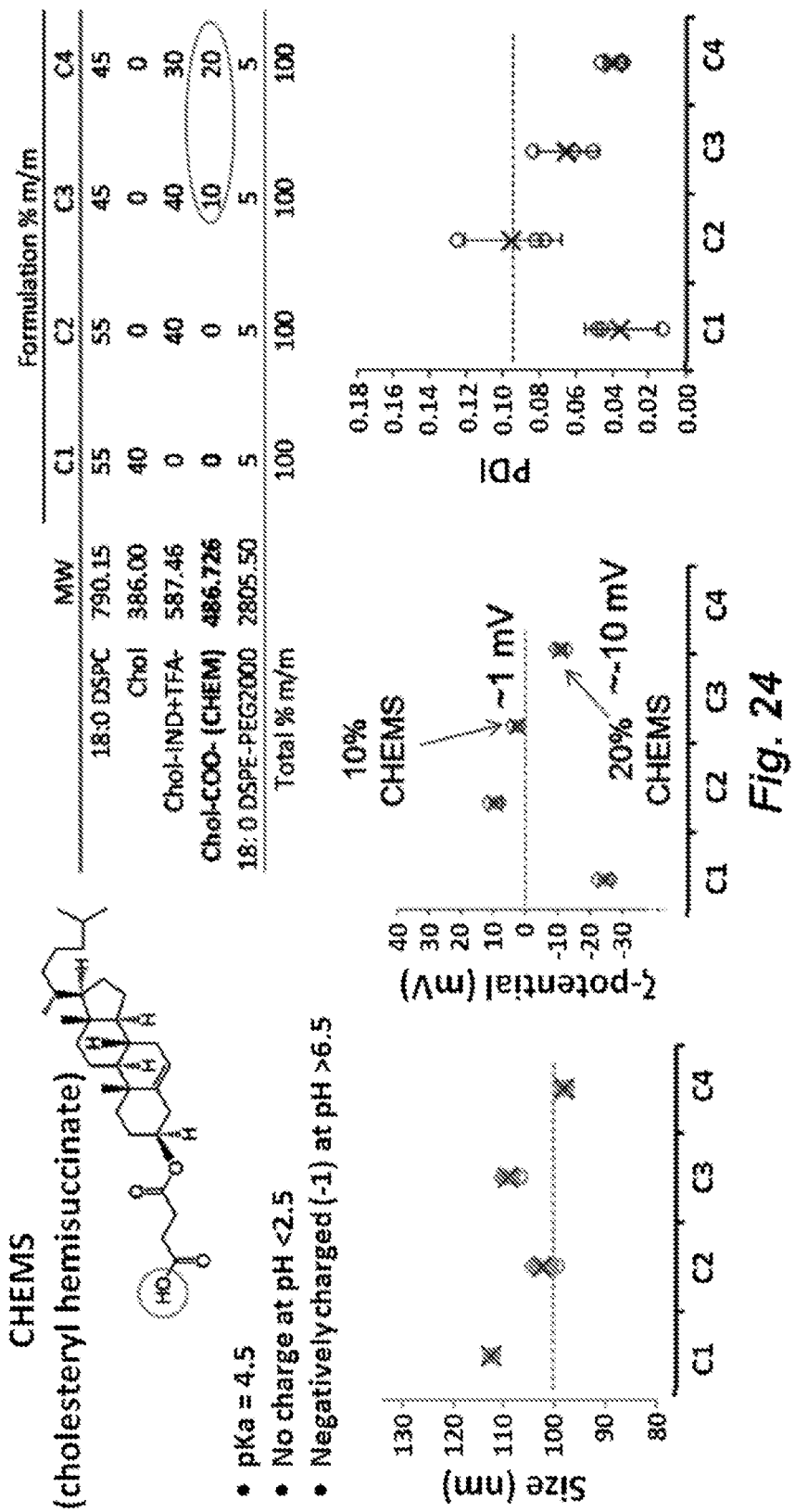
FIG. 24. A list of MTX laden liposomes was made using pristine cholesterol, CHEMS and Chol-IND. We reasoned that the inclusion of CHEMS in the Chol-IND formulation should adjust the particle charge from positive to the neutral or slightly anionic. The design of the formulation is provided in the inserted table. Four formulations (C1-C4) were made, in which C3 contains 10% CHEMS and C4 contains 20% CHEMS. Controls include MTX-only liposome using pristine cholesterol (C1) and DSPC:Cho-IND/DSPE-PEG2K=50:40:5 (molar ratio) without CHEMS (C2). The particles size, charge and PDI were summarized in the lower panel. As expected, use of 10% and 20% CHEMS led to zeta potential values of +1 and −10 mV, respectively. Particle size measurement and PDI were not significantly changed among these formulations. The sizes of these particles are 100~130 nm; the PDI values are <0.15. The loading efficiency of C3 and C4 formulations are 93±4% and 87±17%, respectively. The loading capacity values are 14±0.5% and 13±2.5%, respectively. These values are similar to the results in C1 and C2.

Cholesteryl hemisuccinate (CHEMS) is a cholesterol derivative that is frequently used in formulation studies (see, e.g., Serpe et al. (2004) Eur. J. Pharm. Biopharm. 58: 673-680; Ding et al. (2005) Int. J. Pharam. 300: 38-47). It carries one negative charge at a pH greater than 6.5. Interestingly, a simulation study (membrane protein crystallization) suggested that protonated form of CHEMS mimics many of the membrane properties of cholesterol quite well (Kulig et al. (2014) *J. Mol. Model.* 20: 2121). We therefore introduced 10% and 20% CHEMS in our co-delivery liposome (i.e. MTX/IND liposome) with the view to reducing the surface charge in the Chol-IND particles (FIG. 24).

Update on Biological Experiments

Figure 26:
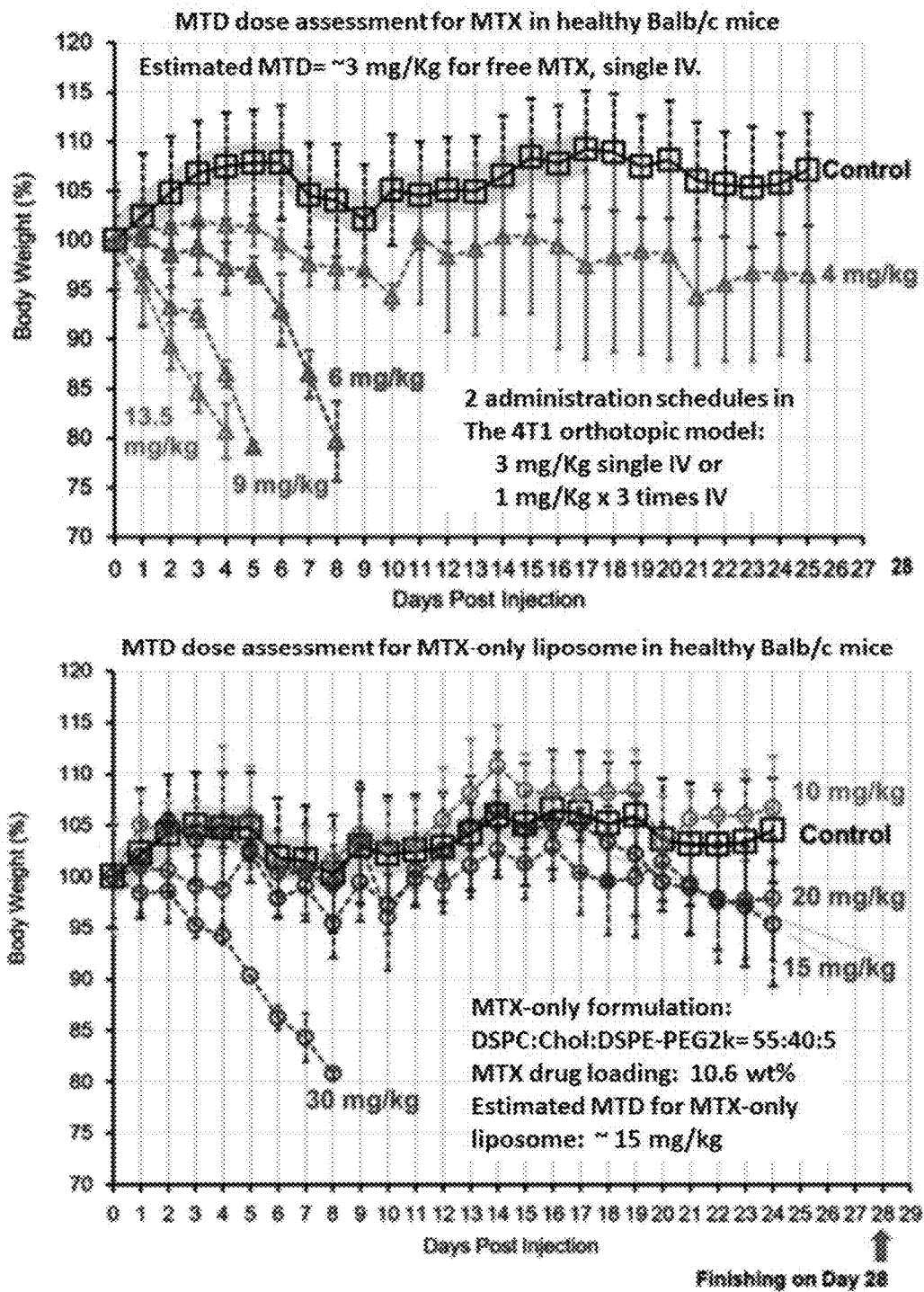
FIG. 26. Panel A) Determination of MTD doses for free MTX and liposomal MTX in normal mice. MTD doses for free MTX and liposomal MTX were 3 and 15 mg/kg for single IV administration. Due to the high MTD of liposomal MTX, we tested the efficacy of the MTX liposome at low dose (1 mg/Kg×3 times) and high dose (3 mg/Kg×3 times). Panel B) Pilot tumor size measurement in 4T1 orthotopic tumor-bearing mice (n=6) receiving IV free drug or MTX-only liposome. For free drug treatment, we have included 2 two schedules namely single IV at 3 mg/kg at Day 8 or IV injections at 1 mg/kg at Day 8, 11 and 14. Since MTX liposome has a 5× higher MTD dose, the tumor mice received single IV at 3 mg/kg at Day 8 or IV injections at Day 8, 11 and 14.

As shown in FIG. 25, the MTX/IND-chol liposome is capable of ICD induction and IDO inhibition in vitro. FIG. 26, panel A, shows a determination of MTD doses for free MTX and liposomal MTX in normal mice. MTD doses for free MTX and liposomal MTX were 3 and 15 mg/kg for single IV administration. FIG. 26, panel B, shows pilot tumor size measurement in 4T1 orthotopic tumor-bearing mice receiving IV free drug or MTX-only liposome.

"Industrial" Synthesis of Chol-IND.

Figure 27:
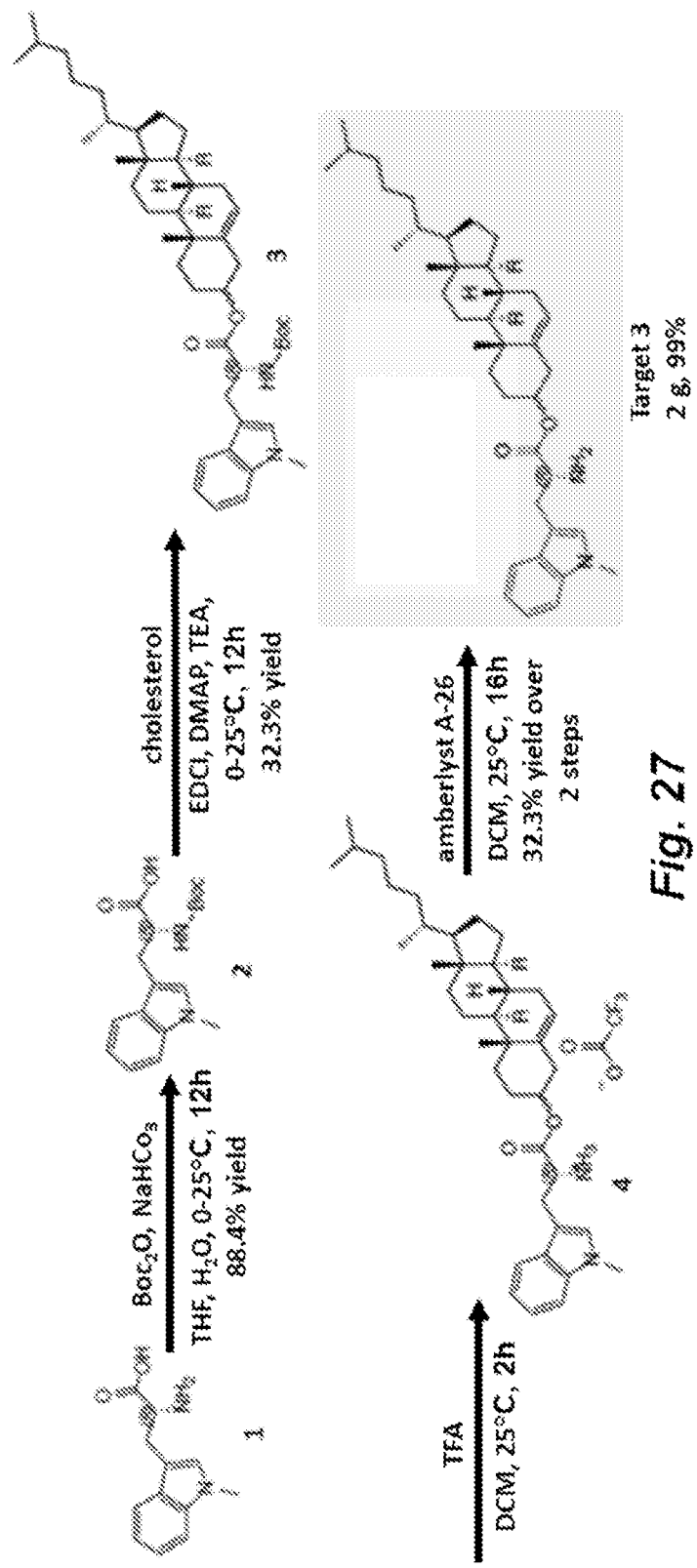
FIG. 27 shows synthetic steps, NMR, MS and HPLC data of Chol-IND.

Using an "industrial" process to implement the steps shown in FIG. 27, a batch of Chol-IND was synthesized to repeat the protocols described abovel. Two grams of the Chol-IND prodrug were successfully synthesized in a 2 week period (see, e.g., FIG. 27).

A portion of MTX/IND liposome (that was used for animal study) was saved for a stability check. The particles were used for size, morphology and charge measurements right after the synthesis and stored at 4° C. for 3 months. We found minimal change with the respect to liposome morphology, size and charge after storage for 3 months (see, e.g., FIG. 28). At 3 moths, majority MTX (quantified via fluorescence) and IDO (quantified via HPLC) remained encapsulated in the liposome. The leakage of MTX and IND was 0.06% and 1.75%, respectively.

Example 8

Animal Study in a 4T1 Orthotopic Breast Cancer Model

Figure 29:
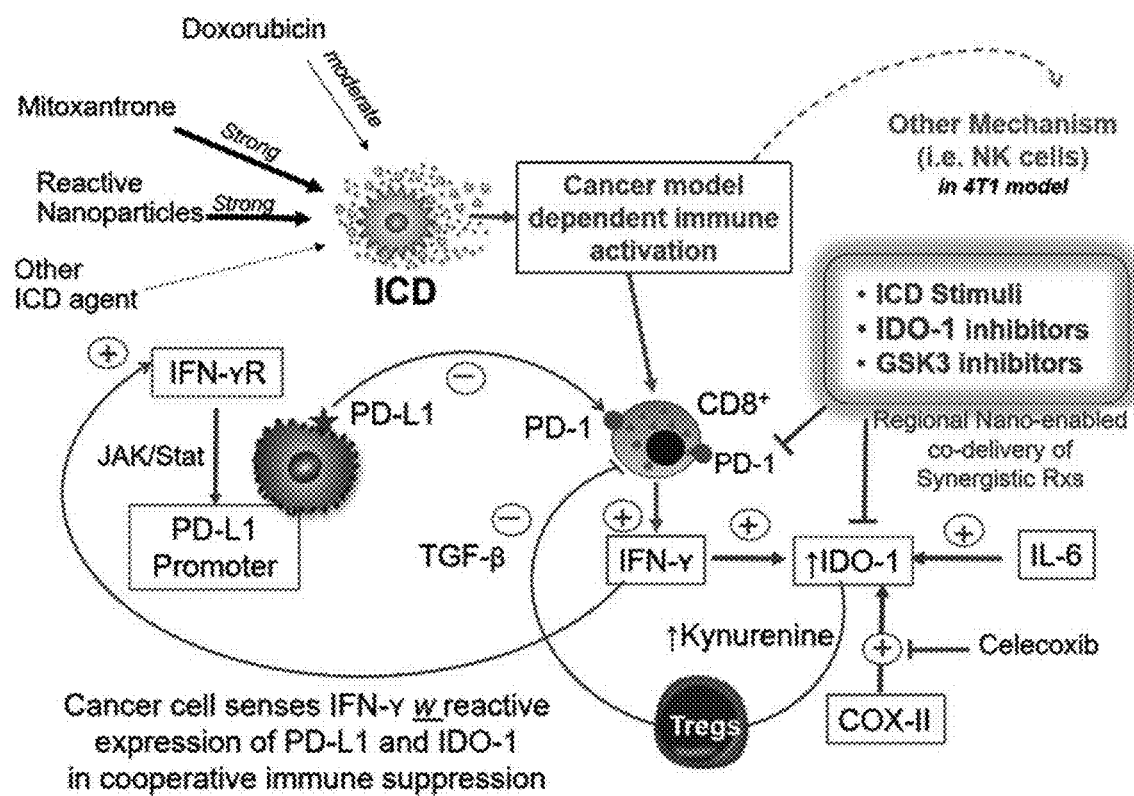
FIG. 29 illustrates mechanisms of immunogenic cell death.

Due to the multifunctionality of nanocarriers described herein it is possible to design a long list of co-delivery carriers that deliver an ICD stimulus plus an immunological agent. The scheme illustrated in FIG. 29 illustrates the principles underlying the design of such a co-delivery carrier including the underling cancer biology. By way of illustration, mitoxatrone (MTX) was selected as an ICD inducer because MTX leads to a very strong ICD effect in multiple cancer types. In illustrative, but non-limiting formulation, we used Cholesterol-IND as an immunological modulation agent based on the formulation work (see, e.g., Example 7).

In this example we show that the use of both of the mitoxantrone-only and mitoxantrone/IND liposomes led to significant anticancer effect in the 4T1 breast cancer model. Moreover these results were dramatically better than the results obtained with a Doxil equivalent doxorubicin only liposome).

Without being bound to a particular theory, it is believed the effect can be attributed to the superior ICD introducing effect of mitoxantrone over doxorubicin, rendering a liposomal mitoxantrone candidate that can be used for multiple cancer types.

It is worth noting that in the 4T1 model, the mitoxantrone-only liposome was so effective that an additional effect for cholesterol-IND could not be observed. Without being bound to a particular theory, it is believed this reflects the possibility that the 4T1 triple negative breast cancer model may represent a TN breast cancer subset in which IDO-1 does not play a major role. In that sense, TN breast cancer is no different from a series of solid cancers in which there is only a 25-30% response rate to checkpoint inhibitors, likely due to a variation on the theme of participation by different immune escape mechanisms. We have clear evidence, however, that in spite of a synergistic effect for IND in the 4T1 model, that there is a strong ICD response in the immunohistochemistry data, implying that the contribution of turning the "cold" tumor "hot" is a valid approach irrespective of the IDO-1 contribution. One could argue that a potent ICD agent such as mitoxantrone could exert similar effects on other solid tumors, increasing the 25% response rate.

In certain embodiments of these observations, in certain embodiments liposomes containing mitoxantrone (MTX), but not containing an IDO inhibitor.

Use of such MTX liposomes would be facilitated by development of a biomarker to determine whether tumors are potentially IDO-1 responsive, similar to the manner in which the expression of PD-1 ligand is currently used, to decide who should receive anti-PD1 therapy for lung cancer.

As illustrated in FIG. 29 immunogenic cell death (ICD) is a specialized form of tumor cell death in response to specific chemotherapeutic drugs (e.g. anthracyclines, MTX, oxaliplatin), radiation therapy, photodynamic therapy or certain engineered nanomaterials. Our data showed MTX and certain nanomaterials led to very strong ICD in multiple models such as breast cancer and colon cancer models. ICD facilitates tumor antigen cross-presentation in dendritic cells as a result of calreticulin (CRT) expression on the dying tumor cell surface. CRT provides an "eat-me" signal for DC uptake via the CD91 receptor. In addition, the stepwise release of adjuvant signals, including high mobility group box 1 (HMGB-1) protein (a TLR-4 ligand) and ATP (activates the NRLP3 inflammasome), allows DC maturation and antigen presentation to naive T cells at the tumor site and regional lymph nodes. Following activation of naïve T-cells, a permissive immune response with recruitment of CTLs (from regional lymph node) can follow if powerful regional immunosuppressive pathways in the TME are overcome or removed. CTLs induce primary and metastatic tumor cell death by perforin and granzyme B release. For certain tumor (e.g., CT26), the reason for using a combinatorial regimen is that the expression of IDO-1 and PD-L1 is paradoxically increased by the recruitment of CTLs at the ICD site. It is also possible to use certain engineered nanomaterials (e.g. metal oxide and graphene) to trigger an ICD effect.

Figure 30:
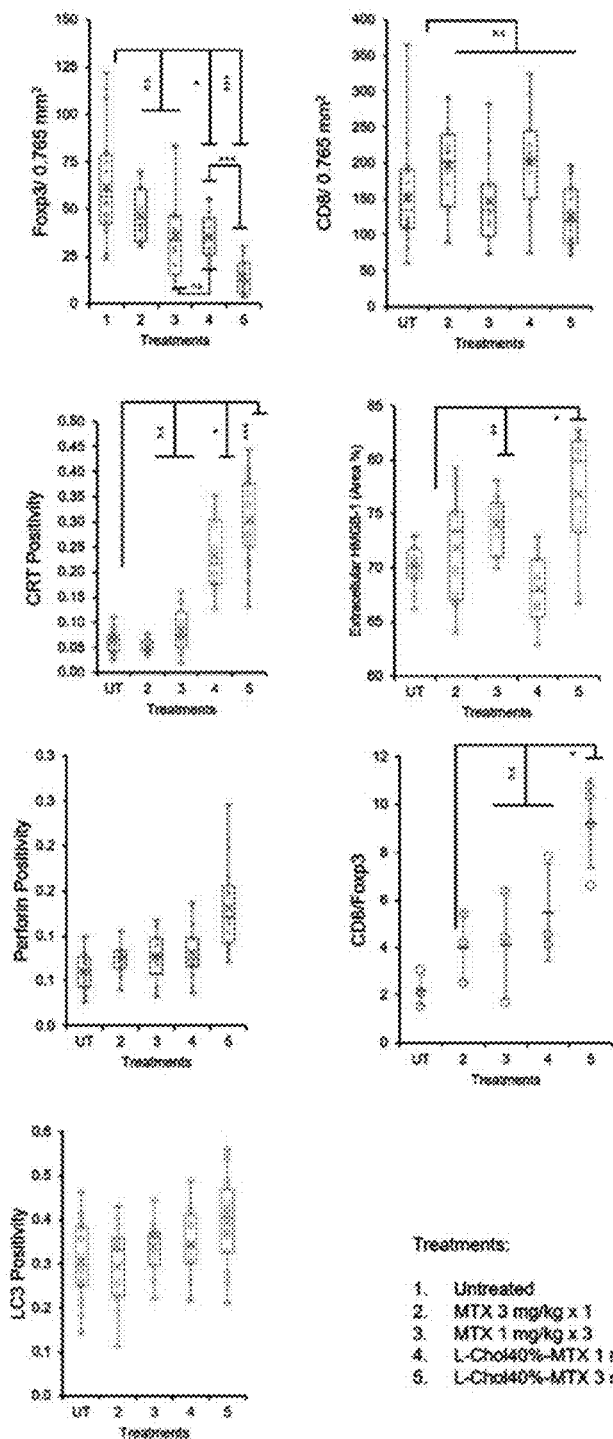
FIG. 30, panels A-B, shows that MTX encapsulated in an IND-Chol liposome leads to stronger ICD induction and immune activation at tumor site. Panel A) IHC study to confirm the effect of ICD induction (e.g. CRT, HMGB1 and LC3) and immune activation (e.g. CD8/Foxp3 ratio, perforin). Panel B) The tumor tissues were fixed and used for IHC staining of CD8, FoxP3, CRT and HMGB1. The IHC staining intensity was quantified using computer software. Panel D) Representative IHC staining of CRT and Perforin were provided.

Before investigating the efficacy of MTX/IND co-delivery liposome in the 4T1-luc orthotopic model, we revisited the tumor samples in FIG. 26 and performed an IHC study to confirm the effect of ICD induction (e.g. CRT, HMGB1 and LC3) and immune activation (e.g. CD8/Foxp3 ratio, perforin) at tumor site (FIG. 30). The overall conclusion was the liposomal MTX introduced more potent ICD and immune activation effect compared to free drug at 4T1 tumor site in a dose-dependent fashion.

We continued to test the anti-cancer effect using MTX/IND liposome in a 4T1 orthotopic model. Two experiments were performed. The $1^{st}$ one is to look at the anticancer efficacy with the objective to investigate the ICD induction and immune activation at 4T1 tumor site. We also performed an independent survival study to compare the survival outcome of each treatment. The results are shown in FIG. 17.

We continued to test the anti-cancer effect using MTX/IND liposome in a 4T1 orthotopic model. Two experiments were performed. The $1^{st}$ one is to look at the anticancer efficacy with the objective to investigate the ICD induction and immune activation at 4T1 tumor site. We also performed an independent survival study to compare the survival outcome of each treatment. The existing results are shown in FIG. 31.

In particular, FIG. 31 illustrates the efficacy of the dual MTX plus Chol-IND delivery by a liposome in the 4T1 model, along with survival data. Orthotopic tumor-bearing 4T1 mice were IV injected with the encapsulated MTX liposomes to deliver 3 mg/kg IND plus 3 mg/kg MTX every 3 days, for a total of 3 administrations, as illustrated in panel A. Flow cytometry was used to assess CRT induction in 4T1 tumor cells, showing the generation of an ICD response by MTX (FIG. 31, panel B). At the conclusion of the experiment, primary tumor and major organs were collected for weighing. Organ index values were calculated (FIG. 31, panel C). The tumor tissues were fixed and used for IHC staining of CD8, FoxP3, CRT and HMGB1 (FIG. 31, panel D). In a separate experiment, we also performed an official survival study using these treatments in the same 4T1 orthotopic model (see, e.g., FIG. 31, panel E).

While we observed an impressive outcome using co-delivery liposome in the 4T1 orthotopic model, we did not achieve statistical significance between "DSPC:CHEMS:Chol-IND:DSPE-PEG2 kDa" (treatment #11 in FIG. 17) vs "DSPC:CHEMS:Chol:DSPE-PEG2 kDa" (treatment #10 in FIG. 31) in the 4T1 model. It is believed that this is partially due to the fact that the MTX-only liposome is so effective that we cannot see an additional effect for cholesterol-IND, reflecting the possibility that the 4T1 triple negative breast cancer model may represent a TN breast cancer subset in which IDO-1 does not play a major role. This has prompted us to test our liposome in a more immune responsive CT26 colon cancer model (see Example Example 9

Animal Study in CT26 Colon Cancer Model

We proceeded to test the MTX/IND liposome in a CT26 colon cancer, a model believed to be more immunologically responsive than the 4T1 orthotopic model. In this case, CT26 subcutaneous tumor bearing mice received 4 IV injection of MTX/IND co-delivery liposome at indicated time points (FIG. 32, panel A). The co-delivery liposome is labeled as "LCIM", in which "I" means IND-Cholesterol; "M" stands for MTX; "C" denotes CHEMS; and "L" means liposome) (FIG. 32). Both MTX and IDO doses in the co-delivery liposome were 3 mg/kg. For comparison, the controls were untreated mice (UT) and MTX only liposomes with or without CHEMS (L50M and LCM). We also included a group called "LCI2M", meaning the LCIM co-delivery plus empty IND liposome.

A stasticial significant difference (p<0.001) emerged as early as day 20 between dual delivery (LCIM) vs MTX only liposome (FIG. 32, panel B). In the MTX/IND liposome group, five out of eight mice have tumor less than 150 mm$^3$, which outperformed all the control groups including MTX-only liposome w/w CHEMS. The addition of empty IND liposome appeared to interfere with the effect of co-delivery via a tumor access compition mechanism.

Example 10

Use of Engineered Nanometerials to Trigger ICD

Various examples described above illustrate chemo-induced ICD, which is usually a "Type 1" ICD agent that primarily induces cell death by impacting the cell nucleus, with secondary effects on the endoplasmic reticulum (ER). It is also possible to use another approach to trigger ICD through a "Type 2" mechanism by which the ICD inducing agent primarily induces ER stress. We envisage that it is possible to use engineered nanomaterials, such as metal oxide and graphene, to induce ICD through "Type 1" or "Type 2" or even both. Accordingly, a CRT cellular screening was performed (see, e.g., FIG. 33).

KPC pancreatic cells were treated by using PBS (negative control), OX (positive control) and indicated engineered nanomaterials at low and high concentrations. The choice of particle concentration is based on an MTS assay (FIG. 33, panel A). Twenty-four hours post incubation, the total cells were harvested for CRT analysis through flow cytometry. This suggested a highly strong CRT induction effects (more potent than OX chemo) by nano-sized Ag, Cu, $SiO_2$, $V_2O_5$, ZnO and graphene (FIG. 33, panel B).

Without being bound to a particular theory, we predict an even better efficacy outcome in a more immune responsive animal model, such as CT26 colon cancer model.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A nanovesicle drug carrier for the combined delivery of an IDO inhibitor and an inducer of immunogenic cell death (ICD), said nanovesicle drug carrier comprising:
   a liposome comprising a lipid bilayer, where said lipid bilayer comprises cholesterol and cholesterol hemisuccinate, wherein said cholesterol or said cholesterol hemisuccinate is conjugated to the IDO inhibitor 1-methyl-D-tryptophan (indoximod); and
   a cargo within said liposome where said cargo comprises an agent that induces immunogenic cell death (ICD) (ICD-inducer), where said agent is mitoxantrone or oxaliplatin.

2. The nanovesicle drug carrier of claim 1, wherein said indoximod is conjugated to cholesterol.

3. The nanovesicle drug carrier of claim 2, wherein said lipid bilayer comprises:
   a phospholipid; and
   cholesterol conjugated to indoximod (Chol-IND).

4. The nanovesicle drug carrier of claim 3, wherein said phospholipid comprises:
   a saturated fatty acid with a C14-C20 carbon chain, and/or an unsaturated fatty acid with a C14-C20 carbon chain, and/or a natural lipid comprising a mixture of fatty acids with C12-C20 carbon chains; and/or
   a phospholipid selected from the group consisting of phosphatidylcholine (DPPC), 1,2-dimyristoleoyl-sn-glycero-3-phosphocholine (DMPC), 1,2-dioleoyl-sn-glycero-3-phosphocholine (DOPC), 1,2-distearoyl-sn-glycero-3-phospho-rac-glycerol (DSPG), 1,2-dipalmitoyl-sn-glycero-3-phosphoglycerol (DPPG), distearoylphosphatidylcholine (DSPC), 1,2-dieicosenoyl-sn-glycero-3-phosphocholine, and diactylphosphatidylcholine (DAPC); or
   a natural lipid selected from the group consisting of egg phosphatidylcholine (egg PC), and soy phosphatidylcholine (soy PC); and/or
   distearoylphosphatidylcholine (DSPC).

5. The nanovesicle drug carrier of claim 3, wherein said lipid bilayer comprises an mPEG phospholipid with a phospholipid C14-C18 carbon chain, and a PEG molecular weight ranging from about 350 Da to 5000 Da.

6. The nanovesicle drug carrier of claim 5, wherein said lipid bilayer comprises 1,2-distearoyl-sn-glycero-3-phosphoethanolamine-PEG (DSPE-PEG).

7. The nanovesicle drug carrier of claim 3, wherein said lipid bilayer comprises DSPC:Chol-IND:DSPE-PEG or DPPG:Chol-IND:DSPE-PEG.

8. The nanovesicle drug carrier of claim 7, wherein:
the ratio of DSPC:Chol-IND:DSPE-PEG ranges from 40-90% DSPC:10%-50% Chol-IND:1%-10% DSPE-PEG (molar ratio); or
the ratio of DSPC:Chol-IND:DSPE-PEG is about 50:40:5 (molar ratio);
the ratio of DPPG:Chol-IND:DSPE-PEG ranges from 40-90% DPPG:10%-50% Chol-IND:1%-10% DSPE-PEG (molar ratio); or
the ratio of DPPG:Chol-IND:DSPE-PEG is about 50:40:5 (molar ratio).

9. The nanovesicle drug carrier of claim 3, wherein said lipid bilayer comprises a cholesterol derivative selected from the group consisting of cholesterol hemisuccinate (CHEMS), lysine-based cholesterol (CHLYS), and PEGylated cholesterol (Chol-PEG).

10. The nanovesicle drug carrier of claim 3, wherein the indoximod conjugated to cholesterol comprises a compound having the structure:

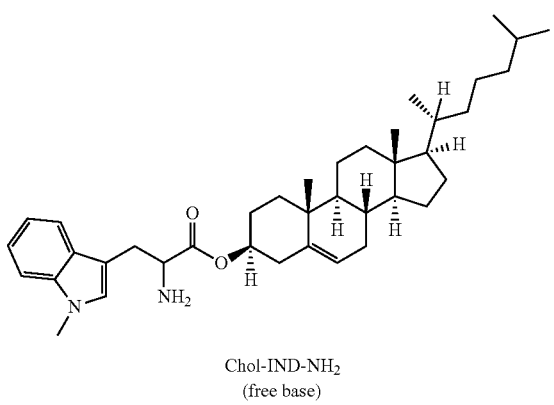

Chol-IND-NH$_2$
(free base)

11. The nanovesicle drug carrier of claim 1, wherein said cargo within said vesicle comprises oxaliplatin.

12. The nanovesicle drug carrier of claim 11, wherein said cargo comprises mitoxantrone (MTX).

13. The nanovesicle drug carrier of claim 1, wherein said liposome contains a cargo-trapping agent.

14. The nanovesicle drug carrier of claim 13, wherein said cargo trapping agent before reaction with the cargo loaded in the vesicle, is selected from the group consisting of citric acid, triethylammonium sucrose octasulfate (TEA$_8$SOS), (NH$_4$)$_2$SO$_4$, an ammonium salt, a trimethylammonium salt, and a triethylammonium salt.

15. The nanovesicle drug carrier of claim 1, wherein said drug carrier is conjugated to a moiety selected from the group consisting of a targeting moiety, a fusogenic peptide, and a transport peptide.

16. The nanovesicle drug carrier of claim 1, wherein the indoximod and the ICD inducer are synergistic in their activity against a cancer.

17. A pharmaceutical formulation comprising a nanovesicle drug carrier of claim 1 and a pharmaceutically acceptable carrier.

18. A method of treating a cancer, said method comprising:
administering to a subject in need thereof an effective amount of a nanovesicle drug carrier of claim 1.

19. A method of treating a cancer in a mammal, said method comprising:
administering to an intra-tumoral or peri-tumoral site an effective amount of a nanovesicle drug carrier of claim 1;
wherein said cancer is selected from the group consisting of colon cancer, pancreatic cancer, and breast cancer.

20. A kit for the treatment or prophylaxis of a cancer said kit comprising:
a container containing:
a nanovesicle drug carrier of claim 1.

21. The method of claim 19, wherein said nanovesicle drug carrier is administered via a route selected from the group consisting of intravenous administration, intraarterial administration, intracerebral administration, intrathecal administration, oral administration, aerosol administration, administration via inhalation, intracranial administration via a cannula, and subcutaneous or intramuscular depot deposition.

* * * * *